(12) United States Patent
Maruyama et al.

(10) Patent No.: US 9,637,469 B2
(45) Date of Patent: May 2, 2017

(54) PYRIDINE DERIVATIVE

(71) Applicant: Teijin Pharma Limited, Tokyo (JP)

(72) Inventors: Akinobu Maruyama, Hino (JP); Hirofumi Kamada, Hino (JP); Mika Fujinuma, Chiyoda-ku (JP); Susumu Takeuchi, Hino (JP); Hiroshi Saitoh, Hino (JP); Yoshimasa Takahashi, Hino (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 0 days.

(21) Appl. No.: 14/441,074

(22) PCT Filed: Nov. 13, 2013

(86) PCT No.: PCT/JP2013/080706
§ 371 (c)(1),
(2) Date: May 6, 2015

(87) PCT Pub. No.: WO2014/077285
PCT Pub. Date: May 22, 2014

(65) Prior Publication Data
US 2015/0284358 A1 Oct. 8, 2015

(30) Foreign Application Priority Data
Nov. 14, 2012 (JP) .................. 2012-250661

(51) Int. Cl.
| C07D 401/04 | (2006.01) |
| C07D 409/14 | (2006.01) |
| A61K 31/4439 | (2006.01) |
| C07D 401/12 | (2006.01) |
| C07D 491/048 | (2006.01) |

(52) U.S. Cl.
CPC ........ *C07D 401/04* (2013.01); *A61K 31/4439* (2013.01); *C07D 401/12* (2013.01); *C07D 409/14* (2013.01); *C07D 491/048* (2013.01)

(58) Field of Classification Search
CPC .................................................. C07D 401/04
USPC ....................... 546/274.1; 514/341
See application file for complete search history.

(56) References Cited

U.S. PATENT DOCUMENTS

| 4,185,992 A | 1/1980 | Gilmour |
| 4,340,598 A | 7/1982 | Furukawa et al. |
| 4,770,689 A | 9/1988 | Van Gestel et al. |
| 4,851,424 A | 7/1989 | Allgeier |
| 2002/0115702 A1 | 8/2002 | Remuzzi |
| 2003/0181496 A1 | 9/2003 | Tokunaga et al. |
| 2010/0056542 A1 | 3/2010 | Gunic et al. |
| 2012/0172345 A1 | 7/2012 | Freeze et al. |

FOREIGN PATENT DOCUMENTS

| JP | 53-111068 A | 9/1978 |
| JP | 56-71073 A | 6/1981 |
| JP | 62-277363 A | 12/1987 |
| JP | 62-292763 A | 12/1987 |
| JP | 08-119936 A | 5/1996 |
| JP | 2001-517698 A | 10/2001 |
| JP | 2010-202575 A | 9/2010 |
| WO | 02/10131 A1 | 2/2002 |
| WO | 2004/108730 A1 | 12/2004 |
| WO | 2011/159839 A2 | 12/2011 |
| WO | 2012/021696 A1 | 2/2012 |

OTHER PUBLICATIONS

Jordan "Tamoxifen . . . " Nature Rev. v.2, p. 205-213 (2003).*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory and Morris (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Ivanisevic et al. "Use of X-ray . . . " Pharm. Sci. Encycl. p. 1-42 (2010).*
Seddon "Pseudopolymorph . . . " Crystal Growth & design v.4(6) p. 1087 (2004) (2 pages from internet).*
Jain et al., "Polymorphism in Pharmacy", Indian Drugs, 1986, 23(6) 315-329.*
Peng Zhang et al., "Synthesis and in vitro anti-hepatitis B and C virus activities of ring-expanded ('fat') nucleobase analogues containing the imidazo [4, 5-e][1,3] diazepine-4, 8-dione ring system", Bioorganic & Medicinal Chemistry Letters, 2005, pp. 5397-5401, vol. 15, No. 15.

(Continued)

*Primary Examiner* — Patricia L Morris
(74) *Attorney, Agent, or Firm* — Sughrue Mion, PLLC

(57) ABSTRACT

Provided is a pyridine derivative represented by formula (I), a prodrug thereof, a pharmaceutically acceptable salt of the pyridine derivative or the prodrug, or a solvate of the pyridine derivative, the prodrug or the pharmaceutically acceptable salt, which is useful for treatment or prophylaxis of diseases associated with URAT1 such as gout, hyperuricemia, hypertension, kidney diseases such as interstitial nephritis, diabetes, arteriosclerosis and Lesch-Nyhan syndrome.

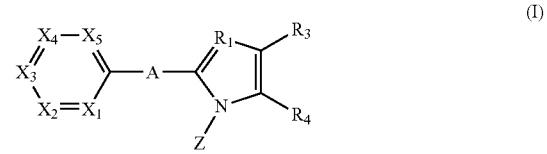

(I)

10 Claims, No Drawings

(56) References Cited

OTHER PUBLICATIONS

Franz Effenberger et al., "Zur Reaktion von Pyroglutaminsaure-Derivaten mit Phosphorpentachlorid Darstellung chlorierter Pyrrol-2-carbonsaure-Derivate", Chemische Berichte, 1987, pp. 45-54, vol. 120, No. 1.
Matthias Eckhardt et al., "Synthesis of 2-bromo-7-methyl-3,5-dihydro-imidazo[4,5-d]pyridazin-4-one and 3-alkyl-2-bromo-3,5-dihydro-imidazo [4,5-d]pyridazin-4-one and their selective elaboration", Tetrahedron Letters, 2008, pp. 1931-1934, vol. 49, No. 12.
Atsushi Enomoto et al., "Molecular identification of a renal urate-anion exchanger that regulates blood urate levels", Letters to Nature, 2002, pp. 447-452, vol. 417.
International Search Report for PCT/JP2013/080706 dated Feb. 4, 2014.

\* cited by examiner

PYRIDINE DERIVATIVE

CROSS REFERENCE TO RELATED APPLICATIONS

This application is a National Stage of International Application No. PCT/JP2013/080706 filed Nov. 13, 2013, claiming priority based on Japanese Patent Application No. 2012-250661, filed Nov. 14, 2012, the contents of all of which are incorporated herein by reference in their entirety.

TECHNICAL FIELD

The present invention relates to a pyridine derivative useful as a pharmaceutical. More particularly, it relates to a pyridine derivative having inhibitory activity against URAT1 and useful in the treatment or prevention of a URAT1-associated disease, such as gout, hyperuricemia, hypertension, renal disease such as interstitial nephritis, diabetes, arteriosclerosis, or Lesch-Nyhan syndrome, or a prodrug thereof, or a pharmaceutically acceptable salt thereof, or a solvate thereof.

BACKGROUND ART

Uric acid is the final product of purine metabolism in the liver. The main route of uric acid excretion is the kidney. Approximately two-thirds of uric acid is excreted in the urine and the remaining is excreted in feces. Although blood uric acid is maintained inappropriate levels in healthy individuals, hyperuricemia is induced when an excessive production of uric acid or a decreased excretion of uric acid occurs.

Hyperuricemia, in which blood uric acid levels become elevated, is a factor that causes gout and urinary calculus, and furthermore it is said to contribute to nephropathy and arteriosclerosis. In addition, there have recently been an increasing number of reports that the higher the blood uric acid level, the higher the incidence rates of lifestyle-related diseases such as metabolic syndrome and hypertension, chronic kidney disease, and the like, and hyperuricemia is being recognized to be a risk factor for these diseases. Thus, an improvement in hyperuricemia is expected to lead to improvements in various diseases (Non-Patent Document 1).

Recently, the gene (SLC22A12) encoding a human renal urate transporter has been identified. The transporter (urate transporter 1, URAT1) encoded by this gene is a 12-transmembrane type molecule belonging to the OAT family. Its mRNA is specifically expressed in the kidney, and further, its localization on apical side of the proximal tubule has been observed in human kidney tissue sections. URAT1-mediated uric acid uptake has been shown by experiments using the *Xenopus* oocyte expression system. Furthermore, it has been reported that probenecid or benzbromarone, which inhibits URAT1, is useful agent for prevention or treatment of hyperuricemia, gout, and the like (Non-Patent Document 2).

RELATED ART DOCUMENTS

Non-Patent Documents

[Non-Patent Document 1] The Guideline Revising Committee of Japanese Society of Gout and Nucleic Acid Metabolism, ed., *Guideline for the management of hyperuricemia and gout*, second edition, Medical Review (2010).

[Non-Patent Document 2] Enomoto A. et al., Nature 417, 447-452 (2002).

SUMMARY OF THE INVENTION

Problems to be Solved by the Invention

It is an object of the present invention to provide a novel compound having URAT1-inhibitory activity.

Additionally, it is another object of the present invention to provide an agent for treatment or prevention of a URAT1-associated disease, such as gout, hyperuricemia, hypertension, renal disease such as interstitial nephritis, diabetes, arteriosclerosis, or Lesch-Nyhan syndrome, containing the novel compound having URAT1-inhibitory activity as an active ingredient

Means of Solving the Problems

As a result of diligent studies with the above objects, the present inventors have reached the following invention.

That is, the present invention is a pyridine derivative represented by the following formula (I) or a pharmaceutically acceptable salt thereof, or a solvate thereof:

[Chemical Formula 1]

$$\begin{array}{c} X_4{=}X_5 \\ \| \\ X_3 \\ \backslash \\ X_2{=}X_1 \end{array} {-} A {-} \begin{array}{c} R_1 \diagup R_3 \\ \diagdown \\ N \diagdown R_4 \\ | \\ Z \end{array} \quad (I)$$

wherein:
A represents a single bond, an oxygen atom, a sulfur atom, NH, or $CH_2$;
$R_1$ represents a nitrogen atom or CH;
one of $X_1$ to $X_5$ represents a nitrogen atom, and the remaining four represent $CR_2$;
$R_2$ each independently represent a hydrogen atom, an alkyl group having 1 to 6 carbon atoms, an alkenyl group having 2 to 6 carbon atoms, an alkynyl group having 2 to 6 carbon atoms, a halogen atom, a trifluoromethyl group, a difluoromethyl group, a cyano group, an alkylcarbonyl group having 2 to 7 carbon atoms, an alkylsulfonyl group having 1 to 6 carbon atoms, a nitro group, an amino group, a dialkylamino group having 1 to 6 carbon atoms which may optionally form a ring, a formyl group, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom), with the proviso that when two $CR_2$'s are adjacent, the two $R_2$'s may optionally be joined together to form a ring;
$R_3$ represents a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkenyl group having 2 to 6 carbon atoms, an alkynyl group having 2 to 6 carbon atoms, an alkoxy group having 1 to 6 carbon atoms (which may optionally be substituted with one or more of a hydroxyl group and a halogen atom), an alkylcarbonyl group having 2 to 7 carbon atoms, an alkylthio group having 1 to 6 carbon atoms, an alkylsulfinyl group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a pyridyl group (which may optionally be substituted with one or more of an alkyl group having 1 to 6 carbon atoms, an alkoxy group having 1 to 6 carbon atoms, and a halogen atom), a phenoxy group (which may optionally be substituted with one or more of an alkyl group having 1 to 6 carbon atoms, an alkoxy group having 1 to 6 carbon atoms, and a halogen atom), a carboxyl group, or —CO$_2$R$_5$;

R$_4$ represents a carboxyl group, a tetrazolyl group, —CONHSO$_2$R$_5$, —CO$_2$R$_5$, or any of the following substituents:

[Chemical Formula 2]

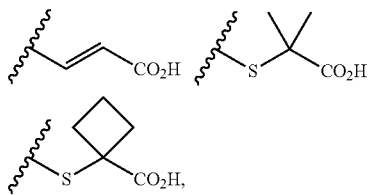

with the proviso that when R$_3$ is an alkyl group having 1 to 6 carbon atoms substituted with a hydroxyl group and when R$_4$ is a carboxyl group, then R$_3$ and R$_4$ may optionally be fused to form a lactone ring;

R$_5$ in R$_3$ and R$_4$ each independently represents an alkyl group having 1 to 6 carbon atoms;

Z represents any of the following substituents, designated Z1 to Z7:

[Chemical Formula 3]

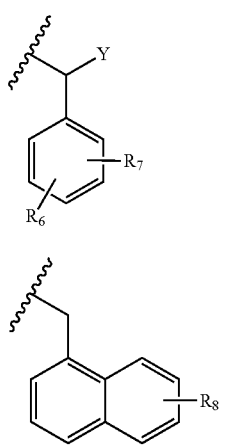

Z1

Z2

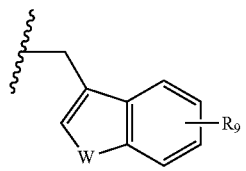

Z3

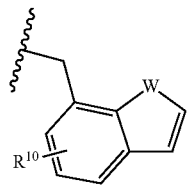

Z4

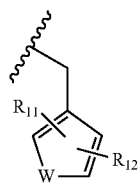

Z5

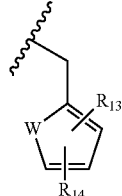

Z6

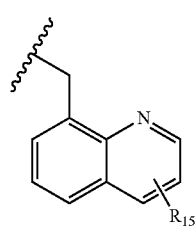

Z7 wherein:

R$_6$ and R$_7$ each independently represent a hydrogen atom, a halogen atom, an alkyl group having 1 to 6 carbon atoms, a trifluoromethyl group, a trifluoromethoxy group, or a cyano group, with the proviso that the case where R$_6$ and R$_7$ are simultaneously hydrogen atoms is excluded;

R$_8$ represents a hydrogen atom, a halogen atom, an alkyl group having 1 to 6 carbon atoms, or a trifluoromethyl group;

R$_9$ represents a hydrogen atom, a halogen atom, an alkyl group having 1 to 6 carbon atoms, or a trifluoromethyl group;

R$_{10}$ represents a hydrogen atom, a halogen atom, an alkyl group having 1 to 6 carbon atoms, or a trifluoromethyl group;

R$_{11}$ and R$_{12}$ each independently represent a hydrogen atom, a halogen atom, an alkyl group having 1 to 6 carbon atoms, or a trifluoromethyl group;

R$_{13}$ and R$_{14}$ each independently represent a hydrogen atom, a halogen atom, an alkyl group having 1 to 6 carbon atoms, or a trifluoromethyl group;

R$_{15}$ represents a hydrogen atom, a halogen atom, an alkyl group having 1 to 6 carbon atoms, or a trifluoromethyl group;

Y represents a hydrogen atom or an alkyl group having 1 to 6 carbon atoms; and

W represents a sulfur atom, an oxygen atom, or $NR_{16}$ (where $R_{16}$ represents a hydrogen atom, an alkyl group having 1 to 6 carbon atoms, or a benzyl group).

The present invention also provides a prodrug of the pyridine derivative represented by the above formula (I) or a pharmaceutically acceptable salt thereof, or a solvate thereof. In addition, the present invention provides: a pharmaceutical composition containing a pyridine derivative represented by the above formula (I) or a prodrug thereof, or a pharmaceutically acceptable salts thereof, or a solvate thereof, and a pharmaceutically acceptable carrier; a URAT1 inhibitor containing as an active ingredient a pyridine derivative represented by the above formula (I) or a prodrug thereof, or a pharmaceutically acceptable salt thereof, or a solvate thereof; and an agent for treatment or prevention of a URAT1-associated disease, such as gout, hyperuricemia, hypertension, renal disease such as interstitial nephritis, diabetes, arteriosclerosis, or Lesch-Nyhan syndrome, containing as an active ingredient a pyridine derivative represented by the above formula (I) or a prodrug thereof, or a pharmaceutically acceptable salt thereof, or a solvate thereof.

Furthermore, the present invention provides compounds represented by the following formula (II) and formula (III) useful in the synthesis of pyridine derivatives represented by the above formula (I) or a pharmaceutically acceptable salt thereof, or a solvate thereof.

[Chemical Formula 4]

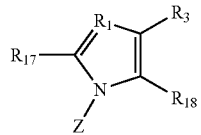

(II)

wherein:

$R_1$ and $R_3$ are as defined in the formula (I);

$R_{17}$ represents a chlorine atom, a bromine atom, or an iodine atom;

$R_{18}$ represents a formyl group or —$CO_2R_5$;

$R_5$ in $R_3$ and $R_{18}$ each independently represents an alkyl group having 1 to 6 carbon atoms; and Z represents any of the following substituents, designated Z1 to Z7:

[Chemical Formula 5]

Z1

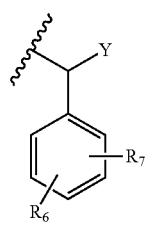

Z2

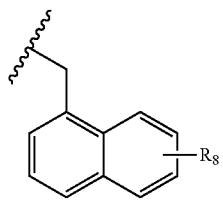

Z3

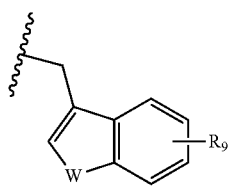

Z4

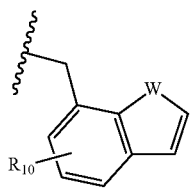

Z5

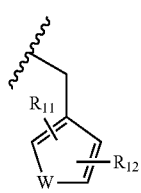

Z6

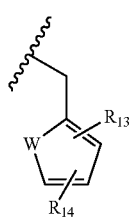

Z7

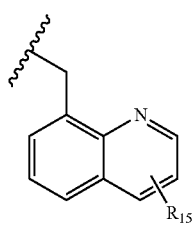

wherein $R_6$ to $R_{15}$, Y, and W are as defined in the formula (I), with the proviso that 2-chloro-1-(thiophen-2-ylmethyl)-1H-pyrrole-5-carbaldehyde, ethyl 2-bromo-1-(4-methylbenzyl)-1H-pyrrole-5-carboxylate, and dimethyl 2-bromo-1-(2-chlorobenzyl)-1H-imidazole-4,5-dicarboxylate are excluded.

[Chemical Formula 6]

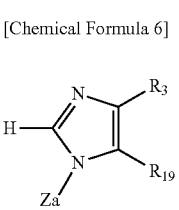

(III)

wherein:

$R_3$ is as defined in the formula (I);

$R_{19}$ represents —$CO_2R_5$;

$R_5$ in $R_3$ and $R_{19}$ each independently represents an alkyl group having 1 to 6 carbon atoms; and Za represents a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group.

Effects of the Invention

According to the present invention, there is provided a novel pyridine derivative or a prodrug thereof, or a pharmaceutically acceptable salt thereof, or a solvate thereof, useful as an agent for treatment or prevention of a URAT1-associated disease, such as gout, hyperuricemia, hypertension, renal disease such as interstitial nephritis, diabetes, arteriosclerosis, or Lesch-Nyhan syndrome.

MODE FOR CARRYING OUT THE INVENTION

Definitions of the terms for the purpose of the present invention are as follows.

An alkyl group, for the purpose of the present invention, refers to a straight-chain, branched, or cyclic saturated aliphatic hydrocarbon group. Specific examples of the alkyl group having 1 to 6 carbon atoms can include, for example, methyl group, ethyl group, propyl group, isopropyl group, butyl group, isobutyl group, tert-butyl group, pentyl group, isopentyl group, hexyl group, cyclopropyl group, cyclopropylmethyl group, cyclopentyl group, or cyclohexyl group.

An alkenyl group, for the purpose of the present invention, refers to a straight-chain, branched, or cyclic unsaturated aliphatic hydrocarbon group containing at least one carbon-carbon double bond. Specific examples of the alkenyl group having 2 to 6 carbon atoms can include, for example, ethenyl group, 1-propenyl group, 2-propenyl group, 2-methyl-1-propenyl group, 1-butenyl group, 2-butenyl group, 3-butenyl group, 3-methyl-2-butenyl group, 1-pentenyl group, 2-pentenyl group, 3-pentenyl group, 4-pentenyl group, 4-methyl-3-pentenyl group, 1-hexenyl group, 3-hexenyl group, 5-hexenyl group, 1-cyclopenten-1-yl group, 3-cyclopenten-1-yl group, 2-cyclohexen-1-yl group, 3-cyclohexen-1-yl group, etc.

An alkynyl group, for the purpose of the present invention, refers to a straight-chain or branched unsaturated aliphatic hydrocarbon group containing at least one carbon-carbon triple bond. Specific examples of the alkynyl group having 2 to 6 carbon atoms can include, for example, ethynyl group, 1-propynyl group, 2-propynyl group, 1-butynyl group, 2-butynyl group, 3-butynyl group, 1-pentynyl group, 2-pentynyl group, 3-pentynyl group, 4-pentynyl group, 1-hexynyl group, 2-hexynyl group, 3-hexynyl group, 4-hexynyl group, 5-hexynyl group, etc.

An alkylcarbonyl group, for the purpose of the present invention, refers to an aforesaid alkyl group attached through a carbonyl group. Specific examples of the alkylcarbonyl group having 2 to 7 carbon atoms can include, for example, acetyl group, propanoyl group, butanoyl group, isobutanoyl group, sec-butanoyl group, tert-butanoyl group, pentanoyl group, isopentanoyl group, hexanoyl group, cyclopropylcarbonyl group, cyclohexylcarbonyl group, etc.

An alkylsulfonyl group, for the purpose of the present invention, refers to an aforesaid alkyl group attached through a sulfonyl group. Specific examples of the alkylsulfonyl group having 1 to 6 carbon atoms can include, for example, methylsulfonyl group, ethylsulfonyl group, isopropylsulfonyl group, or cyclopropylsulfonyl group.

An alkylsulfinyl group, for the purpose of the present invention, refers to an aforesaid alkyl group attached through a sulfinyl group. Specific examples of the alkylsulfinyl group having 1 to 6 carbon atoms can include, for example, methylsulfinyl group, ethylsulfinyl group, isopropylsulfinyl group, or cyclopropylsulfinyl group.

An alkoxy group, for the purpose of the present invention, refers to a straight-chain, branched, or cyclic saturated aliphatic hydrocarbonoxy group. Specific examples of the alkoxy group having 1 to 6 carbon atoms can include, for example, methoxy group, ethoxy group, propoxy group, isopropoxy group, butoxy group, isobutoxy group, pentyloxy group, isopentyloxy group, hexyloxy group, cyclopropoxy group, cyclopropylmethoxy group, or cyclohexyloxy group.

An alkylthio group, for the purpose of the present invention, refers to a straight-chain, branched, or cyclic saturated aliphatic hydrocarbonsulfide group. Specific examples of the alkylthio group having 1 to 6 carbon atoms can include, for example, methylthio group, ethylthio group, propylthio group, isopropylthio group, butylthio group, isobutylthio group, pentylthio group, isopentylthio group, hexylthio group, cyclopropylthio group, cyclopropylmethylthio group, or cyclohexylthio group.

A dialkylamino group, for the purpose of the present invention, refers to an amino group substituted with two identical or different aforesaid alkyl groups. A dialkylamino group having 1 to 6 carbon atoms, for the purpose of the present invention, refers to an amino group substituted with two identical or different alkyl groups each having 1 to 6 carbon atoms. A dialkylamino group, for the purpose of the present invention, may optionally form a ring with the alkyl groups. Specific examples of the dialkylamino groups having 1 to 6 carbon atoms which may optionally form a ring can include, for example, dimethylamino group, diethylamino group, pyrrolidin-1-yl group, or piperidin-1-yl group.

A halogen atom, for the purpose of the present invention, refers to a fluorine atom, a chlorine atom, a bromine atom, and an iodine atom.

For the purpose of the present invention, "when two $CR_2$'s are adjacent, the two $R_2$'s are joined together to form a ring" means that two $R_2$'s are joined together and taken together with the carbon atoms to which they are attached on the pyridine ring to form a nonaromatic or aromatic ring. The joining of two $R_2$'s to form a ring results in the formation of a bicyclic ring in which the ring is fused to a pyridine ring. Such nonaromatic or aromatic ring may be a hydrocarbon ring or a heterocycle having an oxygen atom, a nitrogen atom, or a sulfur atom as a constituent atom.

For the purpose of the present invention, "substituted with an imidazole ring, a pyrazole ring, a pyrrolidine ring, a piperidine ring, a morpholine ring, or a piperazine ring" refers to being substituted with any of the groups derived from each of these rings by the removal of one hydrogen atom therefrom.

[Chemical Formula 7]

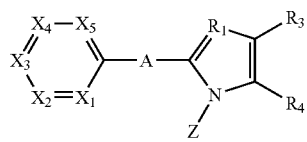

(I)

In the above formula (I), A represents a single bond, an oxygen atom, a sulfur atom, NH, or $CH_2$. Preferably, A is a single bond or an oxygen atom, and more preferably a single bond.

$R_1$ represents a nitrogen atom or CH, and preferably a nitrogen atom.

One of $X_1$ to $X_5$ represents a nitrogen atom, and the remaining four represent $CR_2$. Preferably, $X_1$ or $X_2$ is a nitrogen atom, and more preferably $X_2$ is a nitrogen atom.

$R_2$ each independently represent a hydrogen atom, an alkyl group having 1 to 6 carbon atoms, an alkenyl group having 2 to 6 carbon atoms, an alkynyl group having 2 to 6 carbon atoms, a halogen atom, a trifluoromethyl group, a difluoromethyl group, a cyano group, an alkylcarbonyl group having 2 to 7 carbon atoms, an alkylsulfonyl group having 1 to 6 carbon atoms, a nitro group, an amino group, a dialkylamino group having 1 to 6 carbon atoms which may optionally form a ring, a formyl group, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom), with the proviso that when two $CR_2$s are adjacent, the two $R_2$'s may optionally be joined together to form a ring. The ring formed by two adjacent $CR_2$'s is preferably an aromatic hydrocarbon ring, and more preferably a benzene ring. Preferably, $R_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms which may optionally form a ring, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom). More preferably, $R_2$ is a hydrogen atom, a methyl group, an ethyl group, a cyclopropyl group, a methoxy group, an ethoxy group, a methylthio group, a fluorine atom, a chlorine atom, a bromine atom, a cyano group, a hydroxyl group, a pyrrolidin-1-yl group, a trifluoromethyl group, a difluoromethyl group, a nitro group, a phenyl group, or a phenoxy group. Even more preferably, $R_2$ is a hydrogen atom, a methyl group, an ethyl group, a cyclopropyl group, a fluorine atom, a chlorine atom, a bromine atom, a methoxy group, an ethoxy group, a methylthio group, a trifluoromethyl group, a difluoromethyl group, a nitro group, or a phenyl group.

When three of the four $CR_2$'s are CH, preferred positions of the remaining $CR_2$ can include $X_4$. When three of the four $CR_2$'s are CH, the combination of the positions of a nitrogen atom and the remaining $CR_2$ is preferably the combination in which $X_2$ is a nitrogen atom and $X_4$ is $CR_2$.

When two of the four $CR_2$'s are CH, combinations of the positions of a nitrogen atom and the remaining $CR_2$'s can include, for example, the combination in which $X_2$ is a nitrogen atom and $X_1$ and $X_3$ are $CR_2$, and the combination in which $X_2$ is a nitrogen atom and $X_3$ and $X_4$ are $CR_2$.

$R_3$ represents a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkenyl group having 2 to 6 carbon atoms, an alkynyl group having 2 to 6 carbon atoms, an alkoxy group having 1 to 6 carbon atoms (which may optionally be substituted with one or more of a hydroxyl group and a halogen atom), an alkylcarbonyl group having 2 to 7 carbon atoms, an alkylthio group having 1 to 6 carbon atoms, an alkylsulfinyl group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a pyridyl group (which may optionally be substituted with one or more of an alkyl group having 1 to 6 carbon atoms, an alkoxy group having 1 to 6 carbon atoms, and a halogen atom), a phenoxy group (which may optionally be substituted with one or more of an alkyl group having 1 to 6 carbon atoms, an alkoxy group having 1 to 6 carbon atoms, and a halogen atom), a carboxyl group, or —$CO_2R_5$. Preferably, $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$. More preferably, $R_3$ is a hydrogen atom, a methyl group, an ethyl group, an isopropyl group, a cyclopropyl group, a trifluoromethyl group, a difluoromethyl group, a chlorine atom, a bromine atom, an iodine atom, a methoxy group, a methylthio group, an ethylthio group, a cyano group, a phenyl group, a carboxyl group, —CO$_2$R$_5$, a hydroxymethyl group, a 2-hydroxypropan-2-yl group, a 3-hydroxypentan-3-yl group, or a morpholin-4-ylmethyl group.

R$_4$ represents a carboxyl group, a tetrazolyl group, —CONHSO$_2$R$_5$, or —CO$_2$R$_5$, or any of the following substituents:

[Chemical Formula 8]

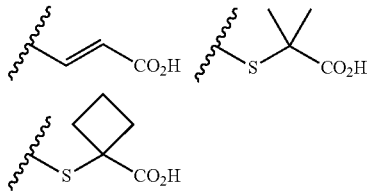

with the proviso that when R$_3$ is an alkyl group having 1 to 6 carbon atoms substituted with a hydroxyl group and when R$_4$ is a carboxyl group, then R$_3$ and R$_4$ may optionally be fused to form a lactone ring. Preferably, R$_4$ is a carboxyl group (which, when R$_3$ is an alkyl group having 1 to 6 carbon atoms substituted with a hydroxyl group, may optionally be fused with R$_3$ to form a lactone ring), a tetrazolyl group, —CONHSO$_2$CH$_3$, —CONHSO$_2$-cyclopropyl, or —CO$_2$R$_5$.

R$_5$ in R$_3$ and R$_4$ each independently represents an alkyl group having 1 to 6 carbon atoms.

Further, Z in the above formula (I) represents any of the following substituents, designated Z1 to Z7.

[Chemical Formula 9]

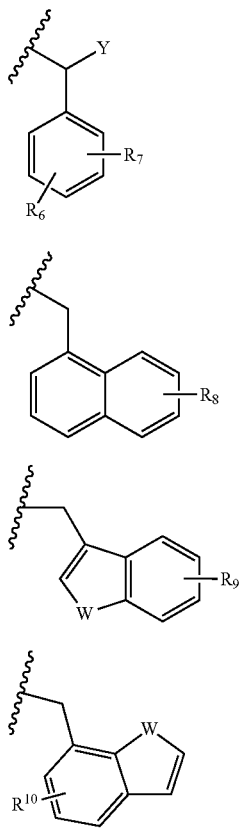

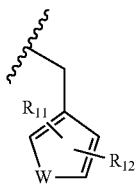

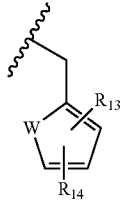

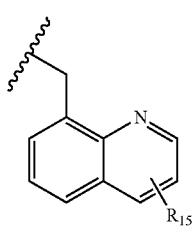

In Z1, R$_6$ and R$_7$ each independently represent a hydrogen atom, a halogen atom, an alkyl group having 1 to 6 carbon atoms, a trifluoromethyl group, a trifluoromethoxy group, or a cyano group, with the proviso that the case where R$_6$ and R$_7$ are simultaneously hydrogen atoms is excluded. Preferably, R$_6$ and R$_7$ are each a methyl group, a fluorine atom, a chlorine atom, a bromine atom, or a trifluoromethyl group. More preferably, R$_6$ and R$_7$ are each a chlorine atom, a methyl group, or a trifluoromethyl group. Preferred substitution positions for R$_6$ and R$_7$ on the benzene ring are 2,5-disubstitution and 3,5-disubstitution, and the more preferred is 2,5-disubstitution. A preferred combination of R$_6$ and R$_7$ with their substitution positions on the benzene ring is 2,5-dichloro substitution, 3,5-dichloro substitution, 2,5-dimethyl substitution, 2,5-bis(trifluoromethyl) substitution, or 2-chloro-5-methyl substitution.

Y represents a hydrogen atom or an alkyl group having 1 to 6 carbon atoms. Preferably, Y is a hydrogen atom.

In Z2, R$_8$ represents a hydrogen atom, a halogen atom, an alkyl group having 1 to 6 carbon atoms, or a trifluoromethyl group. A preferred combination of R$_8$ with its substitution position on the naphthalene ring is a hydrogen atom, a 2-methyl group, a 4-methyl group, an 8-methyl group, or an 8-bromo group.

In Z3, R$_9$ represents a hydrogen atom, a halogen atom, an alkyl group having 1 to 6 carbon atoms, or a trifluoromethyl group. W represents a sulfur atom, an oxygen atom, or NR$_{16}$ (where R$_{16}$ represents a hydrogen atom, an alkyl group having 1 to 6 carbon atoms, or a benzyl group), and preferably a sulfur atom.

A preferred combination of R$_9$ with its substitution position on the benzothiophene, benzofuran, or indole ring is a hydrogen atom, a 4-methyl group, a 4-chloro group, a 4-bromo group, a 4-trifluoromethyl group, a 5-methyl group, a 5-chloro group, or a 5-trifluoromethyl group.

In Z4, R$_{10}$ represents a hydrogen atom, a halogen atom, an alkyl group having 1 to 6 carbon atoms, or a trifluoromethyl group. W represents a sulfur atom, an oxygen atom, or NR$_{16}$ (where R$_{16}$ represents a hydrogen atom, an alkyl group having 1 to 6 carbon atoms, or a benzyl group), and preferably a sulfur atom. A preferred combination of $R_{10}$ with its substitution position on the benzothiophene, benzofuran, or indole ring is a hydrogen atom or a 5-fluoro group.

In Z5, $R_{11}$ and $R_{12}$ each independently represent a hydrogen atom, a halogen atom, an alkyl group having 1 to 6 carbon atoms, or a trifluoromethyl group. W represents a sulfur atom, an oxygen atom, or $NR_{16}$ (where $R_{16}$ represents a hydrogen atom, an alkyl group having 1 to 6 carbon atoms, or a benzyl group), and preferably a sulfur atom. A preferred combination of $R_{11}$ and $R_{12}$ with their substitution positions on the thiophene, furan, or pyrrole ring is 2,5-dichloro substitution.

In Z6, $R_{13}$ and $R_{14}$ each independently represent a hydrogen atom, a halogen atom, an alkyl group having 1 to 6 carbon atoms, or a trifluoromethyl group. W represents a sulfur atom, an oxygen atom, or $NR_{16}$ (where $R_{16}$ represents a hydrogen atom, an alkyl group having 1 to 6 carbon atoms, or a benzyl group), and preferably a sulfur atom. A preferred combination of $R_{13}$ and $R_{14}$ with their substitution positions on the thiophene, furan, or pyrrole ring is 2,4-dichloro substitution.

In Z7, $R_{15}$ represents a hydrogen atom, a halogen atom, an alkyl group having 1 to 6 carbon atoms, or a trifluoromethyl group. Preferably, $R_{15}$ is a hydrogen atom.

Preferred among Z1 to Z7 are Z1 to Z6, and more preferred are Z1 to Z4.

Preferred Z is, in particular, for example, a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group, and more preferred Z is, for example, a 2,5-dichlorobenzyl group, a 2,5-dimethylbenzyl group, a naphthalen-1-ylmethyl group, a (4-chlorobenzo[b]thiophen-3-yl)methyl group, or a benzo[b]thiophen-7-ylmethyl group.

Preferred combinations of the A, $X_1$-$X_5$, $R_1$-$R_4$, and Z present in the formula (I) according to the present invention can include the following combinations 1) to 11).

1) A is a single bond; $R_1$ is a nitrogen atom; $X_1$ is a nitrogen atom; $X_4$ is $CR_2$, and $X_2$, $X_3$, and $X_5$ are CH; $R_2$ is a hydrogen atom, an alkyl group having 1 to 6 carbon atoms, a halogen atom, a trifluoromethyl group, a difluoromethyl group, a cyano group, a nitro group, a dialkylamino group optionally forming a ring with the alkyl groups each having 1 to 6 carbon atoms, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom); $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$; $R_4$ is a carboxyl group (which, when $R_3$ is an alkyl group having 1 to 6 carbon atoms substituted with a hydroxyl group, may optionally be fused with $R_3$ to form a lactone ring), a tetrazolyl group, —$CONHSO_2CH_3$, —$CONHSO_2$-cyclopropyl, or —$CO_2R_5$; and Z is a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group.

2) A is a single bond; $R_1$ is a nitrogen atom; $X_2$ is a nitrogen atom; $X_4$ is $CR_2$, and $X_1$, $X_3$, and $X_5$ are CH; $R_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms which may optionally form a ring, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may, optionally be substituted with one or more of an alkyl group having 1 to 6 carbon atoms, an alkoxy group having 1 to 6 carbon atoms, and a halogen atom); $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$; $R_4$ is a carboxyl group (which, when $R_3$ is an alkyl group having 1 to 6 carbon atoms substituted with a hydroxyl group, may optionally be fused with $R_3$ to form a lactone ring), a tetrazolyl group, —$CONHSO_2CH_3$, —$CONHSO_2$-cyclopropyl, or —$CO_2R_5$; and Z is a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group.

3) A is a single bond; $R_1$ is CH; $X_1$ is a nitrogen atom; $X_4$ is $CR_2$, and $X_2$, $X_3$, and $X_5$ are CH; $R_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms which may optionally form a ring, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom); $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$; $R_4$ is a carboxyl group (which, when $R_3$ is an alkyl group having 1 to 6 carbon atoms substituted with a hydroxyl group, may optionally be fused with $R_3$ to foil a lactone ring), a tetrazolyl group, —$CONHSO_2CH_3$, —$CONHSO_2$-cyclopropyl, or —$CO_2R_5$; and Z is a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group.

4) A is a single bond; $R_1$ is CH; $X_2$ is a nitrogen atom; $X_4$ is $CR_2$, and $X_1$, $X_3$, and $X_5$ are CH; $R_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms which may optionally form a ring, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom); $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$; $R_4$ is a carboxyl group (which, when $R_3$ is an alkyl group having 1 to 6 carbon atoms substituted with a hydroxyl group, may optionally be fused with $R_3$ to form a lactone ring), a tetrazolyl group, —$CONHSO_2CH_3$, —$CONHSO_2$-cyclopropyl, or —$CO_2R_5$; and Z is a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group.

5) A is an oxygen atom; $R_1$ is a nitrogen atom; $X_1$ is a nitrogen atom; $X_4$ is $CR_2$, and $X_2$, $X_3$, and $X_5$ are CH; $R_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms which may optionally form a ring, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom); $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$; $R_4$ is a carboxyl group (which, when $R_3$ is an alkyl group having 1 to 6 carbon atoms substituted with a hydroxyl group, may optionally be fused with $R_3$ to form a lactone ring), a tetrazolyl group, —$CONHSO_2CH_3$, —$CONHSO_2$-cyclopropyl, or —$CO_2R_5$; and Z is a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinoline-8-ylmethyl group.

6) A is an oxygen atom; $R_1$ is a nitrogen atom; $X_2$ is a nitrogen atom; $X_4$ is $CR_2$, and $X_1$, $X_3$, and $X_5$ are CH; $R_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms which may optionally form a ring, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom); $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$; $R_4$ is a carboxyl group (which, when $R_3$ is an alkyl group having 1 to 6 carbon atoms substituted with a hydroxyl group, may optionally be fused with $R_3$ to form a lactone ring), a tetrazolyl group, —$CONHSO_2CH_3$, —$CONHSO_2$-cyclopropyl, or —$CO_2R_5$; and Z is a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group.

7) A is an oxygen atom; $R_1$ is CH; $X_1$ is a nitrogen atom; $X_4$ is $CR_2$, and $X_2$, $X_3$, and $X_5$ are CH; $R_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms which may optionally form a ring, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom); $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$; $R_4$ is a carboxyl group (which, when $R_3$ is an alkyl group having 1 to 6 carbon atoms substituted with a hydroxyl group, may optionally be fused with $R_3$ to form a lactone ring), a tetrazolyl group, —$CONHSO_2CH_3$, —$CONHSO_2$-cyclopropyl, or —$CO_2R_5$; and Z is a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group.

8) A is an oxygen atom; $R_1$ is CH; $X_2$ is a nitrogen atom; $X_4$ is $CR_2$, and $X_1$, $X_3$, and $X_5$ are CH; $R_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms which may optionally form a ring, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom); $R_3$ is a hydrogen atom, an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and a piperazine ring (which may optionally be substituted with one or more of an alkyl group having 1 to 6 carbon atoms and an alkylsulfonyl group having 1 to 6 carbon atoms)), an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$; $R_4$ is a carboxyl group (which, when $R_3$ is an alkyl group having 1 to 6 carbon atoms substituted with a hydroxyl group, may optionally be fused with $R_3$ to form a lactone ring), a tetrazolyl group, —$CONHSO_2CH_3$, —$CONHSO_2$-cyclopropyl, or —$CO_2R_5$; and Z is a 2,5-dichlorobenzyl group, a 3,5-di chlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl) methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl) methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl) methyl group, a (2,5-dichlorothiophen-3-yl)methyl group, a (2,4-dichlorothiophen-5-yl)methyl group, or a quinolin-8-ylmethyl group.

9) In 1) to 8) above, $R_2$ is a hydrogen atom, a methyl group, an ethyl group, a cyclopropyl group, a fluorine atom, a chlorine atom, a bromine atom, a methoxy group, an ethoxy group, a methylthio group, a trifluoromethyl group, a difluoromethyl group, a nitro group, or a phenyl group.

10) In 1) to 9) above, $R_3$ is a hydrogen atom, a methyl group, an ethyl group, an isopropyl group, a cyclopropyl group, a trifluoromethyl group, a difluoromethyl group, a chlorine atom, a bromine atom, an iodine atom, a methoxy group, a methylthio group, an ethylthio group, a cyano group, a phenyl group, a carboxyl group, —$CO_2R_5$, a hydroxymethyl group, a 2-hydroxypropan-2-yl group, a 3-hydroxypentan-3-yl group, or a morpholin-4-ylmethyl group.

11) In 1) to 10) above, Z is a 2,5-dichlorobenzyl group, a 2,5-dimethylbenzyl group, a naphthalen-1-ylmethyl group, a (4-chlorobenzo[b]thiophen-3-yl)methyl group, or a benzo[b]thiophen-7-ylmethyl group.

Synthetic intermediates useful in the synthesis of a pyridine derivative represented by the above formula (I) or a pharmaceutically acceptable salt thereof, or a solvate thereof, can include compounds represented by the following formula (II) and formula (III).

[Chemical Formula 10]

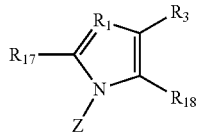

(II)

wherein:
$R_1$ and $R_3$ are as defined in the formula (I);
$R_{17}$ represents a chlorine atom, a bromine atom, or an iodine atom;
$R_{18}$ represents a formyl group or —$CO_2R_5$;
$R_5$ in $R_3$ and $R_{18}$ each independently represents an alkyl group having 1 to 6 carbon atoms; and
Z represents any of the following substituents, designated Z1 to Z7:

[Chemical Formula 11]

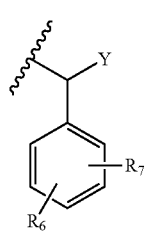

Z1

-continued

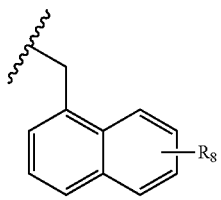
Z2

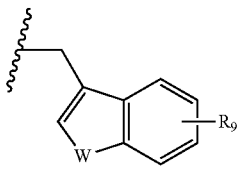
Z3

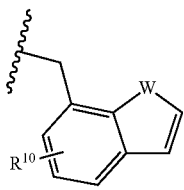
Z4

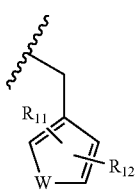
Z5

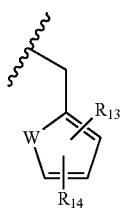
Z6

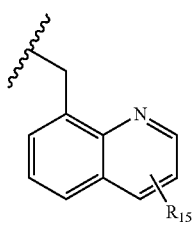
Z7 wherein $R_6$ to $R_{15}$, Y, and W are as defined in the formula (I), with the proviso that 2-chloro-1-(thiophen-2-ylmethyl)-1H-pyrrole-5-carbaldehyde, ethyl 2-bromo-1-(4-methylbenzyl)-1H-pyrrole-5-carboxylate, and dimethyl 2-bromo-1-(2-chlorobenzyl)-1H-imidazole-4,5-dicarboxylate are excluded.

Preferably $R_3$ is a hydrogen atom, an alkyl group having 1 to 6 carbon atoms (which may optionally be substituted with one or more hydroxyl groups), a halogen atom, a trifluoromethyl group, or —$CO_2R_5$. More preferably $R_3$ is a hydrogen atom, a methyl group, an ethyl group, an isopropyl group, a cyclopropyl group, a trifluoromethyl group, a chlorine atom, a bromine atom, or —$CO_2R_5$.

Preferred $R_{17}$ is a bromine atom or an iodine atom.

Preferred $R_{18}$ is a formyl group, —$CO_2CH_3$, or —$CO_2C_2H_5$.

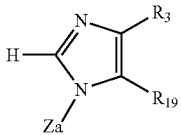

[Chemical Formula 12]

(III)

wherein:

$R_3$ is as defined in the formula (I);

$R_{19}$ represents —$CO_2R_5$;

$R_5$ in $R_3$ and $R_{19}$ each independently represents an alkyl group having 1 to 6 carbon atoms; and Za represents a 2,5-dichlorobenzyl group, a 3,5-dichlorobenzyl group, a 2,5-dimethylbenzyl group, a 2,5-bis(trifluoromethyl)benzyl group, a 2-chloro-5-methylbenzyl group, a naphthalen-1-ylmethyl group, a (2-methylnaphthalen-1-yl)methyl group, a (4-methylnaphthalen-1-yl)methyl group, a (8-methylnaphthalen-1-yl)methyl group, a (8-bromonaphthalen-1-yl)methyl group, a benzo[b]thiophen-3-ylmethyl group, a (4-methylbenzo[b]thiophen-3-yl)methyl group, a (4-chlorobenzo[b]thiophen-3-yl)methyl group, a (4-bromobenzo[b]thiophen-3-yl)methyl group, a (4-(trifluoromethyl)benzo[b]thiophen-3-yl)methyl group, a (5-methylbenzo[b]thiophen-3-yl)methyl group, a (5-chlorobenzo[b]thiophen-3-yl)methyl group, a (5-(trifluoromethyl)benzo[b]thiophen-3-yl)methyl group, a benzo[b]thiophen-7-ylmethyl group, a (5-fluorobenzo[b]thiophen-7-yl)methyl group, a (2,5-dichlorothiophen-3-yl)methyl group, a (2,4-dichlorothiophen-5-yl)methyl group, or a quinolin-8-ylmethyl group.

Preferably $R_3$ is a hydrogen atom, an alkyl group having 1 to 6 carbon atoms (which may optionally be substituted with one or more hydroxyl groups), a halogen atom, a trifluoromethyl group, or —$CO_2R_5$. More preferably $R_3$ is a hydrogen atom, a methyl group, an ethyl group, an isopropyl group, a cyclopropyl group, a trifluoromethyl group, a chlorine atom, a bromine atom, or —$CO_2R_5$.

Preferred $R_{19}$ is —$CO_2CH_3$ or —$CO_2C_2H_5$

Preferred Za is a 2,5-dichlorobenzyl group, a 2,5-dimethylbenzyl group, a naphthalen-1-ylmethyl group, a (4-chlorobenzo[b]thiophen-3-yl)methyl group, or benzo[b]thiophen-7-ylmethyl group.

Specific examples of the pyridine derivative represented by the formula (I) of the present invention can include the following compounds.

| Compound No. | Structure |
|---|---|
| | [Chemical Formula 13] |
| A1 | 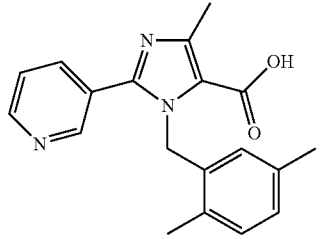 [SMILES: Cc1ccc(C)c(Cn2c(-c3cccnc3)nc(C)c2C(=O)O)c1] |

-continued
| Compound No. | Structure |
|---|---|
| A2 | 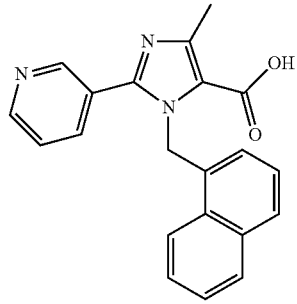 [SMILES: Cc1nc(-c2cccnc2)n(Cc2cccc3ccccc23)c1C(=O)O] |
| A3 | 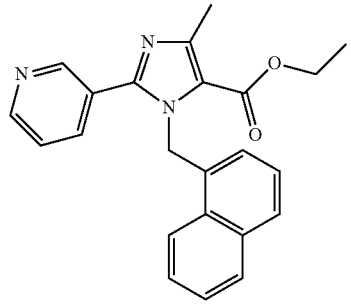 [SMILES: CCOC(=O)c1c(C)nc(-c2cccnc2)n1Cc1cccc2ccccc12] |
| A4 | 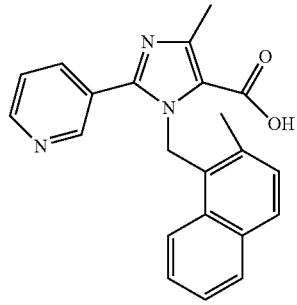 [SMILES: Cc1ccc2ccccc2c1Cn1c(-c2cccnc2)nc(C)c1C(=O)O] |
| A5 | 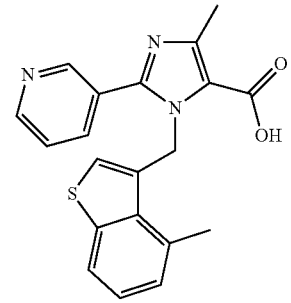 [SMILES: Cc1nc(-c2cccnc2)n(Cc2csc3cccc(C)c23)c1C(=O)O] |
| A6 | 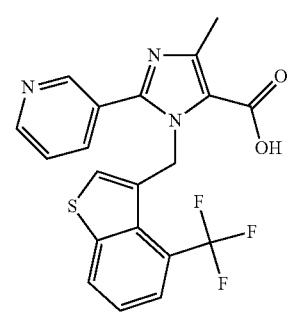 [SMILES: Cc1nc(-c2cccnc2)n(Cc2csc3cccc(C(F)(F)F)c23)c1C(=O)O] |
-continued
| Compound No. | Structure |
|---|---|
| A7 | 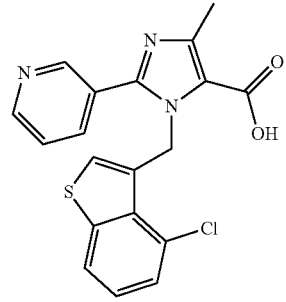 [SMILES: Cc1nc(-c2cccnc2)n(Cc2csc3cccc(Cl)c23)c1C(=O)O] |
| A8 | 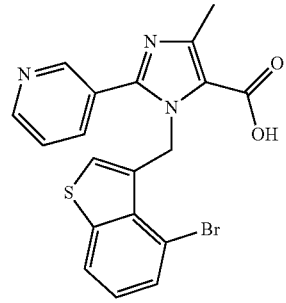 [SMILES: Cc1nc(-c2cccnc2)n(Cc2csc3cccc(Br)c23)c1C(=O)O] |
| A9 | 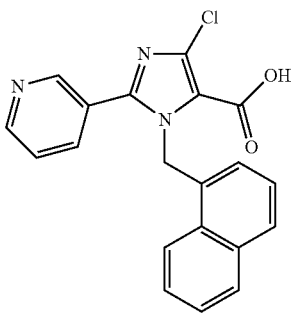 [SMILES: O=C(O)c1c(Cl)nc(-c2cccnc2)n1Cc1cccc2ccccc12] |
| A10 | 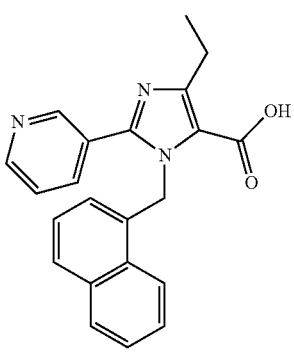 [SMILES: CCc1nc(-c2cccnc2)n(Cc2cccc3ccccc23)c1C(=O)O] |

TABLE-continued
| Compound No. | Structure |
|---|---|
| A11 | 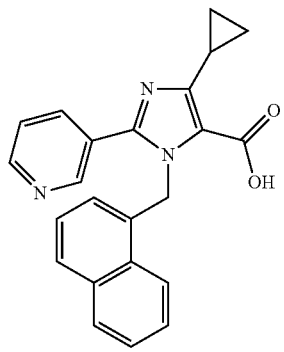 [SMILES: O=C(O)c1c(C2CC2)nc(-c2cccnc2)n1Cc1cccc2ccccc12] |
| A12 | 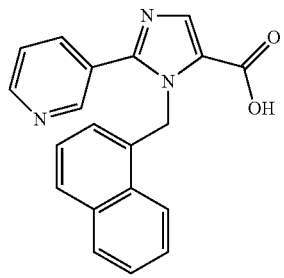 [SMILES: O=C(O)c1cnc(-c2cccnc2)n1Cc1cccc2ccccc12] |
[Chemical Formula 14]
| Compound No. | Structure |
|---|---|
| A13 | 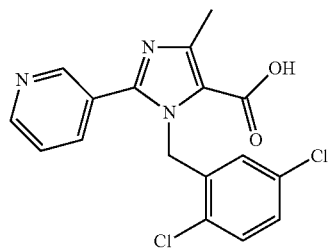 [SMILES: Cc1nc(-c2cccnc2)n(Cc2cc(Cl)ccc2Cl)c1C(=O)O] |
| A14 | 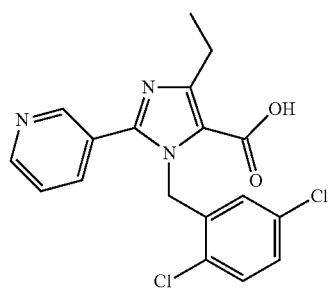 [SMILES: CCc1nc(-c2cccnc2)n(Cc2cc(Cl)ccc2Cl)c1C(=O)O] |
| A15 | 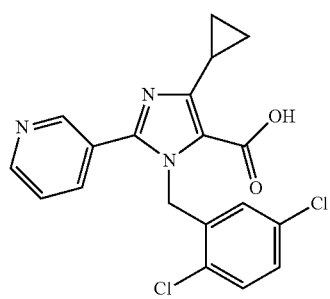 [SMILES: O=C(O)c1c(C2CC2)nc(-c2cccnc2)n1Cc1cc(Cl)ccc1Cl] |
| A16 | 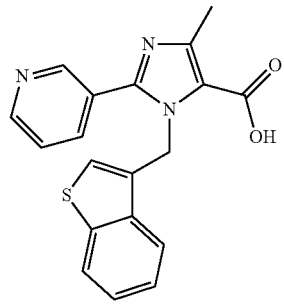 [SMILES: Cc1nc(-c2cccnc2)n(Cc2csc3ccccc23)c1C(=O)O] |
| A17 | 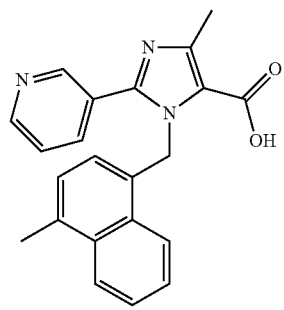 [SMILES: Cc1nc(-c2cccnc2)n(Cc2ccc(C)c3ccccc23)c1C(=O)O] |
| A18 | 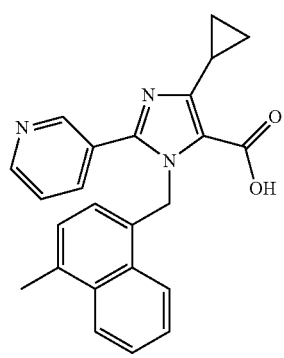 [SMILES: Cc1ccc(Cn2c(-c3cccnc3)nc(C3CC3)c2C(=O)O)c2ccccc12] |
| A19 | 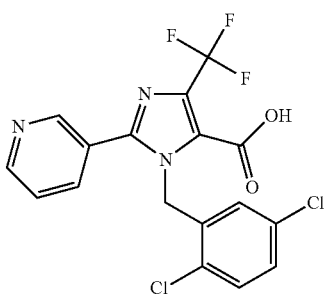 [SMILES: O=C(O)c1c(C(F)(F)F)nc(-c2cccnc2)n1Cc1cc(Cl)ccc1Cl] |

| Compound No. | Structure |
|---|---|
| A20 | 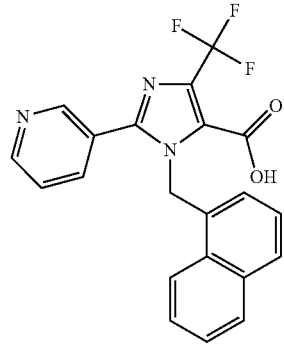 [SMILES: O=C(O)c1c(C(F)(F)F)nc(-c2cccnc2)n1Cc1cccc2ccccc12] |
| A21 | 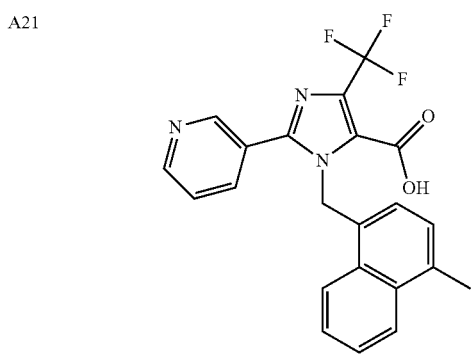 |
| A22 | 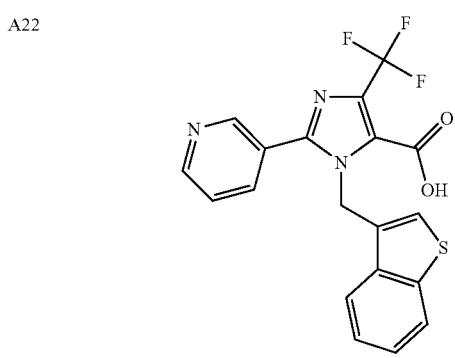 |
| A23 | 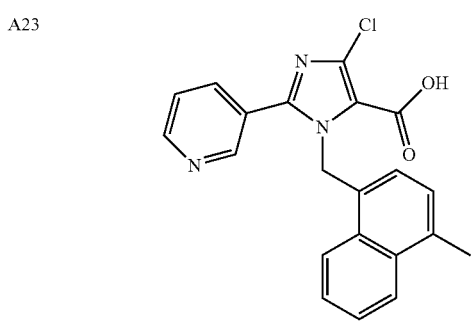 |
| Compound No. | Structure |
|---|---|
| A24 | 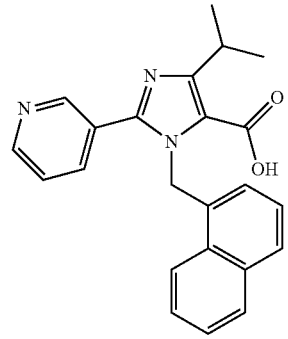 [SMILES: CC(C)c1nc(-c2cccnc2)n(Cc2cccc3ccccc23)c1C(=O)O] |
[Chemical Formula 15]
| Compound No. | Structure |
|---|---|
| A25 | 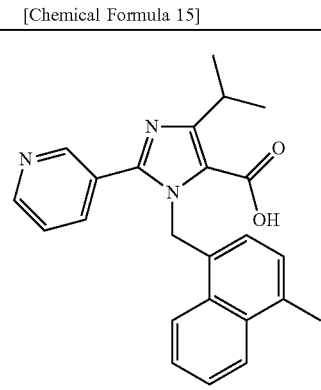 |
| A26 | 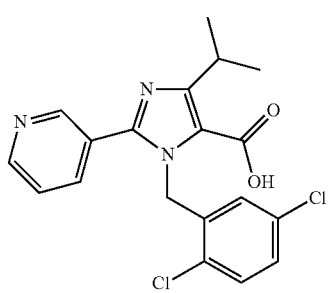 [SMILES: CC(C)c1nc(-c2cccnc2)n(Cc2cc(Cl)ccc2Cl)c1C(=O)O] |
| A27 | 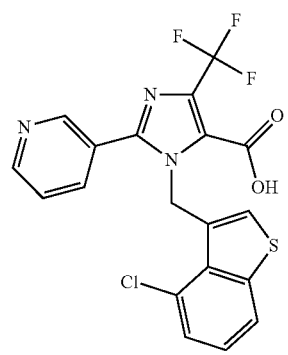 [SMILES: O=C(O)c1c(C(F)(F)F)nc(-c2cccnc2)n1Cc1csc2cccc(Cl)c12] |

-continued
| Compound No. | Structure |
|---|---|
| A28 | 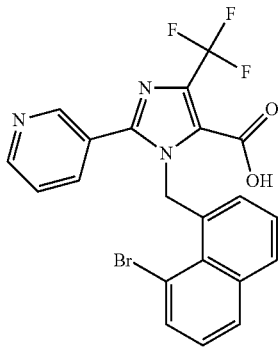 [SMILES: O=C(O)c1c(C(F)(F)F)nc(-c2cccnc2)n1Cc1cccc2cccc(Br)c12] |
| A29 | 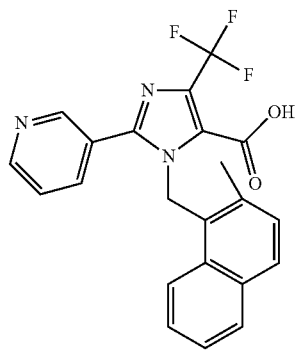 [SMILES: Cc1ccc2ccccc2c1Cn1c(-c2cccnc2)nc(C(F)(F)F)c1C(=O)O] |
| A30 | 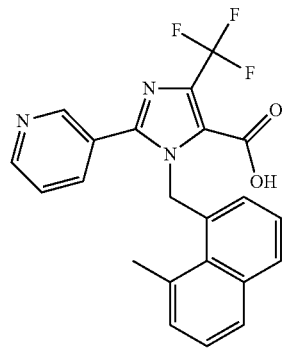 [SMILES: Cc1cccc2cccc(Cn3c(-c4cccnc4)nc(C(F)(F)F)c3C(=O)O)c12] |
| A31 | 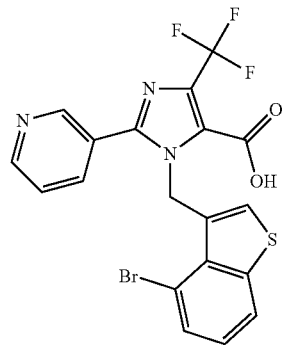 [SMILES: O=C(O)c1c(C(F)(F)F)nc(-c2cccnc2)n1Cc1csc2cccc(Br)c12] |
-continued
| Compound No. | Structure |
|---|---|
| A32 | 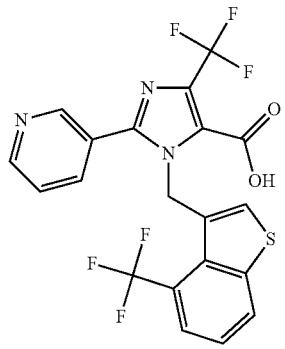 [SMILES: O=C(O)c1c(C(F)(F)F)nc(-c2cccnc2)n1Cc1csc2cccc(C(F)(F)F)c12] |
| A33 | 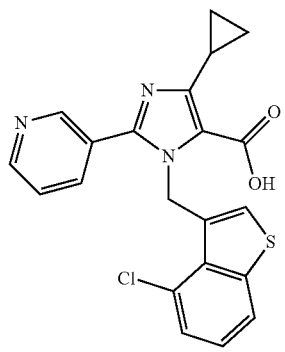 [SMILES: O=C(O)c1c(C2CC2)nc(-c2cccnc2)n1Cc1csc2cccc(Cl)c12] |
| A34 | 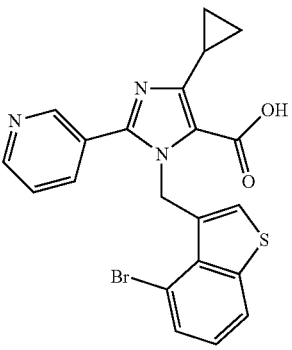 [SMILES: O=C(O)c1c(C2CC2)nc(-c2cccnc2)n1Cc1csc2cccc(Br)c12] |
| A35 | 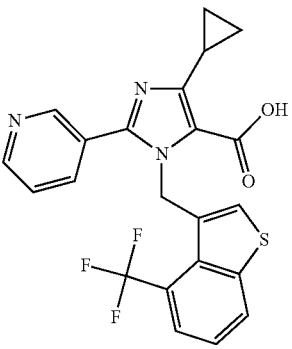 [SMILES: O=C(O)c1c(C2CC2)nc(-c2cccnc2)n1Cc1csc2cccc(C(F)(F)F)c12] |

-continued
| Compound No. | Structure |
|---|---|
| A36 | 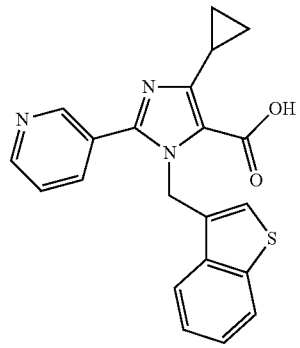 [SMILES: O=C(O)c1c(C2CC2)nc(-c2cccnc2)n1Cc1csc2ccccc12] |
| A37 | 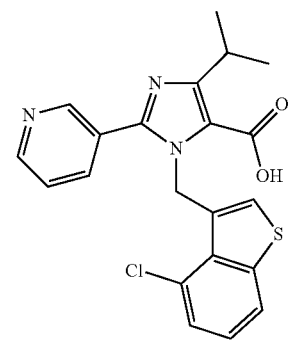 [SMILES: CC(C)c1nc(-c2cccnc2)n(Cc2csc3cccc(Cl)c23)c1C(=O)O] |
| A38 | 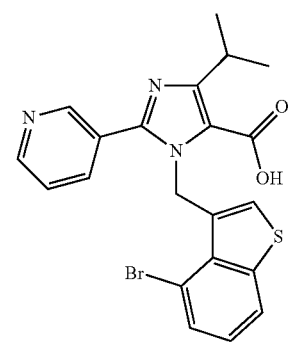 [SMILES: CC(C)c1nc(-c2cccnc2)n(Cc2csc3cccc(Br)c23)c1C(=O)O] |
| A39 | 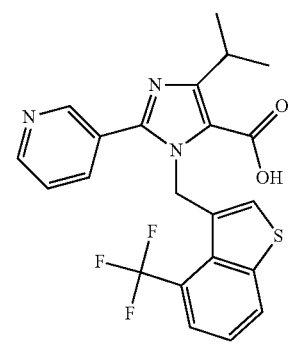 [SMILES: CC(C)c1nc(-c2cccnc2)n(Cc2csc3cccc(C(F)(F)F)c23)c1C(=O)O] |
[Chemical Formula 16]
-continued
| Compound No. | Structure |
|---|---|
| A40 | 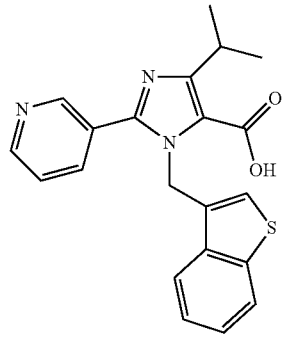 [SMILES: CC(C)c1nc(-c2cccnc2)n(Cc2csc3ccccc23)c1C(=O)O] |
| A41 | 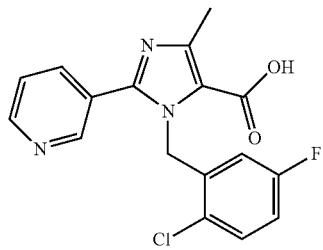 [SMILES: Cc1nc(-c2cccnc2)n(Cc2cc(F)ccc2Cl)c1C(=O)O] |
| A42 | 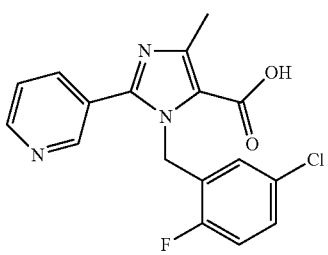 [SMILES: Cc1nc(-c2cccnc2)n(Cc2cc(Cl)ccc2F)c1C(=O)O] |
| A43 | 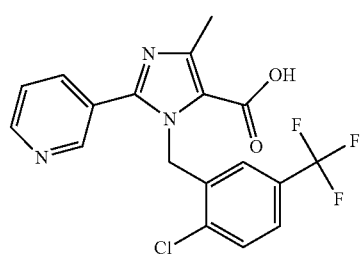 [SMILES: Cc1nc(-c2cccnc2)n(Cc2cc(C(F)(F)F)ccc2Cl)c1C(=O)O] |
| A44 | 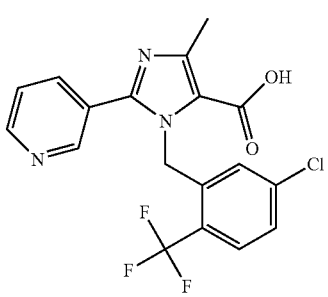 [SMILES: Cc1nc(-c2cccnc2)n(Cc2cc(Cl)ccc2C(F)(F)F)c1C(=O)O] |

| Compound No. | Structure |
|---|---|
| A45 | 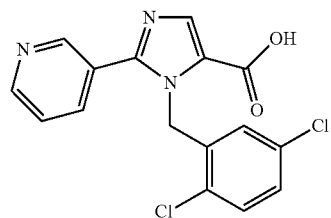 [SMILES: O=C(O)c1cnc(-c2cccnc2)n1Cc1cc(Cl)ccc1Cl] |
| A46 | 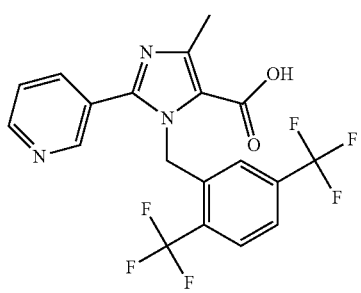 [SMILES: Cc1nc(-c2cccnc2)n(Cc2cc(C(F)(F)F)ccc2C(F)(F)F)c1C(=O)O] |
| A47 | 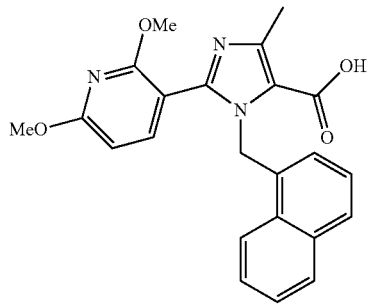 [SMILES: COc1ccc(-c2nc(C)c(C(=O)O)n2Cc2cccc3ccccc23)c(OC)n1] |
| A48 | 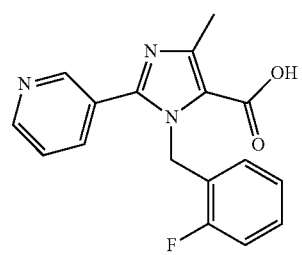 [SMILES: Cc1nc(-c2cccnc2)n(Cc2ccccc2F)c1C(=O)O] |
[Chemical Formula 17]
| Compound No. | Structure |
|---|---|
| A49 | 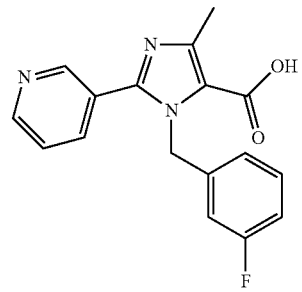 [SMILES: Cc1nc(-c2cccnc2)n(Cc2cccc(F)c2)c1C(=O)O] |
| A50 | 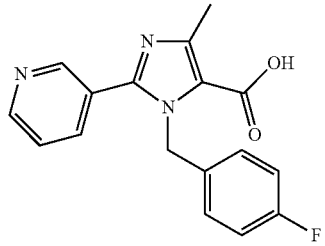 [SMILES: Cc1nc(-c2cccnc2)n(Cc2ccc(F)cc2)c1C(=O)O] |
| A51 | 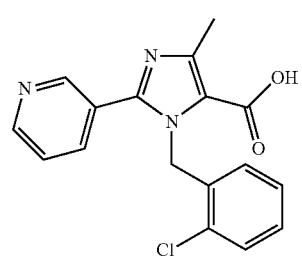 [SMILES: Cc1nc(-c2cccnc2)n(Cc2ccccc2Cl)c1C(=O)O] |
| A52 | 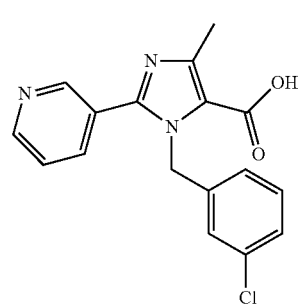 |
| A53 | 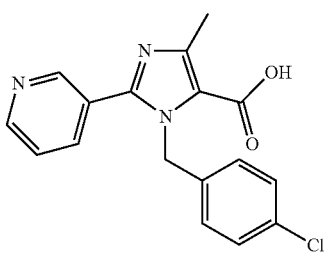 [SMILES: Cc1nc(-c2cccnc2)n(Cc2ccc(Cl)cc2)c1C(=O)O] |
| A54 | 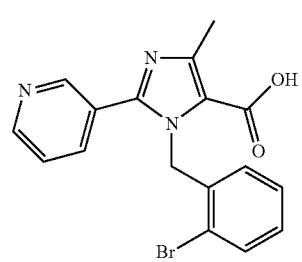 [SMILES: Cc1nc(-c2cccnc2)n(Cc2ccccc2Br)c1C(=O)O] |

| Compound No. | Structure |
|---|---|
| A55 | 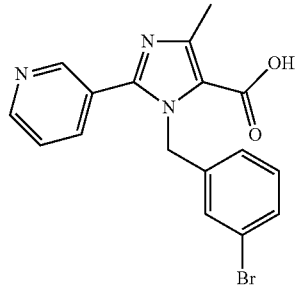 [SMILES: Cc1nc(-c2cccnc2)n(Cc2cccc(Br)c2)c1C(=O)O] |
| A56 | 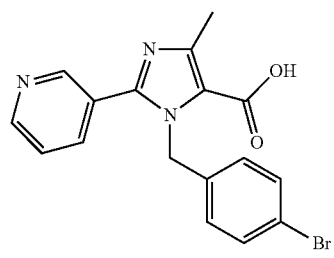 [SMILES: Cc1nc(-c2cccnc2)n(Cc2ccc(Br)cc2)c1C(=O)O] |
| A57 | 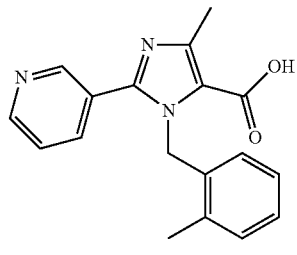 [SMILES: Cc1ccccc1Cn1c(-c2cccnc2)nc(C)c1C(=O)O] |
| A58 | 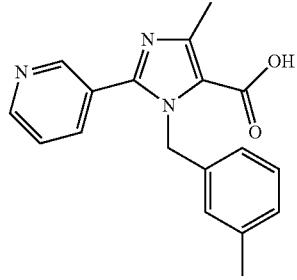 [SMILES: Cc1cccc(Cn2c(-c3cccnc3)nc(C)c2C(=O)O)c1] |
| A59 | 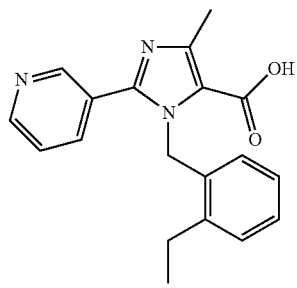 [SMILES: CCc1ccccc1Cn1c(-c2cccnc2)nc(C)c1C(=O)O] |
| Compound No. | Structure |
|---|---|
| A60 | 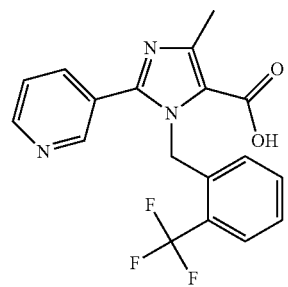 [SMILES: Cc1nc(-c2cccnc2)n(Cc2ccccc2C(F)(F)F)c1C(=O)O] |
[Chemical Formula 18]
| | |
|---|---|
| A61 | 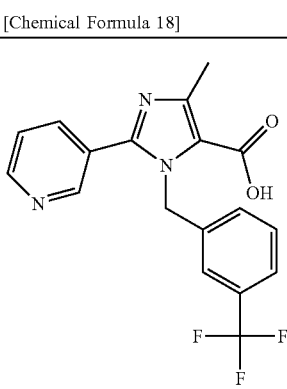 |
| A62 | 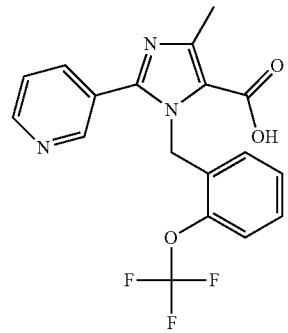 [SMILES: Cc1nc(-c2cccnc2)n(Cc2ccccc2OC(F)(F)F)c1C(=O)O] |
| A63 | 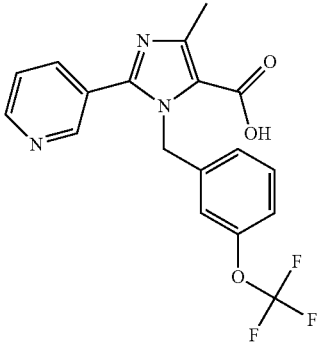 [SMILES: Cc1nc(-c2cccnc2)n(Cc2cccc(OC(F)(F)F)c2)c1C(=O)O] |

TABLE-continued
| Compound No. | Structure |
|---|---|
| A64 | 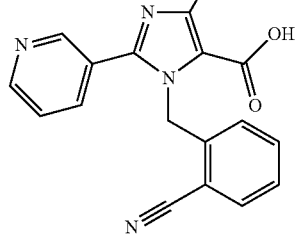 |
| A65 | 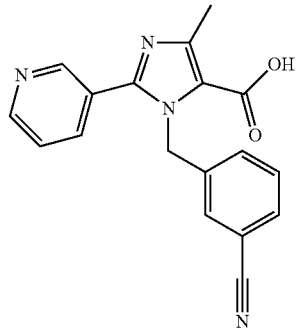 [SMILES: Cc1nc(-c2cccnc2)n(Cc2cccc(C#N)c2)c1C(=O)O] |
| A66 | 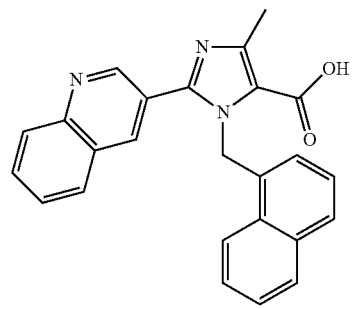 [SMILES: Cc1nc(-c2cnc3ccccc3c2)n(Cc2cccc3ccccc23)c1C(=O)O] |
| A67 | 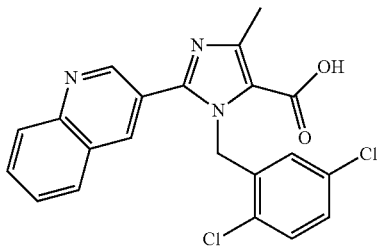 [SMILES: Cc1nc(-c2cnc3ccccc3c2)n(Cc2cc(Cl)ccc2Cl)c1C(=O)O] |
| A68 | 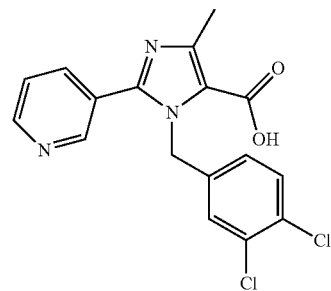 [SMILES: Cc1nc(-c2cccnc2)n(Cc2ccc(Cl)c(Cl)c2)c1C(=O)O] |
TABLE-continued
| Compound No. | Structure |
|---|---|
| A69 | 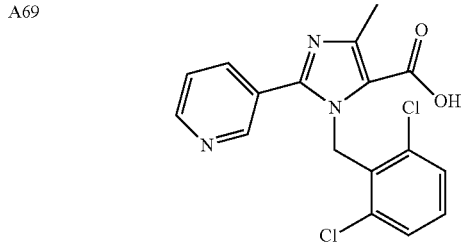 |
| A70 | 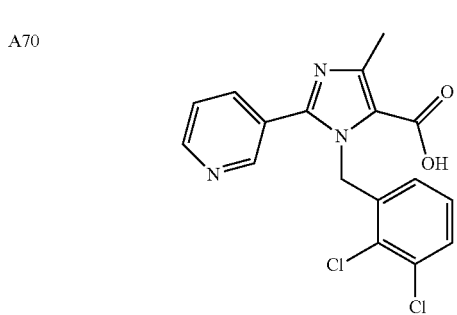 |
| A71 | 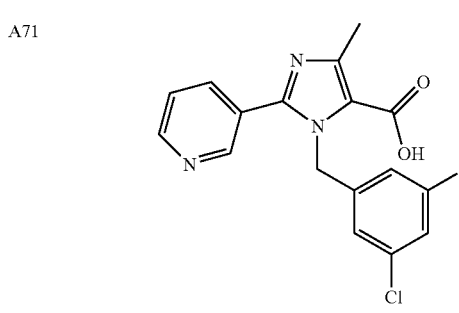 |
| A72 | 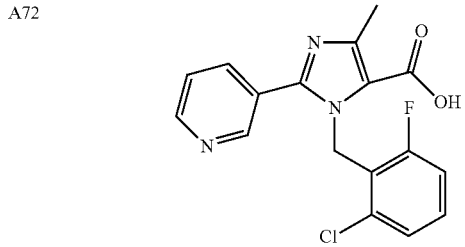 |
[Chemical Formula 19]
| A73 | 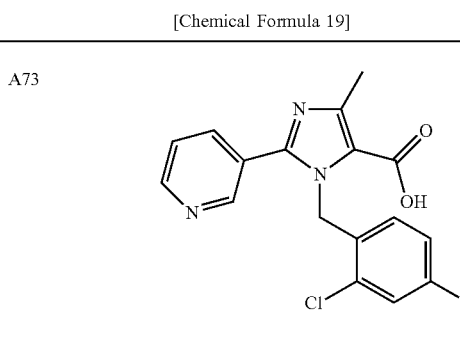 |

| Compound No. | Structure |
|---|---|
| A74 | 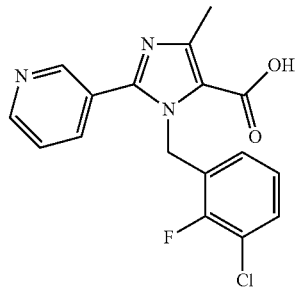 [SMILES: Cc1nc(-c2cccnc2)n(Cc2cccc(Cl)c2F)c1C(=O)O] |
| A75 | 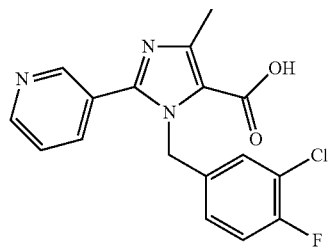 [SMILES: Cc1nc(-c2cccnc2)n(Cc2ccc(F)c(Cl)c2)c1C(=O)O] |
| A76 | 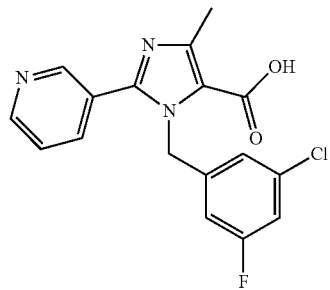 [SMILES: Cc1nc(-c2cccnc2)n(Cc2cc(F)cc(Cl)c2)c1C(=O)O] |
| A77 | 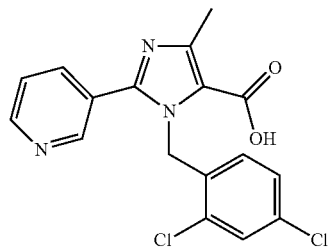 [SMILES: Cc1nc(-c2cccnc2)n(Cc2ccc(Cl)cc2Cl)c1C(=O)O] |
| A78 | 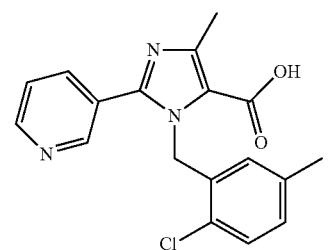 [SMILES: Cc1ccc(Cl)c(Cn2c(-c3cccnc3)nc(C)c2C(=O)O)c1] |
| Compound No. | Structure |
|---|---|
| A79 | 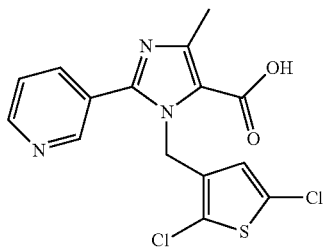 [SMILES: Cc1nc(-c2cccnc2)n(Cc2cc(Cl)sc2Cl)c1C(=O)O] |
| A80 | 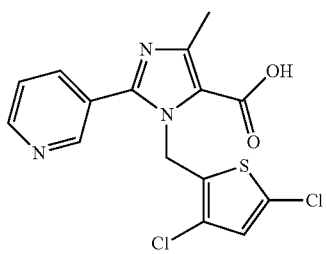 [SMILES: Cc1nc(-c2cccnc2)n(Cc2sc(Cl)cc2Cl)c1C(=O)O] |
| A81 | 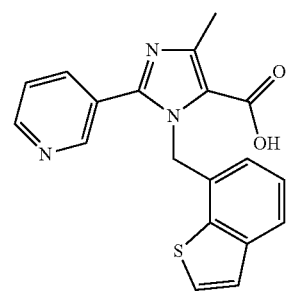 [SMILES: Cc1nc(-c2cccnc2)n(Cc2cccc3ccsc23)c1C(=O)O] |
| A82 | 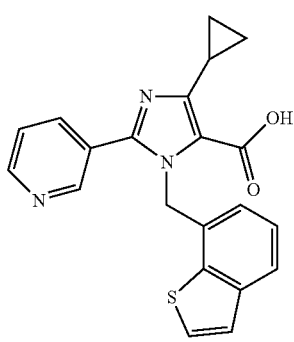 [SMILES: O=C(O)c1c(C2CC2)nc(-c2cccnc2)n1Cc1cccc2ccsc12] |
| A83 | 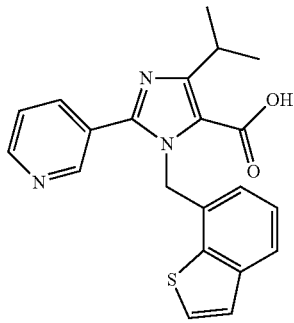 [SMILES: CC(C)c1nc(-c2cccnc2)n(Cc2cccc3ccsc23)c1C(=O)O] |

-continued
| Compound No. | Structure |
|---|---|
| A84 | 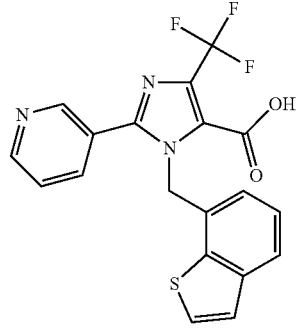 [SMILES: O=C(O)c1c(C(F)(F)F)nc(-c2cccnc2)n1Cc1cccc2ccsc12] |
[Chemical Formula 20]
| Compound No. | Structure |
|---|---|
| A85 | 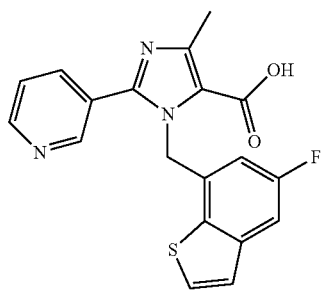 [SMILES: Cc1nc(-c2cccnc2)n(Cc2cc(F)cc3ccsc23)c1C(=O)O] |
| A86 | 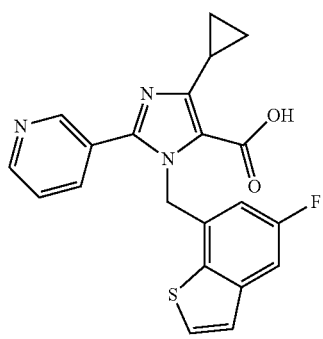 [SMILES: O=C(O)c1c(C2CC2)nc(-c2cccnc2)n1Cc1cc(F)cc2ccsc12] |
| A87 | 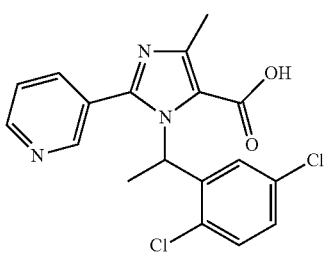 [SMILES: Cc1nc(-c2cccnc2)n(C(C)c2cc(Cl)ccc2Cl)c1C(=O)O] |
| A88 | 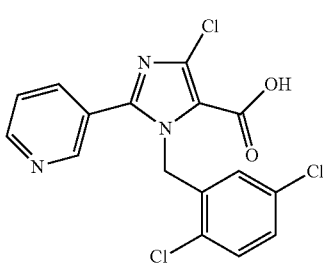 [SMILES: O=C(O)c1c(Cl)nc(-c2cccnc2)n1Cc1cc(Cl)ccc1Cl] |
-continued
| Compound No. | Structure |
|---|---|
| A89 | 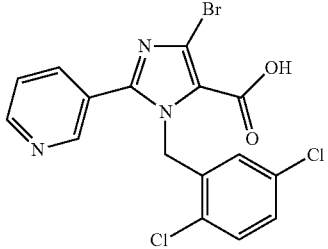 [SMILES: O=C(O)c1c(Br)nc(-c2cccnc2)n1Cc1cc(Cl)ccc1Cl] |
| A90 | 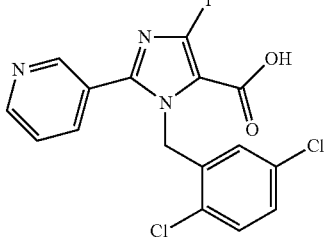 |
| A91 | 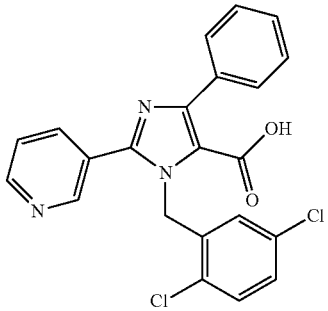 [SMILES: O=C(O)c1c(-c2ccccc2)nc(-c2cccnc2)n1Cc1cc(Cl)ccc1Cl] |
| A92 | 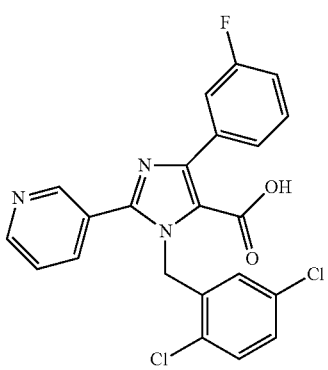 [SMILES: O=C(O)c1c(-c2cccc(F)c2)nc(-c2cccnc2)n1Cc1cc(Cl)ccc1Cl] |
| A93 | 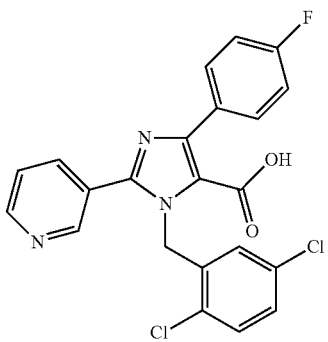 [SMILES: O=C(O)c1c(-c2ccc(F)cc2)nc(-c2cccnc2)n1Cc1cc(Cl)ccc1Cl] |

-continued
| Compound No. | Structure |
|---|---|
| A94 | 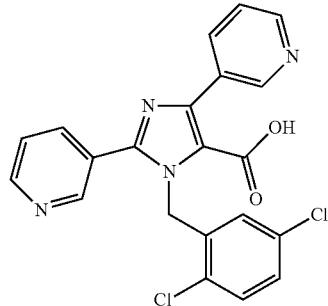 [SMILES: O=C(O)c1c(-c2cccnc2)nc(-c2cccnc2)n1Cc1cc(Cl)ccc1Cl] |
| A95 | 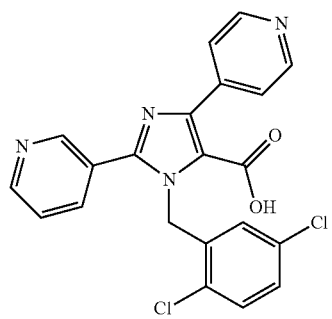 [SMILES: O=C(O)c1c(-c2ccncc2)nc(-c2cccnc2)n1Cc1cc(Cl)ccc1Cl] |
| A96 | 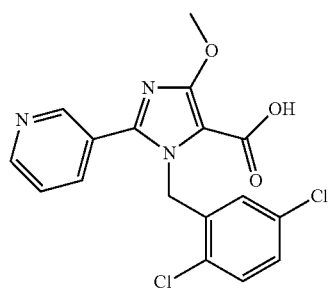 [SMILES: COc1nc(-c2cccnc2)n(Cc2cc(Cl)ccc2Cl)c1C(=O)O] |
[Chemical Formula 21]
| A97 | 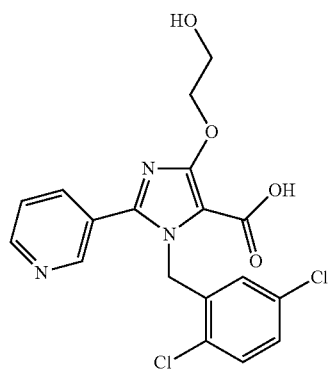 [SMILES: O=C(O)c1c(OCCO)nc(-c2cccnc2)n1Cc1cc(Cl)ccc1Cl] |
-continued
| Compound No. | Structure |
|---|---|
| A98 | 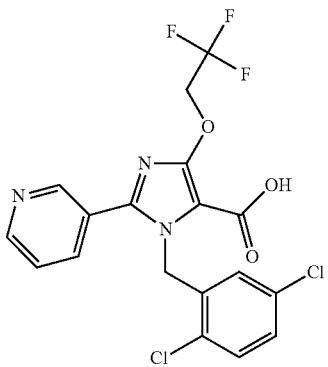 [SMILES: O=C(O)c1c(OCC(F)(F)F)nc(-c2cccnc2)n1Cc1cc(Cl)ccc1Cl] |
| A99 | 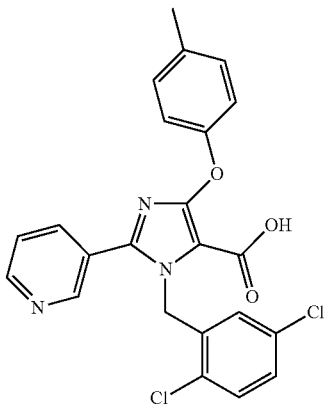 [SMILES: Cc1ccc(Oc2nc(-c3cccnc3)n(Cc3cc(Cl)ccc3Cl)c2C(=O)O)cc1] |
| A100 | 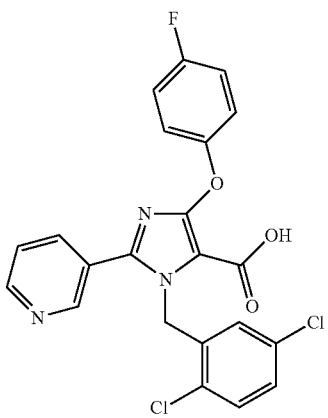 [SMILES: O=C(O)c1c(Oc2ccc(F)cc2)nc(-c2cccnc2)n1Cc1cc(Cl)ccc1Cl] |
| A101 | 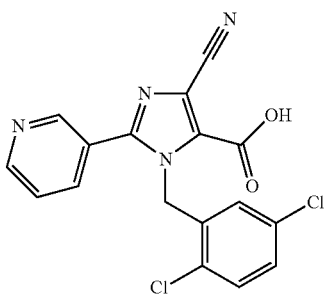 [SMILES: N#Cc1nc(-c2cccnc2)n(Cc2cc(Cl)ccc2Cl)c1C(=O)O] |

45
-continued
| Compound No. | Structure |
|---|---|
| A102 | 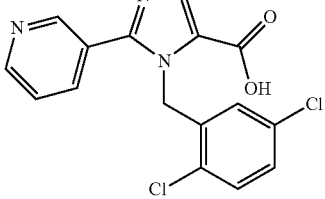 |
| A103 | 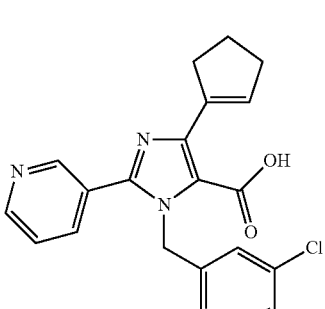 |
| A104 | 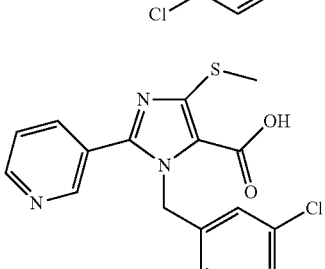 |
| A105 | 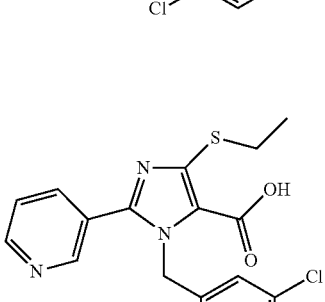 |
| A106 | 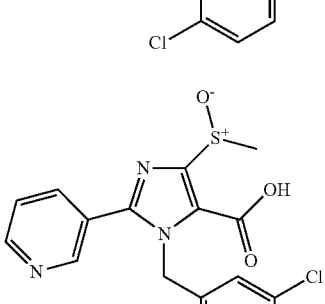 |
46
-continued
| Compound No. | Structure |
|---|---|
| A107 | 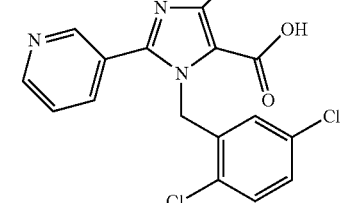 |
| A108 | 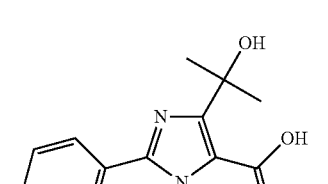 |
[Chemical Formula 22]
| A109 | 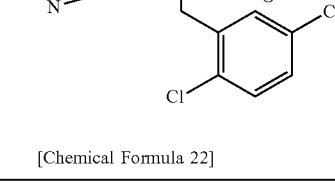 |
| A110 | 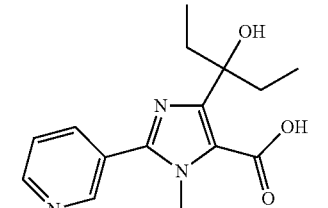 |
| A111 | 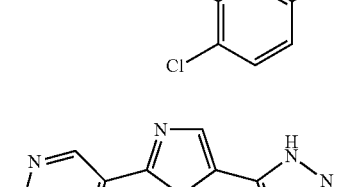 |

| Compound No. | Structure |
|---|---|
| A112 | 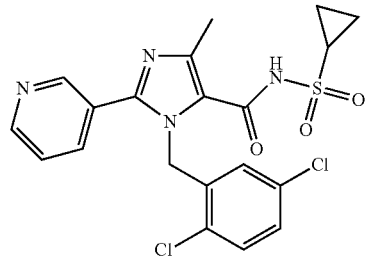 [SMILES: Cc1nc(-c2cccnc2)n(Cc2cc(Cl)ccc2Cl)c1C(=O)NS(=O)(=O)C1CC1] |
| A113 | 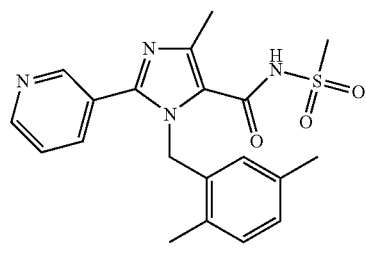 [SMILES: Cc1ccc(C)c(Cn2c(-c3cccnc3)nc(C)c2C(=O)NS(C)(=O)=O)c1] |
| A114 | 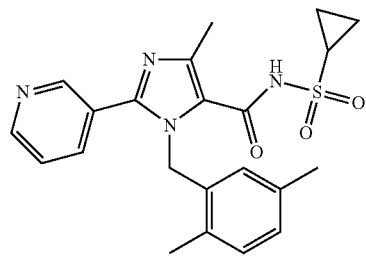 [SMILES: Cc1ccc(C)c(Cn2c(-c3cccnc3)nc(C)c2C(=O)NS(=O)(=O)C2CC2)c1] |
| A115 | 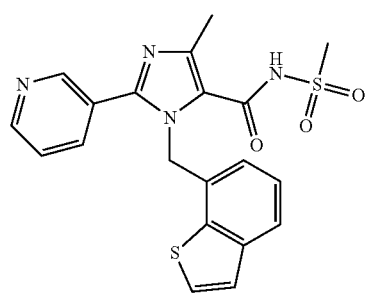 [SMILES: Cc1nc(-c2cccnc2)n(Cc2cccc3ccsc23)c1C(=O)NS(C)(=O)=O] |
| A116 | 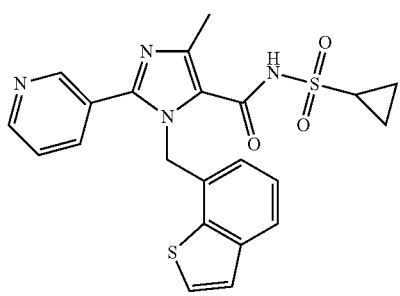 [SMILES: Cc1nc(-c2cccnc2)n(Cc2cccc3ccsc23)c1C(=O)NS(=O)(=O)C1CC1] |
| Compound No. | Structure |
|---|---|
| A117 | 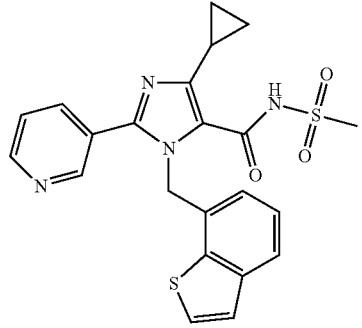 [SMILES: CS(=O)(=O)NC(=O)c1c(C2CC2)nc(-c2cccnc2)n1Cc1cccc2ccsc12] |
| A118 | 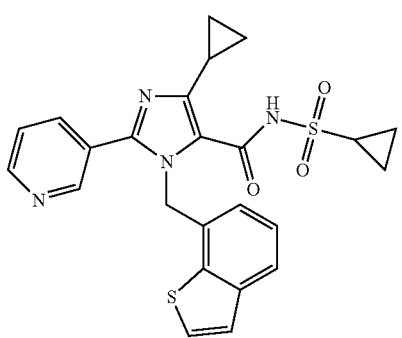 [SMILES: O=C(NS(=O)(=O)C1CC1)c1c(C2CC2)nc(-c2cccnc2)n1Cc1cccc2ccsc12] |
| A119 | 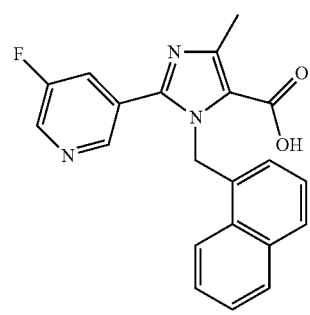 |
| A120 | 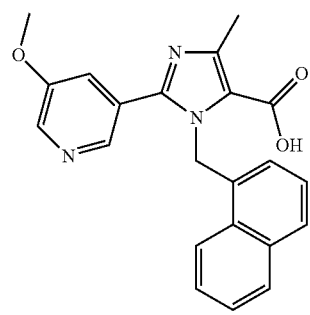 [SMILES: COc1cncc(-c2nc(C)c(C(=O)O)n2Cc2cccc3ccccc23)c1] |

| Compound No. | Structure |
|---|---|
| [Chemical Formula 23] | |
| A121 | 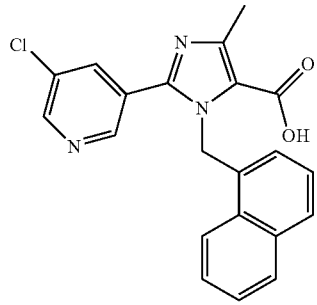 [SMILES: Cc1nc(-c2cncc(Cl)c2)n(Cc2cccc3ccccc23)c1C(=O)O] |
| A122 | 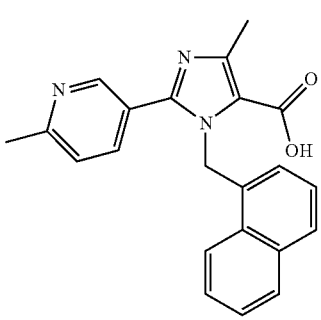 [SMILES: Cc1ccc(-c2nc(C)c(C(=O)O)n2Cc2cccc3ccccc23)cn1] |
| A123 | 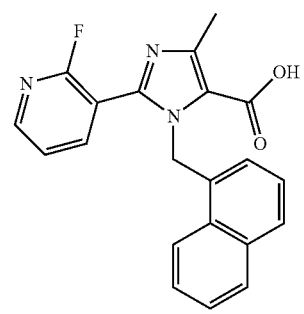 [SMILES: Cc1nc(-c2cccnc2F)n(Cc2cccc3ccccc23)c1C(=O)O] |
| A124 | 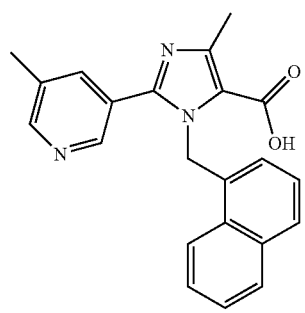 [SMILES: Cc1cncc(-c2nc(C)c(C(=O)O)n2Cc2cccc3ccccc23)c1] |
| Compound No. | Structure |
|---|---|
| A125 | 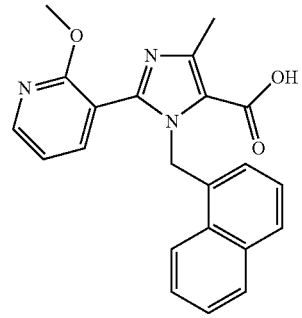 [SMILES: COc1ncccc1-c1nc(C)c(C(=O)O)n1Cc1cccc2ccccc12] |
| A126 | 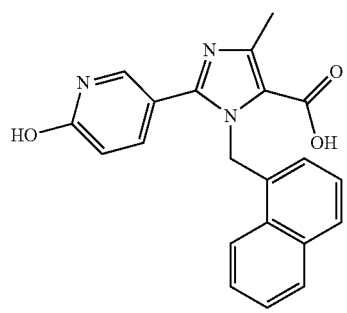 [SMILES: Cc1nc(-c2ccc(O)nc2)n(Cc2cccc3ccccc23)c1C(=O)O] |
| A127 | 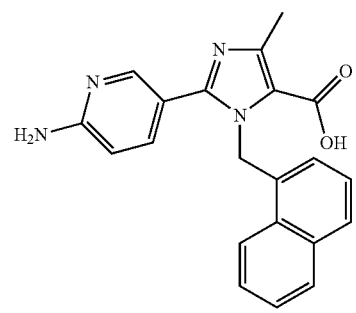 [SMILES: Cc1nc(-c2ccc(N)nc2)n(Cc2cccc3ccccc23)c1C(=O)O] |
| A128 | 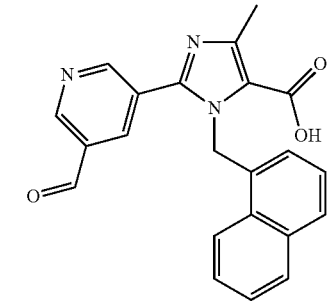 [SMILES: Cc1nc(-c2cncc(C=O)c2)n(Cc2cccc3ccccc23)c1C(=O)O] |
| A129 | 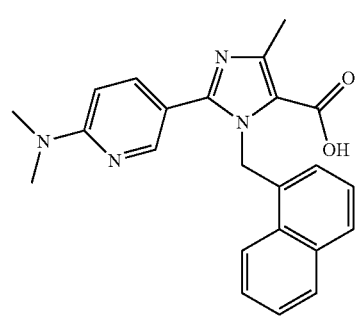 [SMILES: Cc1nc(-c2ccc(N(C)C)nc2)n(Cc2cccc3ccccc23)c1C(=O)O] |

| Compound No. | Structure |
|---|---|
| A130 | 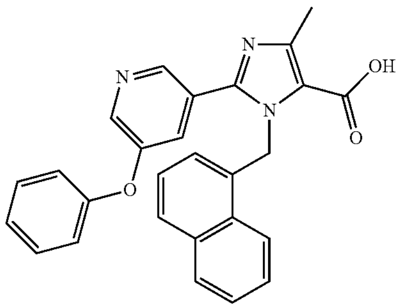 [SMILES: Cc1nc(-c2cncc(Oc3ccccc3)c2)n(Cc2cccc3ccccc23)c1C(=O)O] |
| A131 | 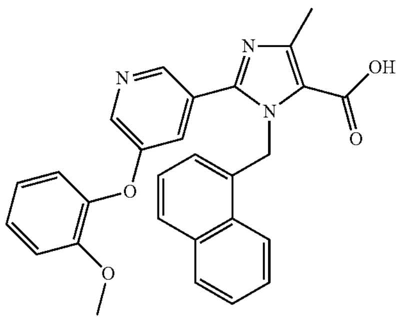 [SMILES: COc1ccccc1Oc1cncc(-c2nc(C)c(C(=O)O)n2Cc2cccc3ccccc23)c1] |
| A132 | 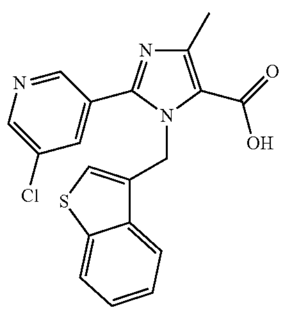 [SMILES: Cc1nc(-c2cncc(Cl)c2)n(Cc2csc3ccccc23)c1C(=O)O] |

[Chemical Formula 24]

| Compound No. | Structure |
|---|---|
| A133 | |
| A134 | |
| A135 | 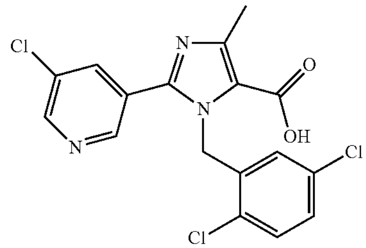 [SMILES: Cc1nc(-c2cncc(Cl)c2)n(Cc2cc(Cl)ccc2Cl)c1C(=O)O] |
| A136 | 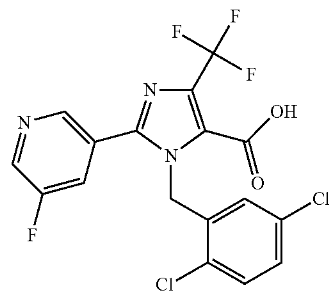 [SMILES: O=C(O)c1c(C(F)(F)F)nc(-c2cncc(F)c2)n1Cc1cc(Cl)ccc1Cl] |
| A137 | 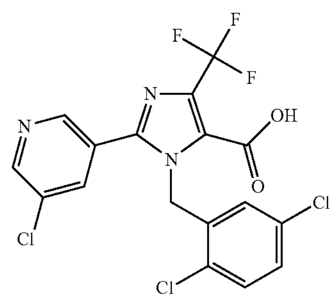 [SMILES: O=C(O)c1c(C(F)(F)F)nc(-c2cncc(Cl)c2)n1Cc1cc(Cl)ccc1Cl] |
| A138 | 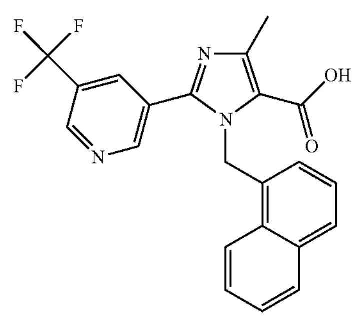 [SMILES: Cc1nc(-c2cncc(C(F)(F)F)c2)n(Cc2cccc3ccccc23)c1C(=O)O] |
| A139 | 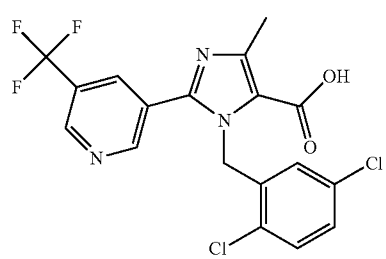 [SMILES: Cc1nc(-c2cncc(C(F)(F)F)c2)n(Cc2cc(Cl)ccc2Cl)c1C(=O)O] |

| Compound No. | Structure |
|---|---|
| A140 | 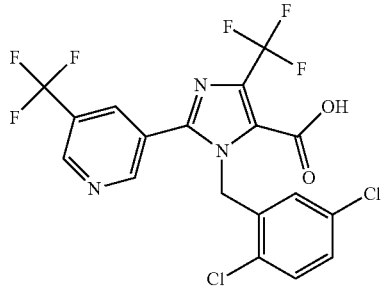 [SMILES: O=C(O)c1c(C(F)(F)F)nc(-c2cncc(C(F)(F)F)c2)n1Cc1cc(Cl)ccc1Cl] |
| A141 | 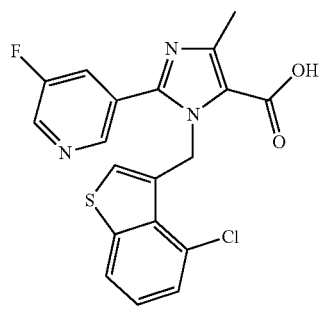 [SMILES: Cc1nc(-c2cncc(F)c2)n(Cc2csc3cccc(Cl)c23)c1C(=O)O] |
| A142 | 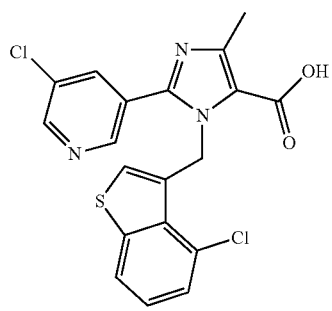 [SMILES: Cc1nc(-c2cncc(Cl)c2)n(Cc2csc3cccc(Cl)c23)c1C(=O)O] |
| A143 | 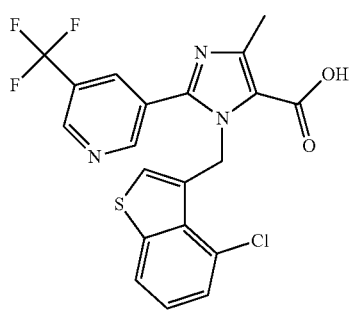 [SMILES: Cc1nc(-c2cncc(C(F)(F)F)c2)n(Cc2csc3cccc(Cl)c23)c1C(=O)O] |
| A144 | 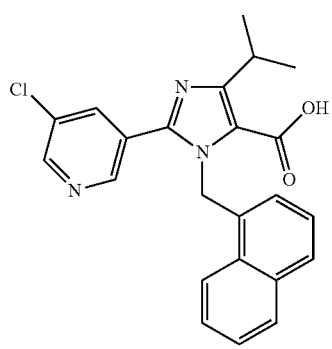 [SMILES: CC(C)c1nc(-c2cncc(Cl)c2)n(Cc2cccc3ccccc23)c1C(=O)O] |
| Compound No. | Structure |
|---|---|
| [Chemical Formula 25] | |
| A145 | 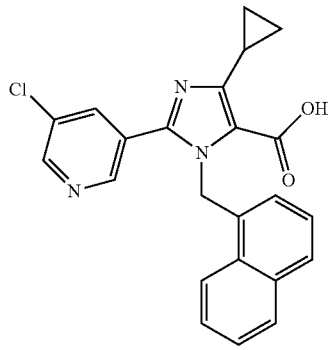 [SMILES: O=C(O)c1c(C2CC2)nc(-c2cncc(Cl)c2)n1Cc1cccc2ccccc12] |
| A146 | 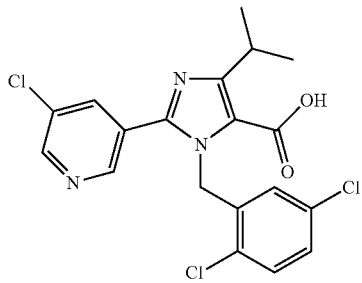 [SMILES: CC(C)c1nc(-c2cncc(Cl)c2)n(Cc2cc(Cl)ccc2Cl)c1C(=O)O] |
| A147 | 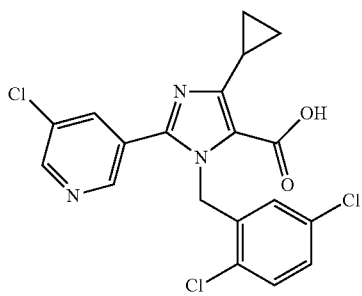 [SMILES: O=C(O)c1c(C2CC2)nc(-c2cncc(Cl)c2)n1Cc1cc(Cl)ccc1Cl] |
| A148 | 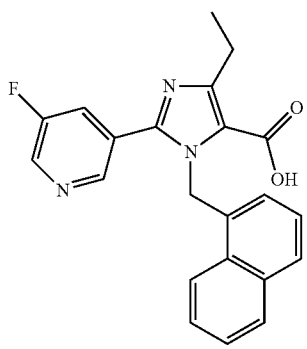 [SMILES: CCc1nc(-c2cncc(F)c2)n(Cc2cccc3ccccc23)c1C(=O)O] |

| Compound No. | Structure |
|---|---|
| A149 | 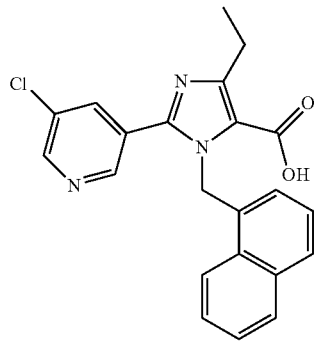 [SMILES: CCc1nc(-c2cncc(Cl)c2)n(Cc2cccc3ccccc23)c1C(=O)O] |
| A150 | 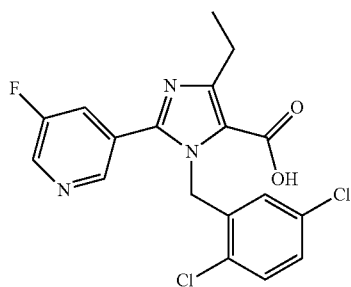 [SMILES: CCc1nc(-c2cncc(F)c2)n(Cc2cc(Cl)ccc2Cl)c1C(=O)O] |
| A151 | 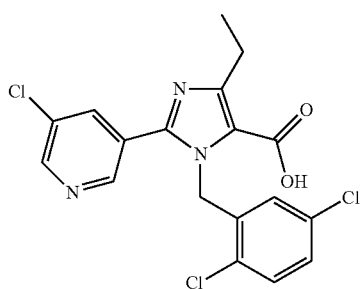 [SMILES: CCc1nc(-c2cncc(Cl)c2)n(Cc2cc(Cl)ccc2Cl)c1C(=O)O] |
| A152 | 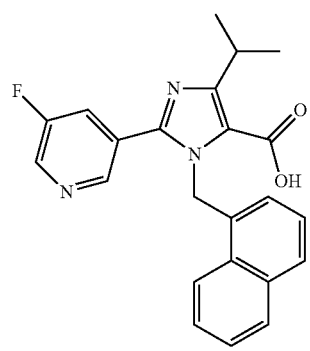 [SMILES: CC(C)c1nc(-c2cncc(F)c2)n(Cc2cccc3ccccc23)c1C(=O)O] |
| Compound No. | Structure |
|---|---|
| A153 | 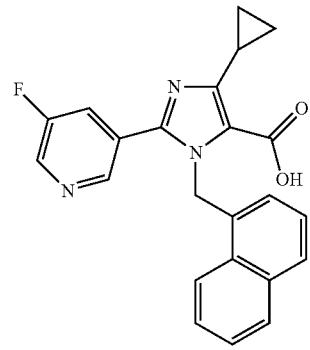 [SMILES: O=C(O)c1c(C2CC2)nc(-c2cncc(F)c2)n1Cc1cccc2ccccc12] |
| A154 | 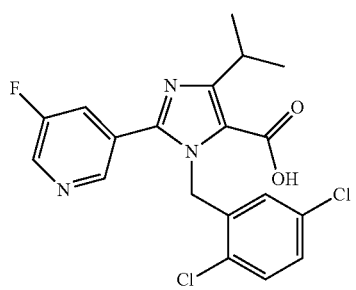 [SMILES: CC(C)c1nc(-c2cncc(F)c2)n(Cc2cc(Cl)ccc2Cl)c1C(=O)O] |
| A155 | 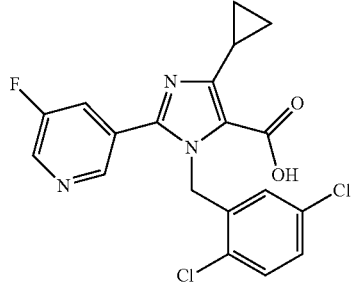 [SMILES: O=C(O)c1c(C2CC2)nc(-c2cncc(F)c2)n1Cc1cc(Cl)ccc1Cl] |
| A156 | 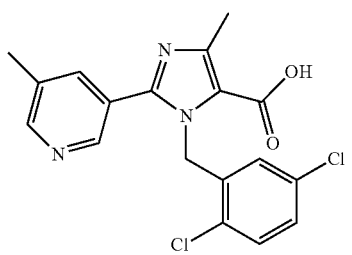 [SMILES: Cc1cncc(-c2nc(C)c(C(=O)O)n2Cc2cc(Cl)ccc2Cl)c1] |
[Chemical Formula 26]
| A157 | 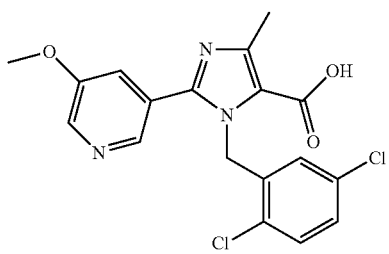 [SMILES: COc1cncc(-c2nc(C)c(C(=O)O)n2Cc2cc(Cl)ccc2Cl)c1] |

-continued
| Compound No. | Structure |
|---|---|
| A158 | 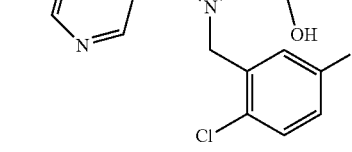 |
| A159 | 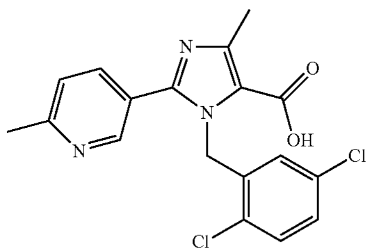 [SMILES: Cc1ccc(-c2nc(C)c(C(=O)O)n2Cc2cc(Cl)ccc2Cl)cn1] |
| A160 | 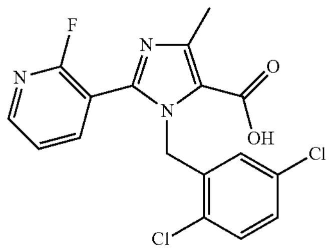 [SMILES: Cc1nc(-c2cccnc2F)n(Cc2cc(Cl)ccc2Cl)c1C(=O)O] |
| A161 | 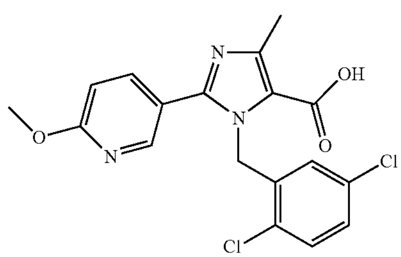 [SMILES: COc1ccc(-c2nc(C)c(C(=O)O)n2Cc2cc(Cl)ccc2Cl)cn1] |
| A162 | 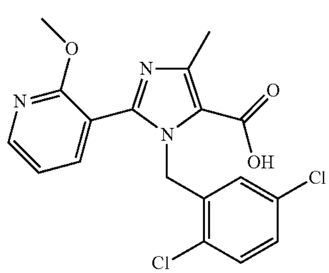 [SMILES: COc1ncccc1-c1nc(C)c(C(=O)O)n1Cc1cc(Cl)ccc1Cl] |
| A163 | 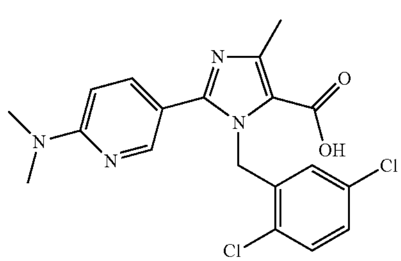 [SMILES: Cc1nc(-c2ccc(N(C)C)nc2)n(Cc2cc(Cl)ccc2Cl)c1C(=O)O] |
-continued
| Compound No. | Structure |
|---|---|
| A164 | 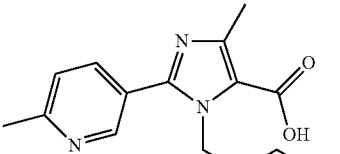 |
| A165 | 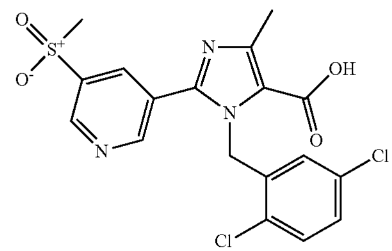 [SMILES: Cc1nc(-c2cncc([S+](C)(=O)[O-])c2)n(Cc2cc(Cl)ccc2Cl)c1C(=O)O] |
| A166 | 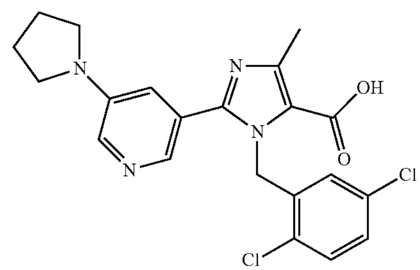 [SMILES: Cc1nc(-c2cncc(N3CCCC3)c2)n(Cc2cc(Cl)ccc2Cl)c1C(=O)O] |
| A167 | 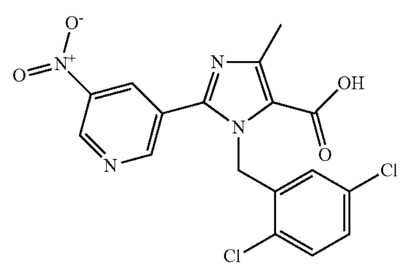 [SMILES: Cc1nc(-c2cncc([N+](=O)[O-])c2)n(Cc2cc(Cl)ccc2Cl)c1C(=O)O] |
| A168 | 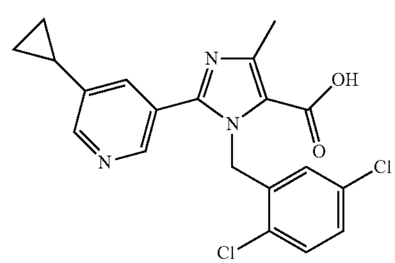 [SMILES: Cc1nc(-c2cncc(C3CC3)c2)n(Cc2cc(Cl)ccc2Cl)c1C(=O)O] |
[Chemical Formula 27]
| A169 | |

| Compound No. | Structure |
|---|---|
| A170 | 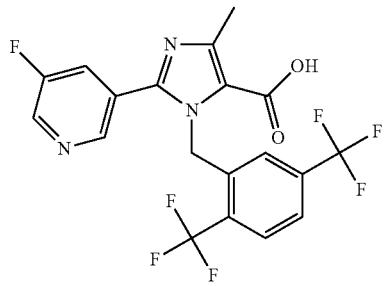 [SMILES: Cc1nc(-c2cncc(F)c2)n(Cc2cc(C(F)(F)F)ccc2C(F)(F)F)c1C(=O)O] |
| A171 | 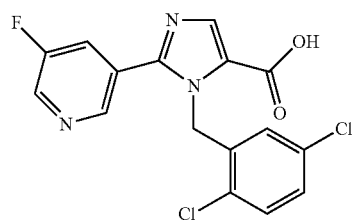 [SMILES: O=C(O)c1cnc(-c2cncc(F)c2)n1Cc1cc(Cl)ccc1Cl] |
| A172 | 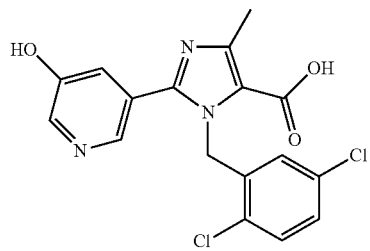 [SMILES: Cc1nc(-c2cncc(O)c2)n(Cc2cc(Cl)ccc2Cl)c1C(=O)O] |
| A173 | 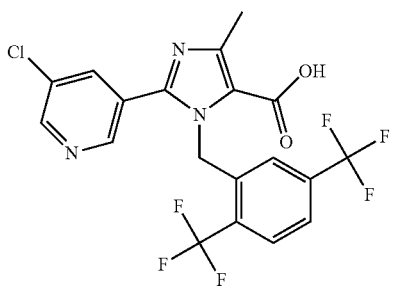 [SMILES: Cc1nc(-c2cncc(Cl)c2)n(Cc2cc(C(F)(F)F)ccc2C(F)(F)F)c1C(=O)O] |
| A174 | 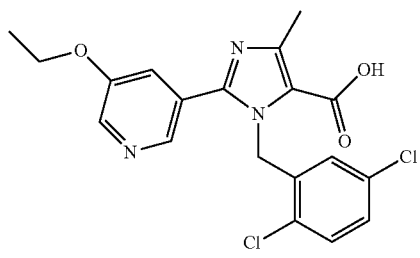 [SMILES: CCOc1cncc(-c2nc(C)c(C(=O)O)n2Cc2cc(Cl)ccc2Cl)c1] |
| Compound No. | Structure |
|---|---|
| A175 | 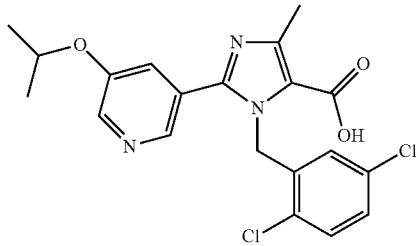 [SMILES: Cc1nc(-c2cncc(OC(C)C)c2)n(Cc2cc(Cl)ccc2Cl)c1C(=O)O] |
| A176 | 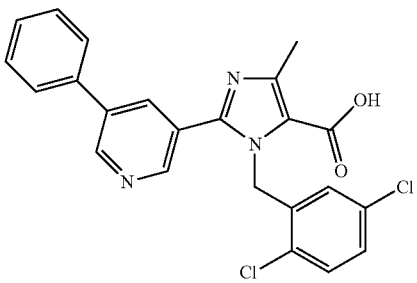 [SMILES: Cc1nc(-c2cncc(-c3ccccc3)c2)n(Cc2cc(Cl)ccc2Cl)c1C(=O)O] |
| A177 | 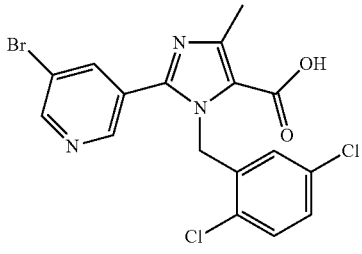 [SMILES: Cc1nc(-c2cncc(Br)c2)n(Cc2cc(Cl)ccc2Cl)c1C(=O)O] |
| A178 | 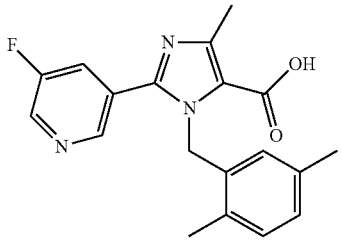 [SMILES: Cc1ccc(C)c(Cn2c(-c3cncc(F)c3)nc(C)c2C(=O)O)c1] |
| A179 | 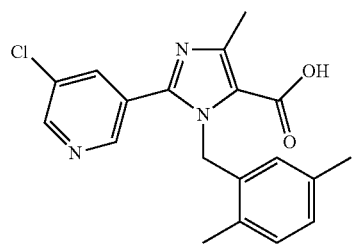 [SMILES: Cc1ccc(C)c(Cn2c(-c3cncc(Cl)c3)nc(C)c2C(=O)O)c1] |
| A180 | 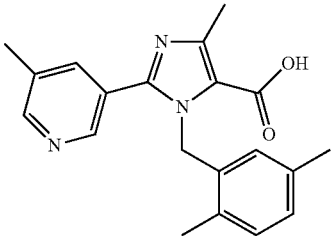 |

| Compound No. | Structure |
|---|---|
| [Chemical Formula 28] | |
| A181 | 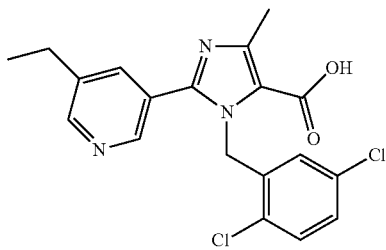 [SMILES: CCc1cncc(-c2nc(C)c(C(=O)O)n2Cc2cc(Cl)ccc2Cl)c1] |
| A182 | 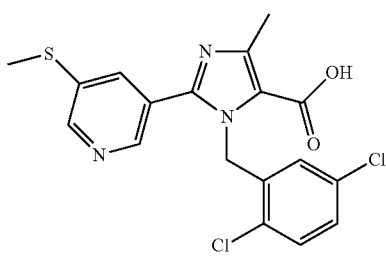 [SMILES: CSc1cncc(-c2nc(C)c(C(=O)O)n2Cc2cc(Cl)ccc2Cl)c1] |
| A183 | 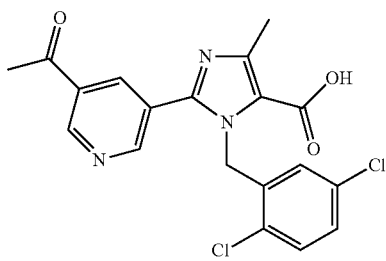 [SMILES: CC(=O)c1cncc(-c2nc(C)c(C(=O)O)n2Cc2cc(Cl)ccc2Cl)c1] |
| A184 | 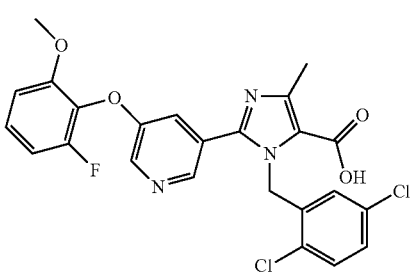 [SMILES: COc1cccc(F)c1Oc1cncc(-c2nc(C)c(C(=O)O)n2Cc2cc(Cl)ccc2Cl)c1] |
| A185 | 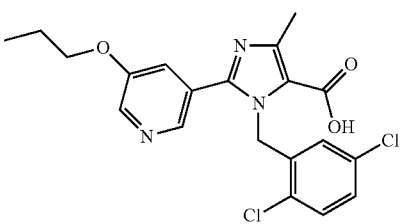 [SMILES: CCCOc1cncc(-c2nc(C)c(C(=O)O)n2Cc2cc(Cl)ccc2Cl)c1] |
| A186 | 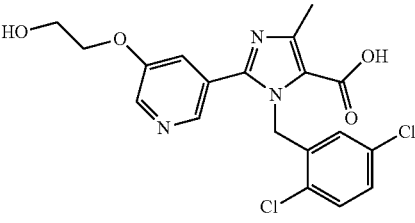 [SMILES: Cc1nc(-c2cncc(OCCO)c2)n(Cc2cc(Cl)ccc2Cl)c1C(=O)O] |
| Compound No. | Structure |
|---|---|
| A187 | 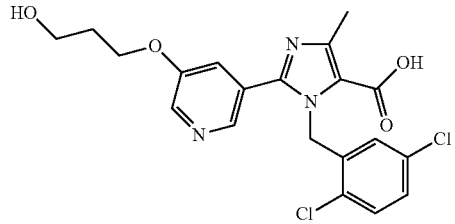 [SMILES: Cc1nc(-c2cncc(OCCCO)c2)n(Cc2cc(Cl)ccc2Cl)c1C(=O)O] |
| A188 | 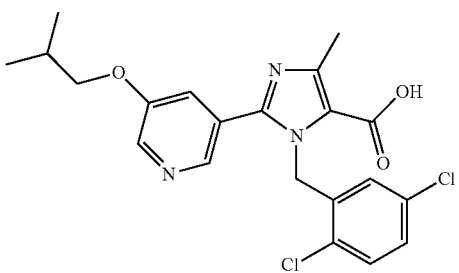 [SMILES: Cc1nc(-c2cncc(OCC(C)C)c2)n(Cc2cc(Cl)ccc2Cl)c1C(=O)O] |
| A189 | 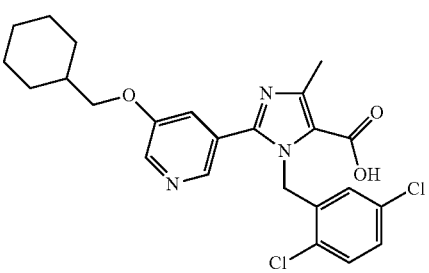 [SMILES: Cc1nc(-c2cncc(OCC3CCCCC3)c2)n(Cc2cc(Cl)ccc2Cl)c1C(=O)O] |
| A190 | 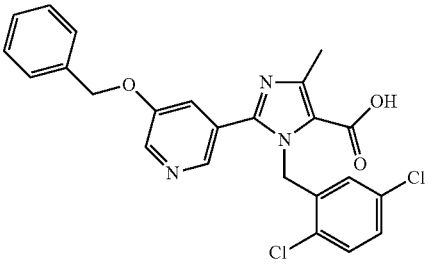 [SMILES: Cc1nc(-c2cncc(OCc3ccccc3)c2)n(Cc2cc(Cl)ccc2Cl)c1C(=O)O] |
| A191 | 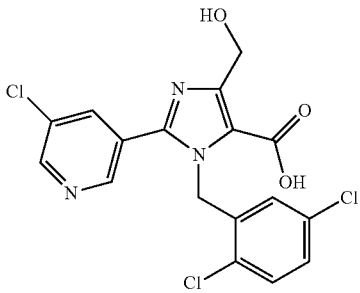 [SMILES: O=C(O)c1c(CO)nc(-c2cncc(Cl)c2)n1Cc1cc(Cl)ccc1Cl] |

-continued
| Compound No. | Structure |
|---|---|
| A192 | 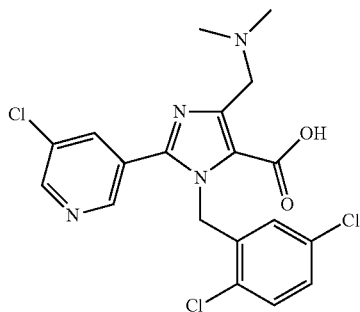 [SMILES: CN(C)Cc1nc(-c2cncc(Cl)c2)n(Cc2cc(Cl)ccc2Cl)c1C(=O)O] |
[Chemical Formula 29]
| Compound No. | Structure |
|---|---|
| A193 | 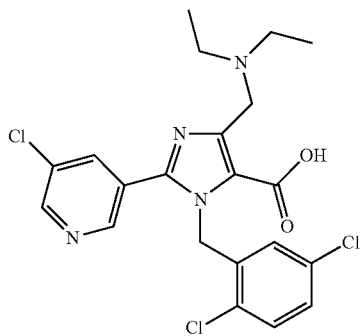 [SMILES: CCN(CC)Cc1nc(-c2cncc(Cl)c2)n(Cc2cc(Cl)ccc2Cl)c1C(=O)O] |
| A194 | 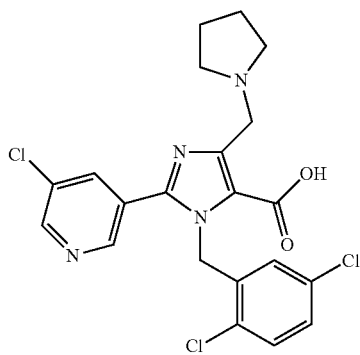 [SMILES: O=C(O)c1c(CN2CCCC2)nc(-c2cncc(Cl)c2)n1Cc1cc(Cl)ccc1Cl] |
| A195 | 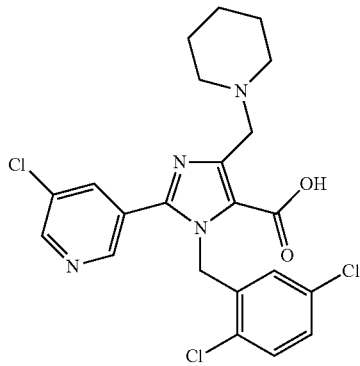 [SMILES: O=C(O)c1c(CN2CCCCC2)nc(-c2cncc(Cl)c2)n1Cc1cc(Cl)ccc1Cl] |
-continued
| Compound No. | Structure |
|---|---|
| A196 | 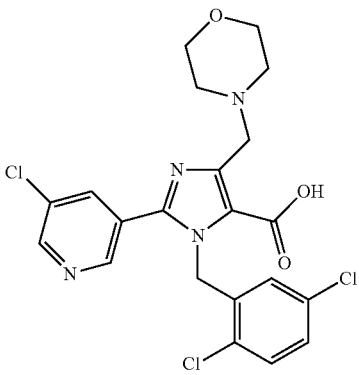 [SMILES: O=C(O)c1c(CN2CCOCC2)nc(-c2cncc(Cl)c2)n1Cc1cc(Cl)ccc1Cl] |
| A197 | 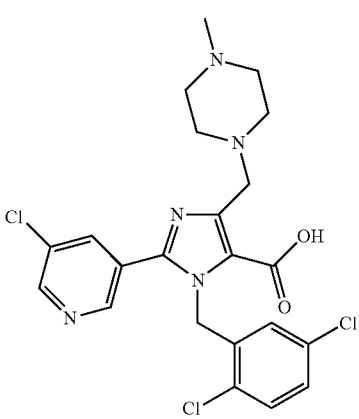 [SMILES: CN1CCN(Cc2nc(-c3cncc(Cl)c3)n(Cc3cc(Cl)ccc3Cl)c2C(=O)O)CC1] |
| A198 | 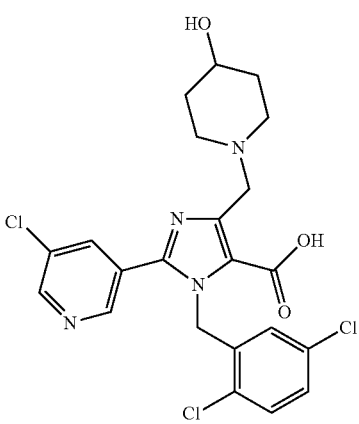 [SMILES: O=C(O)c1c(CN2CCC(O)CC2)nc(-c2cncc(Cl)c2)n1Cc1cc(Cl)ccc1Cl] |
| A199 | 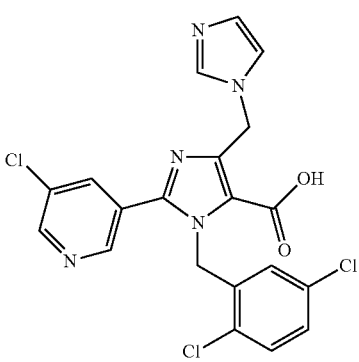 [SMILES: O=C(O)c1c(Cn2ccnc2)nc(-c2cncc(Cl)c2)n1Cc1cc(Cl)ccc1Cl] |

-continued

| Compound No. | Structure |
|---|---|
| A200 | 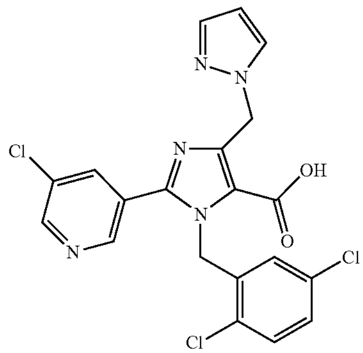 [SMILES: O=C(O)c1c(Cn2cccn2)nc(-c2cncc(Cl)c2)n1Cc1cc(Cl)ccc1Cl] |
| A201 | 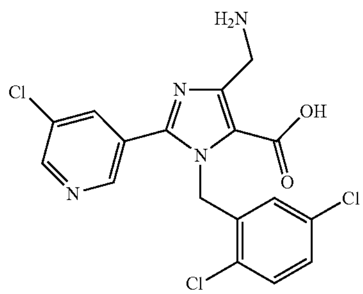 [SMILES: NCc1nc(-c2cncc(Cl)c2)n(Cc2cc(Cl)ccc2Cl)c1C(=O)O] |
| A202 | 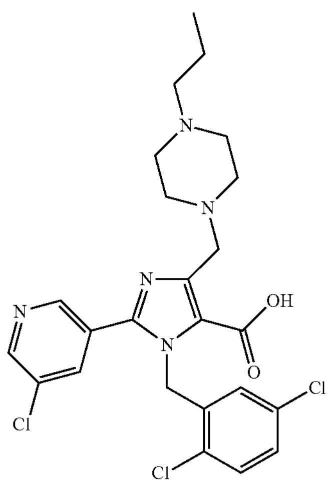 [SMILES: CCCN1CCN(Cc2nc(-c3cncc(Cl)c3)n(Cc3cc(Cl)ccc3Cl)c2C(=O)O)CC1] |
| A203 | 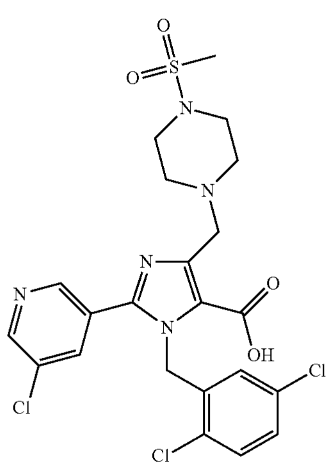 [SMILES: CS(=O)(=O)N1CCN(Cc2nc(-c3cncc(Cl)c3)n(Cc3cc(Cl)ccc3Cl)c2C(=O)O)CC1] |

-continued

| Compound No. | Structure |
|---|---|
| A204 | 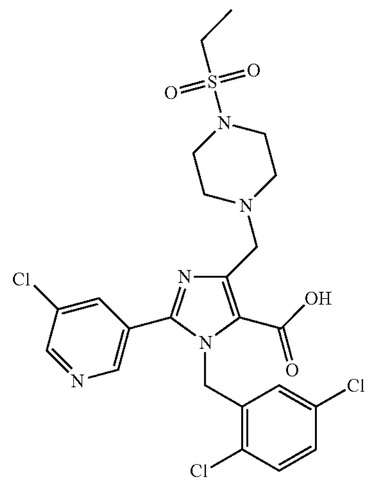 [SMILES: CCS(=O)(=O)N1CCN(Cc2nc(-c3cncc(Cl)c3)n(Cc3cc(Cl)ccc3Cl)c2C(=O)O)CC1] |

[Chemical Formula 30]

| A205 | |
| A206 | |
| A207 | |
| A208 | |

-continued
| Compound No. | Structure |
|---|---|
| A209 | 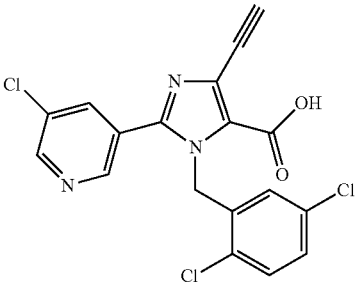 [SMILES: C#Cc1nc(-c2cncc(Cl)c2)n(Cc2cc(Cl)ccc2Cl)c1C(=O)O] |
| A210 | 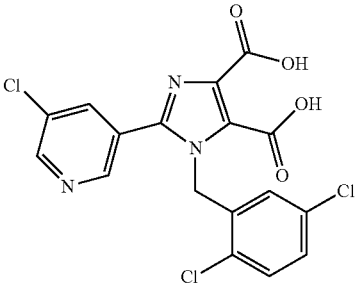 [SMILES: O=C(O)c1nc(-c2cncc(Cl)c2)n(Cc2cc(Cl)ccc2Cl)c1C(=O)O] |
| A211 | 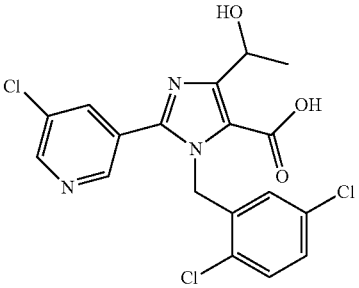 [SMILES: CC(O)c1nc(-c2cncc(Cl)c2)n(Cc2cc(Cl)ccc2Cl)c1C(=O)O] |
| A212 | 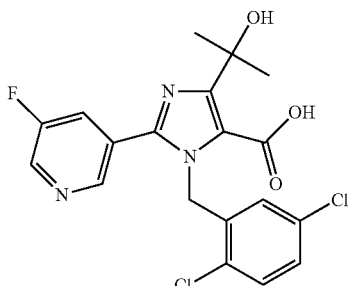 |
| A213 | 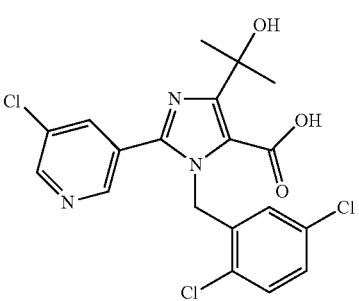 [SMILES: CC(C)(O)c1nc(-c2cncc(Cl)c2)n(Cc2cc(Cl)ccc2Cl)c1C(=O)O] |
-continued
| Compound No. | Structure |
|---|---|
| A214 | 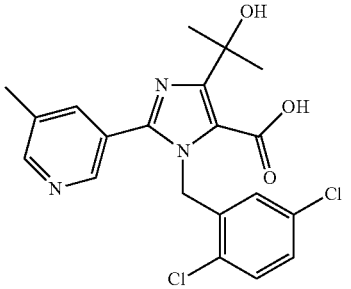 [SMILES: Cc1cncc(-c2nc(C(C)(C)O)c(C(=O)O)n2Cc2cc(Cl)ccc2Cl)c1] |
| A215 | 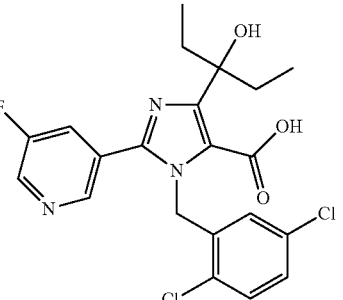 |
| A216 | 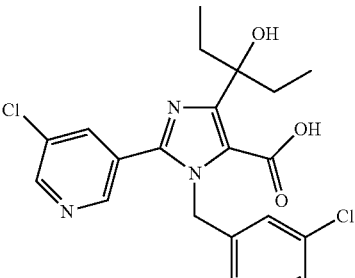 |
[Chemical Formula 31]
| A217 | 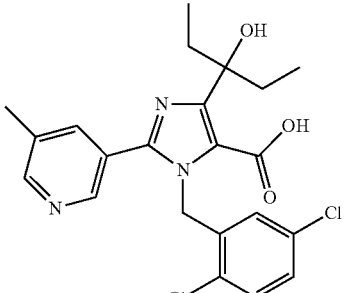 |
| A218 | 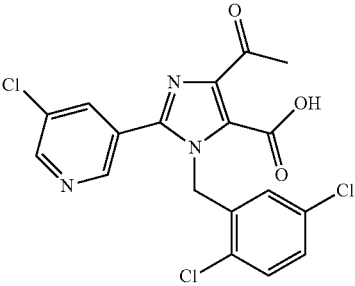 [SMILES: CC(=O)c1nc(-c2cncc(Cl)c2)n(Cc2cc(Cl)ccc2Cl)c1C(=O)O] |

| Compound No. | Structure |
|---|---|
| A219 | 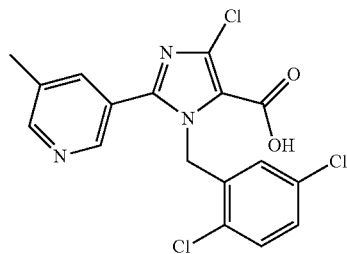 [SMILES: Cc1cncc(-c2nc(Cl)c(C(=O)O)n2Cc2cc(Cl)ccc2Cl)c1] |
| A220 | 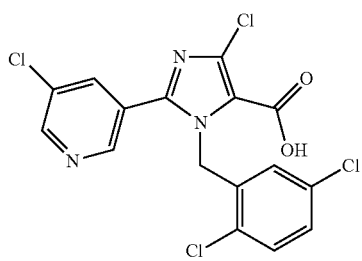 [SMILES: O=C(O)c1c(Cl)nc(-c2cncc(Cl)c2)n1Cc1cc(Cl)ccc1Cl] |
| A221 | 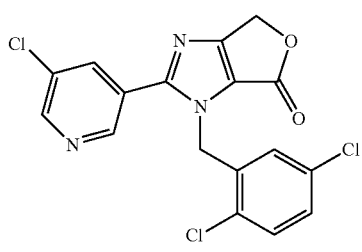 [SMILES: O=C1OCc2nc(-c3cncc(Cl)c3)n(Cc3cc(Cl)ccc3Cl)c21] |
| A222 | 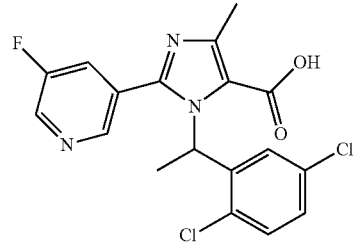 [SMILES: Cc1nc(-c2cncc(F)c2)n(C(C)c2cc(Cl)ccc2Cl)c1C(=O)O] |
| A223 | 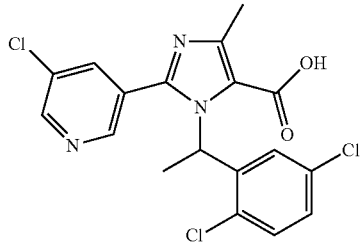 [SMILES: Cc1nc(-c2cncc(Cl)c2)n(C(C)c2cc(Cl)ccc2Cl)c1C(=O)O] |
| A224 | 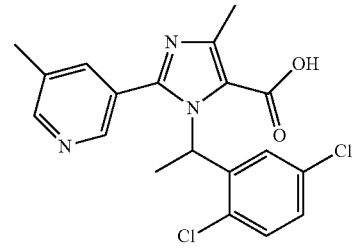 [SMILES: Cc1cncc(-c2nc(C)c(C(=O)O)n2C(C)c2cc(Cl)ccc2Cl)c1] |
| Compound No. | Structure |
|---|---|
| A225 | 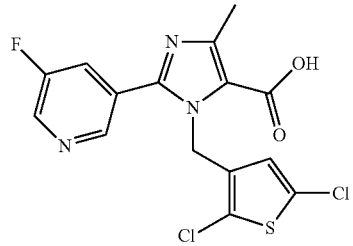 [SMILES: Cc1nc(-c2cncc(F)c2)n(Cc2cc(Cl)sc2Cl)c1C(=O)O] |
| A226 | 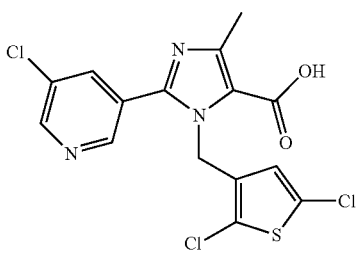 [SMILES: Cc1nc(-c2cncc(Cl)c2)n(Cc2cc(Cl)sc2Cl)c1C(=O)O] |
| A227 | 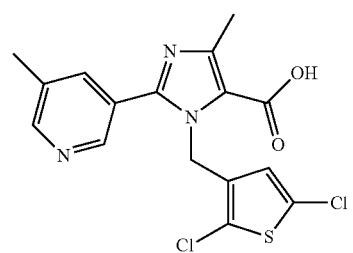 [SMILES: Cc1cncc(-c2nc(C)c(C(=O)O)n2Cc2cc(Cl)sc2Cl)c1] |
| A228 | 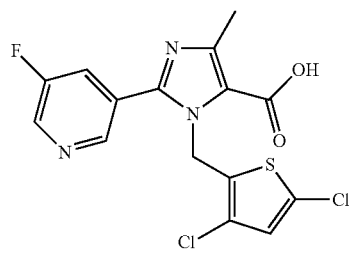 [SMILES: Cc1nc(-c2cncc(F)c2)n(Cc2sc(Cl)cc2Cl)c1C(=O)O] |
[Chemical Formula 32]
| Compound No. | Structure |
|---|---|
| A229 | 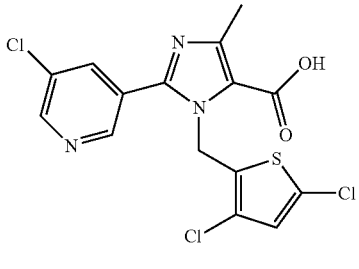 [SMILES: Cc1nc(-c2cncc(Cl)c2)n(Cc2sc(Cl)cc2Cl)c1C(=O)O] |
| A230 | 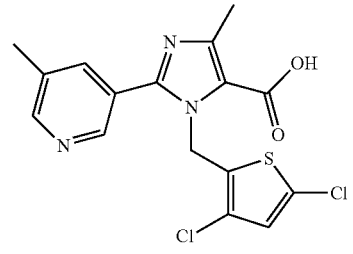 [SMILES: Cc1cncc(-c2nc(C)c(C(=O)O)n2Cc2sc(Cl)cc2Cl)c1] |

-continued
| Compound No. | Structure |
|---|---|
| A231 | 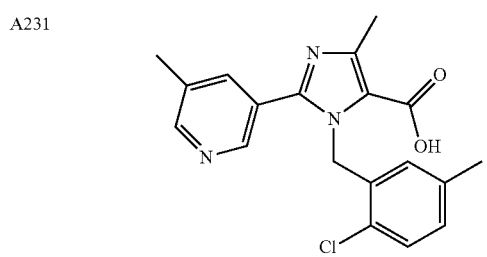 |
| A232 | 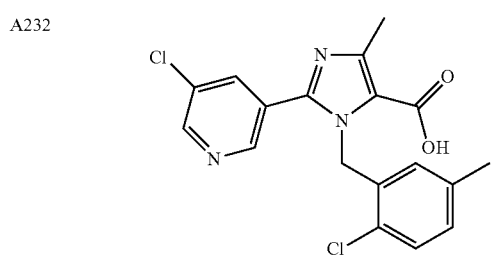 |
| A233 | 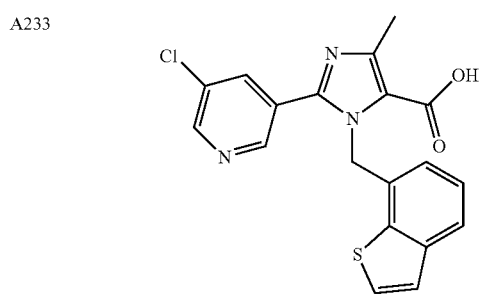 |
| A234 | 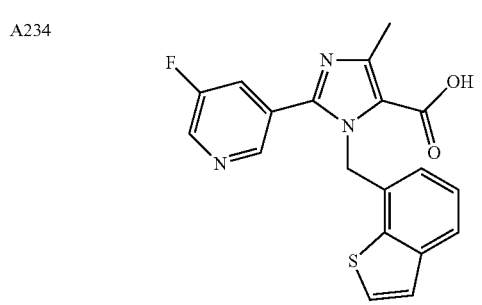 |
| A235 | 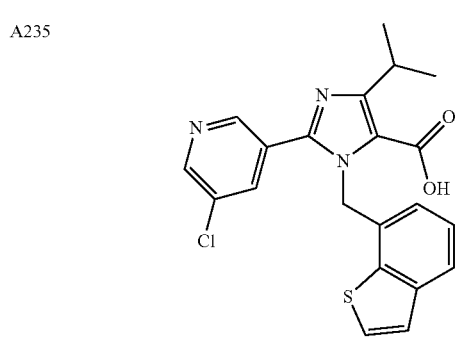 |
-continued
| Compound No. | Structure |
|---|---|
| A236 | 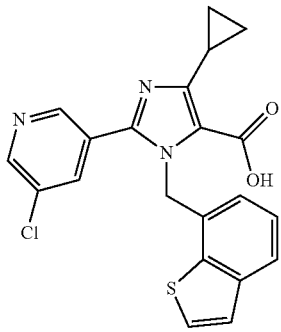 [SMILES: O=C(O)c1c(C2CC2)nc(-c2cncc(Cl)c2)n1Cc1cccc2ccsc12] |
| A237 | 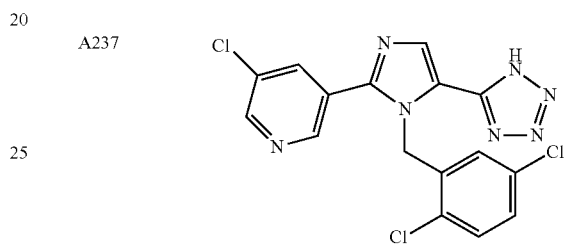 |
| A238 | 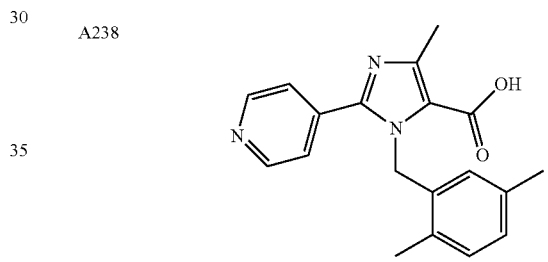 |
| A239 | 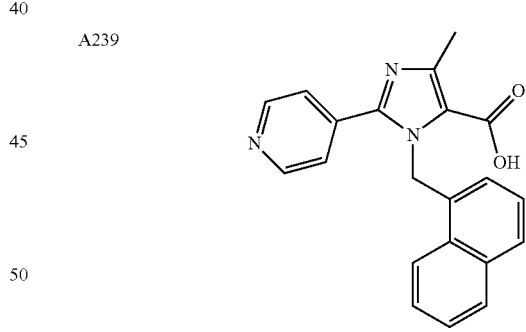 |
| A240 | 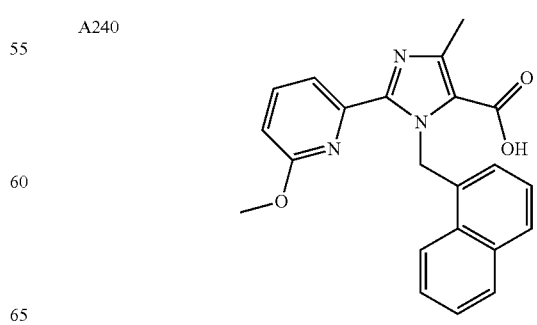 |

-continued
| Compound No. | Structure |
|---|---|
| [Chemical Formula 33] | |
| A241 | 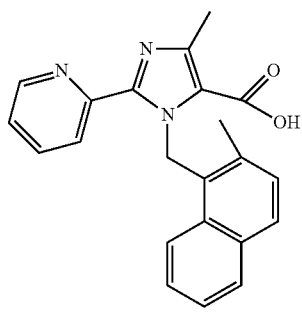 [SMILES: Cc1ccc2ccccc2c1Cn1c(-c2ccccn2)nc(C)c1C(=O)O] |
| A242 | 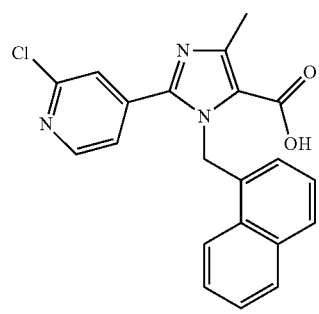 [SMILES: Cc1nc(-c2ccnc(Cl)c2)n(Cc2cccc3ccccc23)c1C(=O)O] |
| A243 | 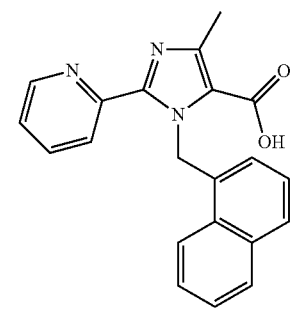 [SMILES: Cc1nc(-c2ccccn2)n(Cc2cccc3ccccc23)c1C(=O)O] |
| A244 | 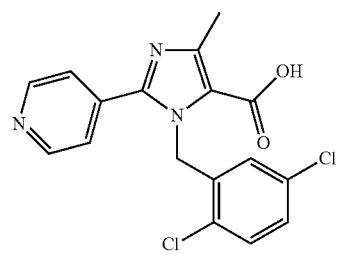 [SMILES: Cc1nc(-c2ccncc2)n(Cc2cc(Cl)ccc2Cl)c1C(=O)O] |
| A245 | 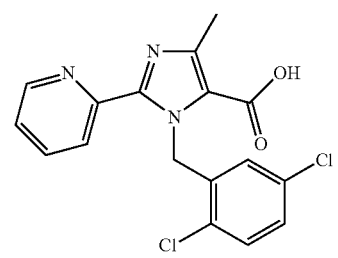 [SMILES: Cc1nc(-c2ccccn2)n(Cc2cc(Cl)ccc2Cl)c1C(=O)O] |
-continued
| Compound No. | Structure |
|---|---|
| A246 | 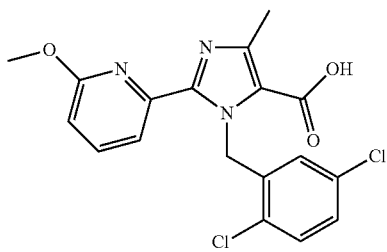 [SMILES: COc1cccc(-c2nc(C)c(C(=O)O)n2Cc2cc(Cl)ccc2Cl)n1] |
| A247 | 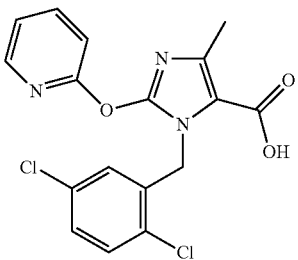 [SMILES: Cc1nc(Oc2ccccn2)n(Cc2cc(Cl)ccc2Cl)c1C(=O)O] |
| A248 | 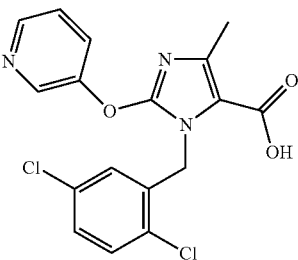 [SMILES: Cc1nc(Oc2cccnc2)n(Cc2cc(Cl)ccc2Cl)c1C(=O)O] |
| A249 | 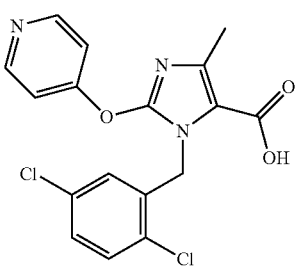 [SMILES: Cc1nc(Oc2ccncc2)n(Cc2cc(Cl)ccc2Cl)c1C(=O)O] |
| A250 | 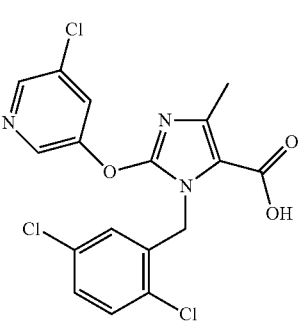 [SMILES: Cc1nc(Oc2cncc(Cl)c2)n(Cc2cc(Cl)ccc2Cl)c1C(=O)O] |

| Compound No. | Structure |
|---|---|
| A251 | 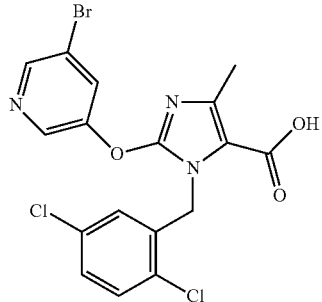 [SMILES: Cc1nc(Oc2cncc(Br)c2)n(Cc2cc(Cl)ccc2Cl)c1C(=O)O] |
| A252 | 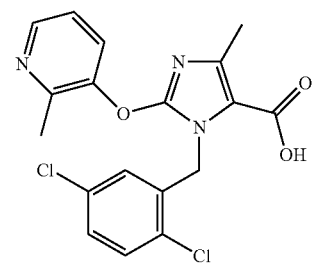 [SMILES: Cc1ncccc1Oc1nc(C)c(C(=O)O)n1Cc1cc(Cl)ccc1Cl] |
[Chemical Formula 34]
| Compound No. | Structure |
|---|---|
| A253 | 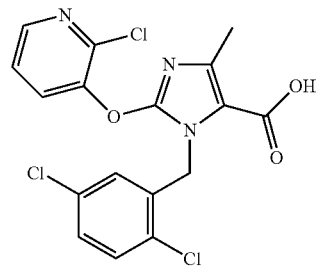 [SMILES: Cc1nc(Oc2cccnc2Cl)n(Cc2cc(Cl)ccc2Cl)c1C(=O)O] |
| A254 | 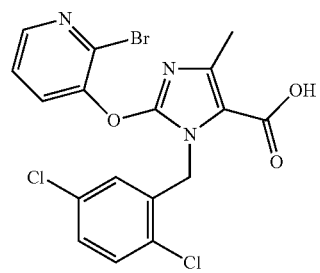 [SMILES: Cc1nc(Oc2cccnc2Br)n(Cc2cc(Cl)ccc2Cl)c1C(=O)O] |
| A255 | 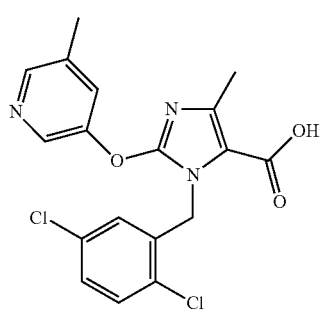 [SMILES: Cc1cncc(Oc2nc(C)c(C(=O)O)n2Cc2cc(Cl)ccc2Cl)c1] |
| Compound No. | Structure |
|---|---|
| A256 | 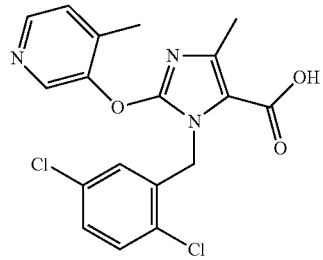 [SMILES: Cc1ccncc1Oc1nc(C)c(C(=O)O)n1Cc1cc(Cl)ccc1Cl] |
| A257 | 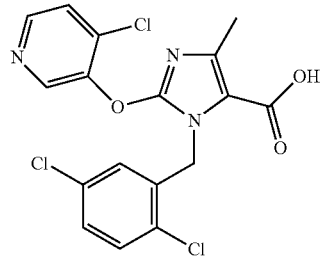 [SMILES: Cc1nc(Oc2cnccc2Cl)n(Cc2cc(Cl)ccc2Cl)c1C(=O)O] |
| A258 | 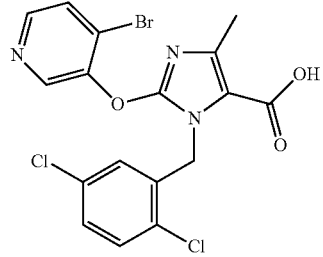 [SMILES: Cc1nc(Oc2cnccc2Br)n(Cc2cc(Cl)ccc2Cl)c1C(=O)O] |
| A259 | 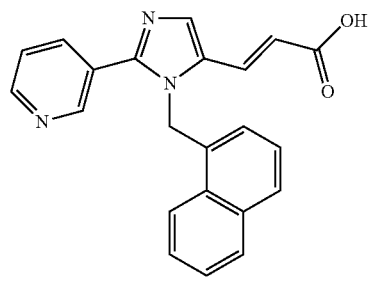 [SMILES: O=C(O)/C=C/c1cnc(-c2cccnc2)n1Cc1cccc2ccccc12] |
| A260 | 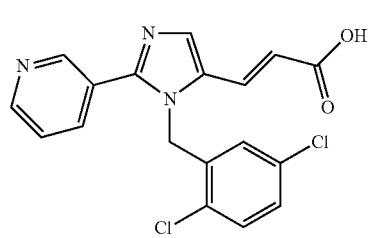 [SMILES: O=C(O)/C=C/c1cnc(-c2cccnc2)n1Cc1cc(Cl)ccc1Cl] |
| A261 | 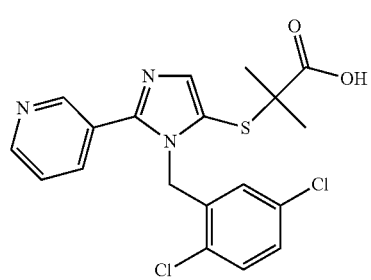 [SMILES: CC(C)(Sc1cnc(-c2cccnc2)n1Cc1cc(Cl)ccc1Cl)C(=O)O] |

| Compound No. | Structure |
|---|---|
| A262 | 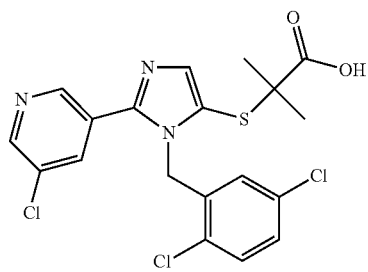 [SMILES: CC(C)(Sc1cnc(-c2cncc(Cl)c2)n1Cc1cc(Cl)ccc1Cl)C(=O)O] |
| A263 | 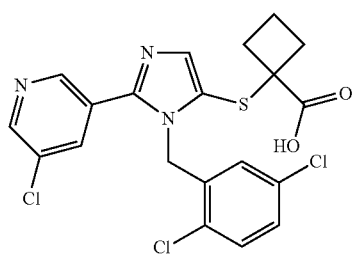 [SMILES: O=C(O)C1(Sc2cnc(-c3cncc(Cl)c3)n2Cc2cc(Cl)ccc2Cl)CCC1] |
| A264 | 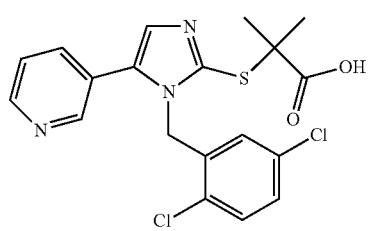 [SMILES: CC(C)(Sc1ncc(-c2cccnc2)n1Cc1cc(Cl)ccc1Cl)C(=O)O] |
[Chemical Formula 35]
| Compound No. | Structure |
|---|---|
| A265 | 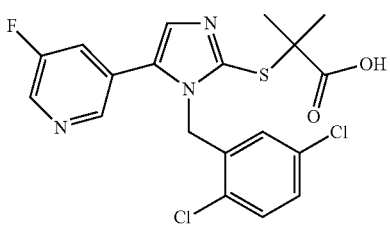 [SMILES: CC(C)(Sc1ncc(-c2cncc(F)c2)n1Cc1cc(Cl)ccc1Cl)C(=O)O] |
| A266 | 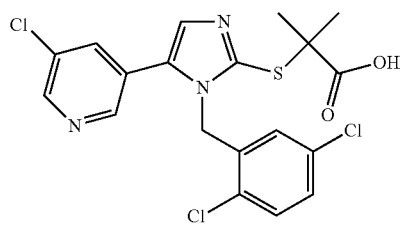 [SMILES: CC(C)(Sc1ncc(-c2cncc(Cl)c2)n1Cc1cc(Cl)ccc1Cl)C(=O)O] |
| A267 | 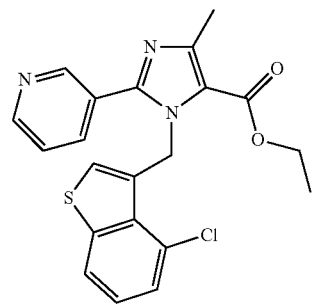 [SMILES: CCOC(=O)c1c(C)nc(-c2cccnc2)n1Cc1csc2cccc(Cl)c12] |
| Compound No. | Structure |
|---|---|
| A268 | 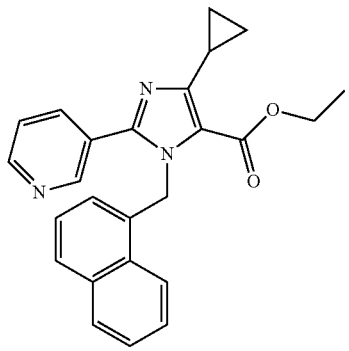 [SMILES: CCOC(=O)c1c(C2CC2)nc(-c2cccnc2)n1Cc1cccc2ccccc12] |
| A269 | 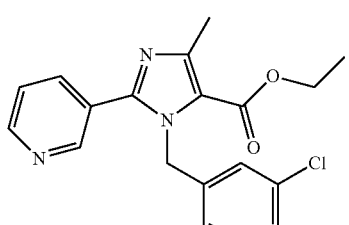 |
| A270 | 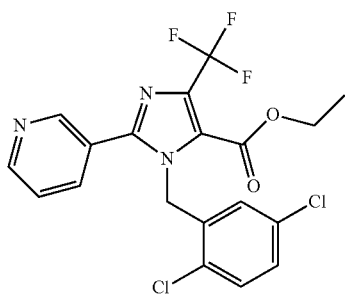 [SMILES: CCOC(=O)c1c(C(F)(F)F)nc(-c2cccnc2)n1Cc1cc(Cl)ccc1Cl] |
| A271 | 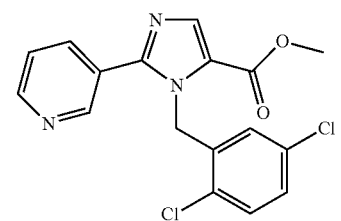 [SMILES: COC(=O)c1cnc(-c2cccnc2)n1Cc1cc(Cl)ccc1Cl] |
| A272 | 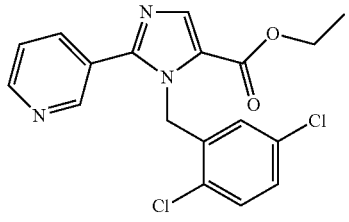 [SMILES: CCOC(=O)c1cnc(-c2cccnc2)n1Cc1cc(Cl)ccc1Cl] |

-continued
| Compound No. | Structure |
|---|---|
| A273 | 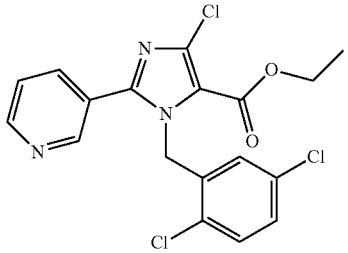 [SMILES: CCOC(=O)c1c(Cl)nc(-c2cccnc2)n1Cc1cc(Cl)ccc1Cl] |
| A274 | 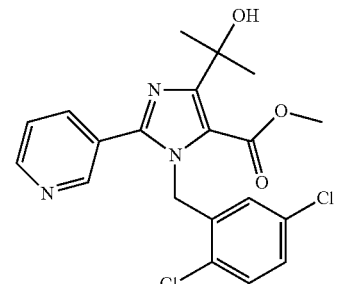 |
| A275 | 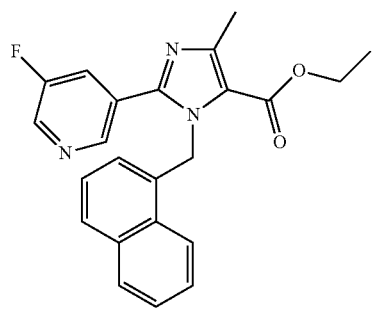 [SMILES: CCOC(=O)c1c(C)nc(-c2cncc(F)c2)n1Cc1cccc2ccccc12] |
| A276 | 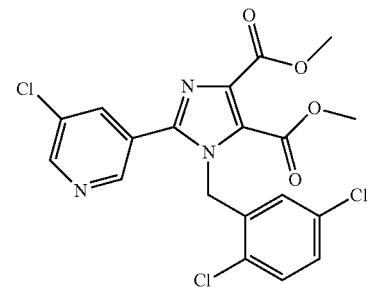 [SMILES: COC(=O)c1nc(-c2cncc(Cl)c2)n(Cc2cc(Cl)ccc2Cl)c1C(=O)OC] |
[Chemical Formula 36]
| Compound No. | Structure |
|---|---|
| A277 | 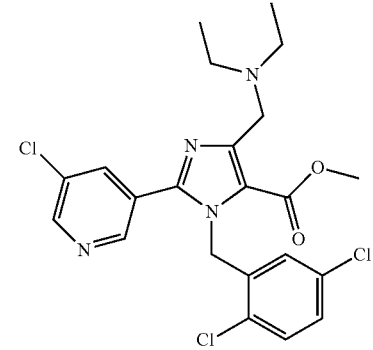 [SMILES: CCN(CC)Cc1nc(-c2cncc(Cl)c2)n(Cc2cc(Cl)ccc2Cl)c1C(=O)OC] |
| A278 | 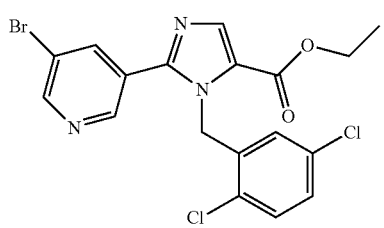 [SMILES: CCOC(=O)c1cnc(-c2cncc(Br)c2)n1Cc1cc(Cl)ccc1Cl] |
| A279 | 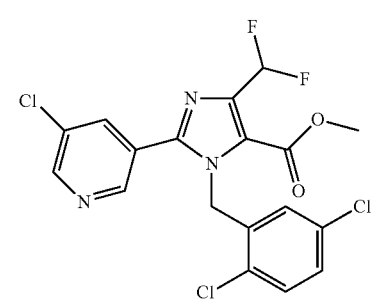 [SMILES: COC(=O)c1c(C(F)F)nc(-c2cncc(Cl)c2)n1Cc1cc(Cl)ccc1Cl] |
| A280 | 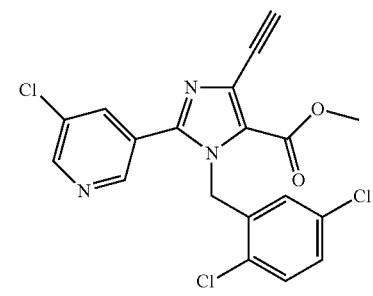 [SMILES: C#Cc1nc(-c2cncc(Cl)c2)n(Cc2cc(Cl)ccc2Cl)c1C(=O)OC] |
| A281 | 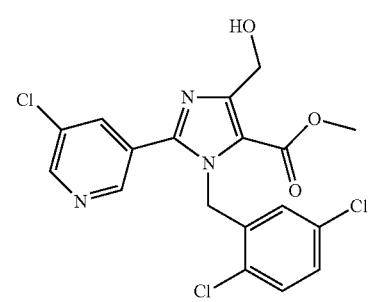 |
| A282 | 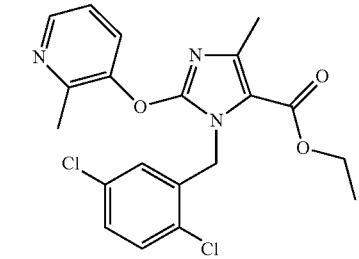 [SMILES: CCOC(=O)c1c(C)nc(Oc2cccnc2C)n1Cc1cc(Cl)ccc1Cl] |

-continued
| Compound No. | Structure |
|---|---|
| B1 | 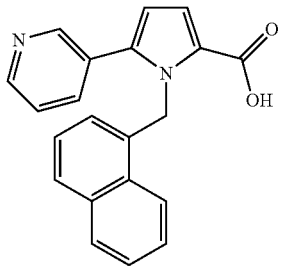 [SMILES: O=C(O)c1ccc(-c2cccnc2)n1Cc1cccc2ccccc12] |
| B2 | 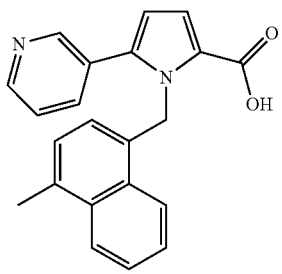 [SMILES: Cc1ccc(Cn2c(C(=O)O)ccc2-c2cccnc2)c2ccccc12] |
| B3 | 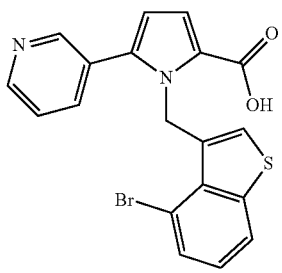 [SMILES: O=C(O)c1ccc(-c2cccnc2)n1Cc1csc2cccc(Br)c12] |
| B4 | 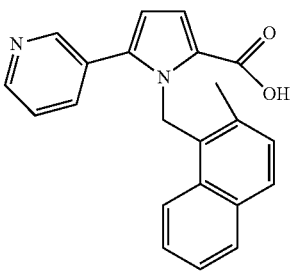 [SMILES: Cc1ccc2ccccc2c1Cn1c(C(=O)O)ccc1-c1cccnc1] |
| B5 | 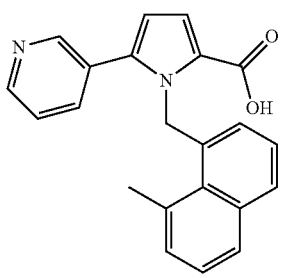 [SMILES: Cc1cccc2cccc(Cn3c(C(=O)O)ccc3-c3cccnc3)c12] |
-continued
| Compound No. | Structure |
|---|---|
| B6 | 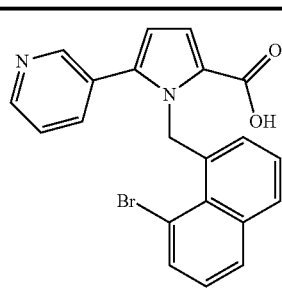 |
[Chemical Formula 37]
| | |
|---|---|
| B7 | 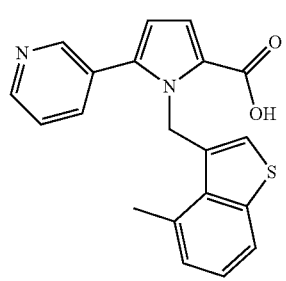 [SMILES: Cc1cccc2scc(Cn3c(C(=O)O)ccc3-c3cccnc3)c12] |
| B8 | 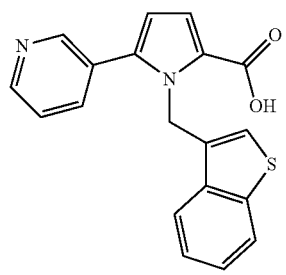 [SMILES: O=C(O)c1ccc(-c2cccnc2)n1Cc1csc2ccccc12] |
| B9 | 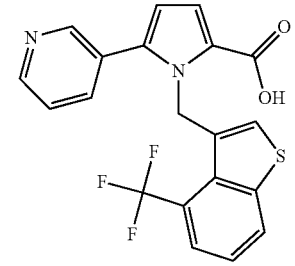 [SMILES: O=C(O)c1ccc(-c2cccnc2)n1Cc1csc2cccc(C(F)(F)F)c12] |
| B10 | 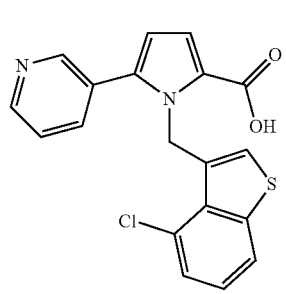 [SMILES: O=C(O)c1ccc(-c2cccnc2)n1Cc1csc2cccc(Cl)c12] |

-continued
| Compound No. | Structure |
|---|---|
| B11 | 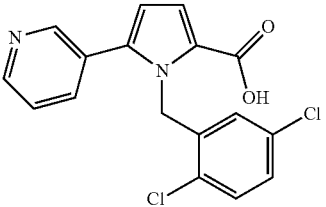 [SMILES: O=C(O)c1ccc(-c2cccnc2)n1Cc1cc(Cl)ccc1Cl] |
| B12 | 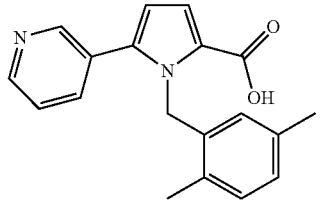 [SMILES: Cc1ccc(C)c(Cn2c(C(=O)O)ccc2-c2cccnc2)c1] |
| B13 | 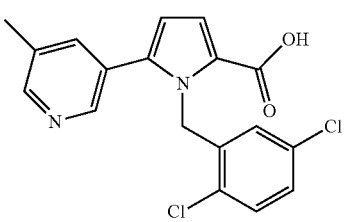 [SMILES: Cc1cncc(-c2ccc(C(=O)O)n2Cc2cc(Cl)ccc2Cl)c1] |
| B14 | 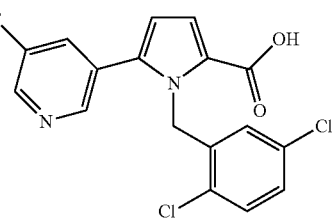 |
| B15 | 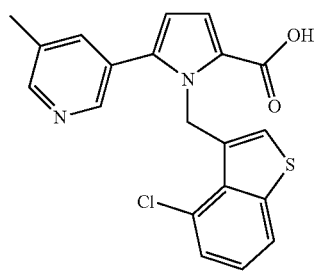 [SMILES: Cc1cncc(-c2ccc(C(=O)O)n2Cc2csc3cccc(Cl)c23)c1] |
| B16 | 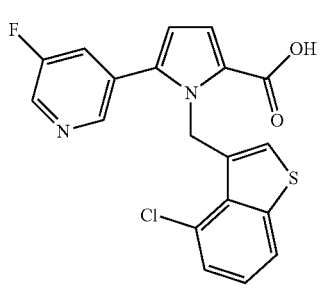 [SMILES: O=C(O)c1ccc(-c2cncc(F)c2)n1Cc1csc2cccc(Cl)c12] |
-continued
| Compound No. | Structure |
|---|---|
| B17 | 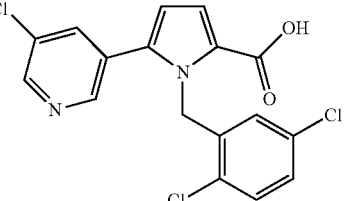 |
| B18 | 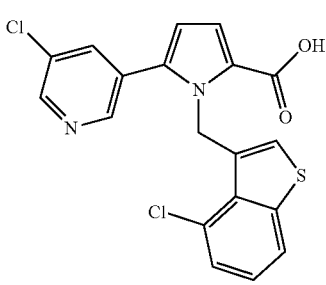 [SMILES: O=C(O)c1ccc(-c2cncc(Cl)c2)n1Cc1csc2cccc(Cl)c12] |
[Chemical Formula 38]
| | |
|---|---|
| B19 | 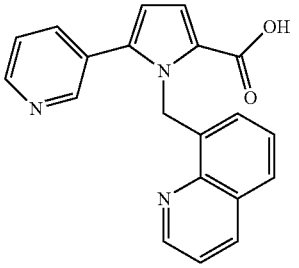 [SMILES: O=C(O)c1ccc(-c2cccnc2)n1Cc1cccc2cccnc12] |
| B20 | 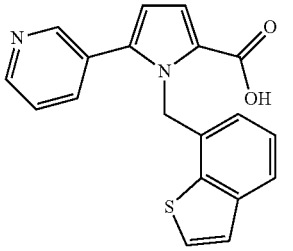 [SMILES: O=C(O)c1ccc(-c2cccnc2)n1Cc1cccc2ccsc12] |
| B21 | 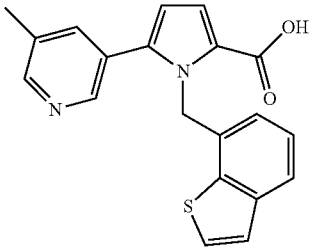 [SMILES: Cc1cncc(-c2ccc(C(=O)O)n2Cc2cccc3ccsc23)c1] |

-continued
| Compound No. | Structure |
|---|---|
| B22 | 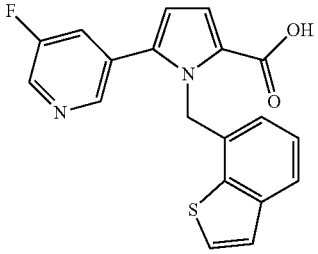 [SMILES: O=C(O)c1ccc(-c2cncc(F)c2)n1Cc1cccc2ccsc12] |
| B23 | 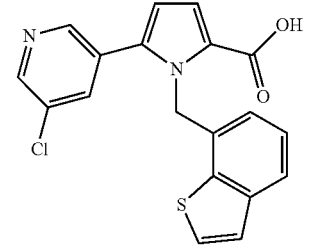 [SMILES: O=C(O)c1ccc(-c2cncc(Cl)c2)n1Cc1cccc2ccsc12] |
| B24 | 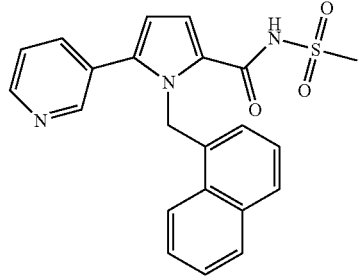 [SMILES: CS(=O)(=O)NC(=O)c1ccc(-c2cccnc2)n1Cc1cccc2ccccc12] |
| B25 | 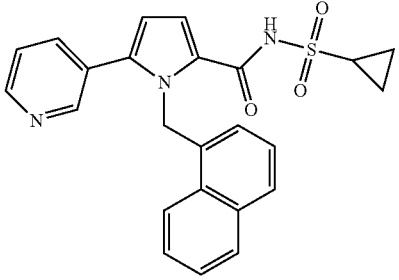 [SMILES: O=C(NS(=O)(=O)C1CC1)c1ccc(-c2cccnc2)n1Cc1cccc2ccccc12] |
| B26 | 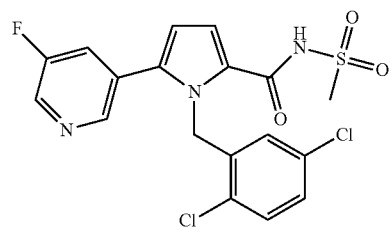 [SMILES: CS(=O)(=O)NC(=O)c1ccc(-c2cncc(F)c2)n1Cc1cc(Cl)ccc1Cl] |
| B27 | 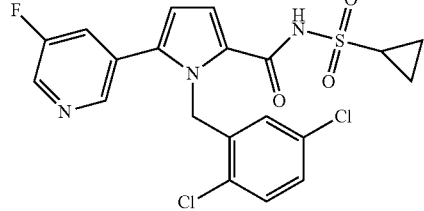 |
-continued
| Compound No. | Structure |
|---|---|
| B28 | 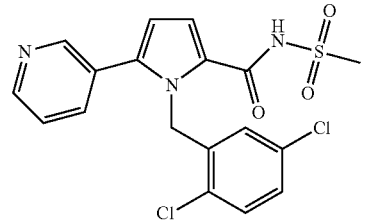 |
| B29 | 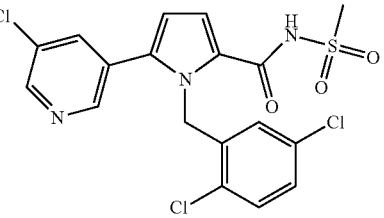 |
| B30 | 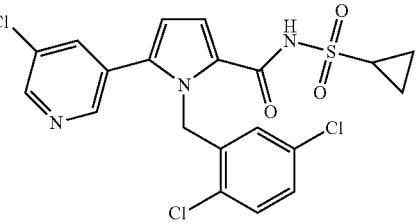 [SMILES: O=C(NS(=O)(=O)C1CC1)c1ccc(-c2cncc(F)c2)n1Cc1cc(Cl)ccc1Cl] |
[Chemical Formula 39]
| B31 | 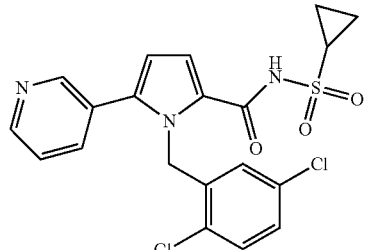 |
| B32 | 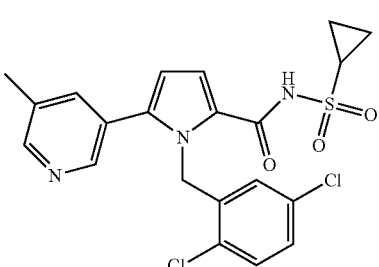 |
| B33 | 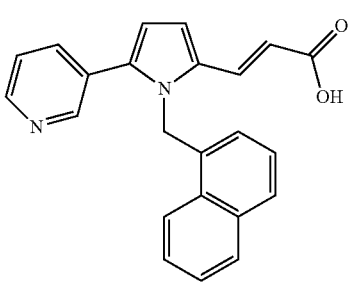 [SMILES: O=C(O)/C=C/c1ccc(-c2cccnc2)n1Cc1cccc2ccccc12] |

| Compound No. | Structure |
|---|---|
| B34 | (5-(5-methylpyridin-3-yl)-1-(2,5-dichlorobenzyl)-1H-pyrrol-2-yl)acrylic acid structure |

| Compound No. | Structure |
|---|---|
| B35 | (5-(5-fluoropyridin-3-yl)-1-(2,5-dichlorobenzyl)-1H-pyrrol-2-yl)acrylic acid structure |

Of these, preferred compounds are those listed in the tables below.

TABLE 1

| Compound No. | Compound Name |
|---|---|
| A1 | 1-(2,5-dimehylbenzyl)-4-methyl-2-(pyridin-3-yl)-1H-imidazole-5-carboxylic acid |
| A2 | 4-methyl-1-(naphthalen-1-ylmethyl)-2-(pyridin-3-yl)-1H-imidazole-5-carboxylic acid |
| A3 | ethyl 4-methyl-1-(naphthalen-1-ylmethyl)-2-(pyridin-3-yl)-1H-imidazole-5-carboxylate |
| A6 | 4-methyl-2-(pyridin-3-yl)-1-((4-(trifluoromethyl)benzo[b]thiophen-3-yl)-methyl)-1H-imidazole-5-carboxylic acid |
| A7 | 1-((4-chlorobenzo[b]thiophen-3-yl)methyl)-4-methyl-2-(pyridin-3-yl)-1H-imidazole-5-carboxylic acid |
| A8 | 1-((4-bromobenzo[b]thiophen-3-yl)methyl)-4-methyl-2-(pyridin-3-yl)-1H-imidazole-5-carboxylic acid |
| A9 | 4-chloro-1-(naphthalen-1-ylmethyl)-2-(pyridin-3-yl)-1H-imidazole-5-carboxylic acid |
| A10 | 4-ethyl-1-(naphthalen-1-ylmethyl)-2-(pyridin-3-yl)-1H-imidazole-5-carboxylic acid |
| A11 | 4-cyclopropyl-1-(naphthalen-1-ylmethyl)-2-(pyridin-3-yl)-1H-imidazole-5-carboxylic acid |
| A13 | 1-(2,5-dichlorobenzyl)-4-methyl-2-(pyridin-3-yl)-1H-imidazole-5-carboxylic acid |
| A14 | 1-(2,5-dichlorobenzyl)-4-ethyl-2-(pyridin-3-yl)-1H-imidazole-5-carboxylic acid |
| A15 | 4-cyclopropyl-1-(2,5-dichlorobenzyl)-2-(pyridin-3-yl)-1H-imidazole-5-carboxylic acid |
| A17 | 4-methyl-1-((4-methylnaphthalen-1-yl)methyl)-2-(pyridin-3-yl)-1H-imidazole-5-carboxylic acid |
| A18 | 4-cyclopropyl-1-((4-methylnaphthalen-1-yl)methyl)-2-(pyridin-3-yl)-1H-imidazole-5-carboxylic acid |
| A19 | 1-(2,5-dichlorobenzyl)-2-(pyridin-3-yl)-4-(trifluoromethyl)-1H-imidazole-5-carboxylic acid |
| A22 | 1-(benzo[b]thiophen-3-ylmethyl)-2-(pyridin-3-yl)-4-(trifluoromethyl)-1H-imidazole-5-carboxylic acid |
| A23 | 4-chloro-1-((4-methylnaphthalen-1-yl)methyl)-2-(pyridin-3-yl)-1H-imidazole-5-carboxylic acid |
| A24 | 4-isopropyl-1-(naphthalen-1-ylmethyl)-2-(pyridin-3-yl)-1H-imidazole-5-carboxylic acid |
| A25 | 4-isopropyl-1-((4-methylnaphthalen-1-yl)methyl)-2-(pyridin-3-yl)-1H-imidazole-5-carboxylic acid |
| A26 | 1-(2,5-dichlorobenzyl)-4-isopropyl-2-(pyridin-3-yl)-1H-imidazole-5-carboxylic acid |
| A27 | 1-((4-chlorobenzo[b]thiophen-3-yl)methyl)-2-(pyridin-3-yl)-4-(trifluoromethyl)-1H-imidazole-5-carboxylic acid |

TABLE 2

| Compound No. | Compound Name |
|---|---|
| A31 | 1-((4-bromobenzo[b]thiophen-3-yl)methyl)-2-(pyridin-3-yl)-4-(trifluoromethyl)-1H-imidazole-5-carboxylic acid |
| A33 | 1-((4-chlorobenzo[b]thiophen-3-yl)methyl)-4-cyclopropyl-2-(pyridin-3-yl)-1H-imidazole-5-carboxylic acid |

TABLE 2-continued

| Compound No. | Compound Name |
|---|---|
| A34 | 1-((4-bromobenzo[b]thiophen-3-yl)methyl)-4-cyclopropyl-2-(pyridin-3-yl)-1H-imidazole-5-carboxylic acid |
| A35 | 4-cyclopropyl-2-(pyridin-3-yl)-1-((4-(trifluoromethyl)benzo[b]thiophen-3-yl)methyl)-1H-imidazole-5-carboxylic acid |
| A36 | 1-(benzo[b]thiophen-3-ylmethyl)-4-cyclopropyl-2-(pyridin-3-yl)-1H-imidazole-5-carboxylic acid |
| A37 | 1-((4-chlorobenzo[b]thiophen-3-yl)methyl)-4-isopropyl-2-(pyridin-3-yl)-1H-imidazole-5-carboxylic acid |
| A38 | 1-((4-bromobenzo[b]thiophen-3-yl)methyl)-4-isopropyl-2-(pyridin-3-yl)-1H-imidazole-5-carboxylic acid |
| A39 | 4-isopropyl-2-(pyridin-3-yl)-1-((4-(trifluoromethyl)benzo[b]thiophen-3-yl)methyl)-1H-imidazole-5-carboxylic acid |
| A40 | 1-(benzo[b]thiophen-3-ylmethyl)-4-isopropyl-2-(pyridin-3-yl)-1H-imidazole-5-carboxylic acid |
| A41 | 1-(2-chloro-5-fluorobenzyl)-4-methyl-2-(pyridin-3-yl)-1H-imidazole-5-carboxylic acid |
| A42 | 1-(5-chloro-2-fluorobenzyl)-4-methyl-2-(pyridin-3-yl)-1H-imidazole-5-carboxylic acid |
| A43 | 1-(2-chloro-5-(trifluoromethyl)benzyl)-4-methyl-2-(pyridin-3-yl)-1H-imidazole-5-carboxylic acid |
| A44 | 1-(5-chloro-2-(trifluoromethyl)benzyl)-4-methyl-2-(pyridin-3-yl)-1H-imidazole-5-carboxylic acid |
| A45 | 1-(2,5-dichlorobenzyl)-2-(pyridin-3-yl)-1H-imidazole-5-carboxylic acid |
| A46 | 1-(2,5-bis(trifluoromethyl)benzyl)-4-methyl-2-(pyridin-3-yl)-1H-imidazole-5-carboxylic acid |
| A54 | 1-(2-bromobenzyl)-4-methyl-2-(pyridin-3-yl)-1H-imidazole-5-carboxylic acid |
| A55 | 1-(3-bromobenzyl)-4-methyl-2-(pyridin-3-yl)-1H-imidazole-5-carboxylic acid |
| A67 | 1-(2,5-dichlorobenzyl)-4-methyl-2-(quinolin-3-yl)-1H-imidazole-5-carboxylic acid |
| A68 | 1-(3,4-dichlorobenzyl)-4-methyl-2-(pyridin-3-yl)-1H-imidazole-5-carboxylic acid |
| A70 | 1-(2,3-dichlorobenzyl)-4-methyl-2-(pyridin-3-yl)-1H-imidazole-5-carboxylic acid |

TABLE 3

| | |
|---|---|
| A71 | 1-(3,5-dichlorobenzyl)-4-methyl-2-(pyridin-3-yl)-1H-imidazole-5-carboxylic acid |
| A76 | 1-(3-chloro-5-fluorobenzyl)-4-methyl-2-(pyridin-3-yl)-1H-imidazole-5-carboxylic acid |
| A77 | 1-(2,4-dichlorobenzyl)-4-methyl-2-(pyridin-3-yl)-1H-imidazole-5-carboxylic acid |
| A78 | 1-(2-chloro-5-methylbenzyl)-4-methyl-2-(pyridin-3-yl)-1H-imidazole-5-carboxylic acid |
| A79 | 1-((2,5-dichlorothiophen-3-yl)methyl)-4-methyl-2-(pyridin-3-yl)-1H-imidazole-5-carboxylic acid |
| A80 | 1-((2,4-dichlorothiophen-5-yl)methyl)-4-methyl-2-(pyridin-3-yl)-1H-imidazole-5-carboxylic acid |
| A81 | 1-(benzo[b]thiophen-7-ylmethyl)-4-methyl-2-(pyridin-3-yl)-1H-imidazole-5-carboxylic acid |
| A82 | 1-(benzo[b]thiophen-7-ylmethyl)-4-cyclopropyl-2-(pyridin-3-yl)-1H-imidazole-5-carboxylic acid |
| A83 | 1-(benzo[b]thiophen-7-ylmethyl)-4-isopropyl-2-(pyridin-3-yl)-1H-imidazole-5-carboxylic acid |
| A84 | 1-(benzo[b]thiophen-7-ylmethyl)-2-(pyridin-3-yl)-4-(trifluoromethyl)-1H-imidazole-5-carboxylic acid |
| A85 | 1-((5-fluorobenzo[b]thiophen-7-yl)methyl)-4-methyl-2-(pyridin-3-yl)-1H-imidazole-5-carboxylic acid |
| A86 | 4-cyclopropyl-1-((5-fluorobenzo[b]thiophen-7-yl)methyl)-2-(pyridin-3-yl)-1H-imidazole-5-carboxylic acid |
| A88 | 4-chloro-1-(2,5-dichlorobenzyl)-2-(pyridin-3-yl)-1H-imidazole-5-carboxylic acid |
| A89 | 4-bromo-1-(2,5-dichlorobenzyl)-2-(pyridin-3-yl)-1H-imidazole-5-carboxylic acid |
| A90 | 1-(2,5-dichlorobenzyl)-4-iodo-2-(pyridin-3-yl)-1H-imidazole-5-carboxylic acid |
| A91 | 1-(2,5-dichlorobenzyl)-4-phenyl-2-(pyridin-3-yl)-1H-imidazole-5-carboxylic acid |
| A92 | 1-(2,5-dichlorobenzyl)-4-(3-fluorophenyl)-2-(pyridin-3-yl)-1H-imidazole-5-carboxylic acid |

TABLE 3-continued

| | |
|---|---|
| A93 | 1-(2,5-dichlorobenzyl)-4-(4-fluorophenyl)-2-(pyridin-3-yl)-1H-imidazole-5-carboxylic acid |
| A94 | 1-(2,5-dichlorobenzyl)-2,4-di(pyridin-3-yl)-1H-imidazole-5-carboxylic acid |
| A96 | 1-(2,5-dichlorobenzyl)-4-methoxy-2-(pyridin-3-yl)-1H-imidazole-5-carboxylic acid |
| A98 | 1-(2,5-dichlorobenzyl)-2-(pyridin-3-yl)-4-(2,2,2-trifluoroethoxy)-1H-imidazole-5-carboxylic acid |

TABLE 4

| Compound No. | Compound Name |
|---|---|
| A99 | 1-(2,5-dichlorobenzyl)-2-(pyridin-3-yl)-4-(p-tolyloxy)-1H-imidazole-5-carboxylic acid |
| A100 | 1-(2,5-dichlorobenzyl)-4-(4-fluorophenoxy)-2-(pyridin-3-yl)-1H-imidazole-5-carboxylic acid |
| A101 | 4-cyano-1-(2,5-dichlorobenzyl)-2-(pyridin-3-yl)-1H-imidazole-5-carboxylic acid |
| A102 | 1-(2,5-dichlorobenzyl)-2-(pyridin-3-yl)-4-vinyl-1H-imidazole-5-carboxylic acid |
| A103 | 4-(1-cyclopenten-1-yl)-1-(2,5-dichlorobenzyl)-2-(pyridin-3-yl)-1H-imidazole-5-carboxylic acid |
| A104 | 1-(2,5-dichlorobenzyl)-4-(methylthio)-2-(pyridin-3-yl)-1H-imidazole-5-carboxylic acid |
| A105 | 1-(2,5-dichlorobenzyl)-4-(ethylthio)-2-(pyridin-3-yl)-1H-imidazole-5-carboxylic acid |
| A108 | 1-(2,5-dichlorobenzyl)-4-(2-hydroxypropan-2-yl)-2-(pyridin-3-yl)-1H-imidazole-5-carboxylic acid |
| A109 | 1-(2,5-dichlorobenzyl)-4-(3-hydroxypentan-3-yl)-2-(pyridin-3-yl)-1H-imidazole-5-carboxylic acid |
| A110 | 3-(1-(2,5-dichlorobenzyl)-5-(1H-tetrazol-5-yl)-1H-imidazol-2-yl)pyridine |
| A117 | 1-(benzo[b]thiophen-7-ylmethyl)-4-cyclopropyl-N-(methylsulfonyl)-2-(pyridin-3-yl)-1H-imidazole-5-carboxamide |
| A118 | 1-(benzo[b]thiophen-7-ylmethyl)-4-cyclopropyl-N-(cyclopropylsulfonyl)-2-(pyridin-3-yl)-1H-imidazole-5-carboxamide |
| A119 | 2-(5-fluoropyridin-3-yl)-4-methyl-1-(naphthalen-1-ylmethyl)-1H-imidazole-5-carboxylic acid |
| A121 | 2-(5-chloropyridin-3-yl)-4-methyl-1-(naphthalen-1-ylmethyl)-1H-imidazole-5-carboxylic acid |
| A130 | 4-methyl-1-(naphthalen-1-ylmethyl)-2-(5-phenoxypyridin-3-yl)-1H-imidazole-5-carboxylic acid |
| A132 | 1-(benzo[b]thiophen-3-ylmethyl)-2-(5-chloropyridin-3-yl)-4-methyl-1H-imidazole-5-carboxylic acid |
| A133 | 1-(benzo[b]thiophen-3-ylmethyl)-2-(5-fluoropyridin-3-yl)-4-methyl-1H-imidazole-5-carboxylic acid |
| A134 | 1-(2,5-dichlorobenzyl)-2-(5-fluoropyridin-3-yl)-4-methyl-1H-imidazole-5-carboxylic acid |
| A135 | 2-(5-chloropyridin-3-yl)-1-(2,5-dichlorobenzyl)-4-methyl-1H-imidazole-5-carboxylic acid |
| A136 | 1-(2,5-dichlorobenzyl)-2-(5-fluoropyridin-3-yl)-4-(trifluoromethyl)-1H-imidazole-5-carboxylic acid |

TABLE 5

| Compound No. | Compound Name |
|---|---|
| A137 | 2-(5-chloropyridin-3-yl)-1-(2,5-dichlorobenzyl)-4-(trifluoromethyl)-1H-imidazole-5-carboxylic acid |
| A138 | 4-methyl-1-(naphthalen-1-ylmethyl)-2-(5-(trifluoromethyl)pyridin-3-yl)-1H-imidazole-5-carboxylic acid |
| A139 | 1-(2,5-dichlorobenzyl)-4-methyl-2-(5-(trifluoromethyl)pyridin-3-yl)-1H-imidazole-5-carboxylic acid |
| A140 | 1-(2,5-dichlorobenzyl)-4-(trifluoromethyl)-2-(5-(trifluoromethyl)pyridin-3-yl)-1H-imidazole-5-carboxylic acid |
| A141 | 1-((4-chlorobenzo[b]thiophen-3-yl)methyl)-2-(5-fluoropyridin-3-yl)-4-methyl-1H-imidazole-5-carboxylic acid |
| A142 | 1-((4-chlorobenzo[b]thiophen-3-yl)methyl)-2-(5-chloropyridin-3-yl)-4-methyl-1H-imidazole-5-carboxylic acid |

TABLE 5-continued

| Compound No. | Compound Name |
|---|---|
| A143 | 1-((4-chlorobenzo[b]thiophen-3-yl)methyl)-4-methyl-2-(5-(trifluoromethyl)pyridin-3-yl)-1H-imidazole-5-carboxylic acid |
| A144 | 2-(5-chloropyridin-3-yl)-4-isopropyl-1-(naphthalen-1-ylmethyl)-1H-imidazole-5-carboxylic acid |
| A145 | 2-(5-chloropyridin-3-yl)-4-cyclopropyl-1-(naphthalen-1-ylmethyl)-1H-imidazole-5-carboxylic acid |
| A146 | 2-(5-chloropyridin-3-yl)-1-(2,5-dichlorobenzyl)-4-isopropyl-1H-imidazole-5-carboxylic acid |
| A147 | 2-(5-chloropyridin-3-yl)-4-cyclopropyl-1-(2,5-dichlorobenzyl)-1H-imidazole-5-carboxylic acid |
| A148 | 4-ethyl-2-(5-fluoropyridin-3-yl)-1-(naphthalen-1-ylmethyl)-1H-imidazole-5-carboxylic acid |
| A149 | 2-(5-chloropyridin-3-yl)-4-ethyl-1-(naphthalen-1-ylmethyl)-1H-imidazole-5-carboxylic acid |
| A150 | 1-(2,5-dichlorobenzyl)-4-ethyl-2-(5-fluoropyridin-3-yl)-1H-imidazole-5-carboxylic acid |
| A151 | 2-(5-chloropyridin-3-yl)-1-(2,5-dichlorobenzyl)-4-ethyl-1H-imidazole-5-carboxylic acid |
| A152 | 2-(5-fluoropyridin-3-yl)-4-isopropyl-1-(naphthalen-1-ylmethyl)-1H-imidazole-5-carboxylic acid |
| A153 | 4-cyclopropyl-2-(5-fluoropyridin-3-yl)-1-(naphthalen-1-ylmethyl)-1H-imidazole-5-carboxylic acid |
| A154 | 1-(2,5-dichlorobenzyl)-2-(5-fluoropyridin-3-yl)-4-isopropyl-1H-imidazole-5-carboxylic acid |
| A155 | 4-cyclopropyl-1-(2,5-dichlorobenzyl)-2-(5-fluoropyridin-3-yl)-1H-imidazole-5-carboxylic acid |
| A156 | 1-(2,5-dichlorobenzyl)-4-methyl-2-(5-methylpyridin-3-yl)-1H-imidazole-5-carboxylic acid |

TABLE 6

| Compound No. | Compound Name |
|---|---|
| A157 | 1-(2,5-dichlorobenzyl)-2-(5-methoxypyridin-3-yl)-4-methyl-1H-imidazole-5-carboxylic acid |
| A158 | 2-(5-cyanopyridin-3-yl)-1-(2,5-dichlorobenzyl)-4-methyl-1H-imidazole-5-carboxylic acid |
| A159 | 1-(2,5-dichlorobenzyl)-4-methyl-2-(6-methylpyridin-3-yl)-1H-imidazole-5-carboxylic acid |
| A160 | 1-(2,5-dichlorobenzyl)-2-(2-fluoropyridin-3-yl)-4-methyl-1H-imidazole-5-carboxylic acid |
| A161 | 1-(2,5-dichlorobenzyl)-2-(6-methoxypyridin-3-yl)-4-methyl-1H-imidazole-5-carboxylic acid |
| A162 | 1-(2,5-dichlorobenzyl)-2-(2-methoxypyridin-3-yl)-4-methyl-1H-imidazole-5-carboxylic acid |
| A164 | 2-(6-chloropyridin-3-yl)-1-(2,5-dichlorobenzyl)-4-methyl-1H-imidazole-5-carboxylic acid |
| A166 | 1-(2,5-dichlorobenzyl)-4-methyl-2-(5-(pyrrolidin-1-yl)pyridin-3-yl)-1H-imidazole-5-carboxylic acid |
| A167 | 1-(2,5-dichlorobenzyl)-4-methyl-2-(5-nitropyridin-3-yl)-1H-imidazole-5-carboxylic acid |
| A168 | 2-(5-cyclopropylpyridin-3-yl)-1-(2,5-dichlorobenzyl)-4-methyl-1H-imidazole-5-carboxylic acid |
| A169 | 2-(5-chloropyridin-3-yl)-1-(2,5-dichlorobenzyl)-1H-imidazole-5-carboxylic acid |
| A170 | 1-(2,5-bis(trifluoromethyl)benzyl)-2-(5-fluoropyridin-3-yl)-4-methyl-1H-imidazole-5-carboxylic acid |
| A171 | 1-(2,5-dichlorobenzyl)-2-(5-fluoropyridin-3-yl)-1H-imidazole-5-carboxylic acid |
| A172 | 1-(2,5-dichlorobenzyl)-2-(5-hydroxypyridin-3-yl)-4-methyl-1H-imidazole-5-carboxylic acid |
| A173 | 1-(2,5-bis(trifluoromethyl)benzyl)-2-(5-chloropyridin-3-yl)-4-methyl-1H-imidazole-5-carboxylic acid |
| A174 | 1-(2,5-dichlorobenzyl)-2-(5-ethoxypyridin-3-yl)-4-methyl-1H-imidazole-5-carboxylic acid |
| A175 | 1-(2,5-dichlorobenzyl)-2-(5-isopropoxypyridin-3-yl)-4-methyl-1H-imidazole-5-carboxylic acid |
| A176 | 1-(2,5-dichlorobenzyl)-4-methyl-2-(5-phenylpyridin-3-yl)-1H-imidazole-5-carboxylic acid |
| A177 | 2-(5-bromopyridin-3-yl)-1-(2,5-dichlorobenzyl)-4-methyl-1H-imidazole-5-carboxylic acid |

TABLE 6-continued

| Compound No. | Compound Name |
|---|---|
| A178 | 1-(2,5-dimethylbenzyl)-2-(5-fluoropyridin-3-yl)-4-methyl-1H-imidazole-5-carboxylic acid |

TABLE 7

| Compound No. | Compound Name |
|---|---|
| A179 | 2-(5-chloropyridin-3-yl)-1-(2,5-dimethylbenzyl)-4-methyl-1H-imidazole-5-carboxylic acid |
| A180 | 1-(2,5-dimethylbenzyl)-4-methyl-2-(5-methylpyridin-3-yl)-1H-imidazole-5-carboxylic acid |
| A181 | 1-(2,5-dichlorobenzyl)-2-(5-ethylpyridin-3-yl)-4-methyl-1H-imidazole-5-carboxylic acid |
| A182 | 1-(2,5-dichlorobenzyl)-4-methyl-2-(5-(methylthio)pyridin-3-yl)-1H-imidazole-5-carboxylic acid |
| A183 | 2-(5-acetylpyridin-3-yl)-1-(2,5-dichlorobenzyl)-4-methyl-1H-imidazole-5-carboxylic acid |
| A185 | 1-(2,5-dichlorobenzyl)-4-methyl-2-(5-propoxypyridin-3-yl)-1H-imidazole-5-carboxylic acid |
| A188 | 1-(2,5-dichlorobenzyl)-2-(5-isobutoxypyridin-3-yl)-4-methyl-1H-imidazole-5-carboxylic acid |
| A189 | 2-(5-(cyclohexylmethoxy)pyridin-3-yl)-1-(2,5-dichlorobenzyl)-4-methyl-1H-imidazole-5-carboxylic acid |
| A190 | 2-(5-(benzyloxy)pyridin-3-yl)-1-(2,5-dichlorobenzyl)-4-methyl-1H-imidazole-5-carboxylic acid |
| A191 | 2-(5-chloropyridin-3-yl)-1-(2,5-dichlorobenzyl)-4-(hydroxymethyl)-1H-imidazole-5-carboxylic acid |
| A192 | 2-(5-chloropyridin-3-yl)-1-(2,5-dichlorobenzyl)-4-((dimethylamino)methyl)-1H-imidazole-5-carboxylic acid |
| A193 | 2-(5-chloropyridin-3-yl)-1-(2,5-dichlorobenzyl)-4-((diethylamino)methyl)-1H-imidazole-5-carboxylic acid |
| A194 | 2-(5-chloropyridin-3-yl)-1-(2,5-dichlorobenzyl)-4-(pyrrolidin-1-ylmethyl)-1H-imidazole-5-carboxylic acid |
| A195 | 2-(5-chloropyridin-3-yl)-1-(2,5-dichlorobenzyl)-4-(piperidin-1-ylmethyl)-1H-imidazole-5-carboxylic acid |
| A196 | 2-(5-chloropyridin-3-yl)-1-(2,5-dichlorobenzyl)-4-(morpholinomethyl)-1H-imidazole-5-carboxylic acid |
| A197 | 2-(5-chloropyridin-3-yl)-1-(2,5-dichlorobenzyl)-4-((4-methylpiperazine-1-yl)methyl)-1H-imidazole-5-carboxylic acid |
| A199 | 4-((1H-imidazol-1-yl)methyl)-2-(5-chloropyridin-3-yl)-1-(2,5-dichlorobenzyl)-1H-imidazole-5-carboxylic acid |
| A200 | 4-((1H-pyrazol-1-yl)methyl)-2-(5-chloropyridin-3-yl)-1-(2,5-dichlorobenzyl)-1H-imidazole-5-carboxylic acid |
| A202 | 2-(5-chloropyridin-3-yl)-1-(2,5-dichlorobenzyl)-4-((4-propylpiperazin-1-yl)methyl)-1H-imidazole-5-carboxylic acid |

TABLE 8

| Compound No. | Compound Name |
|---|---|
| A203 | 2-(5-chloropyridin-3-yl)-1-(2,5-dichlorobenzyl)-4-((4-(methylsulfonyl)piperazin-1-yl)methyl)-1H-imidazole-5-carboxylic acid |
| A204 | 2-(5-chloropyridin-3-yl)-1-(2,5-dichlorobenzyl)-4-((4-(ethylsulfonyl)piperazin-1-yl)methyl)-1H-imidazole-5-carboxylic acid |
| A205 | 2-(5-bromopyridin-3-yl)-1-(2,5-dichlorobenzyl)-1H-imidazole-5-carboxylic acid |
| A206 | 1-(2,5-dichlorobenzyl)-2-(5-methylpyridin-3-yl)-1H-imidazole-5-carboxylic acid |
| A207 | 2-(5-chloropyridin-3-yl)-1-(2,5-dichlorobenzyl)-4-(difluoromethyl)-1H-imidazole-5-carboxylic acid |
| A208 | 1-(2,5-dichlorobenzyl)-2-(5-(difluoromethyl)pyridin-3-yl)-4-methyl-1H-imidazole-5-carboxylic acid |
| A209 | 2-(5-chloropyridin-3-yl)-1-(2,5-dichlorobenzyl)-4-ethynyl-1H-imidazole-5-carboxylic acid |
| A210 | 2-(5-chloropyridin-3-yl)-1-(2,5-dichlorobenzyl)-1H-imidazole-4,5-dicarboxylic acid |

TABLE 8-continued

| Compound No. | Compound Name |
| --- | --- |
| A211 | 2-(5-chloropyridin-3-yl)-1-(2,5-dichlorobenzyl)-4-(1-hydroxyethyl)-1H-imidazole-5-carboxylic acid |
| A212 | 1-(2,5-dichlorobenzyl)-2-(5-fluoropyridin-3-yl)-4-(2-hydroxypropan-2-yl)-1H-imidazole-5-carboxylic acid |
| A213 | 2-(5-chloropyridin-3-yl)-1-(2,5-dichlorobenzyl)-4-(2-hydroxypropan-2-yl)-1H-imidazole-5-carboxylic acid |
| A214 | 1-(2,5-dichlorobenzyl)-4-(2-hydroxypropan-2-yl)-2-(5-methylpyridine-3-yl)-1H-imidazole-5-carboxylic acid |
| A215 | 1-(2,5-dichlorobenzyl)-2-(5-fluoropyridin-3-yl)-4-(3-hydroxypentan-3-yl)-1H-imidazole-5-carboxylic acid |
| A216 | 2-(5-chloropyridin-3-yl)-1-(2,5-dichlorobenzyl)-4-(3-hydroxypentane-3-yl)-1H-imidazole-5-carboxylic acid |
| A217 | 1-(2,5-dichlorobenzyl)-4-(3-hydroxypentan-3-yl)-2-(5-methylpyridin-3-yl)-1H-imidazole-5-carboxylic acid |
| A218 | 4-acetyl-2-(5-chloropyridin-3-yl)-1-(2,5-dichlorobenzyl)-1H-imidazole-5-carboxylic acid |
| A219 | 4-chloro-1-(2,5-dichlorobenzyl)-2-(5-methylpyridin-3-yl)-1H-imidazole-5-carboxylic acid |

TABLE 9

| | |
| --- | --- |
| A220 | 4-chloro-2-(5-chloropyridine-3-yl)-1-(2,5-dichlorobenzyl)-1H-imidazole-5-carboxylic acid |
| A221 | 2-(5-chloropyridin-3-yl)-1-(2,5-dichlorobenzyl)-1H-furo[3,4-d]imidazole-6(4H)-one |
| A223 | 2-(5-chloropyridin-3-yl)-1-(1-(2,5-dichlorophenyl)ethyl)-4-methyl-1H-imidazole-5-carboxylic acid |
| A225 | 1-((2,5-dichlorothiophen-3-yl)methyl)-2-(5-fluoropyridin-3-yl)-4-methyl-1H-imidazole-5-carboxylic acid |
| A226 | 2-(5-chloropyridin-3-yl)-1-((2,5-dichlorothiophen-3-yl)-4-methyl-1H-imidazole-5-carboxylic acid |
| A227 | 1-((2,5-dichlorothiophen-3-yl)methyl)-4-methyl-2-(5-methylpyridin-3-yl)-1H-imidazole-5-carboxylic acid |
| A228 | 1-((2,4-dichlorothiophen-5-yl)methyl)-2-(5-fluoropyridin-3-yl)-4-methyl-1H-imidazole-5-carboxylic acid |
| A229 | 2-(5-chloropyridin-3-yl)-1-((2,4-dichlorothiophen-5-yl)methyl)-4-methyl-1H-imidazole-5-carboxylic acid |
| A230 | 1-((2,4-dichlorothiophen-5-yl)methyl)-4-methyl-2-(5-methylpyridin-3-yl)-1H-imidazole-5-carboxylic acid |
| A231 | 1-(2-chloro-5-methylbenzyl)-4-methyl-2-(5-methylpyridin-3-yl)-1H-imidazole-5-carboxylic acid |
| A232 | 1-(2-chloro-5-methylbenzyl)-2-(5-chloropyridin-3-yl)-4-methyl-1H-imidazole-5-carboxylic acid |
| A233 | 1-(benzo[b]thiophen-7-ylmethyl)-2-(5-chloropyridin-3-yl)-4-methyl-1H-imidazole-5-carboxylic acid |
| A234 | 1-(benzo[b]thiophen-7-ylmethyl)-2-(5-fluoropyridin-3-yl)-4-methyl-1H-imidazole-5-carboxylic acid |
| A235 | 1-(benzo[b]thiophen-7-ylmethyl)-2-(5-chloropyridin-3-yl)-4-isopropyl-1H-imidazole-5-carboxylic acid |
| A236 | 1-(benzo[b]thiophen-7-ylmethyl)-2-(5-chloropyridin-3-yl)-4-cyclopropyl-1H-imidazole-5-carboxylic acid |
| A237 | 3-chloro-5-(1-(2,5-dichlorobenzyl)-5-(1H-tetrazol-5-yl)-1H-imidazol-2-yl)pyridine |
| A238 | 1-(2,5-dimethylbenzyl)-4-methyl-2-(pyridin-4-yl)-1H-imidazole-5-carboxylic acid |
| A240 | 2-(6-methoxypyridin-2-yl)-4-methyl-1-(naphthalen-1-ylmethyl)-1H-imidazole-5-carboxylic acid |
| A244 | 1-(2,5-dichlorobenzyl)-4-methyl-2-(pyridin-4-yl)-1H-imidazole-5-carboxylic acid |
| A245 | 1-(2,5-dichlorobenzyl)-4-methyl-2-(pyridin-2-yl)-1H-imidazole-5-carboxylic acid |
| A246 | 1-(2,5-dichlorobenzyl)-2-(6-methoxypyridin-2-yl)-4-methyl-1H-imidazole-5-carboxylic acid |
| A247 | 1-(2,5-dichlorobenzyl)-4-methyl-2-(pyridin-2-yloxy)-1H-imidazole-5-carboxylic acid |

TABLE 10

| | |
| --- | --- |
| A248 | 1-(2,5-dichlorobenzyl)-4-methyl-2-(pyridin-3-yloxy)-1H-imidazole-5-carboxylic acid |
| A250 | 2-((5-chloropyridin-3-yl)oxy)-1-(2,5-dichlorobenzyl)-4-methyl-1H-imidazole-5-carboxylic acid |

TABLE 10-continued

| | |
|---|---|
| A251 | 2-((5-bromopyridin-3-yl)oxy)-1-(2,5-dichlorobenzyl)-4-methyl-1H-imidazole-5-carboxylic acid |
| A252 | 1-(2,5-dichlorobenzyl)-4-methyl-2-((2-methylpyridin-3-yl)oxy)-1H-imidazole-5-carboxylic acid |
| A253 | 2-((2-chloropyridin-3-yl)oxy)-1-(2,5-dichlorobenzyl)-4-methyl-1H-imidazole-5-carboxylic acid |
| A254 | 2-((2-bromopyridin-3-yl)oxy)-1-(2,5-dichlorobenzyl)-4-methyl-1H-imidazole-5-carboxylic acid |
| A255 | 1-(2,5-dichlorobenzyl)-4-methyl-2-((5-methylpyridin-3-yl)oxy)-1H-imidazole-5-carboxylic acid |
| A256 | 1-(2,5-dichlorobenzyl)-4-methyl-2-((4-methylpyridin-3-yl)oxy)-1H-imidazole-5-carboxylic acid |
| A257 | 2-((4-chloropyridin-3-yl)oxy)-1-(2,5-dichlorobenzyl)-4-methyl-1H-imidazole-5-carboxylic acid |
| A258 | 2-((4-bromopyridin-3-yl)oxy)-1-(2,5-dichlorobenzyl)-4-methyl-1H-imidazole-5-carboxylic acid |
| A262 | 2-((2-(5-chloropyridin-3-yl)-1-(2,5-dichlorobenzyl)-1H-imidazol-5-yl)thio)-2-methylpropanoic acid |
| A263 | 1-((2-(5-chloropyridin-3-yl)-1-(2,5-dichlorobenzyl)-1H-imidazol-5-yl)thio)cyclobutanecarboxylic acid |
| A266 | 2-((5-(5-chloropyridin-3-yl)-1-(2,5-dichlorobenzyl)-1H-imidazol-2-yl)thio)-2-methylpropanoic acid |
| B1 | 1-(naphthalen-1-ylmethyl)-2-(pyridin-3-yl)-1H-pyrrole-5-carboxylic acid |
| B2 | 1-((4-methylnaphthalen-1-yl)methyl)-2-(pyridin-3-yl)-1H-pyrrole-5-carboxylic acid |
| B3 | 1-((4-bromobenzo[b]thiophen-3-yl)methyl)-2-(pyridin-3-yl)-1H-pyrrole-5-carboxylic acid |
| B4 | 1-((2-methylnaphthalen-1-yl)methyl)-2-(pyridin-3-yl)-1H-pyrrole-5-carboxylic acid |
| B6 | 1-((8-bromonaphthalen-1-yl)methyl)-2-(pyridin-3-yl)-1H-pyrrole-5-carboxylic acid |
| B7 | 1-((4-methylbenzo[b]thiophen-3-yl)methyl)-2-(pyridin-3-yl)-1H-pyrrole-5-carboxylic acid |
| B8 | 1-(benzo[b]thiophen-3-ylmethyl)-2-(pyridin-3-yl)-1H-pyrrole-5-carboxylic acid |
| B9 | 2-(pyridin-3-yl)-1-((4-(trifluoromethyl)benzo[b]thiophen-3-yl)methyl)-1H-pyrrole-5-carboxylic acid |

TABLE 11

| Compound No. | Compound Name |
|---|---|
| B10 | 1-((4-chlorobenzo[b]thiophen-3-yl)methyl)-2-(pyridin-3-yl)-1H-pyrrole-5-carboxylic acid |
| B11 | 1-(2,5-dichlorobenzyl)-2-(pyridin-3-yl)-1H-pyrrole-5-carboxylic acid |
| B12 | 1-(2,5-dimethylbenzyl)-2-(pyridin-3-yl)-1H-pyrrole-5-carboxylic acid |
| B13 | 1-(2,5-dichlorobenzyl)-2-(5-methylpyridin-3-yl)-1H-pyrrole-5-carboxylic acid |
| B14 | 1-(2,5-dichlorobenzyl)-2-(5-fluoropyridin-3-yl)-1H-pyrrole-5-carboxylic acid |
| B15 | 1-((4-chlorobenzo[b]thiophen-3-yl)methyl)-2-(5-methylpyridin-3-yl)-1H-pyrrole-5-carboxylic acid |
| B16 | 1-((4-chlorobenzo[b]thiophen-3-yl)methyl)-2-(5-fluoropyridin-3-yl)-1H-pyrrole-5-carboxylic acid |
| B17 | 2-(5-chloropyridin-3-yl)-1-(2,5-dichlorobenzyl)-1H-pyrrole-5-carboxylic acid |
| B18 | 1-((4-chlorobenzo[b]thiophen-3-yl)methyl)-2-(5-chloropyridin-3-yl)-1H-pyrrole-5-carboxylic acid |
| B19 | 2-(pyridin-3-yl)-1-(quinolin-8-ylmethyl)-1H-pyrrole-5-carboxylic acid |
| B20 | 1-(benzo[b]thiophen-7-ylmethyl)-2-(pyridin-3-yl)-1H-pyrrole-5-carboxylic acid |
| B21 | 1-(benzo[b]thiophen-7-ylmethyl)-2-(5-methylpyridin-3-yl)-1H-pyrrole-5-carboxylic acid |
| B22 | 1-(benzo[b]thiophen-7-ylmethyl)-2-(5-fluoropyridin-3-yl)-1H-pyrrole-5-carboxylic acid |
| B23 | 1-(benzo[b]thiophen-7-ylmethyl)-2-(5-chloropyridin-3-yl)-1H-pyrrole-5-carboxylic acid |
| B24 | N-(methylsulfonyl)-1-(naphthalen-1-ylmethyl)-2-(pyridin-3-yl)-1H-pyrrole-5-carboxamide |
| B25 | N-(cyclopropylsulfonyl)-1-(naphthalen-1-ylmethyl)-2-(pyridin-3-yl)-1H-pyrrole-5-carboxamide |
| B26 | 1-(2,5-dichlorobenzyl)-2-(5-fluoropyridin-3-yl)-N-(methylsulfonyl)-1H-pyrrole-5-carboxamide |
| B27 | N-(cyclopropylsulfonyl)-1-(2,5-dichlorobenzyl)-2-(5-fluoropyridin-3-yl)-1H-pyrrole-5-carboxamide |

TABLE 11-continued

| Compound No. | Compound Name |
|---|---|
| B28 | 1-(2,5-dichlorobenzyl)-N-(methylsulfonyl)-2-(pyridin-3-yl)-1H-pyrrole-5-carboxamide |
| B29 | 2-(5-chloropyridin-3-yl)-1-(2,5-dichlorobenzyl)-N-(methylsulfonyl)-1H-pyrrole-5-carboxamide |

TABLE 12

| Compound No. | Compound Name |
|---|---|
| B30 | 2-(5-chloropyridin-3-yl)-N-(cyclopropylsulfonyl)-1-(2,5-dichlorobenzyl)-1H-pyrrole-5-carboxamide |
| B31 | N-(cyclopropylsulfonyl)-1-(2,5-dichlorobenzyl)-2-(pyridin-3-yl)-1H-pyrrole-5-carboxamide |
| B32 | N-(cyclopropylsulfonyl)-1-(2,5-dichlorobenzyl)-2-(5-methylpyridin-3-yl)-1H-pyrrole-5-carboxamide |
| B33 | (E)-3-(1-(naphthalen-1-ylmethyl)-2-(pyridin-3-yl)-1H-pyrrole-5-yl) acrylic acid |
| B34 | (E)-3-(1-(2,5-dichlorobenzyl)-2-(5-methylpyridin-3-yl)-1H-pyrrol-5-yl) acrylic acid |
| B35 | (E)-3-(1-(2,5-dichlorobenzyl)-2-(5-fluoropyridin-3-yl)-1H-pyrrol-5-yl) acrylic acid |

More preferred are the compounds of A1, A2, A7, A13, A14, A15, A18, A19, A25, A26, A37, A38, A39, A43, A45, A71, A78, A81, A85, A86, A88, A89, A90, A91, A92, A93, A96, A98, A99, A100, A101, A104, A105, A108, A119, A121, A134, A135, A136, A137, A139, A140, A142, A143, A144, A145, A146, A147, A149, A150, A151, A154, A155, A156, A157, A166, A167, A168, A169, A171, A173, A174, A176, A177, A179, A180, A181, A182, A183, A185, A188, A191, A193, A194, A195, A196, A197, A200, A202, A204, A205, A206, A207, A208, A209, A210, A211, A212, A213, A214, A215, A216, A217, A218, A219, A220, A221, A225, A226, A227, A231, A232, A233, A235, A236, A237, A245, A248, A250, A251, A252, A253, A254, A255, A256, A257, A258, B1, B2, B3, B6, B7, B8, B9, B10, B11, B12, B13, B14, B15, B16, B17, B18, B20, B21, B22, B23, B24, B25, B26, B27, B28, B29, B30, B31, B32, B33, B34, and B35. Even more preferred are A1, A2, A7, A13, A14, A15, A19, A26, A81, A119, A121, A134, A135, A137, A139, A147, A156, A169, A233, B1, and B11.

The pyridine derivative represented by the above formula (I) can be converted into its prodrugs by conventional means. A prodrug refers to a compound that is converted into a pyridine derivative represented by the formula (I) in the body by enzymes, gastric acids, etc. Prodrugs for the pyridine derivative represented by the formula (I) include compounds in which the carboxyl group in the pyridine derivative has been esterified or amidated (such as those in which the carboxyl group has been $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, or methylamidated), compounds in which the hydroxyl group in the pyridine derivative has been acylated, alkylated, phosphorylated, or borated (such as those in which the hydroxyl group has been acetylated, palmitoylated, propanoylated, pivaloylated, succinylated, fumarylated, alanylated, dimethylaminomethylcarbonylated, or tetrahydropyranylated), or compounds in which the amino group in the pyridine derivative has been acylated, alkylated, or phosphorylated (such as those in which the amino group has been eicosanoylated, alanylated, pentylaminocarbonylated, (5-methyl-2-oxo-1,3-dioxolen-4-yl) methoxycarbonylated, tetrahydrofuranylated, tetrahydropyranylated, pyrrolidylmethylated, pivaloyloxymethylated, or tert-butylated). In addition, prodrugs for the pyridine derivative represented by the formula (I) may be compounds which are converted into a pyridine derivative represented by the formula (I) under physiological conditions, such as those described on pages 163 to 198 of "Iyakuhin no Kaihatsu [Development of Pharmaceuticals]," volume 7, Bunshi Sekkei [Molecular Design], published in 1990 by Hirokawa Shoten. Note that, among the pyridine derivatives represented by the formula (I), a compound in which $R_3$ and/or $R_4$ is —$CO_2R_5$ or a compound in which $R_3$ and $R_4$ are fused to form a lactone ring can also be a prodrug which yields in the body a compound in which $R_3$ and/or $R_4$ is a carboxylic acid or a compound in which $R_3$ is an alkyl group substituted with a hydroxyl group and $R_4$ is a carboxyl group. Such pyridine derivatives represented by the formula (I) that can also be a prodrug include A3, A221, A267, A268, A269, A270, A271, A272, A273, A274, A275, A276, A277, A278, A279, A280, A281, and A282.

If necessary, the pyridine derivative represented by formula (I), or a prodrug thereof, of the present invention can be converted into its pharmaceutically acceptable salts. Such salts include, for example, salts with inorganic acids, such as hydrochloric acid, hydrobromic acid, hydriodic acid, sulfuric acid, nitric acid, phosphoric acid, and carbonic acid; salts with organic acids, such as formic acid, acetic acid, propionic acid, trifluoroacetic acid, phthalic acid, oxalic acid, malonic acid, succinic acid, fumaric acid, maleic acid, lactic acid, malic acid, tartaric acid, citric acid, benzoic acid, methanesulfonic acid, ethanesulfonic acid, benzenesulfonic acid, and p-toluenesulfonic acid; salts with amino acids, such as lysine, arginine, ornithine, glutamic acid, and aspartic acid; salts with alkali metals, such as sodium, potassium, and lithium; salts with alkaline-earth metals, such as calcium and magnesium; salts with metals, such as aluminium, zinc, and iron; salts with organic bases, such as methylamine, ethylamine, diethylamine, trimethylamine, triethylamine, ethylenediamine, piperidine, piperazine, pyridine, picoline, ethanolamine, diethanolamine, triethanolamine, cyclohexylamine, dicyclohexylamine, N-methyl glucamine, and N,N-dibenzylethylenediamine; ammonium salts, and the like.

If necessary, the pyridine derivative represented by the above formula (I), or a prodrug thereof, or a pharmaceutically acceptable salt thereof, can be converted into its solvates. Such solvents can include water, methanol, ethanol, 1-propanol, 2-propanol, butanol, t-butanol, acetonitrile, acetone, methyl ethyl ketone, chloroform, ethyl acetate, diethyl ether, t-butyl methyl ether, benzene, toluene, DMF, DMSO, etc. Particularly, water, methanol, ethanol, 1-propanol, 2-propanol, acetonitrile, acetone, methyl ethyl ketone, and ethyl acetate can be mentioned as being preferred.

Although synthesis of the pyridine derivatives represented by the above formula (I) may be carried out by any method, the present derivatives can be synthesized as shown in Scheme A below when A is a single bond; $R_1$ is a nitrogen atom; $R_3$ is an alkyl group having 1 to 6 carbon atoms or a trifluoromethyl group; and $R_4$ is a carboxyl group, $-CO_2R_5$, or $-CONHSO_2R_5$. That is, after the imidazole derivative (IV) is brominated to give the compound (V), N-alkylation is carried out by a reaction using a base and a halide compound, or by a Mitsunobu reaction using an alcohol, to give the compound (II-1). The compound (I-1) is obtained by a Suzuki coupling reaction of the compound (II-1) and a boronate derivative. The compound (I-2) can be obtained by hydrolyzing the ester group. Furthermore, if necessary, the acylsulfonamide (I-3) can also be obtained by carrying out a condensation reaction with an alkylsulfonamide.

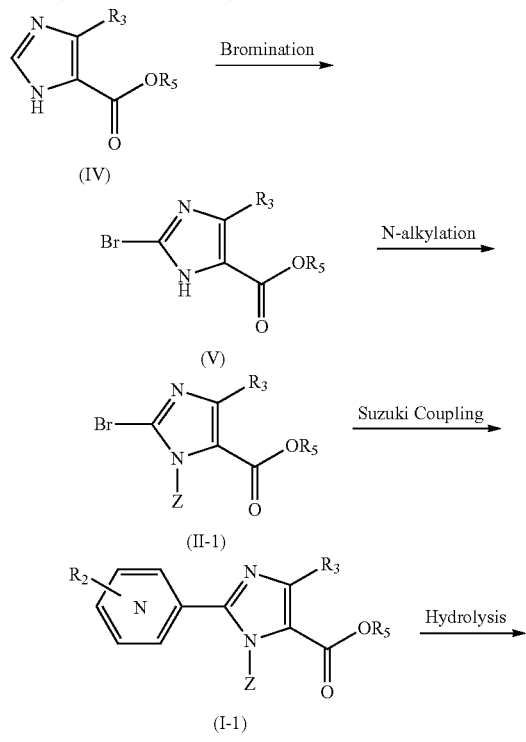

Scheme A

Suitable reagents for the bromination of the compound (IV) to (V) in Scheme A can include bromine, N-bromosuccinimide (NBS), etc. Solvents in this reaction include, but are not particularly limited to, for example, ethers such as tetrahydrofuran (THF), 1,4-dioxane, 1,2-dimethoxyethane, or 1,2-diethoxyethane, halogenated solvents such as dichloromethane or carbon tetrachloride, acetonitrile, mixed solvents thereof, or the like. This reaction proceeds at 0° C. to 100° C., but it is preferably carried out at room temperature to 50° C.

The N-alkylation of the compound (V) to the compound (II-1) proceeds in a reaction using a base and a halide compound, or by a Mitsunobu reaction using an alcohol. When a base and a halide compound are used, the base can include potassium carbonate, cesium carbonate, triethylamine, diisopropylethylamine, sodium hydride, etc., among which the preferred base is potassium carbonate, cesium carbonate, triethylamine, or diisopropylethylamine. The halide compound includes chloride, bromide, or iodide, among which the preferred halide compound is a chloride or bromide. The temperature for the reaction in the presence of a base and a halide compound is preferably from room temperature to 150° C., and more preferably from 50° C. to 120° C. Solvents in this reaction include, but are not particularly limited to, for example, ethers such as tetrahydrofuran (THF), 1,4-dioxane, 1,2-dimethoxyethane, or 1,2-diethoxyethane, amides such as dimethylformamide or N-methylpyrrolidone, dimethyl sulfoxide (DMSO), toluene, xylene, mixed solvents thereof, or the like. The N-alkylation of the compound (V) to the compound (II-1) also proceeds by a Mitsunobu reaction with an alcohol. As for conditions for the Mitsunobu reaction, a phosphine compound, a condensation agent, an alcohol, and the compound (V) react in an inert solvent to give the compound (II-1). The phosphine includes tributylphosphine, triphenylphosphine, tricyclohexylphosphine, etc., but preferably triphenylphosphine. A preferred condensation agent is diethyl azodicarboxylate (DEAD) or diisopropyl azodicarboxylate (DIAD). The reaction temperature for this Mitsunobu reaction may be anywhere from 0° C. to 100° C., but the preferred reaction temperature is from room temperature to 80° C. The solvent in the Mitsunobu reaction includes, but is not particularly limited to, for example, ethers such as tetrahydrofuran (THF), 1,4-dioxane, 1,2-dimethoxyethane, or 1,2-diethoxyethane, amides such as dimethylformamide or N-methylpyrrolidone, halogenated solvents such as dichloromethane, toluene, xylene, mixed solvents thereof, or the like.

The Suzuki coupling reaction of the compound (II-1) to the compound (I-1) proceeds by heating the compound (II-1), a boronate derivative, a palladium catalyst, and a base in a reaction-inert solvent. Preferably, this reaction is carried out under an inert gas atmosphere. Preferred examples of the boronate derivative can include boronic acid and boronic acid pinacol ester. As the palladium catalyst, [1,1'-bis(diphenylphosphino)ferrocene]dichloropalladium (II) (PdCl$_2$(dppf)), tetrakis(triphenylphosphine)palladium (Pd(PPh$_3$)$_4$), or the like is preferably used. As the base, potassium carbonate, cesium carbonate, or potassium phosphate can be mentioned as being preferred. Although the solvent in this reaction is not particularly limited, it is preferable to use, for example, ethers such as tetrahydrofuran (THF), 1,4-dioxane, 1,2-dimethoxyethane, or 1,2-diethoxyethane, amides such as dimethylformamide or N-methylpyrrolidone, alcohols such as ethanol, 2-propanol, or butanol, toluene, xylene, water, or mixed solvents thereof. This reaction proceeds at 50° C. to 150° C., but it is preferably carried out at 80° C. to 120° C.

The hydrolysis reaction of the compound (I-1) to the compound (I-2) proceeds by reacting the compound (I-1) with an equivalent or a slight excess of a base in a mixed solvent of a reaction-inert solvent and water. Preferred bases can include sodium hydroxide, potassium hydroxide, or lithium hydroxide. Although the solvent is not particularly limited, it is preferable to use, for example, a mixed solvent of an organic solvent, such as tetrahydrofuran (THF) or alcohol (such as methanol or ethanol), and water for the reaction. This reaction proceeds at 0° C. to 100° C., but it is preferably carried out at room temperature to 60° C.

The condensation reaction of the compound (I-2) to the compound (I-3) proceeds by reacting the compound (I-2) with an alkylsulfonamide in the presence of a base and a condensation agent in an inert solvent. The solvent includes, for example, ethers such as tetrahydrofuran (THF), 1,4-dioxane, 1,2-dimethoxyethane, or 1,2-diethoxyethane, halogenated solvents such as dichloromethane or carbon tetrachloride, acetonitrile, mixed solvents thereof, or the like. The preferred solvent is tetrahydrofuran (THF), dimethylformamide, or dichloromethane. The base can include potassium carbonate, cesium carbonate, triethylamine, diisopropylethylamine, sodium hydride, etc., but the preferred base is triethylamine or diisopropylethylamine. The condensation agent includes dicyclohexylcarbodiimide (DCC), diphenylphosphoryl azide (DPPA), 1-ethyl-3-(3-dimethylaminopropyl)carbodiimide hydrochloride (EDCI or WSC), O-(7-azabenzotriazol-1-yl)-N,N,N',N'-tetramethyluronium hexafluorophosphate (HATU), O-(7-azabenzotriazol-1-yl)-N,N,N',N'-tetramethyluronium tetrafluoroborate (TATU), etc., but preferably WSC. The reaction temperature may be anywhere from 0° C. to 100° C., but the preferred reaction temperature is from room temperature to 50° C.

Note that the compound of the formula (II) discussed above can be used as the compound (II-1) in Scheme A above.

The present derivatives can also be synthesized according to Scheme B below, for example, when A is a single bond, R$_1$ is a nitrogen atom, R$_3$ is an alkyl group having 1 to 6 carbon atoms, and R$_4$ is a carboxyl group, —CO$_2$R$_5$, or —CONHSO$_2$R$_5$. That is, after the compound (VIII) is obtained by an imidazole ring-forming reaction using the compound (VI) and the compound (VII), N-alkylation is carried out by a reaction using a base and a halide compound, or by a Mitsunobu reaction using an alcohol, to give the compound (I-1). As in Scheme A, the compound (I-2) can be obtained by hydrolyzing the ester group. Furthermore, if necessary, the acylsulfonamide compound (I-3) can also be obtained by carrying out condensation with an alkylsulfonamide.

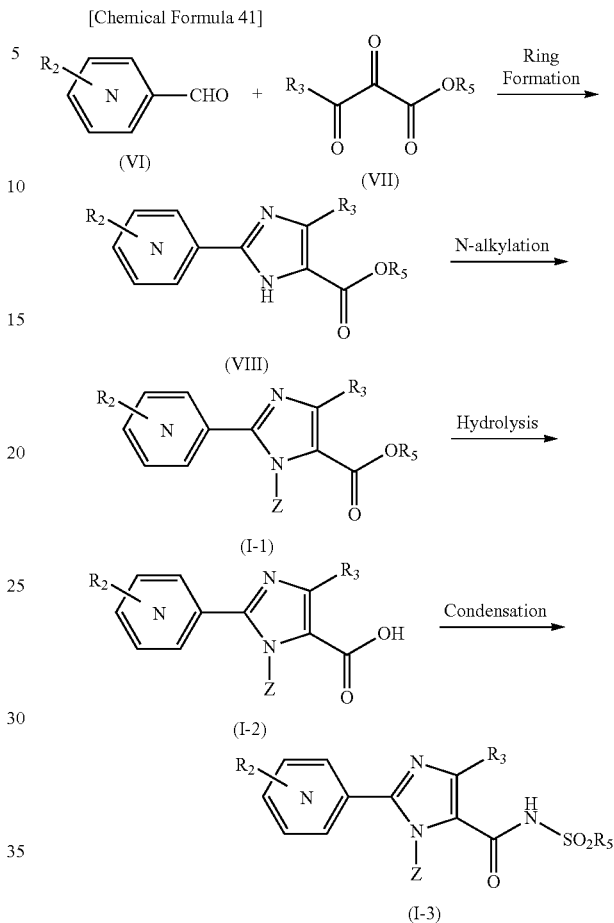

Scheme B

[Chemical Formula 41]

Here, the imidazole ring-forming reaction using the compound (VI) and the compound (VII) proceeds, for example, by heating the compound (VI) and the compound (VII) in a mixed solvent of toluene and water in the presence of 2 or more equivalents, preferably 10 or more equivalents, of ammonium acetate. The reaction temperature for this reaction is preferably from room temperature to 150° C., and more preferably from 50° C. to 120° C. Preferably, the N-alkylation reaction of the compound (VIII) to the compound (I-1), the hydrolysis reaction of the compound (I-1) to the compound (I-2), and the condensation reaction of the compound (I-2) to the compound (I-3) are carried out under the conditions described in Scheme A.

The present derivatives can be synthesized according to Scheme C below when A is a single bond, R$_1$ is a nitrogen atom, R$_3$ is a hydrogen atom or an alkyl group having 1 to 6 carbon atoms, and R$_4$ is a carboxyl group or —CO$_2$R$_5$. That is, after the compound (III-1) is obtained by an N-alkylation reaction of the imidazole derivative (IV), the compound (II-1) is obtained by bromination. As in Scheme A, Suzuki coupling of the compound (II-1) and a boronate derivative is carried out to give the compound (I-1). Furthermore, the compound (I-2) can be obtained by hydrolyzing the ester group. In addition, as an alternative route when R$_3$ is a hydrogen atom, the compound (I-1) can also be obtained by an N-alkylation reaction of the easily synthesizable compound (IX) to give the compound (X), followed by a bromination reaction to give the compound (XI), and further followed by a CO-insertion reaction in an alcohol using palladium.

[Chemical Formula 42]
Scheme C
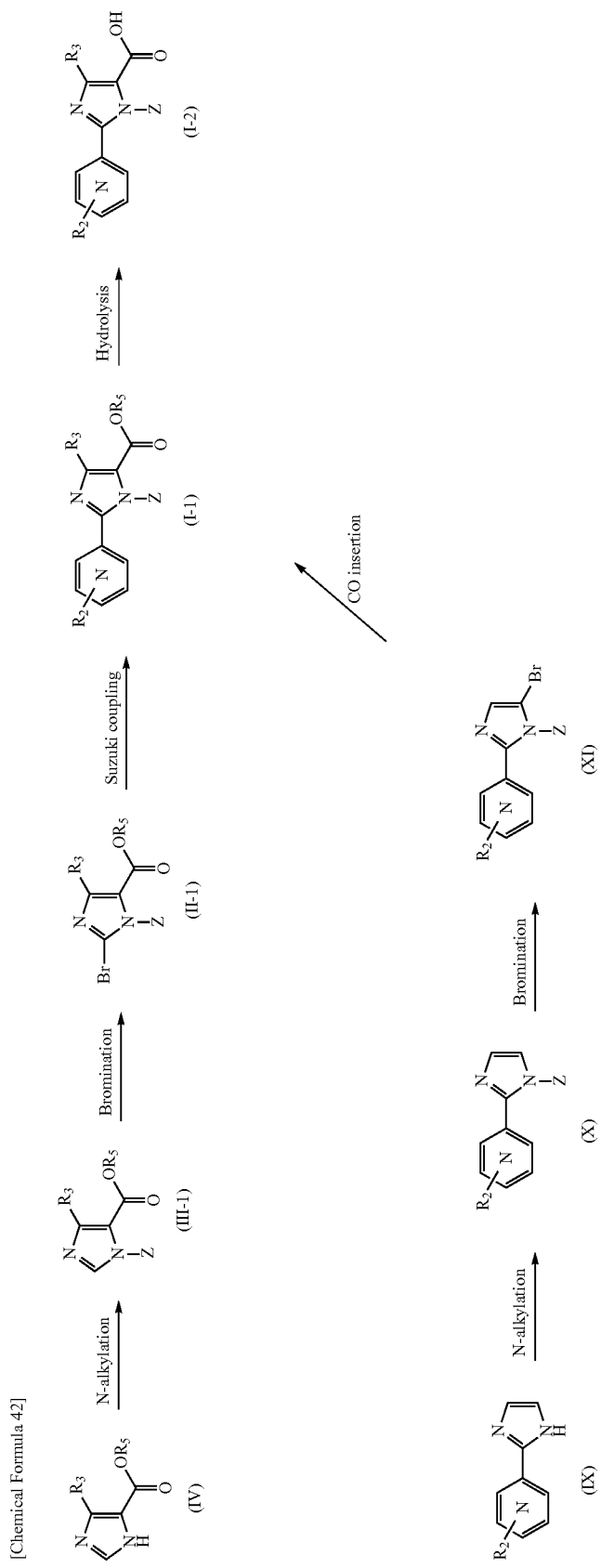

For the N-alkylation reaction of the compound (IV) to the compound (III-1) in Scheme C, the conditions described in Scheme A are preferred. For the bromination of the compound (III-1) to the compound (II-1), the conditions described in Scheme A are preferred, and the conditions of further adding a catalytic amount of 2,2'-azobis(isobutyronitrile) (AIBN) are more preferred. Preferably, the Suzuki coupling reaction of the compound (II-1) to the compound (I-1) and the subsequent hydrolysis reaction are carried out under the conditions described in Scheme A. The N-alkylation reaction of the compound (IX) to the compound (X) and the bromination of the compound (X) to the compound (XI) are preferably carried out under the conditions described in Scheme A. The CO-insertion reaction of the compound (XI) to the compound (I-1) proceeds by using a palladium catalyst, a base, and the compound (XI) in an alcohol solvent under a CO atmosphere. As the alcohol solvent, methanol or ethanol is preferred. As the palladium catalyst, [1,1'-bis(diphenylphosphino)ferrocene]dichloropalladium (II) (PdCl$_2$(dppf)), tetrakis(triphenylphosphine)palladium (Pd(PPh$_3$)$_4$), etc. is preferred. The base is preferably triethylamine or diisopropylethylamine. The reaction temperature for this reaction is preferably from room temperature to 150° C., and more preferably from 50° C. to 90° C.

Note that the compound of the formula (II) discussed above can be used as the compound (II-1) in Scheme C above, and the compound of the formula (III) discussed above can be used as the compound (III-1) in Scheme C above.

The present derivative can be synthesized according to Scheme D below when A is a single bond, R$_1$ is a nitrogen atom, R$_3$ is a chlorine atom, and R$_4$ is a carboxyl group. That is, the amidine hydrochloride (XII) and dihydroxyacetone dimer are used to form an imidazole ring to obtain the alcohol compound (XIII). After the compound (XIV) is obtained by chlorination, the aldehyde compound (XV) is obtained by oxidation. The compound (I-4) can be obtained by N-alkylation to give the compound (XVI), followed by, further oxidation. In addition, as an alternative route, the compound (I-4) can also be obtained by chlorination of the compound (I-5) which corresponds to the compound (I-1) in Scheme C above wherein R$_3$ is a hydrogen atom to give the compound (I-6), followed by hydrolysis.

The imidazole ring-forming reaction of the compound (XII) to the compound (XIII), is preferably carried out under the conditions where ammonium chloride and dihydroxyacetone dimer are used in aqueous ammonia. This reaction proceeds at 50° C. to 100° C., but it is preferably carried out at 80 to 100° C. Chlorinating agents for the compound (XIII) can include N-chlorosuccinimide (NCS), chlorine, etc., but preferably N-chlorosuccinimide (NCS). This reaction proceeds at room temperature to 50° C., but it is more preferable to perform the reaction at room temperature in order to reduce side reactions. The oxidation of the compound (XIV) to the compound (XV) is preferably carried out using manganese dioxide, and the reaction solvent is preferably a halogenated solvent such as dichloromethane. The N-alkylation of the compound (XV) to the compound (XVI) is preferably carried out under the conditions described in Scheme A. For the oxidation reaction of the compound (XVI) to the compound (I-4), the Pinnick reaction is widely known, and the conditions of using sodium chlorite and sodium dihydrogenphosphate in the presence of 2-methyl-2-butene are preferred. As the reaction solvent, it is preferable to use a mixed solvent of tetrahydrofuran (THF), or an alcohol such as t-butanol or propanol, and water. The reaction temperature is preferably from room temperature to 50° C. As for the chlorination of the compound (I-5) to the compound (I-6), it is preferable to perform the reaction using Scheme D

[Chemical Formula 43]

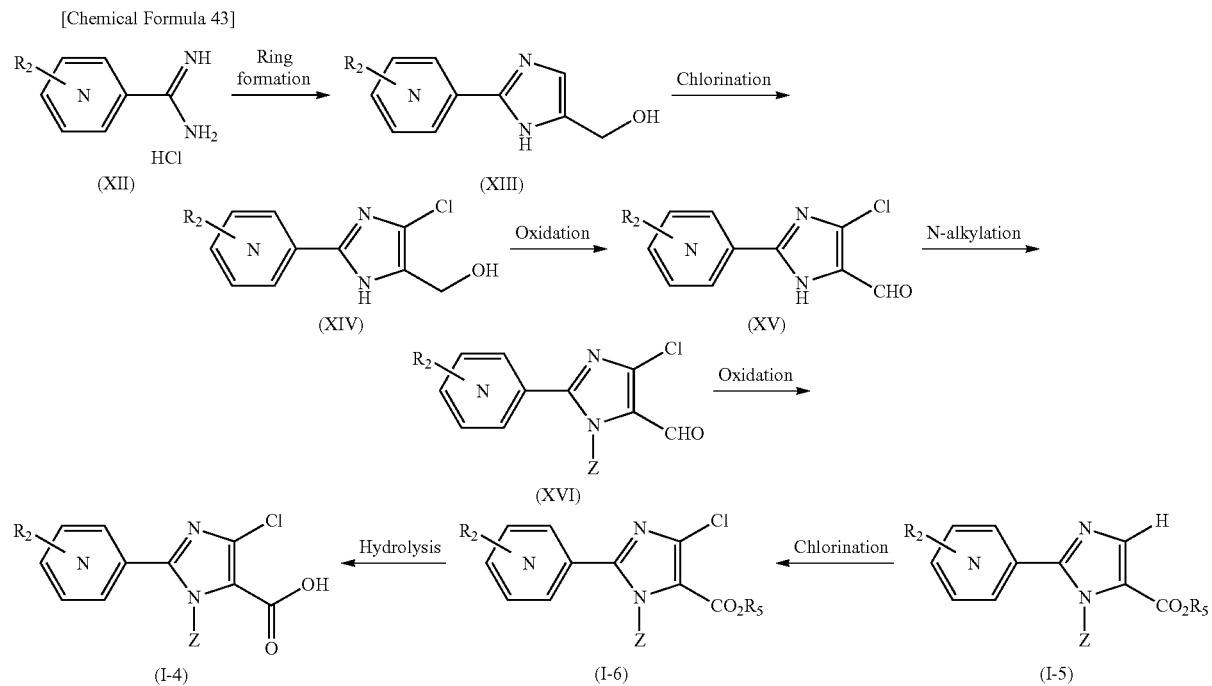

N-chlorosuccinimide (NCS) in acetonitrile. This reaction proceeds at room temperature to 100° C., but it is preferably carried out at 50° C. to 80° C. The hydrolysis of the compound (I-6) to the compound (I-4) is preferably carried out under the conditions described in Scheme A.

The present derivatives can be synthesized according to Scheme E below when A is a single bond, $R_1$ is a nitrogen atom, $R_3$ is an alkyl group having 1 to 6 carbon atoms (which may optionally be substituted with one or more of a hydroxyl group, an amino group, a dialkylamino group having 1 to 6 carbon atoms which may optionally form a ring, an imidazole ring, a pyrazole ring, a pyrrolidine ring, a piperidine ring, a morpholine ring, and piperazine ring (which may optionally be substituted with one or more of an alkyl group having 1 to 6 carbon atoms and an alkylsulfonyl group having 1 to 6 carbon atoms)), an acetyl group, a difluoromethyl group, or an ethynyl group, and $R_4$ is a carboxyl group. That is, the diester compound (XVII) is converted into the compound (XVIII) by a bromination reaction and then into the compound (II-2) by an N-alkylation reaction. After the compound (I-7) is subsequently obtained by a Suzuki coupling reaction, the hydroxymethyl compound (I-8), reduced only at the 4-position, is obtained by a selective reduction reaction using diisobutylaluminum hydride (DIBAL-H). The compound (I-2) can be synthesized by converting the hydroxymethyl moiety into various $R_3$ moieties through various common conversion reactions in organic synthesis, finally followed by a hydrolysis reaction.

Scheme E

[Chemical Formula 44]

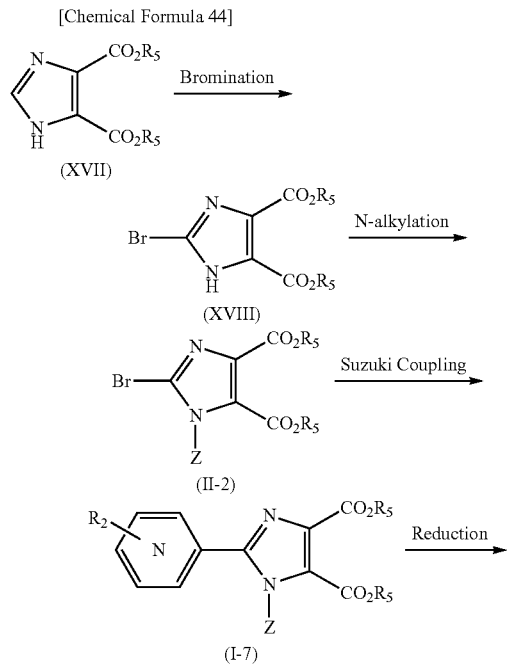

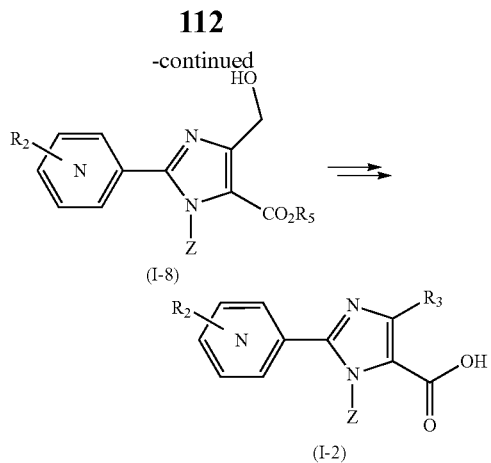

In Scheme E, the bromination of the compound (XVII) to the compound (XVIII), the N-alkylation reaction of the compound (XVIII) to the compound (II-2), and the Suzuki coupling reaction of the compound (II-2) to the compound (I-7) are preferably carried out under the conditions described in Scheme A. As for the reduction reaction of the compound (I-7) to the compound (I-8), it is preferable to carry out a reduction reaction in tetrahydrofuran (THF) solvent using diisobutylaluminum hydride (DIBAL-H). This reaction proceeds at −50° C. to 50° C., but it is preferably carried out at −40° C. to room temperature. As for the conversion of the hydroxymethyl moiety of the compound (I-8), further conversion into various $R_3$ moieties is made possible by converting the alcohol moiety into an aldehyde through oxidation with manganese dioxide, or by converting the alcohol moiety into a bromo group using tribromophosphine, followed by further transformations of these aldehyde and bromo group into $R_3$ moieties. The hydrolysis is preferably carried out under the conditions described in Scheme A.

Note that the compound of the formula (II) discussed above can be used as the compound (II-2) in Scheme E above.

The present derivatives can be synthesized according to Scheme F below when A is a single bond, $R_1$ is a nitrogen atom, $R_3$ is an iodine atom, a phenyl group, a pyridyl group, a phenoxy group, a cyano group, an alkoxy group having 1 to 6 carbon atoms, or an alkenyl group having 2 to 6 carbon atoms, and $R_4$ is a carboxyl group. That is, the compound (X) obtained in Scheme (C) is iodinated to give the compound (XIX), followed by selective formylation to give the compound (XX). After the compound (XXI) is subsequently obtained by Suzuki coupling, cyanation, or etherification through the introduction of alcohol, thiol, phenol, or the like, etc. under the conditions of using palladium, the compound (I-2) can be obtained by carrying out the Pinnick oxidation. When $R_3$ is an iodine atom, the compound (XX) is directly oxidated to give the compound (I-2).

Scheme F

[Chemical Formula 45]

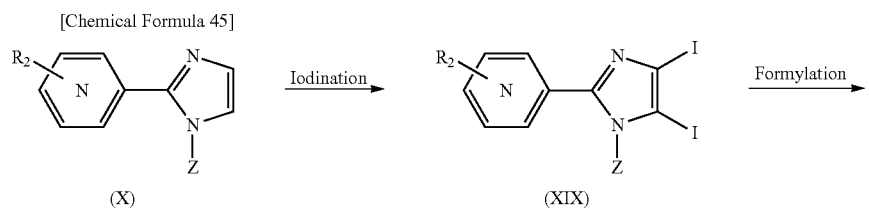

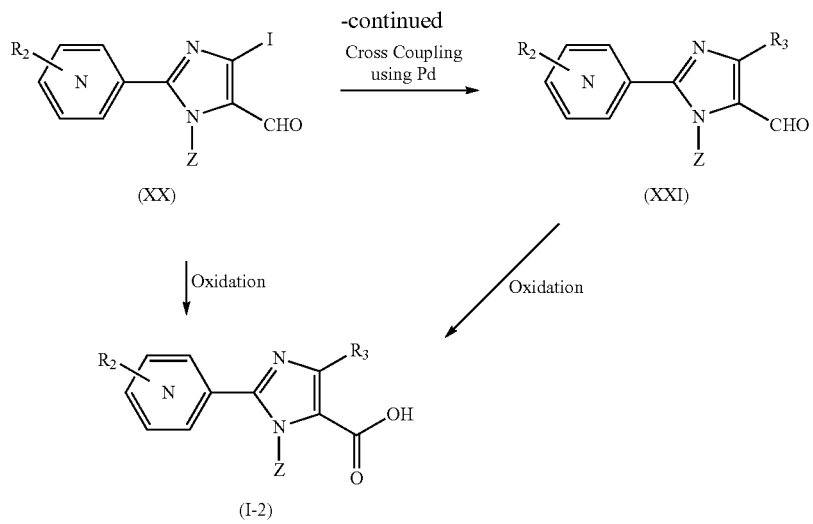

Preferably, the iodination reaction of the compound (X) to the compound (XIX) in Scheme F is carried out in methanol using iodine and silver sulfate. This reaction proceeds at 0° C. to 100° C., but it is preferably carried out at room temperature to 50° C. As for the selective formylation of the compound (XIX) to the compound (XX), it is preferable to perform the reaction using a Grignard reagent such as EtMgBr, or a lithium reagent such as nBuLi, in DMF, or in a mixed solvent of tetrahydrofuran (THF) and DMF. This reaction proceeds at −50° C. to 50° C., but it is preferably carried out at 0° C. to room temperature. In the conversion of the compound (XX) to the compound (XXI), the Suzuki coupling reaction is preferably carried out under the conditions described in Scheme A. The cyanation using palladium, is carried out preferably under the conditions where a palladium catalyst, such as [1,1'-bis(diphenylphosphino)ferrocene]dichloropalladium (II) ($PdCl_2$ (dppf)) or tetrakis(triphenylphosphine)palladium ($Pd(PPh_3)_4$), and $ZnCN_2$ are heated in DMF. This reaction proceeds at 50° C. to 150° C., but it is preferably carried out at 80° C. to 100° C. For the etherification through the introduction of alcohol, thiol, phenol, or the like, the conditions of using CuI, 1,10-phenanthroline, and cesium carbonate in the presence of the compound (XX) and any of the alcohol, thiol, phenol, or the like in toluene solvent are preferred. The reaction temperature is preferably from 50° C. to 100° C. The Pinnick oxidation reaction of the compound (XX) or the compound (XXI) is preferably carried out under the conditions described in Scheme D.

The present derivatives can be synthesized according to Scheme G below when A is a single bond, $R_1$ is a nitrogen atom, $R_3$ is a hydrogen atom, $R_4$ is a tetrazolyl group, acrylic acid, or thiomethylpropanoic acid. That is, for a tetrazole compound, the compound (I-9) can be obtained by introducing a cyano group using palladium into the compound (XI) obtained in Scheme C above to give the compound (XXII) and then converting the cyano group into tetrazolyl group using sodium azide. For acrylic acid, the compound (I-10) can be obtained by performing a Heck reaction on the compound (XI) to give the compound (XXIII), followed by a hydrolysis reaction. For thiomethylpropanoic acid, the compound (I-11) can be obtained by the introduction of a SH group using palladium to give the compound (XXIV), followed by S-alkylation to give the compound (XXV), and finally followed by hydrolysis.

Scheme G

[Chemical Formula 46]

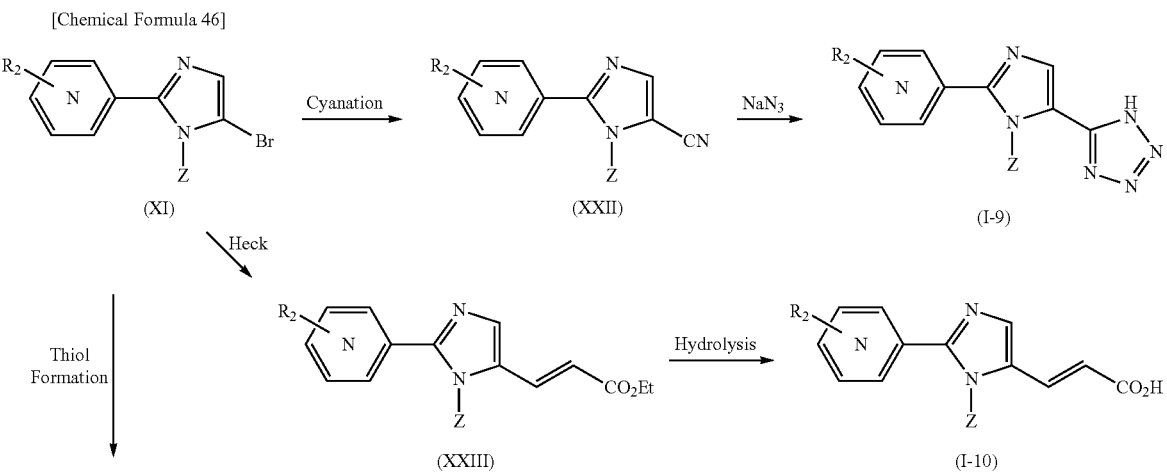

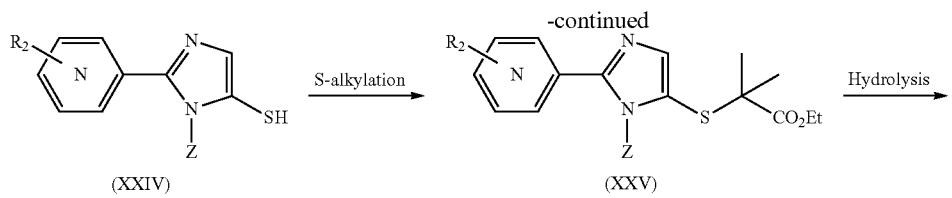

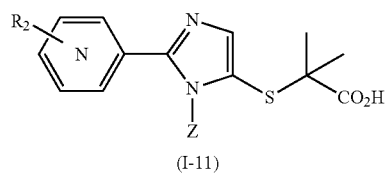

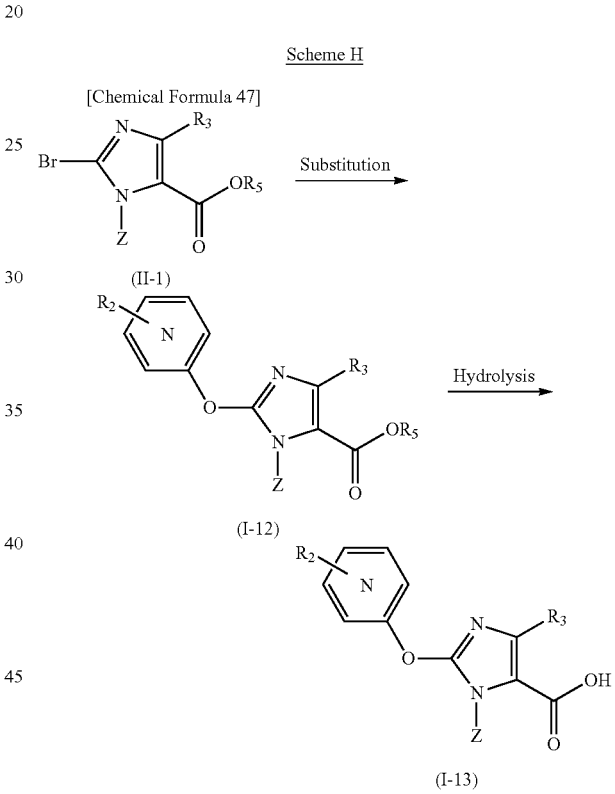

For the cyanation reaction of the compound (XI) to the compound (XXII), the conditions of heating in DMF with a palladium catalyst, such as [1,1'-bis(diphenylphosphino)ferrocene]dichloropalladium (II) ($PdCl_2$ (dppf)) or tetrakis(triphenylphosphine)palladium ($Pd(PPh_3)_4$), and $ZnCN_2$ are preferred. This reaction proceeds at 50° C. to 150° C., but it is preferably carried out at 80° C. to 100° C. The conversion of the compound (XXII) to the compound (I-9), is carried out preferably by using triethylamine hydrochloride and sodium azide in DMF. This reaction proceeds at 100° C. to 170° C., but it is preferably carried out at 120° C. to 150° C. The Heck reaction for converting the compound (XI) to the compound (XXIII) proceeds by using a palladium catalyst such as [1,1'-bis(diphenylphosphino)ferrocene]dichloropalladium (II) ($PdCl_2$ (dppf)) or tetrakis(triphenylphosphine) palladium ($Pd(PPh_3)_4$), a base such as potassium carbonate, potassium acetate, triethylamine, or diisopropylethylamine, the compound (XI), and an acrylic acid ester in acetonitrile, or in an amide type solvent such as DMF or DMA, under heated conditions. This reaction proceeds at room temperature to 150° C., but it is preferably carried out at 80° C. to 140° C. The hydrolysis is preferably carried out under the conditions described in Scheme A. As for the introduction of a SH group into the compound (XI) to give the compound (XXIV), an alkylthiol moiety is introduced by heating the compound (XI), 2-ethylhexyl 3-mercaptopropionate, $Pd_2(dba)_3$, Xantphos, and diisopropylethylamine in 1,4-dioxane under a nitrogen atmosphere, and then a β-elimination reaction is carried out under basic conditions to give the compound (XXIV), with reference to the document: Org. Lett. 2004, 6, 4587-4590; or Org. Lett. 2007, 9, 3687-3689. For the β-elimination reaction, the conditions of using a slight excess of KOtBu in DMF at room temperature are preferred. The S-alkylation of the compound (XXIV) to the compound (XXV) is preferably carried out under conditions similar to those for the N-alkylation in Scheme A, and more preferably under the conditions of using a base and a halide compound. The hydrolysis is preferably carried out under the conditions described in Scheme A.

The present derivatives can be synthesized according to Scheme H below when A is an oxygen atom, $R_1$ is a nitrogen atom, $R_3$ is an alkyl group having 1 to 6 carbon atoms, and $R_4$ is a carboxyl group. That is, the compound (I-13) can be synthesized by performing a substitution reaction using a phenol and a base on the compound (II-1) obtained in Scheme A above to give the compound (I-12), and then performing a hydrolysis reaction.

The substitution reaction of the compound (II-1) to the compound (I-12) proceeds by reacting compound (II-1) with a phenol in DMF, in the presence of a base, such as potassium carbonate or cesium carbonate. This reaction proceeds at 50° C. to 150° C., but it is preferably carried out at 90° C. to 130° C. The hydrolysis of the compound (I-12) to the compound (I-13) is preferably carried out under the conditions described in Scheme A.

Note that the compound of the formula (II) discussed above can be used as the compound (II-1) in Scheme H above.

Furthermore, the present derivatives can be synthesized according to Scheme I below when A is a single bond, $R_1$ is CH, $R_3$ is a hydrogen atom, and $R_4$ is a carboxyl group or acrylic acid. That is, for a carboxylic acid, after the known pyrrole derivative (XXVI) is N-alkylated to give the compound (II-3), the compound (XXVII) is obtained by a Suzuki coupling reaction with a boronate derivative. The target compound (I-14) can be obtained by a subsequent oxidation reaction. For an acrylic acid, the compound (I-15) can be obtained by performing a Horner-Emmons reaction on the compound (XXVII) to give the compound (XXVIII), followed by hydrolysis.

tration such as via injections, such as intravenous injection and intramuscular injection, suppositories, or transdermal administration.

For the purpose of the present invention, "preventing" refers to obviating contraction or development of a disease in an individual who has not yet contracted or developed it, Scheme I

[Chemical Formula 48]

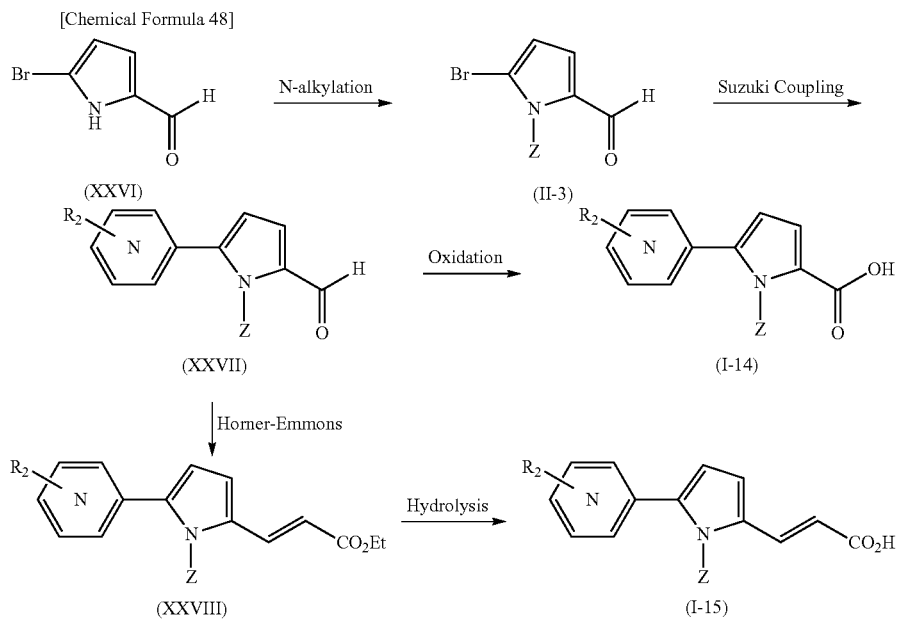

Preferably, the N-alkylation reaction of the compound (XXVI) to the compound (II-3) in Scheme I and the subsequent Suzuki coupling reaction of the compound (II-3) are carried out under the conditions described in Scheme A. Preferably, the oxidation reaction of the compound (XXVII) is carried out under the conditions described in Scheme D. The Horner-Emmons reaction of the compound (XXVII) to the compound (XXVIII) proceeds by reacting the compound (XXVII) with ethyl diethylphosphonoacetate in THF, in the presence of a base, such as sodium hydride or nBuLi. The reaction temperature is preferably from 0° C. to room temperature. The subsequent hydrolysis is preferably carried out under the conditions described in Scheme A.

Note that the compound of the formula (II) discussed above can be used as the compound (II-3) in Scheme I above.

An agent for treatment or prevention of gout, hyperuricemia, and the like, containing a pyridine derivative or a prodrug thereof, or a pharmaceutically acceptable salt thereof, or a solvate thereof, of the present invention as an active ingredient is prepared with carriers, excipients, and other additives commonly used to formulate pharmaceutical preparations. The carriers and excipients to formulate pharmaceutical preparations may be either solid or liquid and include, for example, lactose, magnesium stearate, starch, talc, gelatin, agar, pectin, Arabian gum, olive oil, sesame oil, cocoa butter, ethylene glycol, etc., and others that are commonly used. Administration may be in any form of oral administration such as via tablets, pills, capsules, granules, powders, or liquid preparations, or of parenteral adminisand "treating" refers to curing, suppressing, or ameliorating a disease or symptom in an individual who has already contracted or developed it.

The effective dose of the active ingredient in a URAT1-inhibitor or an agent for treatment or prevention of the present invention may vary depending upon the route of administration, the age and sex of the patient, the extent of the disease, and the like, but it is generally about 0.1 to 100 mg/day. The dose frequency is generally 1 to 3 times/day or 1 to 7 times/week. It is preferred that pharmaceutical preparations be prepared to meet these conditions.

EXAMPLES

Hereinafter, the present invention will be described in greater detail by way of working examples, without being limited thereto. Abbreviations in the present invention are as follows:
DMF=N,N-dimethylformamide
THF=tetrahydrofuran
NBS=N-bromosuccinimide
NCS=N-chlorosuccinimide
DEAD=diethyl azodicarboxylate
DIAD=diisopropyl azodicarboxylate
$PdCl_2$ (dppf)=[1,1'-bis(diphenylphosphino)ferrocene]dichloropalladium(II)
$PdCl_2$ (dppf). $CH_2Cl_2$=[1,1'-bis(diphenylphosphino)ferrocene]dichloropalladium(II) dichloromethane complex
BSA=N,O-bis(trimethylsilyl)acetamide
AIBN=2,2'-azobis(isobutyronitrile)

HATU=O-(7-azabenzotriazol-1-yl)-N,N,N',N'-tetramethyl-uronium hexafluorophosphate
WSC=1-ethyl-3-(3-dimethylaminopropyl)carbodiimide hydrochloride
DMAP=N,N-dimethylamino-4-aminopyridine
DIBAL-H=diisobutylaluminum hydride
DAST=diethylaminosulfur trifluoride The structures of the isolated, novel compounds were confirmed by $^1$H-NMR and/or mass spectrometry using single quadrupole instrumentation equipped with an electrospray source, and other appropriate analytical methods.

For the compounds whose $^1$H-NMR spectra (400 MHz, DMSO-$d_6$, CDCl$_3$, or CD$_3$OD) were measured, their chemical shifts (δ: ppm) and coupling constants (J: Hz) are shown. For the mass spectroscopy results, the observed measurement is shown as M$^+$+H, i.e., the value of compound's molecular mass (M) plus a proton (H+). Abbreviations below refer respectively to the following.
s=singlet, d=doublet, t=triplet, q=quartet, brs=broad singlet, m=multiplet.

The compounds synthesized according to the methods of the following Examples were also analyzed by high-performance liquid chromatography (HPLC) analysis and by mass spectroscopy using a time-of-flight mass spectrometer (TOF-MS: Time of Flight-Mass Spectroscopy) equipped with an electrospray ion source.

The retention time (in minutes) of a compound in the HPLC analysis under the following analytical conditions is shown as HPLC retention time.
HPLC measurement conditions
Instrument: Hewlett-Packard 1100HPLC
Column: Imtakt Cadenza CD-C18 100 mm×4.6 mm 3 μm
UV: PDA detection (254 nm)
Column temperature: 40° C.
Gradient conditions:
Solvents: A: H$_2$O/acetonitrile=95/5
  0.05% TFA (trifluoroacetic acid)
B: H$_2$O/acetonitrile=5/95
  0.05% TFA (trifluoroacetic acid)
Flow rate: 1.0 mL/min
Gradients: 0 to 1 minute, Solvent B: 2%, Solvent A: 98%
  1 to 14 minutes, Solvent B: 2%→100%, Solvent A: 98%→0%
  14 to 17 minutes, Solvent B: 100%, Solvent A: 0%
  17 to 19 minutes, Solvent B: 100%→2%, Solvent A: 0%→98%

For the mass spectroscopy results, the value of "M$^+$+H" observed using the apparatus and analytical conditions listed below (Obs. Mass: i.e., the observed value of compound's molecular mass (M) plus a proton (H$^+$)) and the calculated value of "M$^+$+H" (Pred. Mass), as well as the compositional formula calculated from the observed value of "M$^+$+H," are shown.
TOF-MS measurement conditions
Mass spectrometer: Shimadzu Corporation LCMS-IT-TOF
LC: Prominence
Column: Phenomenex Synergi Hydro-RP 4.0 mm×20 mm 2.5 μm
UV: PDA detection (254 nm)
Flow rate: 0.6 mL/min
Column temperature: 40° C.
Detection voltage: 1.63 kV
Gradient conditions:
Solvents: A: H$_2$O/acetonitrile=95/5
  0.1% HCO$_2$H
B: H$_2$O/acetonitrile=5/95
  0.1% HCO$_2$H
Flow rate: 0.5 mL/min
Gradients: 0 to 0.2 minutes, Solvent B: 2%, Solvent A: 98%
  0.2 to 2.5 minutes, Solvent B: 2%→100%, Solvent A: 98%→0%
  2.5 to 3.8 minutes, Solvent B: 100%, Solvent A: 0%
  3.8 to 4.0 minutes, Solvent B: 100%→2%, Solvent A: 0%→98%
  4.0 to 5.0 minutes, Solvent B: 2%, Solvent A: 98%

Example 1

Production of 4-methyl-1-(naphthalen-1-ylmethyl)-2-(pyridin-3-yl)-1H-imidazole-5-carboxylic acid (Compound A2) (Scheme A)

[Chemical Formula 49]

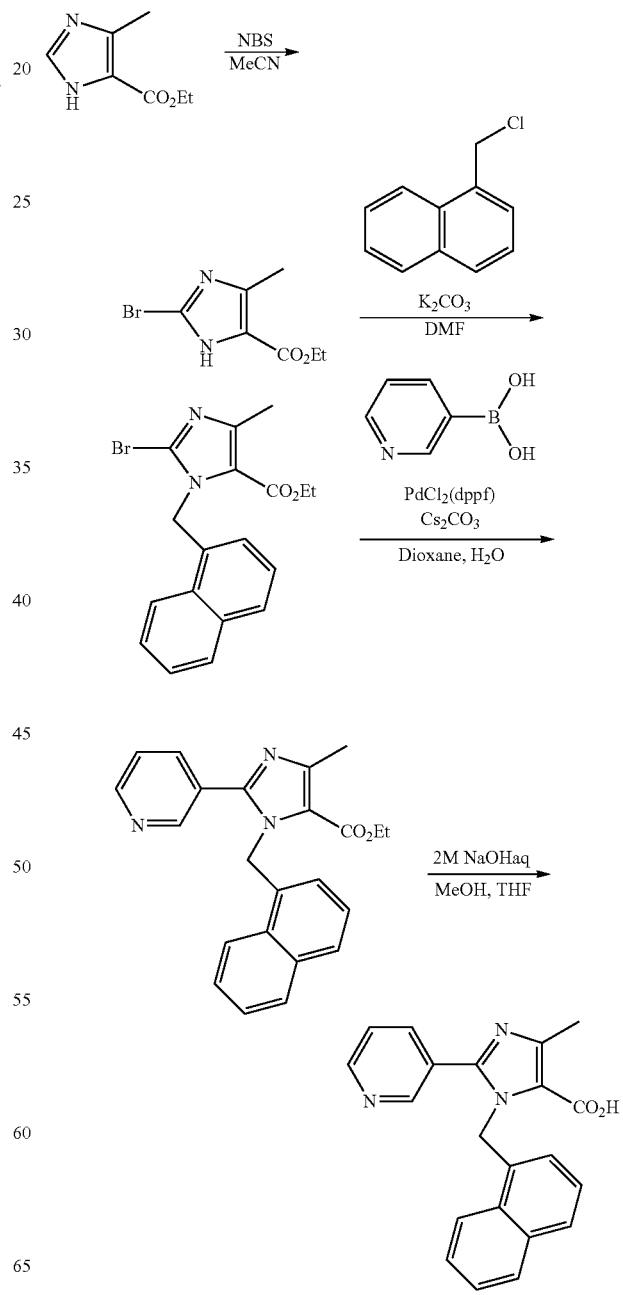

(1) Ethyl 4-methyl-1H-imidazole-5-carboxylate (7.5 g, 48.7 mmol) was dissolved in acetonitrile (120 mL), N-bromosuccinimide (10.4 g, 58.4 mmol) was added thereto, and then the mixture was stirred at room temperature for 3 hours. After the reaction, saturated aqueous sodium hydrogen carbonate was added and the mixture was extracted twice with ethyl acetate. After washing with saturated aqueous sodium chloride, the organic layer was dried over anhydrous sodium sulfate. After concentrating the organic layer, the residue was purified by column chromatography to obtain ethyl 2-bromo-4-methyl-1H-imidazole-5-carboxylate (3.6 g):

$^1$H-NMR (CDCl$_3$) δ: 4.35 (2H, q, J=7.1 Hz), 2.51 (3H, s), 1.37 (3H, t, J=7.1 Hz);

ESI-MS m/z=233 (M$^+$+H).

(2) Ethyl 2-bromo-4-methyl-1H-imidazole-5-carboxylate (5 g, 21.45 mmol) was dissolved in DMF (40 mL), potassium carbonate (5.93 g, 42.9 mmol) and 1-(chloromethyl)naphthalene (4.56 g, 25.8 mmol) were added thereto, and the mixture was stirred at 80° C. for 2 hours. After the reaction, water was added and the mixture was extracted twice with ethyl acetate. The organic layer was washed with saturated aqueous sodium chloride and dried over anhydrous sodium sulfate. After concentrating the organic layer, the residue was purified by column chromatography to obtain ethyl 2-bromo-4-methyl-1-(naphthalen-1-ylmethyl)-1H-imidazole-5-carboxylate (3.25 g):

$^1$H-NMR (CDCl$_3$) δ: 8.01 (1H, d, J=8.3 Hz), 7.91 (1H, d, J=7.8 Hz), 7.77 (1H, d, J 8.3 Hz), 7.63-7.53 (2H, m), 7.33 (1H, t, J=7.6 Hz), 6.43 (1H, dd, J=7.3, 1.0 Hz), 6.07 (2H, s), 4.13 (2H, q, J=7.1 Hz), 2.58 (3H, s), 1.11 (3H, t, J=7.1 Hz);

ESI-MS m/z=373 (M$^+$+H).

(3) Ethyl 2-bromo-4-methyl-1-(naphthalen-1-ylmethyl)-1H-imidazole-5-carboxylate (1.5 g, 4.0 mmol), pyridin-3-ylboronic acid (0.74 g, 6.0 mmol), cesium carbonate (2.62 g, 8.0 mmol), and PdCl$_2$ (dppf) (0.3 g, 0.4 mmol) were dissolved in a mixed solvent of dioxane (15 mL) and water (3 mL), and the solution was heated and stirred at 100° C. for 6 hours under a nitrogen atmosphere. After cooling, the reaction mixture was concentrated under reduced pressure, ethyl acetate was added to the residue, and the solution was washed with water and saturated aqueous sodium chloride. The organic layer was dried over anhydrous sodium sulfate and subsequently concentrated under vacuum. The residue obtained was purified by column chromatography to obtain ethyl 4-methyl-1-(naphthalen-1-ylmethyl)-2-(pyridin-3-yl)-1H-imidazole-5-carboxylate (Compound A3, 1.46 g):

$^1$H-NMR (CDCl$_3$) δ: 8.78 (1H, d, J=2.0 Hz), 8.58 (1H, dd, J=4.9, 1.5 Hz), 7.93-7.85 (2H, m), 7.82-7.77 (2H, m), 7.57-7.53 (2H, m), 7.38 (1H, t, J=7.6 Hz), 7.24-7.20 (1H, m), 6.73 (1H, d, J=6.3 Hz), 6.03 (2H, s), 4.13 (2H, q, J=7.2 Hz), 2.67 (3H, s), 1.07 (3H, t, J=7.1 Hz);

ESI-MS m/z=372 (M$^+$+H).

(4) Ethyl 4-methyl-1-(naphthalen-1-ylmethyl)-2-(pyridin-3-yl-1H-imidazole-5-carboxylate (1.46 g, 3.93 mmol) was dissolved in a mixed solvent of THF (10 mL) and methanol (10 mL), and 2 M aqueous sodium hydroxide (4 mL, 8.0 mmol) was added to the solution, and then the mixture was heated and stirred at 50° C. for 1 hour. After cooling to room temperature, 2 M hydrochloric acid (4 ml, 8.0 mmol) was added and the mixture was concentrated under reduced pressure. The residue was purified according to the conventional method to obtain 4-methyl-1-(naphthalen-1-ylmethyl)-2-(pyridin-3-yl)-1H-imidazole-5-carboxylic acid (Compound A2, 0.88 g):

$^1$H-NMR (DMSO-D$_6$) δ: 8.69 (1H, d, J=2.0 Hz), 8.60 (1H, dd, J=4.9, 1.5 Hz), 8.05-8.01 (1H, m), 7.99-7.95 (1H, m), 7.93 (1H, dt, J=8.0, 2.0 Hz), 7.84 (1H, d, J=8.3 Hz), 7.60-7.57 (2H, m), 7.46-7.40 (2H, m), 6.59 (1H, d, J=7.3 Hz), 6.09 (2H, s), 2.56 (3H, s);

HPLC retention time=7.40 min;

Pred. Mass=344.1394 (M$^+$+H, C$_{21}$H$_{17}$N$_3$O$_2$);

Obs. Mass=344.1391 (M$^+$+H).

Example 2

Production of 1-((4-chlorobenzo[b]thiophen-3-yl)methyl)-4-methyl-2-(pyridin-3-yl)-1H-imidazole-5-carboxylic acid (Compound A7) (Scheme A)

[Chemical Formula 50]

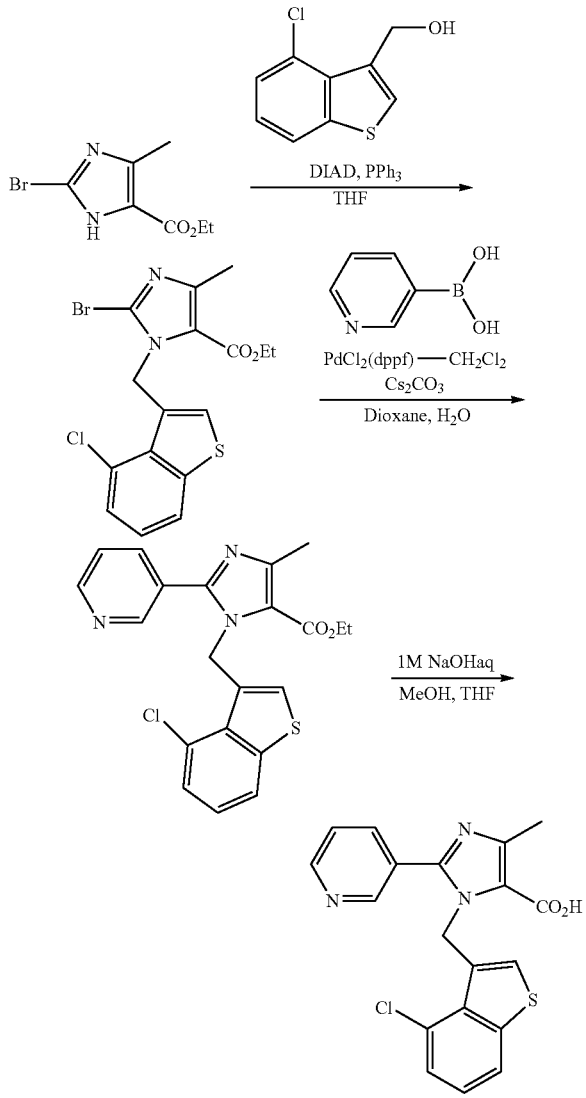

(1) Ethyl 2-bromo-4-methyl-1H-imidazole-5-carboxylate (1.52 g, 6.0 mmol), (4-chlorobenzo[b]thiophen-3-yl)methanol (1.79 g, 9.0 mmol) obtained according to a method described in a literature (for example, WO 2002/066457), and triphenylphosphine (2.36 g, 9.0 mmol) were dissolved in THF (15 mL), a 1.9 M solution of DIAD in toluene (4.73 mL, 9.0 mmol) was added dropwise thereto under cooling at 0° C., and the mixture was stirred at 30° C. for 10 hours. The solvent was distilled away and the residue was purified by column chromatography to obtain ethyl 2-bromo-1-((4-chlorobenzo[b]thiophen-3-yl)methyl)-4-methyl-1H-imidazole-5-carboxylate (1.73 g):

$^1$H-NMR (CDCl$_3$) δ: 7.72 (1H, d, J=8.3 Hz), 7.41-7.24 (3H, m), 6.15 (2H, s), 4.21 (2H, q, J=7.1 Hz), 2.57 (3H, s), 1.20 (3H, t, J=7.1 Hz);

ESI-MS m/z=413 (M$^+$+H).

(2) Ethyl 2-bromo-1-((4-chlorobenzo[b]thiophen-3-yl)methyl)-4-methyl-1H-imidazole-5-carboxylate (800 mg, 1.93 mmol), pyridin-3-ylboronic acid (366 mg, 3.0 mmol), cesium carbonate (1.06 g, 3.0 mmol), PdCl$_2$ (dppf). CH$_2$Cl$_2$ (245 mg, 0.3 mmol) were dissolved in a mixed solvent of dioxane (19 mL) and water (1 mL), and the solution was heated and stirred at 100° C. for 5 hours under a nitrogen atmosphere. After cooling, ethyl acetate was added to extract the reaction mixture, the organic layer was washed with saturated aqueous sodiumchloride, dried with anhydrous magnesium sulfate, and concentrated under reduced pressure. The residue obtained was purified by column chromatography to obtain ethyl 1-((4-chlorobenzo[b]thiophen-3-yl)methyl)-4-methyl-2-(pyridin-3-yl)-1H-imidazole-5-carboxylate (Compound A267, 0.63 g):

ESI-MS m/z=412 (M$^+$+H).

(3) Ethyl 1-((4-chlorobenzo[b]thiophen-3-yl)methyl)-4-methyl-2-(pyridin-3-yl)-1H-imidazole-5-carboxylate (0.63 g, 1.53 mmol) was dissolved in a mixed solvent of THF (6 mL), methanol (6 mL), and water (3 mL), 1 M aqueous sodium hydroxide (3 mL, 3.0 mmol) was added to the solution, and the mixture was stirred at 60° C. for 3 hours. After cooling, the reaction mixture was neutralized by the addition of 1 M hydrochloric acid (3 mL, 3.0 mmol) and the organic solvent was distilled away. The residue was extracted with ethyl acetate and the organic layer was washed with saturated aqueous sodium chloride. After being dried over anhydrous magnesium sulfate, the organic layer was concentrated under reduced pressure. The residue was purified by a conventional method to obtain 1-((4-chlorobenzo[b]thiophen-3-yl)methyl)-4-methyl-2-(pyridin-3-yl)-1H-imidazole-5-carboxylic acid (Compound A7, 0.26 g):

$^1$H-NMR (DMSO-D$_6$) δ: 8.72 (1H, d, J=2.0 Hz), 8.60 (1H, dd, J=4.9, 2.0 Hz), 7.99-7.93 (2H, m), 7.47-7.44 (2H, m), 7.37 (1H, t, J=8.0 Hz), 6.87 (1H, s), 6.05 (2H, s), 2.60 (3H, s);

HPLC retention time=7.76 min:
Pred. Mass=384.0568 (M$^+$+H, C$_{19}$H$_{14}$ClN$_3$O$_2$S);
Obs. Mass=384.0564 (M$^+$+H).

Example 3

Production of 4-chloro-1-(napthalen-1-ylmethyl)-2-(pyridin-3-yl)-1H-imidazole-5-carboxylic acid (Compound A9) (Scheme D)

[Chemical Formula 51]

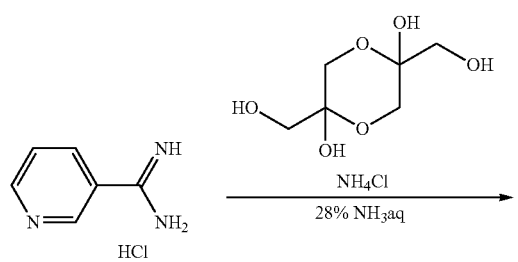

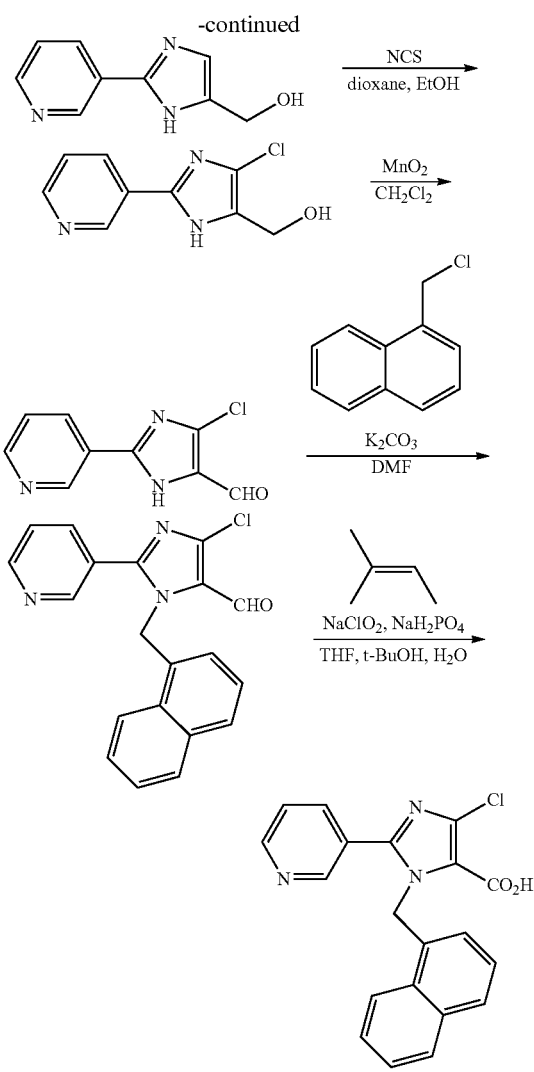

(1) 3-Amidinopyridine hydrochloride (10 g, 63.5 mmol), dihydroxyacetone dimer (11.43 g, 63.6 mmol) and ammonium chloride (17 g, 317 mmol) were dissolved in 28% aqueous ammonia (100 mL), and the solution was stirred at 80° C. for 2 hours. After the reaction, saturated aqueous sodium chloride (50 mL) was added and the aqueous layer was extracted three times with a mixed solvent of ethyl acetate and THF. The organic layer was dried over anhydrous sodium sulfate and concentrated to obtain a crude product, which was subsequently washed with acetonitrile and hexane to obtain (2-(pyridin-3-yl)-1H-imidazol-5-yl)methanol (3 g):

ESI-MS m/z=176 (M$^+$+H).

(2) In a mixed solvent of ethanol (30 mL) and 1,4-dioxane (30 mL) was dissolved (2-(pyridin-3-yl)-1H-imidazol-5-yl)methanol (2.1 g, 12 mmol), N-chlorosuccinimide (1.6 g, 12 mmol) was added thereto, and the mixture was stirred at room temperature for 48 hours. After the reaction, water (50 mL) and saturated aqueous sodium chloride (50 mL) were added and the mixture was extracted twice with a mixed solvent of ethyl acetate and THF. After being dried over anhydrous sodium sulfate, the organic layer was concentrated and the residue was purified by column chromatography to obtain (4-chloro-2-(pyridin-3-yl)-1H-imidazol-5-yl)methanol (600 mg):

$^1$H-NMR (DMSO-d$_6$) δ: 13.16 (1H, s), 9.09 (1H, d, J=2.0 Hz), 8.54 (1H, dd, J=4.9, 1.5 Hz), 8.24 (1H, dt, J=8.1, 2.0 Hz), 7.47 (1H, dd, J=7.8, 4.9 Hz), 5.31 (1H, t, J=5.1 Hz), 4.45 (2H, d, J=4.9 Hz);

ESI-MS m/z=210 (M$^+$+H).

(3) In dichloromethane (7 mL) was suspended (4-chloro-2-(pyridin-3-yl)-1H-imidazol-5-yl)methanol (600 mg, 2.86 mmol), manganese dioxide (4 g, 46 mmol) was added thereto, and the mixture was stirred at room temperature for 20 hours. After the reaction, the reaction mixture was filtered using celite and subsequently the filtrate was concentrated to obtain 4-chloro-2-(pyridin-3-yl)-1H-imidazole-5-carbaldehyde (460 mg). This material was used as is for the next reaction without further purification:

$^1$H-NMR (DMSO-d$_6$) δ: 14.22 (1H, s), 9.72 (1H, s), 9.24 (1H, s), 8.66 (1H, d, J=4.4 Hz), 8.42 (1H, d, J=7.3 Hz), 7.54 (1H, dd, J=7.8, 4.9 Hz); ESI-MS m/z=208 (M$^+$+H).

(4) In DMF (1 mL) was dissolved 4-chloro-2-(pyridin-3-yl)-1H-imidazole-5-carbaldehyde (50 mg, 0.241 mmol), potassium carbonate (66.6 mg, 0.482 mmol) and 1-(chloromethyl)naphthalene (51.0 mg, 0.289 mmol) were added to the solution, and the mixture was heated and stirred at 80° C. for 5 hours. After the reaction, water (5 mL) was added and the mixture was extracted twice with ethyl acetate (5 mL). After being washed with saturated aqueous sodium chloride, the organic layer was dried over anhydrous sodium sulfate and subsequently concentrated to obtain 4-chloro-1-(napthalen-1-ylmethyl)-2-(pyridin-3-yl)-1H-imidazole-5-carbaldehyde (100 mg). This material was used as is for the next reaction without further purification: ESI-MS m/z=348 (M$^+$+H).

(5) 4-Chloro-1-(napthalen-1-ylmethyl)-2-(pyridin-3-yl)-1H-imidazol-5-carbaldehyde (100 mg) and 2-methyl-2-butene (141 mg, 2 mmol) were dissolved in a mixed solvent of THF (1 mL) and t-butanol (1 mL), an aqueous solution (2 mL) of sodium chlorite (221 mg, 2.44 mmol) and sodium dihydrogen phosphate (292 mg, 1.87 mmol) was added dropwise thereto, and the mixture was stirred at room temperature for 6 hours. After the reaction, water (5 mL) was added and the mixture was extracted twice with ethyl acetate (5 mL). After being washed with saturated aqueous sodium chloride, the organic layer was dried over sodium sulfate. After concentrating the organic layer, the residue was purified by HPLC to obtain 4-chloro-1-(napthalen-1-ylmethyl)-2-(pyridin-3-yl)-1H-imidazole-5-carboxylic acid (Compound A9, 2.53 mg):

HPLC retention time=8.52 min;
Pred. Mass=364.0847 (M$^+$+H, C$_{20}$H$_{14}$ClN$_3$O$_2$);
Obs. Mass=364.0847 (M$^+$+H).

Example 4

Production of 4-cyclopropyl-1-(napthalen-1-ylmethyl)-2-(pyridin-3-yl)-1H-imidazole-5-carboxylic acid (Compound A11) (Scheme B)

[Chemical Formula 52]

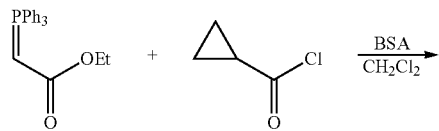

(1) Ethyl 2-(triphenylphosphoranylidene)acetate (16.3 g, 47 mmol) was dissolved in dichloromethane (160 mL), cyclopropanecarbonyl chloride (5.4 g, 51 mmol) and N,O-bis(trimethylsilyl)acetamide (BSA) (11.9 g, 58 mmol) were added thereto under ice cooling, and the mixture was stirred at room temperature for 3 hours. After the reaction, water (100 mL) was added and the aqueous layer was extracted twice with dichloromethane. After being washed with saturated aqueous sodium chloride, the organic layer was dried over anhydrous magnesium sulfate and was concentrated to obtain ethyl 3-cyclopropyl-3-oxo-2-(triphenylphosphoranylidene)propanoate (19.0 g):

$^1$H-NMR (CDCl) δ: 7.67-7.40 (15H, m), 3.74 (2H, q, J=7.2 Hz), 3.35-3.33 (1H, m), 0.85-0.81 (2H, m), 0.71-0.67 (2H, m), 0.65 (3H, t, J=7.3 Hz); ESI-MS m/z=417 (M$^+$+H).

(2) Ethyl 3-cyclopropyl-3-oxo-2-(triphenylphosphoranylidene)propanoate (19.0 g, 47 mmol) was dissolved in a mixed solvent of tetrahydrofuran (300 mL) and water (200 mL), oxone (34.7 g, 56 mmol) was added thereto under ice cooling, and the mixture was stirred at room temperature for 4 hours. After the reaction, insoluble matter was removed by filtration and the solid was washed with ethyl acetate. The filtrate was concentrated and the solvent was distilled away. The aqueous layer was extracted twice with ethyl acetate (100 mL). After being washed with saturated aqueous sodium chloride, the organic layer was dried over anhydrous magnesium sulfate. The residue obtained by concentrating the organic layer was purified by column chromatography to obtain ethyl 3-cyclopropyl-2,3-dioxopropanoate (7.47 g):

$^1$H-NMR (CDCl$_3$) δ: 4.34 (2H, q, J=7.1 Hz), 2.16-2.11 (1H, m), 1.31 (3H, t, J=7.1 Hz), 1.25-1.22 (2H, m), 1.15-1.10 (2H, m).

(3) Ethyl 3-cyclopropyl-2,3-dioxopropanoate (500 mg, 2.9 mmol), nicotine aldehyde (315 mg, 2.9 mmol), and ammonium acetate (2.26 g, 29 mmol) were dissolved in a mixed solvent of toluene (4 mL) and water (2 mL), and the mixture was heated and stirred at 70° C. for 3 hours. After the reaction, the residue obtained by distilling away toluene was purified by a conventional method to obtain ethyl 4-cyclopropyl-2-(pyridin-3-yl)-1H-imidazole-5-carboxylate (416 mg):

$^1$H-NMR (DMSO-d$_6$) δ: 13.07 (1H, brs), 9.16 (1H, brs), 8.56 (1H, d, J=4.9 Hz), 8.33 (1H, brs), 7.46 (1H, dd, J=7.8, 4.9 Hz), 4.30 (2H, brs), 2.59 (1H, brs), 1.32 (3H, t, J=7.1 Hz), 0.97 (4H, brs); ESI-MS m/z=258 (M$^+$+H).

(4) Ethyl 4-cyclopropyl-2-(pyridin-3-yl)-1H-imidazole-5-carboxylate (50 mg, 0.194 mmol) was dissolved in DMF (1 mL), potassium carbonate (53.7 mg, 0.389 mmol) and 1-(chloromethyl)naphthalene (41.2 mg, 0.233 mmol) were added to the solution, and the mixture was stirred at 90° C. for 3 hours. After the reaction, water (5 mL) was added and the mixture was extracted twice with ethyl acetate (5 mL). After being washed with saturated aqueous sodium chloride, the organic layer was dried over anhydrous sodium sulfate. After concentrating the organic layer, the residue was purified by column chromatography to obtain ethyl 4-cyclopropyl-1-(napthalen-1-ylmethyl)-2-(pyridin-3-yl)-1H-imidazole-5-carboxylate (Compound A268, 40 mg):

ESI-MS m/z=398 (M$^+$+H).

(5) Ethyl 4-cyclopropyl-1-(napthalen-1-ylmethyl)-2-(pyridin-3-yl)-1H-imidazol-5-carboxylate (40 mg) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 3 hours. After the reaction, the reaction mixture was neutralized by the addition of 2 M aqueous hydrochloric acid (0.2 mL, 0.4 mmol) and was concentrated. The residue was purified by HPLC to obtain 4-cyclopropyl-1-(napthalen-1-ylmethyl)-2-(pyridin-3-yl)-1H-imidazole-5-carboxylic acid (Compound A11, 30 mg):

$^1$H-NMR (DMSO-d$_6$) δ: 8.62 (1H, d, J=2.0 Hz), 8.56 (1H, dd, J=4.9, 1.5 Hz), 8.05-7.95 (2H, m), 7.89-7.82 (2H, m), 7.60-7.56 (2H, m), 7.45-7.38 (2H, m), 6.55 (1H, d, J=6.8 Hz), 6.05 (2H, s), 2.78-2.71 (1H, m), 1.04-0.96 (4H, m);

HPLC retention time=8.28 min;
Pred. Mass=370.1550 (M$^+$+H, C$_{23}$H$_{19}$N$_3$O$_2$);
Obs. Mass=370.1548 (M$^+$+H).

Example 5

Production of 1-(2,5-dichlorobenzyl)-2-(pyridin-3-yl)-4-methyl-1H-imidazole-5-carboxylic acid (Compound A13) (Scheme A)

[Chemical Formula 53]

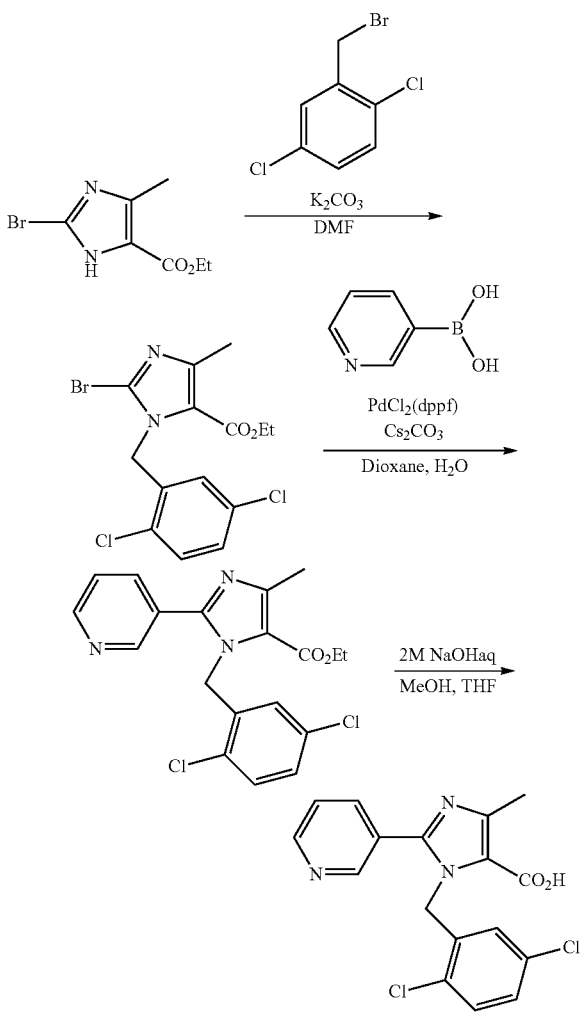

(1) Ethyl 2-bromo-4-methyl-1H-imidazole-5-carboxylate (2.75 g, 11.81 mmol) described in Example 1 (1) was dissolved in DMF (20 mL), potassium carbonate (3.26 g, 23.62 mmol) and 2,5-dichlorobenzyl bromide (3.4 g, 14.17 mmol) were added thereto, and the mixture was stirred at 90° C. for 3 hours. After the reaction, water (50 mL) was added and the mixture was extracted twice with ethyl acetate (50 mL). The organic layer was washed with saturated aqueous sodium chloride and subsequently dried over sodium sulfate. After concentrating the organic layer, the residue was purified by column chromatography to obtain ethyl 2-bromo-1-(2,5-dichlorobenzyl)-4-methyl-1H-imidazole-5-carboxylate (1.72 g):

$^1$H-NMR (CDCl$_3$) δ: 7.34 (1H, d, J=8.8 Hz), 7.20 (1H, dd, J=8.8, 2.4 Hz), 6.40 (1H, d, J=2.4 Hz), 5.60 (2H, s), 4.25 (2H, q, J=7.2 Hz), 2.56 (3H, s), 1.27 (3H, t, J=7.1 Hz);
ESI-MS m/z=391 (M$^+$+H).

(2) Ethyl 2-bromo-1-(2,5-dichlorobenzyl)-4-methyl-1H-imidazole-5-carboxylate (1 g, 2.55 mmol), pyridin-3-ylboronic acid (627 mg, 5.1 mmol), PdCl$_2$(dppf) (467 mg, 0.64 mmol), and cesium carbonate (1.66 g, 5.1 mmol) were dissolved in a mixed solvent of 1.4-dioxane (7 mL) and water (1.5 mL), and the solution was stirred at 100° C. for 3 hours under a nitrogen atmosphere. After the reaction, water (50 mL) was added and the mixture was extracted twice with ethyl acetate (50 mL). The organic layer was washed with saturated aqueous sodium chloride and subsequently dried over sodium sulfate. After concentrating the organic layer, the residue was purified by column chromatography to obtain ethyl 1-(2,5-dichlorobemzyl)-4-methyl-2-(pyridin-3-yl)-1H-imidazole-5-carboxylate (Compound A269, 565 mg):

$^1$H-NMR (CDCl$_3$) δ: 8.69-8.66 (2H, m), 7.82-7.78 (1H, m), 7.37-7.33 (2H, m), 7.26-7.22 (1H, m), 6.66 (1H, d, J=2.4 Hz), 5.53 (2H, s), 4.25 (2H, q, J=7.2 Hz), 2.65 (3H, s), 1.27 (3H, t, J=7.1 Hz);

ESI-MS m/z=391 (M$^+$+H).

(3) Ethyl 1-(2,5-di chlorobenzyl)-4-methyl-2-(pyridin-3-yl)-1H-imidazole-5-carboxylate (859 mg, 2.2 mmol) was dissolved in a mixed solvent of THF (8 ml) and methanol (3 ml), 2 M aqueous sodium hydroxide (2.2 mL, 4.4 mmol) was added to the solution, and the mixture was stirred at 50° C. for 3 hours. After the reaction, the reaction mixture was neutralized by the addition of a 2M hydrochloric acid (2.2 mL, 4.4 mmol) and was concentrated. The residue was purified by a conventional method to obtain 1-(2,5-dichlorobenzyl)-4-methyl-2-(pyridine-3-yl)-1H-imidazole-5-carboxylic acid (Compound A13, 393 mg):

$^1$H-NMR (DMSO-d$_6$) δ: 13.01 (1H, s), 8.64-8.61 (2H, m), 7.84 (1H, d, J=7.8 Hz), 7.52-7.44 (2H, m), 7.37 (1H, dd, J=8.5, 2.2 Hz), 6.54 (1H, d, J=2.0 Hz), 5.55 (2H, s), 2.49 (3H, s);

HPLC retention time=7.33 min;

Pred. Mass=362.0458 (M$^+$+H, C$_{17}$H$_{13}$Cl$_2$N$_3$O$_2$);

Obs. Mass=362.0455 (M$^+$+H).

Example 6

Production of 1-(2,5-dichlorobenzyl)-2-(pyridin-3-yl)-4-(trifluoromethyl)-1H-imidazole-5-carboxylic acid (Compound A19) (Scheme A)

[Chemical Formula 54]

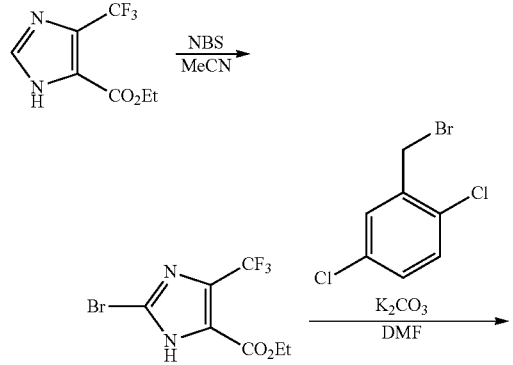

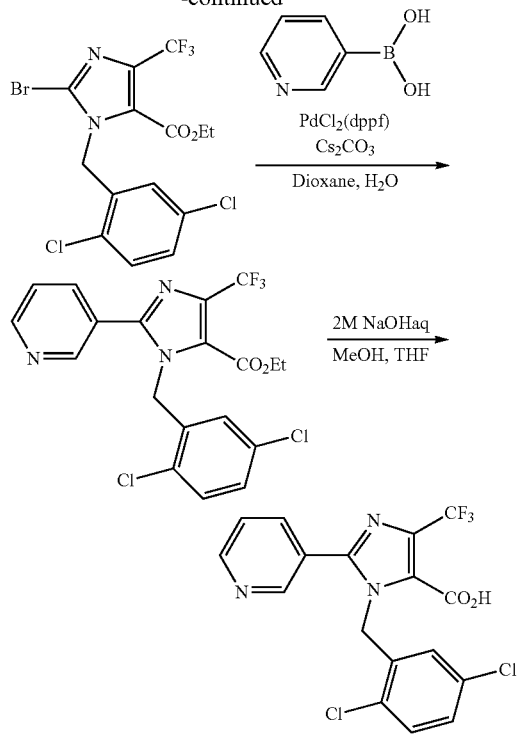

(1) Ethyl 4-trifluoromethyl-1H-imidazole-5-carboxylate (5.73 g, 27 mmol), which is publicly known through publication (for example, Journal of Medicinal Chemistry, 2011, 54, 7621-7638), was dissolved in acetonitrile (100 mL), N-bromosuccinimide (5.88 g, 33 mmol) was added thereto, and the mixture was stirred at 50° C. for 2 hours. After the reaction, acetonitrile was distilled away, saturated aqueous sodium bicarbonate (50 mL) was added, and mixture was extracted twice with ethyl acetate (50 mL). After being washed with saturated aqueous magnesium chloride, the organic layer was dried over sodium sulfate. After concentrating the organic layer, the residue was purified by column chromatography to obtain ethyl 2-bromo-4-trifluoromethyl-1H-imidazole-5-carboxylate (5.71 g):

$^1$H-NMR (CDCl$_3$) δ: 4.44 (2H, q, J=7.2 Hz), 1.40 (3H, t, J=7.2 Hz);

ESI-MS m/z=287 (M$^+$+H).

(2) Ethyl 2-bromo-4-trifluoromethyl-1H-imidazole-5-carboxylate (1.57 g, 5.47 mmol) was dissolved in DMF (11 mL), potassium carbonate (1.51 g, 10.9 mmol) and 2,5-dichlorobenzyl bromide (1.58 g, 6.56 mmol) were added thereto, and the mixture was stirred at 90° C. for 3 hours. After the reaction, water (50 mL) was added and the mixture was extracted twice with ethyl acetate (50 mL). After being washed with saturated aqueous sodium chloride, the organic layer was dried over sodium sulfate. After concentrating the organic layer, the residue was purified by column chromatography to obtain ethyl 2-bromo-1-(2,5-dichlorobenzyl)-4-trifluoromethyl-1H-imidazole-5-carboxylate (2.07 g):

$^1$H-NMR (CDCl$_3$) δ: 7.38 (1H, d, J=8.3 Hz), 7.26-7.23 (1H, m), 6.43 (1H, d, J=2.4 Hz), 5.66 (2H, s), 4.32 (2H, q, J=7.1 Hz), 1.32 (3H, t, J=7.1 Hz);

ESI-MS m/z=445 (M$^+$+H).

(3) Ethyl 2-bromo-1-(2,5-dichlorobenzyl)-4-trifluoromethyl-1H-imidazole-5-carboxylate (2.05 g, 4.6 mmol), pyridin-3-ylboronic acid (847 mg, 6.89 mmol), PdCl$_2$ (dppf) (673 mg, 0.92 mmol), and cesium carbonate (2.99 g, 9.19 mmol) were dissolved in a mixed solvent of 1,4-dioxane (13 mL) and water (3 mL), and the solution was heated and stirred at 100° C. for 3 hours under a nitrogen atmosphere. After the reaction, water (50 mL) was added and the mixture was extracted twice with ethyl acetate (50 mL). After being washed with a saturated aqueous sodium chloride solution, the organic layer was dried over sodium sulfate. After concentrating the organic layer, the residue was purified by column chromatography to obtain ethyl 1-(2,5-dichlorobenzyl)-2-(pyridin-3-yl)-4-trifluoromethyl-1H-imidazole-5-carboxylate (Compound A270, 1.42 g):

$^1$H-NMR (CDCl$_3$) δ: 8.72 (1H, dd, J=4.9, 1.5 Hz), 8.68 (1H, d, J=1.2 Hz), 7.85-7.81 (1H, m), 7.41-7.35 (2H, m), 7.28-7.25 (1H, m), 6.64 (1H, d, J=2.0 Hz), 5.60 (2H, s), 4.33 (2H, q, J=7.1 Hz), 1.32 (3H, t, J=7.1 Hz);

ESI-MS m/z=444 (M$^+$+H).

(4) Ethyl 1-(2,5-dichlorobenzyl)-2-(pyridin-3-yl)-4-trifluoromethyl-1H-imidazole-5-carboxylate (1.42 g, 3.2 mmol) was dissolved in a mixed solvent of THF (13 ml) and methanol (3 mL), and 2 M aqueous sodium hydroxide (3.2 mL, 6.4 mmol) was added to the solution, and then the mixture was stirred at 50° C. for 3 hours. After the reaction, the reaction mixture was neutralized by the addition of 2 M hydrochloric acid (3.2 mL, 6.4 mmol) and was concentrated. The residue was purified by a conventional method to obtain 1-(2,5-dichlorobenzyl)-2-(pyridyn-3-yl)-4-trifluoromethyl-1H-imidazole-5-carboxylic acid (Compound A19, 683 mg):

$^1$H-NMR (DMSO-d$_6$) δ: 14.13 (1H, s), 8.70-8.66 (2H, m), 7.92 (1H, dt, J=7.8, 2.0 Hz), 7.53-7.47 (2H, m), 7.39 (1H, dd, J=8.8, 2.4 Hz), 6.80 (1H, d, J=2.4 Hz), 5.60 (2H, s);

HPLC retention time=9.32 min;

Pred. Mass=416.0175 (M$^+$+H, C$_{17}$H$_{10}$Cl$_2$F$_3$N$_3$O$_2$);

Obs. Mass=416.0175+H).

Example 7

Production of 1-(2,5-dichlorobenzyl)-2-(pyridin-3-yl)-1H-imidazole-5-carboxylic acid (Compound A45) (Scheme C)

[Chemical Formula 55]

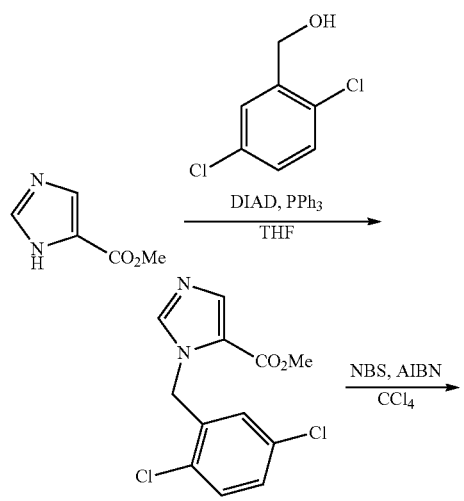

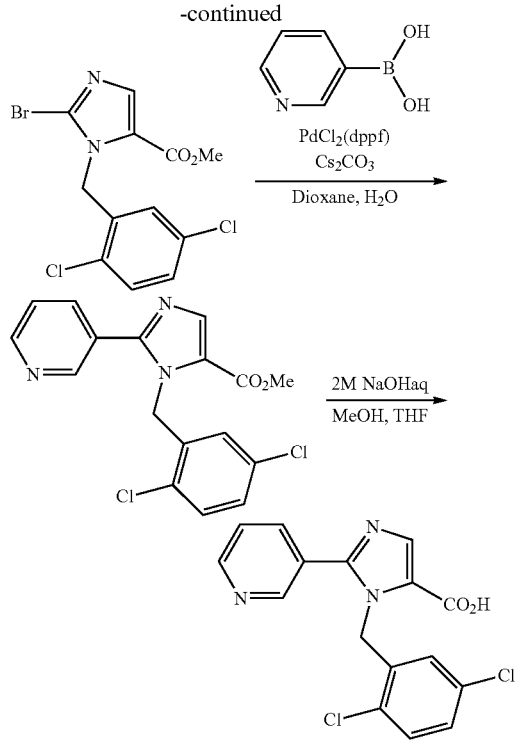

(1) Methyl 1H-imidazole-4-carboxylate (1 g, 7.93 mmol), (2,5-dichlorophenyl)methanol (1.68 g, 9.52 mmol), and triphenylphosphine (3.12 g, 11.89 mmol) were dissolved in THF (15 mL), and a toluene solution of DIAD (2.4 g, 11.89 mmol) was dropwise added thereto, and then the mixture was stirred at 50° C. for 2 hours. After the reaction, water (50 mL) was added and the mixture was extracted twice with ethyl acetate (50 mL). After being washed with saturated aqueous sodium chloride, the organic layer was dried over sodium sulfate. After concentrating the organic layer, the residue was purified by column chromatography to obtain methyl 1-(2,5-dichlorobenzyl)-1H-imidazole-5-carboxylate (4 g):

$^1$H-NMR (CDCl$_3$) δ: 7.83 (1H, s), 7.67 (1H, s), 7.36 (1H, d, J=8.8 Hz), 7.24 (1H, dd, J=8.3, 2.4 Hz), 6.78 (1H, d, J=2.4 Hz), 5.61 (2H, s), 3.83 (3H, s);

ESI-MS m/z=285 (M$^+$+H).

(2) Methyl 1-(2,5-dichlorobenzyl)-1H-imidazole-5-carboxylate (2.4 g), 2,2'-azobis(isobutyronitrile) (AIBN) (69 mg, 0.421 mmol) was dissolved in carbon tetrachloride (20 mL), and N-bromosuccinimide (3 g, 16.83 mmol) was added thereto, and then mixture was stirred at 50° C. for 20 hours. After the reaction, water (50 mL) was added and the mixture was extracted twice with dichloromethane (50 mL). After being washed with aqueous sodium thiosulfate and saturated aqueous sodium chloride, the organic layer was dried over sodium sulfate. After concentrating the organic layer, the residue was purified by column chromatography to obtain methyl 2-bromo-1-(2,5-dichlorobenzyl)-1H-imidazole-5-carboxylate (890 mg):

$^1$H-NMR (CDCl$_3$) δ: 7.83 (1H, s), 7.36 (1H, d, J=8.3 Hz), 7.21 (1H, dd, J=8.8, 2.4 Hz), 6.34 (1H, d, J=2.4 Hz), 5.66 (2H, s), 3.82 (3H, s); ESI-MS m/z=363 (M$^+$+H).

(3) Under a nitrogen atmosphere, methyl 2-bromo-1-(2,5-dichlorobenzyl)-1H-imidazole-5-carboxylate (100 mg, 0.275 mmol), pyridin-3-ylboronic acid (67.5 mg, 0.55 mmol), PdCl$_2$ (dppf) (40.2 mg, 0.055 mmol), and cesium carbonate (179 mg, 0.55 mmol) were dissolved in a mixed solvent of 1,4-dioxane (1 mL) and water (0.2 mL), and the solution was stirred at 100° C. for 20 hours. After the reaction, water (5 mL) was added and the mixture was extracted twice with ethyl acetate (5 mL). After being washed with saturated aqueous sodium chloride, the organic layer was dried over sodium sulfate. After concentrating the organic layer, the residue was purified by column chromatography to obtain methyl 1-(2,5-dichlorobenzyl)-2-(pyridin-3-yl)-1H-imidazole-5-carboxylate (Compound A271, 15 mg):

ESI-MS m/z=362 (M$^+$+H).

(4) Methyl 1-(2,5-dichlorobenzyl)-2-(pyridin-3-yl)-1H-imidazole-5-carboxylate (15 mg) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 3 hours. After the reaction, the reaction mixture was neutralized by the addition of 2 M hydrochloric acid (0.2 mL, 0.4 mmol) and was concentrated. The residue was purified by HPLC to obtain 1-(2,5-dichlorobenzyl)-2-(pyridyn-3-yl)-1H-imidazole-5-carboxylic acid (Compound A45, 9.43 mg):

$^1$H-NMR (DMSO-d$_6$) δ: 8.71 (2H, s), 7.98 (1H, s), 7.94 (1H, d, J=8.3 Hz), 7.57-7.49 (2H, m), 7.39 (1H, dd, J=8.8, 2.4 Hz), 6.54 (1H, d, J=2.4 Hz), 5.65 (2H, s);

HPLC retention time=7.25 min;

Pred. Mass=348.0301 (M$^+$+H, C$_{16}$H$_{11}$Cl$_2$N$_3$O$_2$);

Obs. Mass=348.0296 (M$^+$+H).

Example 8

Production of 4-chloro-1-(2,5-dichlorobenzyl)-2-(pyridin-3-yl)-1H-imidazole-5-carboxylic acid (Compound A88) (Scheme D)

[Chemical Formula 56]

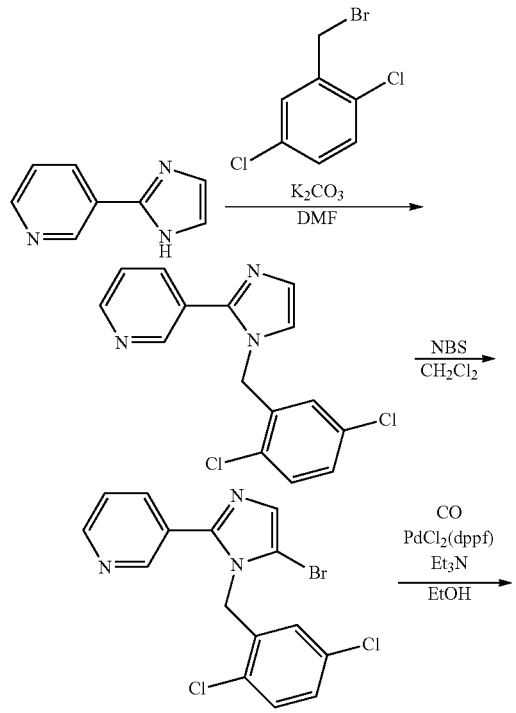

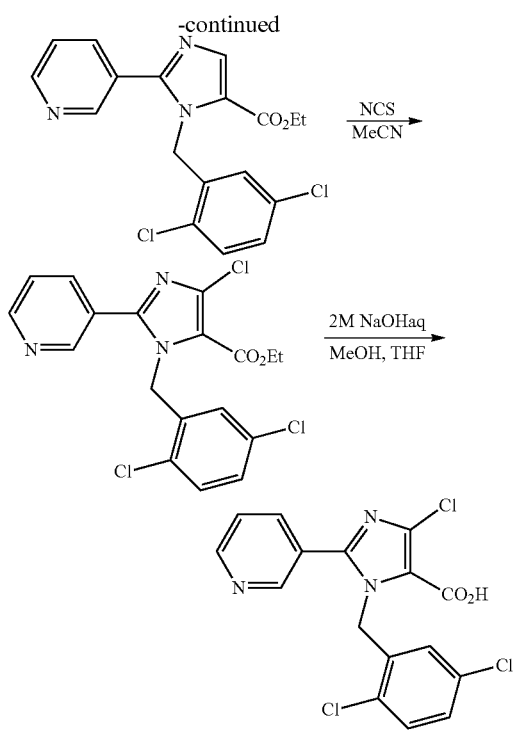

(1) In DMF (70 mL) was dissolved 3-(1H-imidazol-2-yl)pyridine (10 g, 68.9 mmol) which is publicly known through publication, potassium carbonate (19 g, 138 mmol) and 2,5-dichlorobenzyl bromide (19.83 g, 83 mmol) were added thereto, and the mixture was stirred at room temperature for 7 hours. After the reaction, water was added and the mixture was extracted twice with ethyl acetate (100 mL). After being washed with saturated aqueous sodium chloride, the organic layer was dried over anhydrous sodium sulfate. After concentrating the organic layer, the residue was purified by column chromatography to obtain 3-O-(2,5-dichlorobenzyl)-1H-imidazol-2-yl)pyridine (12.49 g):

$^1$H-NMR (DMSO-d$_6$) δ: 8.71 (1H, d, J=2.0 Hz), 8.58 (1H, dd, J=4.9, 1.5 Hz), 7.92 (1H, dt, J=8.1, 2.0 Hz), 7.52-7.36 (4H, m), 7.15 (1H, d, J=1.5 Hz), 6.81 (1H, d, J=2.4 Hz), 5.41 (2H, s);

ESI-MS m/z=304 (M$^+$+H).

(2) In dichloromethane (65 mL) was dissolved 3-(1-(2,5-dichlorobenzyl)-1H-imidazol-2-yl)pyridine (6.4 g, 21.1 mmol), N-bromosuccinimide (3.76 g, 21.1 mmol) was added thereto, and the mixture was stirred at room temperature for 16 hours. After the reaction, water was added and the mixture was extracted twice with dichloromethane (100 mL). After being washed with saturated aqueous sodium chloride, the organic layer was dried over anhydrous sodium sulfate. After concentrating the organic layer, the residue was purified by column chromatography to obtain 3-(5-bromo-1-(2,5-dichlorobenzyl)-1H-imidazol-2-yl)pyridine (3.5 g):

$^1$H-NMR (CDCl$_3$) δ: 8.67-8.63 (2H, m), 7.80 (1H, dt, J=7.8, 2.0 Hz), 7.40-7.33 (3H, m), 7.30-7.26 (1H, m), 6.64 (1H, s), 5.28 (2H, s);

ESI-MS m/z=382 (M$^+$+H).

(3) Under a nitrogen atmosphere, 3-(5-bromo-1-(2,5-dichlorobenzyl)-1H-imidazol-2-yl)pyridine (1.74 g, 4.54 mmol), PdCl$_2$ (dppf) (500 mg, 0.68 mmol), and triethylamine (5.4 mL, 39.1 mmol) were dissolved in ethanol (10 mL) and, after replacing the atmosphere with CO gas, the solution was stirred at 70° C. for 16 hours. After the reaction, the solvent was distilled away, water (20 mL) was added to the residue, and the mixture was extracted twice with ethyl acetate (30 mL). After being washed with saturated aqueous sodium chloride, the organic layer was dried over anhydrous sodium sulfate. After concentrating the organic layer, and the residue was purified by column chromatography to obtain ethyl 1-(2,5-dichlorobenzyl)-2-(pyridin-3-yl)-1H-imidazole-5-carboxylate (Compound A272, 1.2 g):

$^{1}$H-NMR (CDCl$_{3}$) δ: 8.72-8.67 (2H, m), 8.03 (1H, s), 7.82 (1H, td, J=5.0, 2.8 Hz), 7.39-7.34 (2H, m), 7.24 (1H, dd, J=8.8, 2.4 Hz), 6.59 (1H, d, J=2.4 Hz), 5.61 (2H, s), 4.28 (2H, q, J=7.2 Hz), 1.31 (3H, t, J=7.1 Hz);

ESI-MS m/z=376 (M$^{+}$+H).

(4) Ethyl 1-(2,5-dichlorobenzyl)-2-(pyridin-3-yl)-1H-imidazole-5-carboxylate (100 mg, 0.266 mmol) was dissolved in acetonitrile (0.5 mL), and N-chlorosuccinimide (71 mg, 0.532 mmol) was added thereto, and then the mixture was stirred at 60° C. for 2 hours. After the reaction, water (5 mL) was added and the mixture was extracted twice with ethyl acetate (5 mL). After being washed with saturated aqueous sodium chloride, the organic layer was dried over anhydrous sodium sulfate. After concentrating the organic layer, the residue was purified by column chromatography to obtain ethyl 4-chloro-1-(2,5-dichlorobenzyl)-2-(pyridin-3-yl)-1H-imidazole-5-carboxylate (Compound A273, 100 mg):

$^{1}$H-NMR (CDCl$_{3}$) δ: 8.72-8.67 (2H, m), 7.83 (1H, dt, J=8.1, 2.0 Hz), 7.40-7.35 (2H, m), 7.26 (1H, dd, J=8.8, 2.4 Hz), 6.70 (1H, d, J=2.0 Hz), 5.58 (2H, s), 4.30 (2H, q, J 7.2 Hz), 1.30 (3H, t, J=7.3 Hz);

ESI-MS m/z=410 (M$^{+}$+H).

(5) Ethyl 4-chloro-1-(2,5-dichlorobenzyl)-2-(pyridin-3-yl)-1H-imidazole-5-carboxylate (100 mg) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 3 hours. After the reaction, the reaction mixture was neutralized by the addition of 2 M hydrochloric acid (0.2 mL, 0.4 mmol) and was concentrated. The residue was purified by HPLC to obtain 4-chloro-1-(2,5-dichlorobenzyl)-2-(pyridin-3-yl)-1H-imidazole-5-carboxylic acid (Compound A88, 71 mg):

$^{1}$H-NMR (DMSO-d$_{6}$) δ: 13.57 (1H, s), 8.69-8.64 (2H, m), 7.88 (1H, dt, J=8.1, 2.0 Hz), 7.53-7.48 (2H, m), 7.39 (1H, dd, J=8.5, 2.7 Hz), 6.79 (1H, d, J=2.4 Hz), 5.57 (2H, s);

HPLC retention time=8.74 min;

Pred. Mass=381.9911 (M$^{+}$+H, C$_{16}$H$_{10}$Cl$_{3}$N$_{3}$O$_{2}$);

Obs. Mass=381.9908 (M$^{+}$+H).

Example 9

Production of 1-(2,5-dichlorobenzyl)-4-iodo-2-(pyridin-3-yl)-1H-imidazole-5-carboxylic acid (Compound A90) (Scheme F)

[Chemical Formula 57]

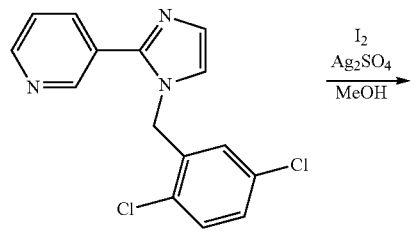

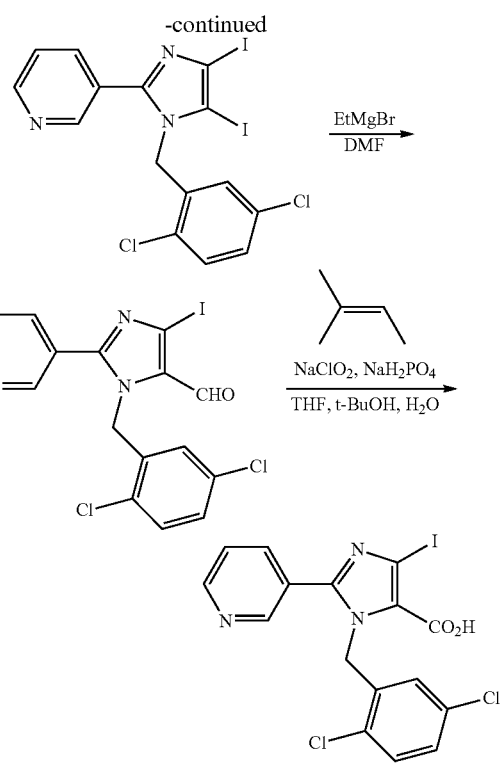

(1) In methanol (250 mL) was dissolved 3-(1-(2,5-dichlorobenzyl)-1H-imidazol-2-yl)pyridine (16.1 g, 52.9 mmol) obtained in Example 8, iodine (26.9 g, 106 mmol) and silver nitrate (16.5 g, 52.9 mmol) were added thereto, and the mixture was stirred at 50° C. for 1 hour. After allowing the reaction mixture to cool, iodine (13.4 g, 52.9 mmol) and silver nitrate (8.2 g, 26.4 mmol) were added, and the mixture was further stirred at 50° C. for 1 hour. After the reaction, the reaction mixture was filtered by using methanol and the filtrate was concentrated. To the residue were added aqueous sodium thiosulfate and aqueous sodium hydrogen carbonate, and the mixture was extracted twice with dichloromethane (100 mL). After being washed with saturated aqueous sodium chloride, the organic layer was dried over anhydrous sodium sulfate. After concentrating the organic layer, the residue was purified by column chromatography to obtain 3-(1-(2,5-dichlorobenzyl)-4,5-diiodo-1H-imidazol-2-yl)pyridine (5.1 g):

$^{1}$H-NMR (CDCl$_{3}$) δ: 8.67-8.62 (2H, m), 7.81 (1H, dt, J=8.0, 2.0 Hz), 7.40-7.27 (3H, m), 6.66 (1H, d, J=2.4 Hz), 5.32 (2H, s);

ESI-MS m/z=556 (M$^{+}$+H).

(2) Under a nitrogen atmosphere, 3-(1-(2,5-dichlorobenzyl)-4,5-diiodo-1H-imidazol-2-yl)pyridine (3.87 g, 6.96 mmol) was dissolved in DMF (130 mL) and, at 0° C., a 1 M solution (13.9 mL, 13.9 mmol) of EtMgBr in THF was added dropwise thereto over a period of 10 minutes. After being stirred as is for further 10 minutes, the mixture was further stirred at room temperature for 1 hour. Water was added to the reaction mixture and the mixture was extracted twice with ethyl acetate. After being washed with saturated aqueous sodium chloride, the organic layer was dried over anhydrous sodium sulfate. After concentrating the organic layer, the residue was purified by column chromatography to obtain 1-(2,5-di chlorobenzyl)-4-iodo-2-(pyridin-3-yl)-1H-imidazole-5-carbaldehyde (2.5 g):

$^1$H-NMR (CDCl$_3$) δ: 9.69 (1H, s), 8.74-8.68 (2H, m), 7.84 (1H, dt, J=8.1, 1.7 Hz), 7.42-7.36 (2H, m), 7.27-7.25 (1H, m), 6.63 (1H, d, J=2.0 Hz), 5.61 (2H, s);

ESI-MS m/z=458 (M$^+$+H).

(3) 1-(2,5-Dichlorobenzyl)-4-iodo-2-(pyridin-3-yl)-1H-imidazole-5-carbaldehyde (50 mg, 0.109 mmol) and 2-methyl-2-butene (23 mg, 0.33 mmol) were dissolved in a mixed solvent of THF (0.5 mL) and t-butanol (0.5 mL), and an aqueous solution (0.25 mL) of sodium chlorite (30 mg, 0.332 mmol) and sodium dihydrogen phosphate (51 mg, 0.327 mmol) was added dropwise thereto, and then the mixture was stirred at room temperature for 16 hours. After the reaction, saturated aqueous sodium chloride was added and the mixture was extracted twice with ethyl acetate (1 mL). The organic layer was dried over anhydrous sodium sulfate. After concentrating the organic layer, the residue was purified by HPLC to obtain 1-(2,5-dichlorobenzyl)-4-iodo-2-(pyridin-3-yl)-1H-imidazole-5-carboxylic acid (Compound A90, 14.2 mg):

$^1$H-NMR (DMSO-d$_6$) δ: 8.69-8.64 (2H, m), 7.90 (1H, dt, J=7.8, 2.0 Hz), 7.54-7.48 (2H, m), 7.39 (1H, dd, J=8.8, 2.4 Hz), 6.69 (1H, d, J=2.4 Hz), 5.57 (2H, s);

HPLC retention time=8.71 min;

Pred. Mass=473.9268 (M$^+$+H, C$_{16}$H$_{10}$Cl$_2$IN$_3$O$_2$);

Obs. Mass=473.9277 (M$^+$+H).

Example 10

Production of 1-(2,5-dichlorobenzyl)-4-phenyl-2-(pyridin-3-yl)-1H-imidazole-5-carboxylic acid (Compound A91) (Scheme F)

[Chemical Formula 58]

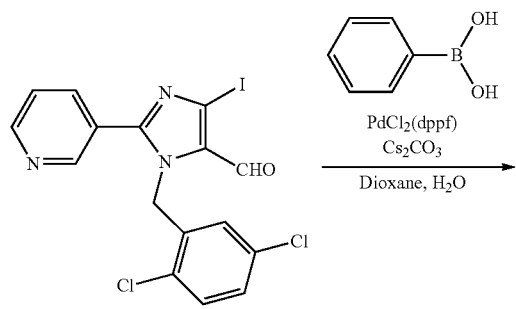

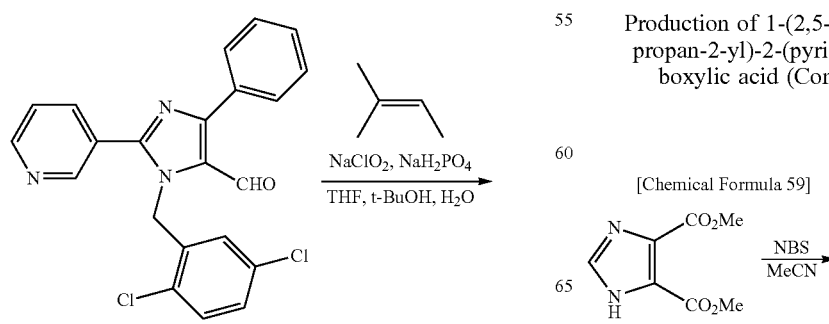

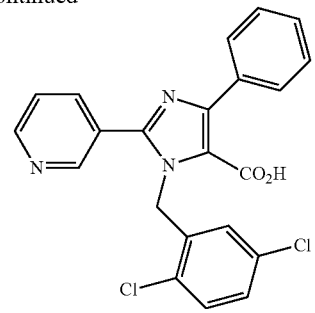

(1) Under a nitrogen atmosphere, 1-(2,5-dichlorobenzyl)-4-iodo-2-(pyridin-3-yl)-1H-imidazole-5-carbaldehyde (69 mg, 0.151 mmol), phenylboronic acid (22 mg, 0.180 mmol), PdCl$_2$(dppf) (11 mg, 0.015 mmol), and cesium carbonate (100 mg, 0.31 mmol) were dissolved in a mixed solvent of 1,4-dioxane (2 mL) and water (0.5 mL), and the solution was stirred at 100° C. for 1 hour. After the reaction, water (5 mL) was added and the mixture was extracted twice with ethyl acetate (5 mL). After being washed with saturated aqueous sodium chloride, the organic layer was dried over sodium sulfate. After concentrating the organic layer, the residue was purified by column chromatography to obtain 1-(2,5-dichlorobenzyl)-4-phenyl-2-(pyridin-3-yl)-1H-imidazole-5-carbaldehyde (48.3 mg):

ESI-MS m/z=408 (M$^+$+H).

(2) 1-(2,5-Dichlorobenzyl)-4-phenyl-2-(pyridin-3-yl)-1H-imidazole-5-carbaldehyde (48.3 mg, 0.118 mmol) and 2-methyl-2-butene (25 mg, 0.36 mmol) were dissolved in a mixed solvent of THF (0.5 mL) and t-butanol (0.5 mL), and an aqueous solution (0.25 mL) of sodium chlorite (32 mg, 0.354 mmol) and sodium dihydrogen phosphate (55 mg, 0.352 mmol) was added dropwise thereto, and then the mixture was stirred at room temperature for 16 hours. After the reaction, saturated aqueous sodium chloride was added and the mixture was extracted twice with ethyl acetate (1 mL). The organic layer was dried over sodium sulfate. After concentrating the organic layer, the residue was purified by HPLC to obtain 1-(2,5-dichlorobenzyl)-4-phenyl-2-(pyridin-3-yl)-1H-imidazole-5-carboxylic acid (Compound A91, 20 mg):

$^1$H-NMR (DMSO-d$_6$) δ: 8.73 (1H, s), 8.68 (1H, d, J=3.9 Hz), 7.95 (1H, d, J=8.0 Hz), 7.78-7.74 (2H, m), 7.54-7.50 (2H, m), 7.45-7.35 (4H, m), 6.73 (1H, d, J=2.0 Hz), 5.61 (2H, s);

HPLC retention time=9.08 min;

Pred. Mass=424.0614 (M$^+$+H, C$_{22}$H$_{15}$Cl$_2$N$_3$O$_2$);

Obs. Mass=424.0602 (M$^+$+H).

Example 11

Production of 1-(2,5-dichlorobenzyl)-4-(2-hydroxypropan-2-yl)-2-(pyridin-3-yl)-1H-imidazole-5-carboxylic acid (Compound A108) (Scheme A)

[Chemical Formula 59]

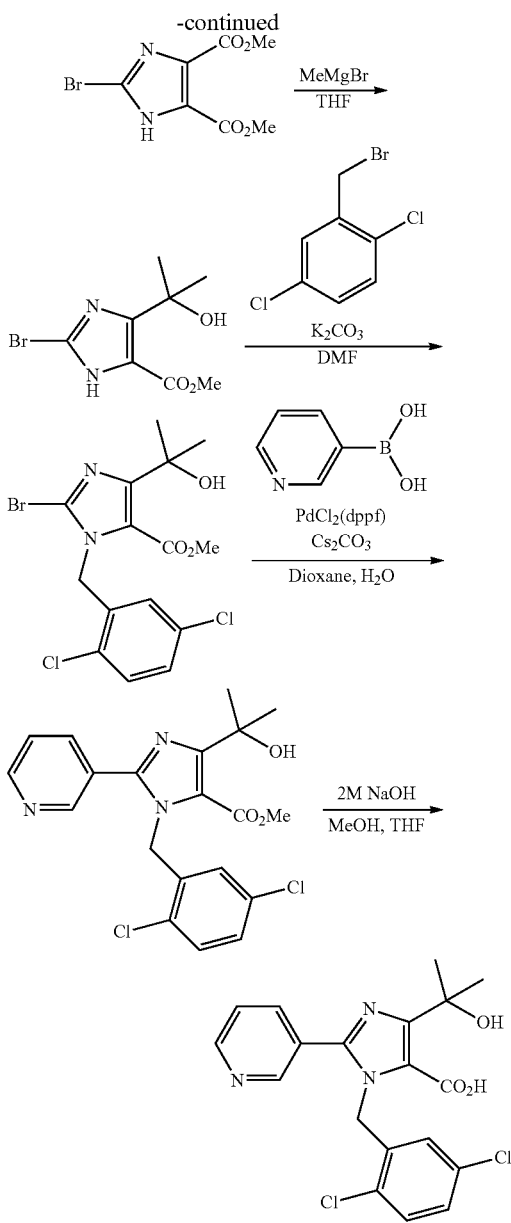

(1) Dimethyl 1H-imidazole-4,5-dicarboxylate (9.6 g, 52 mmol) was dissolved in acetonitrile (200 mL), and N-bromosuccinimide (13.92 g, 78 mmol) was added thereto, and then the mixture was stirred at 50° C. for 4 hours. After the reaction, water was added and the mixture was extracted twice with ethyl acetate. After being washed with saturated aqueous sodium thiosulfate and saturated aqueous sodium chloride, the organic layer was dried over anhydrous sodium sulfate. The organic layer was concentrated to obtain dimethyl 2-bromo-1H-imidazole-4,5-dicarboxylate (8.3 g). This material was used as is in the next reaction without further purification:

$^1$H-NMR (CDCl$_3$) δ: 10.56 (1H, s), 3.96 (6H, s);
ESI-MS m/z=263 (M$^+$+H).

(2) Under a nitrogen atmosphere, dimethyl 2-bromo-1H-imidazole-4,5-dicarboxylate (2 g, 7.6 mmol) was dissolved in THF (38 mL) and, at −10° C., a 1 M solution (30 mL) of EtMgBr in THF was added dropwise thereto over a period of 10 minutes. After allowing the mixture to react for further 30 minutes, the reaction was quenched by the addition of aqueous ammonium chloride. Water was added and the mixture was extracted twice with ethyl acetate. After being washed with saturated aqueous sodium chloride, the organic layer was dried over anhydrous sodium sulfate. After concentrating the organic layer, the residue was purified by column chromatography to obtain methyl 2-bromo-4-(2-hydroxypropan-2-yl)-1H-imidazole-5-dicarboxylate (830 mg):

$^1$H-NMR (CDCl$_3$) δ: 9.78 (1H, s), 3.93 (3H, s), 1.68 (3H, s), 1.61 (3H, s);
ESI-MS m/z=263 (M$^+$+H).

(3) Methyl 2-bromo-4-(2-hydroxypropan-2-yl)-1H-imidazole-4,5-dicarboxylate (830 mg, 3.15 mmol) was dissolved in DMF (3 mL), and potassium carbonate (872 mg, 6.31 mmol) and 2,5-dichlorobenzyl bromide (908 mg, 3.79 mmol) were added thereto, and then the mixture was stirred at 90° C. for 1 hour. After the reaction, water was added and the mixture was extracted twice with ethyl acetate. After being washed with saturated aqueous sodium chloride, the organic layer was dried over anhydrous sodium sulfate. After concentrating the organic layer, the residue was purified by column chromatography to obtain methyl 2-bromo-1-(2,5-dichlorobenzyl)-4-(2-hydroxypropan-2-yl)-1H-imidazole-5-carboxylate (673 mg):

$^1$H-NMR (CDCl$_3$) δ: 7.37 (1H, d, J=8.8 Hz), 7.24 (1H, d, J=8.8 Hz), 6.46 (1H, s), 5.55 (2H, s), 3.77 (3H, s), 1.65 (6H, s);
ESI-MS m/z=421 (M$^+$+H).

(4) Methyl 2-bromo-1-(2,5-dichlorobenzyl)-4-(2-hydroxypropan-2-yl)-1H-imidazole-5-carboxylate (100 mg, 0.237 mmol), pyridin-3-ylboronic acid (58.2 mg, 0.474 mmol), cesium carbonate (154 mg, 0.474 mmol), and PdCl$_2$ (dppf) (34.7 mg, 0.047 mmol) were dissolved in a mixed solvent of dioxane (1 mL) and water (0.2 mL). Under a nitrogen atmosphere, the solution was heated and stirred at 100° C. for 3 hours. After cooling, the reaction mixture was concentrated under reduced pressure and ethyl acetate was added to the residue. The organic layer was washed with water and saturated aqueous sodium chloride, dried over anhydrous magnesium sulfate, and subsequently concentrated under reduced pressure. The residue was purified by column chromatography to obtain methyl 1-(2,5-dichlorobenzyl)-4-(2-hydroxypropan-2-yl)-2-(pyridin-3-yl)-1H-imidazole-5-carboxylate (Compound A274, 71 mg):

ESI-MS m/z=420 (M$^+$+H).

(5) Methyl 1-(2,5-dichlorobenzyl)-4-(2-hydroxypropan-2-yl)-2-(pyridin-3-yl)-1H-imidazole-5-carboxylate (71 mg, 0.169 mmol) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 2 hours. After the reaction, the reaction mixture was neutralized by the addition of 2 M hydrochloric acid (0.2 mL, 0.4 mmol) and was concentrated. The residue was purified by HPLC to obtain 1-(2,5-dichlorobenzyl)-4-(2-hydroxypropan-2-yl)-2-(pyridin-3-yl)-1H-imidazole-5-carboxylic acid (Compound A108, 61 mg):

$^1$H-NMR (DMSO-d$_6$) δ: 8.71-8.65 (2H, m), 7.91 (1H, d, J=7.8 Hz), 7.56-7.48 (2H, m), 7.39 (1H, dd, J=8.5, 2.2 Hz), 6.56 (1H, d, J=1.5 Hz), 5.59 (2H, s), 1.62 (6H, s);
HPLC retention time=8.16 min;
Pred. Mass=406.0720 (M$^+$+H, C$_{19}$H$_{17}$Cl$_2$N$_3$O$_3$);
Obs. Mass=406.0725 (M$^+$+H).

Example 12

Production of 3-(1-(2,5-dichlorobenzyl)-5-(1H-tetrazol-5-yl)-1H-imidazol-2-yl)pyridine (Compound A110) (Scheme G)

[Chemical Formula 60]

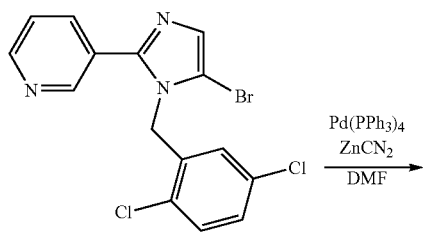

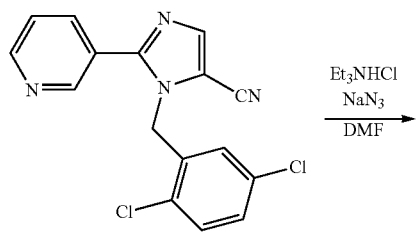

(1) Under a nitrogen atmosphere, 3-(5-bromo-1-(2,5-dichlorobenzyl)-1H-imidazol-2-yl)pyridine (300 mg, 0.784 mmol) obtained in Example 8, $ZnCN_2$ (138 mg, 1.174 mmol), tetrakis(triphenylphosphine)palladium (272 mg, 0.117 mmol) were dissolved in DMF (3 mL), and the mixture was stirred at 100° C. for 16 hours. After the reaction, water was added and the mixture was extracted twice with ethyl acetate (10 mL). After being washed with saturated aqueous sodium chloride, the organic layer was dried over anhydrous sodium sulfate. After concentrating the organic layer, the residue was purified by column chromatography to obtain 1-(2,5-dichlorobenzyl)-2-(pyridin-3-yl)-1H-imidazole-5-carbonitrile (83 mg):

$^1$H-NMR (CDCl$_3$) δ: 8.74-8.71 (2H, m), 7.92 (1H, s), 7.86 (1H, dt, J=8.3, 2.0 Hz), 7.43-7.38 (2H, m), 7.31 (1H, dd, J=8.3, 2.4 Hz), 6.67 (1H, d, J=2.4 Hz), 5.41 (2H, s);

ESI-MS m/z=329 (M$^+$+H).

(2) In DMF (1 mL) was dissolved 1-(2,5-dichlorobenzyl)-2-(pyridin-3-yl)-1H-imidazole-5-carbonitrile (83 mg, 0.252 mmol), and triethylamine hydrochloride (34.7 mg, 0.252 mmol) and sodium azide (82 mg, 1.26 mmol) were added thereto, and then the mixture was stirred at 140° C. for 3 hours. After filtering the reaction solution, the filtrate was purified by HPLC to obtain 3-(1-(2,5-dichlorobenzyl)-5-(1H-tetrazol-5-yl)-1H-imidazol-2-yl)pyridine (Compound A110, 80 mg):

$^1$H-NMR (DMSO-d$_6$) δ: 8.75 (1H, d, J=2.0 Hz), 8.69-8.65 (1H, m), 8.00-7.96 (2H, m), 7.56-7.48 (2H, m), 7.35 (1H, dd, J=8.3, 2.4 Hz), 6.51 (1H, d, J=2.4 Hz), 5.83 (2H, s);

HPLC retention time=7.97 min;

Pred. Mass=372.0526 (M$^+$+H, C$_{16}$H$_{11}$Cl$_2$N$_7$);

Obs. Mass=372.0527 (M$^+$+H).

Example 13

Production of 1-(2,5-dichlorobenzyl)-4-methyl-N-(methylsulfonyl)-2-(pyridin-3-yl)-1H-imidazole-5-carboxamide (Compound A111) (Scheme A)

[Chemical Formula 61]

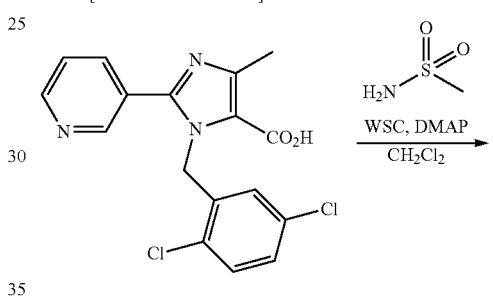

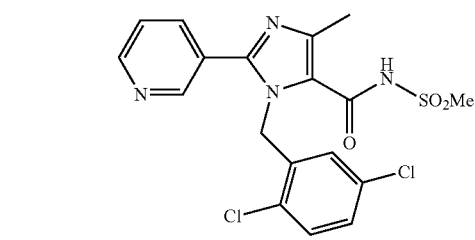

(1) In dichloromethane (1 mL) were dissolved 1-(2,5-dichlorobenzyl)-4-methyl-2-(pyridin-3-yl)-1H-imidazole-5-carboxlic acid (30 mg, 0.083 mmol), methanesulfonamide (15.76 mg, 0.166 mmol) and DMAP (20.24 mg, 0.166 mmol), 1-ethyl-3-(3-dimethylaminopropyl)carbodiimide hydrochloride (WSC) (31.8 mg, 0.166 mmol) was added thereto, and the mixture was stirred at room temperature for 16 hours. Purification by HPLC was performed to obtain 1-(2,5-dichlorobenzyl)-4-methyl-N-(methylsulfonyl)-2-(pyridin-3-yl)-1H-imidazole-5-carboxamide (Compound A111, 18 mg):

$^1$H-NMR (DMSO-d$_6$) δ: 8.74 (1H, d, J=2.0 Hz), 8.69 (1H, dd, J=4.9, 2.0 Hz), 7.99 (1H, dt, J=8.0, 1.8 Hz), 7.58-7.53 (1H, m), 7.46 (1H, d, J=8.3 Hz), 7.38 (1H, dd, J=8.5, 2.7 Hz), 6.78 (1H, d, J=2.4 Hz), 5.50 (2H, s), 3.13 (3H, s), 2.45 (3H, s);

HPLC retention time=7.76 min;

Pred. Mass=439.0393 (M$^+$+H, C$_{18}$H$_{16}$Cl$_2$N$_4$O$_3$S);

Obs. Mass=439.0397 (M$^+$+H).

Example 14

Production of 2-(5-fluoropyridin-3-yl)-4-methyl-1-(naphthalen-1-ylmethyl)-1H-imidazole-5-carboxylic acid (Compound A119) (Scheme A)

[Chemical Formula 62]

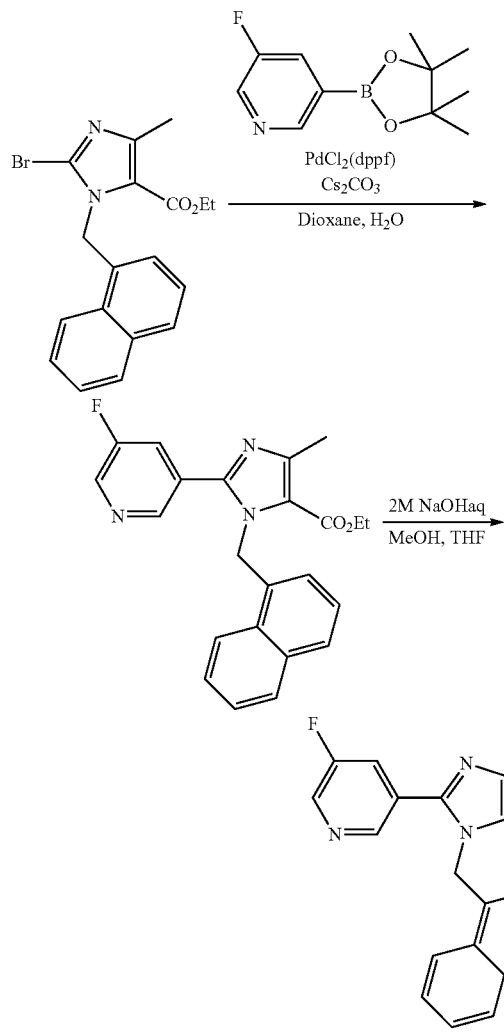

(1) Ethyl 2-bromo-4-methyl-1-(naphthalen-1-ylmethyl)-1H-imidazole-5-carboxylate (1.26 g, 3.39 mmol) described in Example 1 (2), 3-fluoro-5-(4,4,5,5-tetramethyl-1,3,2-dioxaborolan-2-yl)pyridine (800 mg, 3.59 mmol), PdCl$_2$ (dppf) (496 mg, 0.678 mmol), and cesium carbonate (2.2 g, 6.78 mmol) were dissolved in a mixed solvent of 1,4-dioxane (9 mL) and water (2 mL), and the solution was stirred at 100° C. for 3 hours under a nitrogen atmosphere. After the reaction, water (50 mL) was added and the mixture was extracted twice with ethyl acetate (50 mL). After being washed with saturated aqueous sodium chloride, the organic layer was dried over anhydrous sodium sulfate. After concentrating the organic layer, the residue was purified by column chromatography to obtain ethyl 2-(5-fluoropyridin-3-yl)-4-methyl-1-(naphthalen-1-ylmethyl)-1H-imidazole-5-carboxylate (Compound A275, 1.2 g):

$^1$H-NMR (CDCl$_3$) δ: 8.53 (1H, s), 8.44 (1H, d, J=2.9 Hz), 7.94-7.85 (2H, m), 7.80 (1H, d, J=8.3 Hz), 7.63-7.53 (3H, m), 7.38 (1H, t, J=7.8 Hz), 6.70 (1H, d, J=6.8 Hz), 6.06 (2H, s), 4.14 (2H, q, J=7.2 Hz), 2.67 (3H, s), 1.09 (3H, t, J=7.2 Hz); ESI-MS m/z=390 (M$^+$+H).

(2) Ethyl 2-(5-fluoropyridin-3-yl)-4-methyl-1-(naphthalen-1-ylmethyl)-1H-imidazole-5-carboxylate (1.2 g, 3.08 mmol) was dissolved in a mixed solvent of THF (12 mL) and methanol (3 mL), 2 M aqueous sodium hydroxide (3 mL, 6 mmol) was added thereto, and the mixture was stirred at 40° C. for 3 hours. After the reaction, the reaction mixture was neutralized by the addition of 2 M hydrochloric acid (3 mL, 6 mmol) and was subsequently concentrated. The residue was purified by a conventional method to obtain 2-(5-fluoropyridin-3-yl)-4-methyl-1-(naphthalen-1-ylmethyl)-1H-imidazole-5-carboxylic acid (Compound A119, 648 mg):

$^1$H-NMR (DMSO-d$_6$) δ: 12.95 (1H, s), 8.58 (1H, d, J=2.9 Hz), 8.48 (1H, s), 8.06-7.95 (2H, m), 7.85-7.80 (2H, m), 7.61-7.57 (2H, m), 7.40 (1H, t, J=7.6 Hz), 6.52 (1H, d, J=7.3 Hz), 6.12 (2H, s), 2.53 (3H, s);

HPLC retention time=8.53 min;

Pred. Mass=362.1299 (M$^+$+H, C$_{21}$H$_{16}$FN$_3$O$_2$);

Obs. Mass=362.1300 (M$^+$+H).

Example 15

Production of 2-(5-chloropyridin-3-yl)-1-(2,5-dichlorobenzyl)-4-(hydroxymethyl)-1H-imidazole-5-carboxylic acid (Compound A191) (Scheme E)

[Chemical Formula 63]

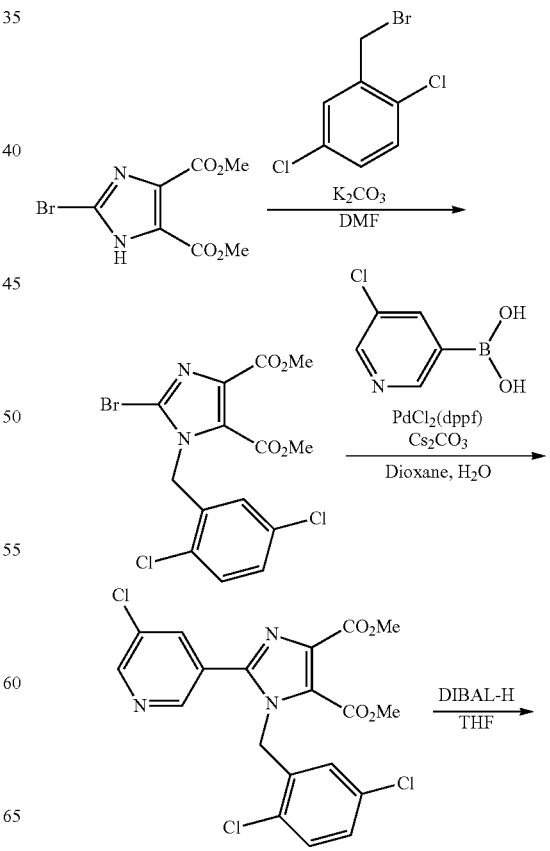

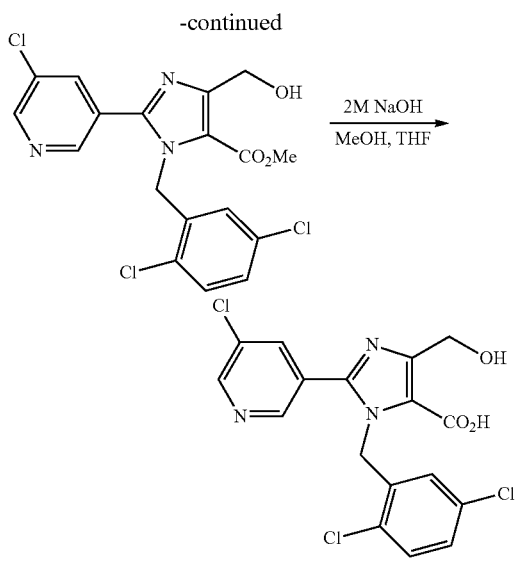

(1) Dimethyl 2-bromo-1H-imidazole-4,5-carboxylate (1.1 g, 4.18 mmol) obtained in Example 11 was dissolved in DMF (4 mL), and potassium carbonate (1.15 g, 8.36 mmol) and 2,5-dichlorobenzyl bromide (1.3 g, 5.44 mmol) were added thereto, and then the mixture was stirred at 100° C. for 2 hours. After the reaction, water was added and the mixture was extracted twice with ethyl acetate. After being washed with saturated aqueous sodium chloride, the organic layer was dried over anhydrous sodium sulfate. After concentrating the organic layer, the residue was purified by column chromatography to obtain 2-bromo-1-(2,5-dichlorobenzyl)-1H-imidazole-4,5-dicarboxylate (1.54 g):

$^1$H-NMR (CDCl$_3$) δ: 7.36 (1H, d, J=8.8 Hz), 7.24 (1H, dd, J=8.8, 3.0 Hz), 6.52 (1H, d, J=2.4 Hz), 5.54 (2H, s), 3.96 (3H, s), 3.85 (3H, s);

ESI-MS m/z=421 (M$^+$+H).

(2) Dimethyl 2-bromo-1-(2,5-dichlorobenzyl)-1H-imidazole-4,5-dicarboxylate (300 mg, 0.711 mmol), (5-chloropyridyn-3-yl)boronic acid (244 mg, 1.422 mmol), cesium carbonate (463 mg, 1.422 mmol) and PdCl$_2$ (dppf) (104 mg, 0.142 mmol) were dissolved in a mixed solvent of dioxane (2 mL) and water (0.5 mL). The solution was heated and stirred at 100° C. for 3 hours under a nitrogen atmosphere. After cooling, the reaction mixture was concentrated under reduced pressure. To the residue was added ethyl acetate and the organic layer was washed with water and saturated aqueous sodium chloride. After being dried over anhydrous magnesium sulfate, the organic layer was concentrated under reduced pressure. The residue was purified by column chromatography to obtain dimethyl 2-(5-chloropyridin-3-yl)-1-(2,5-dichlorobenzyl)-1H-imidazole-4,5-dicarboxylate (Compound A276, 168 mg):

$^1$H-NMR (CDCl$_3$) δ: 8.66 (1H, d, J=2.0 Hz), 8.50 (1H, d, J=2.0 Hz), 7.91 (1H, t, J=2.0 Hz), 7.36 (1H, d, J=8.3 Hz), 7.29-7.26 (1H, in), 6.72 (1H, d, J=2.4 Hz), 5.51 (2H, s), 3.99 (3H, s), 3.86 (3H, s);

ESI-MS m/z=454 (M$^+$+H).

(3) Dimethyl 2-(5-chloropyridin-3-yl)-1-(2,5-dichlorobenzyl)-1H-imidazole-4,5-dicarboxylate (168 mg, 0.369 mmol) was dissolved in THF (3 mL), a 1 M solution of diisobutylaluminum hydride (DIBAL-H) (0.739 mL, 0.739 mmol) was added dropwise thereto over a period of 5 minutes at −40° C. under a nitrogen atmosphere, and the mixture was stirred as is for 5 hours. After being allowed to warm to room temperature, the reaction was quenched with aqueous ammonium chloride, followed by the addition of water, and the mixture was extracted twice with ethyl acetate. After being washed with saturated aqueous sodium chloride, the organic layer was dried over anhydrous sodium sulfate. After concentrating the organic layer, the residue was purified by column chromatography to obtain methyl 2-(5-chloropyridin-3-yl)-1-(2,5-dichlorobenzyl)-4-(hydroxymethyl)-1H-imidazole-5-carboxylate (Compounds A277, 57 mg):

$^1$H-NMR (CDCl$_3$) δ: 8.65 (1H, d, J=2.4 Hz), 8.50 (1H, d, J=2.0 Hz), 7.91 (1H, t, J=2.2 Hz), 7.39 (1H, d, J=8.8 Hz), 7.27 (1H, dd, J=8.3, 2.4 Hz), 6.63 (1H, d, J=2.4 Hz), 5.59 (2H, s), 4.99-4.96 (2H, m), 3.85 (3H, s), 3.21 (1H, t, J=5.6 Hz);

ESI-MS m/z=426 (M$^+$+H).

(4) Methyl 2-(5-chloropyridin-3-yl)-1-(2,5-dichlorobenzyl)-4-(hydroxymethyl)-1H-imidazole-5-carboxylate (57 mg, 0.134 mmol) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 2 hours. After the reaction, the reaction mixture was neutralized by the addition of 2 M hydrochloric acid (0.2 mL, 0.4 mmol) and was concentrated. The residue was purified by HPLC to obtain 2-(5-chloropyridin-3-yl)-1-(2,5-dichlorobenzyl)-4-(hydroxymethyl)-1H-imidazole-5-carboxylic acid (Compound A191, 35 mg):

$^1$H-NMR (DMSO-d$_6$) δ: 8.72 (1H, d, J=2.4 Hz), 8.56 (1H, d, J=2.0 Hz), 8.04 (1H, t, J=2.0 Hz), 7.51 (1H, d, J=8.8 Hz), 7.39 (1H, dd, J=8.3, 2.4 Hz), 6.60 (1H, d, J=2.4 Hz), 5.64 (2H, s), 4.71 (2H, s); HPLC retention time=8.81 min; Pred. Mass=412.0017 (M$^+$+H, C$_{17}$H$_{12}$Cl$_3$N$_3$O$_3$); Obs. Mass=412.0018 (M$^+$+H).

Example 16

Production of 2-(5-chloropyridin-3-yl)-1-(2,5-dichlorobenzyl)-4-((diethylamino)methyl)-1H-imidazole-5-carboxylic acid (Compound A193) (Scheme E)

[Chemical Formula 64]

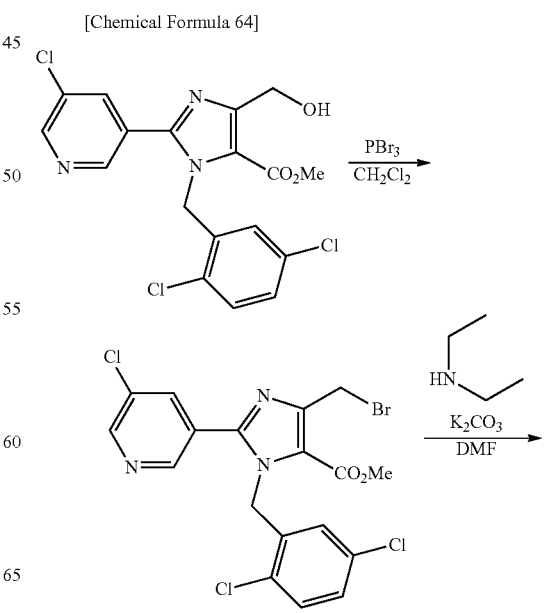

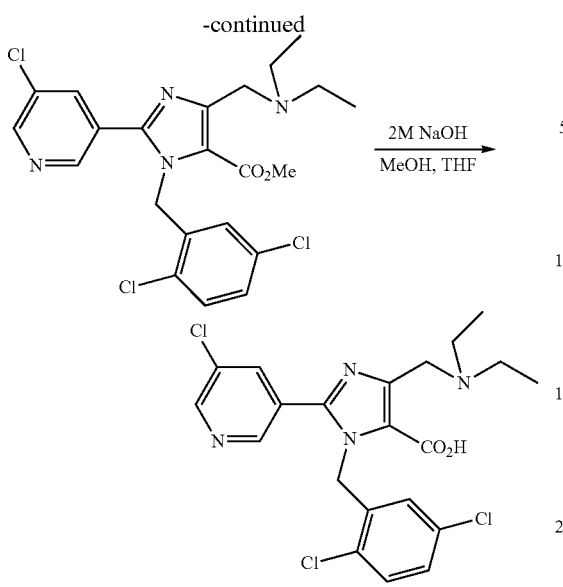

(1) Methyl 2-(5-chloropyridin-3-yl)-1-(2,5-dichlorobenzyl)-4-(hydroxymethyl)-1H-imidazole-5-carboxylate (500 mg, 1.17 mmol) was dissolved in dichloromethane (5 mL), and tribromophosphine (317 mg, 1.17 mmol) was added thereto, and then the mixture was stirred at room temperature for 2 hours. After the reaction, water was added and the mixture was extracted twice with ethyl acetate. After being washed with saturated aqueous sodium chloride, the organic layer was dried over anhydrous sodium sulfate. The organic layer was concentrated to obtain methyl 4-(bromomethyl)-2-(5-chloropyridin-3-yl)-1-(2,5-dichlorobenzyl)-1H-imidazole-5-carboxylate (500 mg). This material was used as is for the next reaction without further purification.

(2) Methyl 4-(bromomethyl)-2-(5-chloropyridin-3-yl)-1-(2,5-dichlorobenzyl)-1H-imidazole-5-carboxylate (90 mg, 0.184 mmol) was dissolved in DMF (1 mL), and potassium carbonate (50 mg, 0.368 mmol) and diethylamine (26.9 mg, 0.368 mmol) were added thereto, and then the mixture was stirred at 40° C. for 3 hours. After the reaction, water was added, the reaction mixture was extracted twice with ethyl acetate, and the organic layer was dried over anhydrous sodium sulfate. The organic layer was concentrated to obtain methyl 2-(5-chloropyridin-3-yl)-1-(2,5-dichlorobenzyl)-4-((diethylamino)methyl)-1H-imidazole-5-carboxylate (Compound A278, 100 mg). This material was used as is for the next reaction without further purification:
ESI-MS m/z=481 (M$^+$+H).

(3) Methyl 2-(5-chloropyridin-3-yl)-1-(2,5-dichlorobenzyl)-4-((diethylamino)methyl)-1H-imidazole-5-carboxylate (100 mg) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 2 hours. After the reaction, the reaction mixture was neutralized by the addition of 2 M hydrochloric acid (0.2 mL, 0.4 mmol) and was concentrated. The residue was purified by HPLC to obtain 2-(5-chloropyridin-3-yl)-1-(2,5-dichlorobenzyl)-4-((diethylamino)methyl)-1H-imidazole-5-carboxylic acid (Compound A193, 55 mg):
$^1$H-NMR (DMSO-d$_6$) δ: 9.58 (1H, s), 8.76 (1H, d, J=2.4 Hz), 8.61 (1H, d, J=2.0 Hz), 8.10 (1H, t, J=2.2 Hz), 7.51 (1H, d, J=8.8 Hz), 7.39 (1H, dd, J=8.3, 2.4 Hz), 6.69 (1H, d, J=2.4 Hz), 5.70 (2H, s), 4.60 (2H, d, J=4.4 Hz), 3.35-3.19 (4H, m), 1.27 (6H, t, J=7.3 Hz);

HPLC retention time=8.55 min;
Pred. Mass=467.0803 (M$^+$+H, C$_{21}$H$_{21}$Cl$_3$N$_4$O$_2$);
Obs. Mass=467.0806 (M$^F$+H).

Example 17

Production of 2-(5-bromopyridin-3-yl)-1-(2,5-dichlorobenzyl)-1H-imidazole-5-carboxylic acid (Compound A205) (Scheme C)

[Chemical Formula 65]

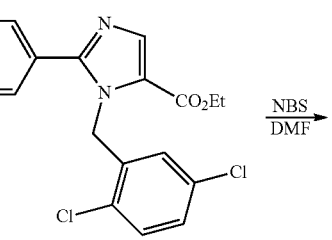
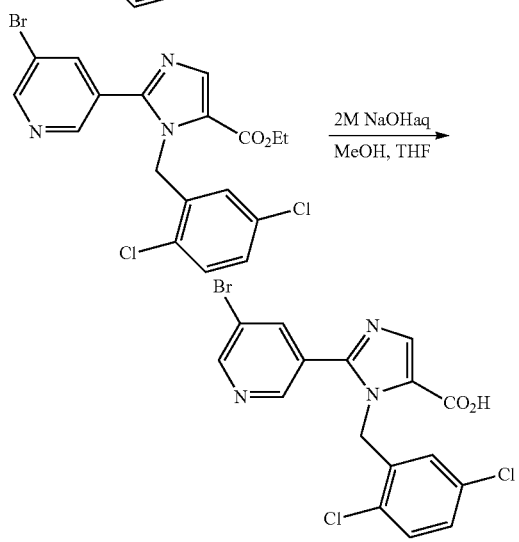

(1) Ethyl 1-(2,5-dichlorobenzyl)-2-(pyridin-3-yl)-1H-imidazole-5-carboxylate (50 mg, 0.133 mmol) was dissolved in DMF (1 mL), and N-bromosuccinimide (48 mg, 0.266 mmol) was added thereto, and then the mixture was stirred at 100° C. for 2 hours. After the reaction, water (5 mL) was added and the mixture was extracted twice with ethyl acetate (5 mL). After being washed with saturated aqueous sodium chloride, the organic layer was dried over sodium sulfate. After concentrating the organic layer, the residue was purified by column chromatography to obtain ethyl 2-(5-bromopyridin-3-yl)-1-(2,5-dichlorobenzyl)-1H-imidazole-5-carboxylate (Compound A279, 39 mg):
$^1$H-NMR (CDCl$_3$) δ: 8.74 (1H, d, J=2.0 Hz), 8.53 (1H, d, J=1.5 Hz), 8.05-8.01 (2H, m), 7.38 (1H, d, J=8.8 Hz), 7.25 (1H, dd, J=9.0, 2.2 Hz), 6.59 (1H, d, J=2.0 Hz), 5.63 (2H, s), 4.29 (2H, q, J=7.2 Hz), 1.32 (3H, t, J=7.3 Hz); ESI-MS m/z=454 (M$^+$+H).

(2) Ethyl 2-(5-bromopyridin-3-yl)-1-(2,5-dichlorobenzyl)-1H-imidazole-5-carboxylate (39 mg) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 3 hours. After the reaction, the reaction mixture was neutralized by the addition of 2 M hydrochloric acid (0.2 mL, 0.4 mmol) and was concentrated. The residue was purified by HPLC to obtain 2-(5-bromopyridin-3-yl)-1-(2,5-dichlorobenzyl)-1H-imidazole-5-carboxylic acid (Compound A205, 23 mg):

$^1$H-NMR (DMSO-$d_6$) δ: 13.23 (1H, s), 8.79 (1H, d, J=2.0 Hz), 8.61 (1H, d, J=2.0 Hz), 8.15 (1H, t, J=2.2 Hz), 7.93 (1H, s), 7.51 (1H, d, J=8.8 Hz), 7.38 (1H, dd, J=8.3, 2.4 Hz), 6.56 (1H, d, J=2.4 Hz), 5.70 (2H, s);

HPLC retention time=9.99 min;

Pred. Mass=425.9406 (M$^+$+H, C$_{16}$H$_{10}$BrCl$_2$N$_3$O$_2$);

Obs. Mass=425.9404 (M$^+$+H).

Example 18

Production of 2-(5-chloropyridin-3-yl)-1-(2,5-dichlorobenzyl)-4-(difluoromethyl)-1H-imidazole-5-carboxylic acid (Compound A207) (Scheme E)

[Chemical Formula 66]

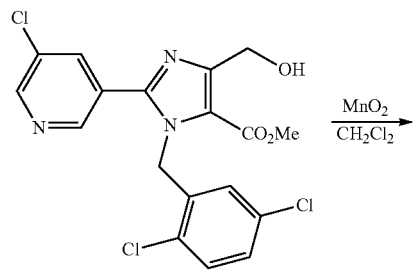

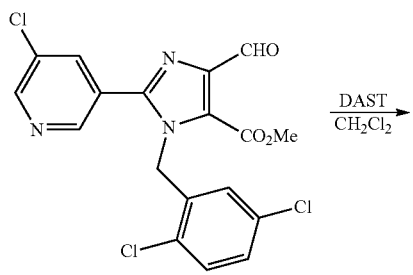

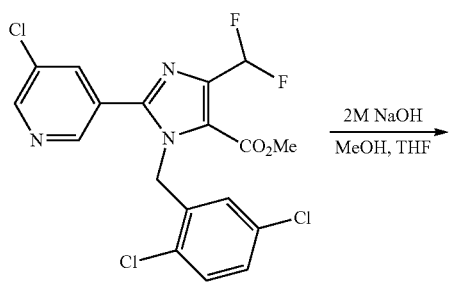

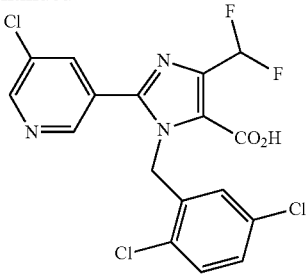

(1) Methyl 2-(5-chloropyridin-3-yl)-1-(2,5-dichlorobenzyl)-4-(hydroxymethyl)-1H-imidazole-5-carboxylate (620 mg, 1.45 mmol) was dissolved in dichloromethane (10 mL), and manganese dioxide (1.426 g, 16.41 mmol) was added thereto, and then the mixture was stirred at room temperature for 96 hours. After the reaction, the reaction mixture was filtered through celite and the residue was washed with dichloromethane. After concentrating the solution, the residue was purified by column chromatography to obtain methyl 2-(5-chloropyridin-3-yl)-1-(2,5-dichlorobenzyl)-4-formyl-1H-imidazole-5-carboxylate (413 mg):

$^1$H-NMR (CDCl$_3$) δ: 10.51 (1H, s), 8.68 (1H, d, J=2.4 Hz), 8.50 (1H, d, J=2.0 Hz), 7.98 (1H, t, J=2.2 Hz), 7.40 (1H, d, J=8.3 Hz), 7.29 (1H, dd, J=8.8, 2.4 Hz), 6.59 (1H, d, J=2.4 Hz), 5.66 (2H, s), 3.97 (3H, s); ESI-MS m/z=424 (M$^+$+H).

(2) Under a nitrogen atmosphere, methyl 2-(5-chloropyridin-3-yl)-1-(2,5-dichlorobenzyl)-4-formyl-1H-imidazole-5-carboxylate (100 mg, 0.235 mmol) was dissolved in dichloromethane (1 mL), and diethylaminosulfur trifluoride (DAST) (49.3 mg, 0.306 mmol) was added thereto, and then the mixture was stirred at room temperature for 6 hours. After the reaction, water was added, followed by the addition of an aqueous sodium hydrogen carbonate solution, and the mixture was extracted twice with ethyl acetate. After being washed with saturated aqueous sodium chloride, the organic layer was dried over sodium sulfate. After concentrating the organic layer, the residue was purified by column chromatography to obtain methyl 2-(5-chloropyridin-3-yl)-1-(2,5-dichlorobenzyl)-4-(difluoromethyl)-1H-imidazole-5-carboxylate (Compound A280, 86 mg):

$^1$H-NMR (CDCl$_3$) δ: 8.67 (1H, d, J=2.4 Hz), 8.49 (1H, d, J=2.0 Hz), 7.95 (1H, t, J=2.2 Hz), 7.39 (1H, d, J=8.8 Hz), 7.28 (1H, dd, J=8.8, 2.2 Hz), 7.21 (1H, t, J=54.1 Hz), 6.60 (1H, d, J=2.4 Hz), 5.63 (2H, s), 3.91 (3H, s); ESI-MS m/z=446 (M$^+$+H).

(3) Methyl 2-(5-chloropyridin-3-yl)-1-(2,5-dichlorobenzyl)-4-(difluoromethyl)-1H-imidazole-5-carboxylate (86 mg) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 7 hours. After the reaction, the reaction mixture was neutralized with 2 M hydrochloric acid (0.2 mL, 0.4 mmol) and was concentrated. The residue was purified by HPLC to obtain 2-(5-chloropyridin-3-yl)-1-(2,5-dichlorobenzyl)-4-(difluoromethyl)-1H-imidazole-5-carboxylic acid (Compound A207, 42 mg):

$^1$H-NMR (DMSO-$d_6$) δ: 14.16 (1H, s), 8.75 (1H, d, J=2.4 Hz), 8.58 (1H, d, J=2.0 Hz), 8.07 (1H, t, J=2.2 Hz), 7.53-7.20 (3H, in), 6.75 (1H, d, J=2.4 Hz), 5.66 (2H, s);

HPLC retention time=11.04 min;

Pred. Mass=431.9879 (M$^+$+H, C$_{17}$H$_{10}$Cl$_3$F$_2$N$_3$O$_2$);

Obs. Mass=431.9878 (M$^+$+H).

Example 19

Production of 2-(5-chloropyridin-3-yl)-1-(2,5-dichlorobenzyl)-4-ethynyl-1H-imidazole-5-carboxylic acid (Compound A209) (Scheme E)

[Chemical Formula 67]

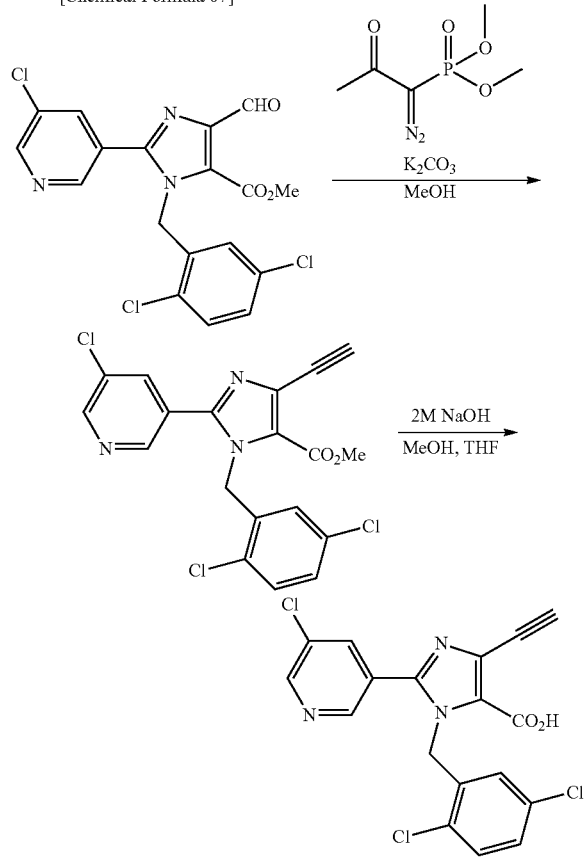

(1) Methyl 2-(5-chloropyridin-3-yl)-1-(2,5-dichlorobenzyl)-4-formyl-1H-imidazole-5-carboxylate (70 mg, 0.165 mmol) was dissolved in methanol (2 mL), and potassium carbonate (45.6 mg, 0.33 mmol) and dimethyl (1-diazo-2-oxopropyl) phosphonate (44.3 mg, 0.231 mmol) were added thereto, and then the mixture was stirred at room temperature for 16 hours. After the reaction, water was added and the mixture was extracted twice with ethyl acetate. After being washed with saturated aqueous sodium chloride, the organic layer was dried over sodium sulfate. After concentrating the organic layer, the residue was purified by column chromatography to obtain methyl 2-(5-chloropyridin-3-yl)-1-(2,5-dichlorobenzyl)-4-ethynyl-1H-imidazole-5-carboxylate (Compound A281, 51 mg):

ESI-MS m/z=420 (M$^+$+H).

(2) Methyl 2-(5-chloropyridin-3-yl)-1-(2,5-dichlorobenzyl)-4-ethynyl-1H-imidazole-5-carboxylate (51 mg) was dissolved in a mixed solvent of THF (1 mL) and methanol (0.5 mL), and 2 M aqueous sodium hydroxide (0.2 mL, 0.4 mmol) was added thereto, and then mixture was stirred at 50° C. for 3 hours. After the reaction, the reaction mixture was neutralized by the addition of 2 M hydrochloric acid (0.2 mL, 0.4 mmol) and was concentrated. The residue was purified by HPLC to obtain 2-(5-chloropyridin-3-yl)-1-(2,5-dichlorobenzyl)-4-ethynyl-1H-imidazole-5-carboxylic acid (Compound A209, 35 mg):

$^1$H-NMR (DMSO-d$_6$) δ: 13.59 (1H, s), 8.73 (1H, d, J=2.0 Hz), 8.57 (1H, d, J=1.5 Hz), 8.06 (1H, t, J=2.2 Hz), 7.48 (1H, d, J=8.3 Hz), 7.38 (1H, d, J=8.8 Hz), 6.73 (1H, s), 5.62 (2H, s), 4.44 (1H, s);
HPLC retention time=10.67 min;
Pred. Mass=405.9911 (M$^+$+H, C$_{18}$H$_{10}$Cl$_3$N$_3$O$_2$);
Obs. Mass=405.9922 (M$^+$+H).

Example 20

Production of 2-(5-chloropyridin-3-yl)-1-(2,5-dichlorobenzyl)-1H-furo[3,4-d]imidazol-6(4H)-one (Compound A221) (Scheme E)

[Chemical Formula 68]

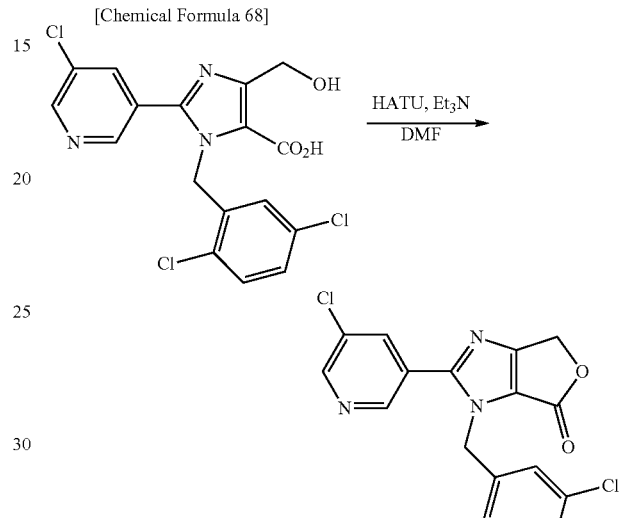

(1) 2-(5-Chloropyridin-3-yl)-1-(2,5-dichlorobenzyl)-4-(hydroxymethyl)-1H-imidazole-5-carboxylic acid (100 mg, 0.242 mmol) was dissolved in DMF (1 mL), and HATU (138 mg, 0.364 mmol) and triethylamine (49 mg, 0.485 mmol) were added thereto, and then the mixture was stirred at room temperature for 1 hour. The reaction mixture was purified by HPLC to obtain 2-(5-chloropyridin-3-yl)-1-(2,5-dichlorobenzyl)-1H-furo[3,4-d]imidazole-6(4H)-one (Compound A221, 38 mg):

$^1$H-NMR (DMSO-d$_6$) δ: 8.79 (1H, d, J=2.2 Hz), 8.75 (1H, d, J=2.0 Hz), 8.23 (1H, t, J=2.2 Hz), 7.47-7.37 (2H, m), 7.30 (1H, d, J=2.0 Hz), 5.51 (2H, s), 5.34 (2H, s);
HPLC retention time=11.16 min;
Pred. Mass=393.9911 (M$^+$+H, C$_{17}$H$_{10}$Cl$_3$N$_3$O$_2$);
Obs. Mass=393.9911 (M$^+$+H).

Example 21

Production of 1-(2,5-dichlorobenzyl)-4-methyl-2-((2-methylpyridin-3-yl)oxy)-1H-imidazole-5-carboxylic acid (Compound A252) (Scheme H)

[Chemical Formula 69]

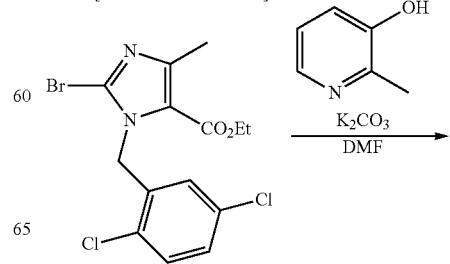

-continued

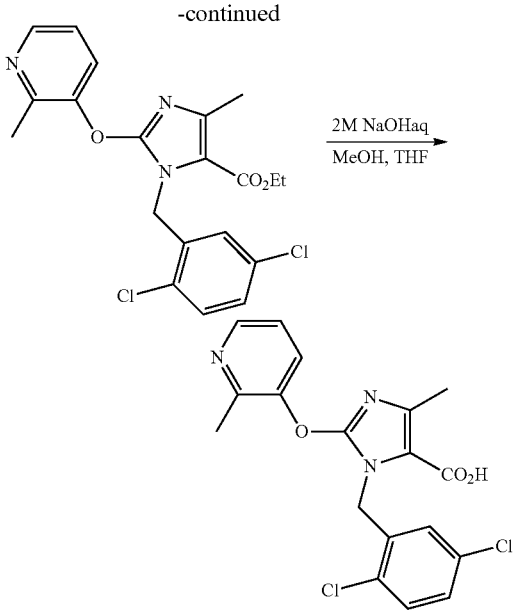

2M NaOHaq
MeOH, THF (1) Ethyl 2-bromo-1-(2,5-dichlorobenzyl)-4-methyl-1H-imidazole-5-carboxylate (60 mg, 0.153 mmol) was dissolved in DMF (1 mL), and potassium carbonate (43 mg, 0.306 mmol) and 2-methylpyridin-3-ol (25 mg, 0.23 mmol) were added thereto, and then the mixture was stirred at 120° C. for 12 hours. After the reaction, water (5 mL) was added and the mixture was extracted twice with ethyl acetate (5 mL). After being washed with saturated aqueous sodium chloride, the organic layer was dried over sodium sulfate. After concentrating the organic layer, the residue was purified by column chromatography to obtain ethyl 1-(2,5-dichlorobenzyl)-4-methyl-2-((2-methylpyridin-3-yl)oxy-1H-imidazole-5-carboxylate (Compound A282, 44 mg): ESI-MS m/z=420 (M$^+$+H).

(2) Ethyl 1-(2,5-dichlorobenzyl)-4-methyl-2-((2-methyl-pyridin-3-yl)oxy-1H-imidazole-5-carboxylate (44 mg, 0.105 mmol) was dissolved in a mixed solvent of THF (1 mL) and methanol (0.5 mL), and 2 M aqueous sodium hydroxide (0.2 mL, 0.4 mmol) was added thereto, and then the mixture was stirred at 50° C. for 7 hours. After the reaction, the reaction mixture was neutralized by the addition of 2 M hydrochloric acid (0.2 mL, 0.4 mmol) and was concentrated. The residue was purified by HPLC to obtain 1-(2,5-dichlorpbenzyl)-4-methyl-2-((2-methylpyridin-3-yl)oxy)-1H-imidazole-5-carboxylic acid (Compound A252, 30 mg):

$^1$H-NMR (DMSO-d$_6$) δ: 8.43 (1H, dd, J=4.9, 1.0 Hz), 7.95 (1H, d, J=8.3 Hz), 7.58-7.40 (3H, m), 6.77 (1H, d, J=2.4 Hz), 5.55 (2H, s), 2.33 (3H, s), 2.28 (3H, s);

HPLC retention time=8.20 min;
Pred. Mass=392.0563 (M$^+$+H, C$_{18}$H$_{15}$Cl$_2$N$_3$O$_3$);
Obs. Mass=392.0570 (M+H).

Compounds having compound numbers A1 to A266 were synthesized in a manner similar to any of Example 1 to Example 21.

TABLE 13

| Example | Compound No. | Scheme | HPLC Retention time | Obs. Mass (M$^+$ + H) | Pred. Mass (M$^+$ + H) | Formula(M) | $^1$H-NMR |
|---|---|---|---|---|---|---|---|
| 22 | A1 | A | 7.18 | 322.1552 | 322.1550 | C$_{19}$H$_{19}$N$_3$O$_2$ | (DMSO-d6) δ: 12.83 (1H, s), 8.63 (1H, dd, J = 2.2, 0.7 Hz), 8.60 (1H, dd, J = 4.9, 1.5 Hz), 7.85 (1H, dt, J = 7.8, 2.0 Hz), 7.44 (1H, dd, J = 7.3, 4.9 Hz), 7.05 (1H, d, J = 7.8 Hz), 6.93 (1H, d, J = 7.3 Hz), 6.16 (1H, s), 5.50 (2H, s), 2.49 (3H, s), 2.13 (3H, s), 2.12 (3H, s). |
| 23 | A3 | A | 9.55 | 372.1704 | 372.1707 | C$_{23}$H$_{21}$N$_3$O$_2$ | (CDCl3) δ: 8.78 (1H, d, J = 2.0 Hz), 8.58 (1H, dd, J = 4.9, 1.5 Hz), 7.93-7.85 (2H, m), 7.82-7.77 (2H, m), 7.57-7.53 (2H, m), 7.38 (1H, t, J = 7.6 Hz), 7.24-7.20 (1H, m), 6.73 (1H, d, J = 6.3 Hz), 6.03 (2H, s), 4.13 (2H, q, J = 7.2 Hz), 2.67 (3H, s), 1.07 (3H, t, J = 7.1 Hz). |
| 24 | A4 | A | 7.02 | 358.1548 | 358.1550 | C$_{22}$H$_{19}$N$_3$O$_2$ | |
| 25 | A5 | A | 7.78 | 364.1119 | 364.1114 | C$_{20}$H$_{17}$N$_3$O$_2$S | (DMSO-d6) δ: 8.77 (1H, dd, J = 2.0, 1.5 Hz), 8.62 (1H, dd, J = 4.9, 1.5 Hz), 8.01 (1H, dt, J = 8.0, 2.0 Hz), 7.73 (1H, d, J = 8.3 Hz), 7.48 (1H, dd, J = 8.3, 4.0 Hz), 7.20 (1H, t, J = 8.0 Hz), 7.10 (1H, d, J = 6.8 Hz), 6.70 (1H, s), 6.00 (2H, s), 2.64 (3H, s), 2.49 (3H, s). |
| 26 | A6 | A | 8.23 | 418.0828 | 418.0832 | C$_{20}$H$_{14}$F$_3$N$_3$O$_2$S | (DMSO-d6) δ: 8.73 (1H, d, J = 2.0 Hz), 8.64 (1H, dd, J = 4.9, 1.5 Hz), 8.40 (1H, d, J = 8.3 Hz), 7.98 (1H, dt, J = 8.3, 2.0 Hz), 7.88 (1H, d, J = 7.5 Hz), 7.58 (1H, t, J = 7.5 Hz), 7.50 (1H, dd, J = 8.0, 4.9 Hz), 7.17 (1H, s), 5.75 (2H, s), 2.56 (3H, s). |
| 27 | A8 | B | 7.88 | 428.0062 | 428.0063 | C$_{19}$H$_{14}$BrN$_3$O$_2$S | (DMSO-d6) δ: 8.75 (1H, d, J = 1.5 Hz), 8.65 (1H, dd, J = 4.9, 1.5 Hz), 8.04 (1H, d, J = 7.8 Hz), 7.99 (1H, dt, J = 7.8, 1.5 Hz), 7.65 (1H, d, J = 7.8 Hz), 7.51 (1H, dd, J = 7.8, 4.9 Hz), 7.29 (1H, t, J = 7.8 Hz), 6.98 (1H, s), 6.11 (2H, s), 2.54 (3H, s). |

TABLE 14

| Example | Compound No. | Scheme | HPLC Retention time | Obs. Mass (M+ + H) | Pred. Mass (M+ + H) | Formula(M) | $^1$H-NMR |
|---|---|---|---|---|---|---|---|
| 28 | A10 | B | 7.76 | 358.1541 | 358.1550 | $C_{22}H_{19}N_3O_2$ | (DMSO-d6) δ: 8.68 (1H, d, J = 2.0 Hz), 8.59 (1H, dd, J = 4.9, 1.5 Hz), 8.04-7.91 (3H, m), 7.84 (1H, d, J = 8.3 Hz), 7.60-7.56 (2H, m), 7.45-7.40 (2H, m), 6.56 (1H, d, J = 7.3 Hz), 6.08 (2H, s), 2.98 (2H, q, J = 7.5 Hz) 1.28 (3H, t, J = 7.6 Hz). |
| 29 | A12 | C | 7.28 | 330.1234 | 330.1237 | $C_{20}H_{15}N_3O_2$ | |
| 30 | A14 | B | 7.79 | 376.0618 | 376.0614 | $C_{18}H_{15}Cl_2N_3O_2$ | (DMSO-d6) δ: 12.99 (1H, brs), 8.63 (2H, d, J = 3.4 Hz), 7.85 (1H, dt, J = 8.0, 2.0 Hz), 7.51-7.45 (2H, m), 7.38 (1H, dd, J = 8.5, 2.2 Hz), 6.49 (1H, s), 5.57 (2H, s), 2.92 (2H, dd, J = 14.9, 7.4 Hz), 1.23 (3H, t, J = 7.6 Hz) |
| 31 | A15 | B | 8.50 | 388.0607 | 388.0614 | $C_{19}H_{15}Cl_2N_3O_2$ | (DMSO-d6) δ: 8.63 (1H, dd, J = 4.9, 1.5 Hz), 8.58 (1H, d, J = 2.0 Hz), 7.80 (1H, dt, J = 8.1, 2.0 Hz), 7.51 (1H, d, J = 8.8 Hz), 7.46 (1H, dd, J = 7.8, 4.9 Hz), 7.39 (1H, dd, J = 8.8, 2.4 Hz), 6.55 (1H, d, J = 2.4 Hz), 5.53 (2H, s), 2.74-2.68 (1H, m), 0.99-0.93 (4H, m). |
| 32 | A16 | A | 7.26 | 350.0952 | 350.0958 | $C_{19}H_{15}N_3O_2S$ | (DMSO-d6) δ: 8.76 (1H, d, J = 2.4 Hz), 8.66 (1H, dd, J = 4.9, 1.5 Hz), 8.01 (1H, dt, J = 8.0, 2.0 Hz), 7.99-7.96 (1H, m), 7.72-7.69 (1H, m), 7.51 (1H, dd, J = 7.8, 4.9 Hz), 7.42-7.38 (2H, m), 7.04 (1H, s), 5.82 (2H, s), 2.53 (3H, s). |
| 33 | A17 | A | 7.93 | 358.1539 | 358.1550 | $C_{22}H_{19}N_3O_2$ | (DMSO-d6) δ: 8.70 (1H, d, J = 2.4 Hz), 8.62 (1H, dd, J = 4.9, 1.0 Hz), 8.07 (1H, dd, J = 7.3, 2.0 Hz), 8.02 (1H, dd, J = 7.8, 1.5 Hz), 7.95 (1H, dt, J = 8.0, 1.7 Hz), 7.64-7.58 (2H, m), 7.46 (1H, dd, J = 7.8, 4.9 Hz), 7.26 (1H, d, J = 7.3 Hz), 6.50 (1H, d, J = 8.0 Hz), 6.06 (2H, s), 2.61 (3H, s), 2.57 (3H, s). |

TABLE 15

| Example | Compound No. | Scheme | HPLC Retention time | Obs. Mass (M+ + H) | Pred. Mass (M+ + H) | Formula(M) | $^1$H-NMR |
|---|---|---|---|---|---|---|---|
| 34 | A18 | B | 8.79 | 384.1700 | 384.1707 | $C_{24}H_{21}N_3O_2$ | (DMSO-d6) δ: 8.64 (1H, s), 8.58 (1H, d, J = 4.9 Hz), 8.06 (1H, d, J = 8.3 Hz), 8.02 (1H, d, J = 7.8 Hz), 7.89 (1H, d, J = 7.8 Hz), 7.64-7.57 (2H, m), 7.43 (1H, dd, J = 7.8, 4.9 Hz), 7.27 (1H, d, J = 6.8 Hz), 6.45 (1H, d, J = 7.3 Hz), 6.02 (2H, s), 2.78-2.71 (1H, m), 2.60 (3H, s), 1.03-0.96 (4H, m). |
| 35 | A20 | A | 9.24 | 398.1104 | 398.1111 | $C_{21}H_{14}F_3N_3O_2$ | |
| 36 | A21 | A | 8.91 | 412.1274 | 412.1267 | $C_{22}H_{16}F_3N_3O_2$ | |
| 37 | A22 | A | 9.06 | 404.0679 | 404.0675 | $C_{19}H_{12}F_3N_3O_2S$ | |
| 38 | A23 | D | 9.11 | 378.1018 | 378.1004 | $C_{21}H_{16}ClN_3O_2$ | (DMSO-d6) δ: 8.67 (1H, s), 8.60 (1H, d, J = 4.9 Hz), 8.12-7.97 (2H, m), 7.91 (1H, dt, J = 7.8, 1.5 Hz), 7.65-7.58 (2H, m), 7.43 (1H, dd, J = 7.8, 4.9 Hz), 7.27 (1H, d, J = 7.3 Hz), 6.52 (1H, d, J = 7.3 Hz), 6.06 (2H, s), 2.61 (3H, s). |
| 39 | A24 | B | 8.19 | 372.1704 | 372.1707 | $C_{23}H_{21}N_3O_2$ | (DMSO-d6) δ: 8.67 (1H, d, J = 2.4 Hz), 8.59 (1H, d, J = 4.4 Hz), 8.05-7.92 (3H, m), 7.84 (1H, d J = 8.3 Hz), 7.60-7.40 (4H, m), 6.56 (1H, d, J = 6.8 Hz), 6.07 (2H, s), 3.78-3.71 (1H, m), 1.31 (6H, d, J = 6.8 Hz). |
| 40 | A25 | B | 8.64 | 386.1860 | 386.1863 | $C_{24}H_{23}N_3O_2$ | (DMSO-d6) δ: 8.68 (1H, d, J = 1.5 Hz), 8.60 (1H, dd, J = 4.9, 1.5 Hz), 8.08-8.00 (2H, m), 7.94 (1H, dt, J = 7.5, 2.0 Hz), 7.65-7.56 (2H, m), 7.46 (1H, dd, J = 8.0, 5.1 Hz), 7.27 (1H, d, J = 7.8 Hz), 6.44 (1H, d, J = 7.3 Hz), 6.04 (2H, s), 3.78-3.71 (1H, m), 2.61 (3H, s), 1.31 (6H, d, J = 7 Hz). |

TABLE 16

| Example | Compound No. | Scheme | HPLC Retention time | Obs. Mass (M⁺ + H) | Pred. Mass (M⁺ + H) | Formula(M) | ¹H-NMR |
|---|---|---|---|---|---|---|---|
| 41 | A26 | B | 8.34 | 390.0770 | 390.0771 | $C_{19}H_{17}Cl_2N_3O_2$ | (DMSO-d6) δ: 8.66-8.61 (2H, m), 7.85 (1H, dt, J = 8.1, 2.0 Hz), 7.52-7.46 (2H, m), 7.38 (1H, dd, J = 8.5, 2.7 Hz), 6.45 (1H, d, J = 2.4 Hz), 5.56 (2H, s), 3.72-3.65 (1H, m), 1.26 (6H, d, J = 7 Hz). |
| 42 | A27 | A | 9.64 | 438.0288 | 438.0285 | $C_{19}H_{11}ClF_3N_3O_2S$ | (DMSO-d6) δ: 8.75 (1H, d, J = 2.0 Hz), 8.66 (1H, dd, J = 4.9, 1.5 Hz), 8.01-7.98 (2H, m), 7.51-7.46 (2H, m), 7.38 (1H, t, J = 8.0 Hz), 7.08 (1H, s), 6.08 (2H, s). |
| 43 | A28 | B | 8.85 | 476.0213 | 476.0216 | $C_{21}H_{13}BrF_3N_3O_2$ | |
| 44 | A29 | A | 8.77 | 412.1273 | 412.1267 | $C_{22}H_{16}F_3N_3O_2$ | |
| 45 | A30 | A | 9.76 | 412.1265 | 412.1267 | $C_{22}H_{16}F_3N_3O_2$ | |
| 46 | A31 | B | 9.78 | 481.9778 | 481.9780 | $C_{19}H_{11}BrF_3N_3O_2S$ | |
| 47 | A32 | B | 10.17 | 472.0548 | 472.0549 | $C_{20}H_{11}F_6N_3O_2S$ | |
| 48 | A33 | B | 8.72 | 410.0728 | 410.0725 | $C_{21}H_{16}ClN_3O_2S$ | (DMSO-d6) δ: 8.72 (1H, d, J = 1.5 Hz), 8.64 (1H, dd, J = 4.9, 1.5 Hz), 8.00-7.98 (2H, m), 7.54-7.50 (1H, m), 7.46 (1H, dd, J = 7.8, 1.0 Hz), 7.37 (1H, t, J = 7.8 Hz), 6.90 (1H, s), 6.04 (2H, s), 2.77-2.70 (1H, m), 1.04-0.95 (4H, m). |

TABLE 17

| Example | Compound No. | Scheme | HPLC Retention time | Obs. Mass (M⁺ + H) | Pred. Mass (M⁺ + H) | Formula(M) | ¹H-NMR |
|---|---|---|---|---|---|---|---|
| 49 | A34 | B | 8.87 | 454.0212 | 454.0219 | $C_{21}H_{16}BrN_3O_2S$ | (DMSO-d6) δ: 8.79 (1H, d, J = 2.0 Hz), 8.71 (1H, dd, J = 4.9, 1.5 Hz), 8.11 (1H, dt, J = 8.1, 1.8 Hz), 8.04 (1H, d, J = 7.8 Hz), 7.66-7.60 (2H, m), 7.29 (1H, t, J = 7.8 Hz), 7.00 (1H, s), 6.10 (2H, s), 2.78-2.71 (1H, m), 1.08-0.98 (4H, m). |
| 50 | A35 | B | 9.25 | 444.0978 | 444.0988 | $C_{22}H_{16}F_3N_3O_2S$ | (DMSO-d6) δ: 8.62 (1H, d, J = 2.4 Hz), 8.56 (1H, dd, J = 4.9, 1.5 Hz), 8.38 (1H, d, J = 7.8 Hz), 7.88-7.84 (2H, m), 7.57 (1H, t, J = 7.6 Hz), 7.40 (1H, dd, J = 8.3, 4.9 Hz), 7.02 (1H, s), 5.74 (2H, brs), 2.80-2.73 (1H, m), 0.99-0.96 (4H, m). |
| 51 | A36 | B | 8.14 | 376.1101 | 376.1114 | $C_{21}H_{17}N_3O_2S$ | |
| 52 | A37 | B | 8.53 | 412.0878 | 412.0881 | $C_{21}H_{18}ClN_3O_2S$ | (DMSO-d6) δ: 8.77 (1H, d, J = 2.0 Hz), 8.67 (1H, dd, J = 5.1, 1.7 Hz), 8.04-7.98 (2H, m), 7.54 (1H, dd, J = 8.3, 4.9 Hz), 7.46 (1H, d, J = 7.8 Hz), 7.37 (1H, t, J = 7.8 Hz), 6.90 (1H, s), 6.06 (2H, s), 3.78-3.71 (1H, m), 1.30 (6H, d, J = 7.3 Hz). |
| 53 | A38 | B | 8.66 | 456.0360 | 456.0376 | $C_{21}H_{18}BrN_3O_2S$ | (DMSO-d6) δ: 8.76 (1H, d, J = 2.3 Hz), 8.67 (1H, dd, J = 2.4, 1.2 Hz), 8.06-8.01 (2H, m), 7.65 (1H, d, J = 7.8 Hz), 7.55 (1H, dd, J = 8.0, 5.1 Hz), 7.30 (1H, t, J = 7.8 Hz), 6.94 (1H, s), 6.11 (2H, s), 3.79-3.72 (1H, m), 1.31 (6H, d, J = 6.8 Hz). |
| 54 | A39 | B | 9.01 | 446.1155 | 446.1145 | $C_{22}H_{18}F_3N_3O_2S$ | (DMSO-d6) δ: 8.70 (1H, d, J = 2.0 Hz), 8.62 (1H, dd, J = 4.9, 1.5 Hz), 8.39 (1H, d, J = 8.3 Hz), 7.96 (1H, dt, J = 7.8, 2.0 Hz), 7.88 (1H, d, J = 7.3 Hz), 7.58 (1H, t, J = 7.8 Hz), 7.48 (1H, dd, J = 7.8, 4.9 Hz), 7.05 (1H, s), 5.74 (2H, brs), 3.80-3.69 (1H, m), 1.31 (6H, d, J = 6.8 Hz). |

TABLE 18

| Example | Compound No. | Scheme | HPLC Retention time | Obs. Mass (M⁺ + H) | Pred. Mass (M⁺ + H) | Formula(M) | ¹H-NMR |
|---|---|---|---|---|---|---|---|
| 55 | A40 | B | 8.02 | 378.1273 | 378.1271 | $C_{21}H_{19}N_3O_2S$ | (DMSO-d6) δ: 8.76 (1H, d, J = 1.5 Hz), 8.66 (1H, dd, J = 4.9, 1.5 Hz), 8.04-7.96 (2H, m), 7.68 (1H, t, J = 5.0 Hz), 7.51 (1H, dd, J = 13.4, 1.5 Hz), 7.41-7.37 (2H, m), 6.98 (1H, |

TABLE 18-continued

| Example | Compound No. | Scheme | HPLC Retention time | Obs. Mass (M$^+$ + H) | Pred. Mass (M$^+$ + H) | Formula(M) | $^1$H-NMR |
|---|---|---|---|---|---|---|---|
| | | | | | | | s), 5.80 (2H, s), 3.75-3.68 (1H, m), 1.28 (6H, d, J = 6.8 Hz). |
| 56 | A41 | A | 6.85 | 346.0748 | 346.0753 | $C_{17}H_{13}ClFN_3O_2$ | (DMSO-d6) δ: 8.72-8.69 (2H, m), 7.95 (1H, dt, J = 7.5, 2.0 Hz), 7.58-7.50 (2H, m), 7.19 (1H, td, J = 8.5, 2.9 Hz), 6.48 (1H, dd, J = 9.3, 2.4 Hz), 5.56 (2H, s), 2.51 (3H, t, J = 6.3 Hz). |
| 57 | A42 | A | 6.90 | 346.0750 | 346.0753 | $C_{17}H_{13}ClFN_3O_2$ | (DMSO-d6) δ: 8.77 (1H, s), 8.73 (1H, d, J = 4.9 Hz), 8.03 (1H, dt, J = 8.3, 1.8 Hz), 7.59 (1H, dd, J = 7.8, 4.9 Hz), 7.40-7.33 (1H, m), 7.21 (1H, t, J = 9.5 Hz), 6.82 (1H, dd, J = 7.0, 1.8 Hz), 5.61 (2H, s), 2.49 (3H, s). |
| 58 | A43 | A | 7.85 | 396.0718 | 396.0721 | $C_{18}H_{13}ClF_3N_3O_2$ | (DMSO-d6) δ: 8.69 (2H, d, J = 2.4 Hz), 7.94 (1H, dt, J = 8.0, 2.0 Hz), 7.70 (2H, q, J = 8.0 Hz), 7.55 (1H, dd, J = 8.0, 5.1 Hz), 6.93 (1H, s), 5.68 (2H, s), 2.52 (3H, d, J = 4.9 Hz). |
| 59 | A44 | A | 7.90 | 396.0726 | 396.0721 | $C_{18}H_{13}ClF_3N_3O_2$ | (DMSO-d6) δ: 8.68-8.65 (2H, m), 7.88 (1H, dt, J = 7.8, 2.0 Hz), 7.80 (1H, d, J = 8.3 Hz), 7.59 (1H, d, J = 8.8 Hz), 7.51 (1H, dd, J = 7.8, 4.9 Hz), 6.67 (1H, s), 5.70 (2H, s), 2.54 (3H, s). |
| 60 | A46 | A | 8.42 | 430.0991 | 430.0985 | $C_{19}H_{13}F_6N_3O_2$ | (DMSO-d6) δ: 8.63 (1H, dd, J = 4.9, 1.7 Hz), 8.61 (1H, d, J = 2.4 Hz), 8.01 (1H, d, J = 8.3 Hz), 7.89 (1H, d, J = 8.3 Hz), 7.85 (1H, dt, J = 7.8, 1.7 Hz), 7.47 (1H, dd, J = 8.3, 4.9 Hz), 6.84 (1H, s), 5.78 (2H, s), 2.53 (3H, s). |

TABLE 19

| Example | Compound No. | Scheme | HPLC Retention time | Obs. Mass (M$^+$ + H) | Pred. Mass (M$^+$ + H) | Formula(M) | $^1$H-NMR |
|---|---|---|---|---|---|---|---|
| 61 | A47 | A | 9.12 | 404.1599 | 404.1605 | $C_{23}H_{21}N_3O_4$ | |
| 62 | A48 | B | 6.09 | 312.1136 | 312.1143 | $C_{17}H_{14}FN_3O_2$ | (CD3OD-d4) δ: 8.71-8.68 (2H, m), 7.98 (1H, d, J = 7.9 Hz), 7.58-7.54 (1H, m), 7.31-7.27 (1H, m), 7.12-7.01 (2H, m), 6.83 (1H, t, J = 7.5 Hz), 5.72 (2H, s), 2.60 (3H, s). |
| 63 | A49 | B | 6.23 | 312.1143 | 312.1143 | $C_{17}H_{14}FN_3O_2$ | (CD3OD-d4) δ: 8.73-8.69 (2H, m), 7.99 (1H, d, J = 7.9 Hz), 7.61-7.56 (1H, m), 7.34-7.28 (1H, m), 6.99 (1H, t, J = 8.2 Hz), 6.75-6.71 (2H, m), 5.71 (2H, s), 2.62 (3H, s). |
| 64 | A50 | B | 6.26 | 312.1142 | 312.1143 | $C_{17}H_{14}FN_3O_2$ | (DMSO-d6) δ: 8.73-8.69 (2H, m), 7.97 (1H, d, J = 8.1 Hz), 7.56-7.52 (1H, m), 7.14-7.09 (2H, m), 6.95-6.90 (2H, m), 5.61 (2H, s), 2.50 (3H, s). |
| 65 | A51 | B | 6.65 | 328.0853 | 328.0847 | $C_{17}H_{14}ClN_3O_2$ | (CD3OD-d4) δ: 8.71-8.63 (2H, m), 7.93 (1H, d, J = 8.1 Hz), 7.58-7.53 (1H, m), 7.43-7.39 (1H, m), 7.30-7.25 (2H, m), 6.75-6.71 (1H, m), 5.71 (2H, s), 2.64 (3H, s). |
| 66 | A52 | B | 6.83 | 328.0844 | 328.0847 | $C_{17}H_{14}ClN_3O_2$ | (DMSO-d6) δ: 8.71-8.68 (2H, m), 7.95 (1H, d, J = 8.0 Hz), 7.56-7.52 (1H, m), 7.34-7.30 (2H, m), 7.01 (1H, s), 6.80 (1H, d, J = 6.4 Hz), 5.62 (2H, s), 2.50 (3H, s). |
| 67 | A53 | B | 6.95 | 328.0832 | 328.0847 | $C_{17}H_{14}ClN_3O_2$ | (CD3OD-d4) δ: 8.85-8.78 (2H, m), 8.11 (1H, d, J = 8.0 Hz), 7.72-7.68 (1H, m), 7.33 (2H, d, J = 8.3 Hz), 7.02 (2H, d, J = 8.3 Hz), 5.76 (2H, s), 2.70 (3H, s). |
| 68 | A54 | B | 6.82 | 372.0339 | 372.0342 | $C_{17}H_{14}BrN_3O_2$ | (CD3OD-d4) δ: 8.72-8.65 (2H, m), 7.94 (1H, d, J = 8.0 Hz), 7.62-7.56 (2H, m), 7.32 (1H, t, J = 7.4 Hz), 7.22 (1H, t, J = 7.2 Hz), 6.73 (1H, d, J = 7.6 Hz), 5.68 (2H, s), 2.66 (3H, s). |

TABLE 20

| Example | Compound No. | Scheme | HPLC Retention time | Obs. Mass (M⁺ + H) | Pred. Mass (M⁺ + H) | Formula(M) | ¹H-NMR |
|---|---|---|---|---|---|---|---|
| 69 | A55 | B | 7.00 | 372.0339 | 372.0342 | $C_{17}H_{14}BrN_3O_2$ | (CD3OD-d4) δ: 8.61-8.57 (2H, m), 7.89 (1H, d, J = 8.0 Hz), 7.52-7.47 (1H, m), 7.33 (1H, d, J = 7.9 Hz), 7.14 (1H, t, J = 7.8 Hz), 7.06 (1H, s), 6.85 (1H, d, J = 7.5 Hz), 5.73 (2H, s), 2.53 (3H, s). |
| 70 | A56 | B | 7.14 | 372.0330 | 372.0342 | $C_{17}H_{14}BrN_3O_2$ | (DMSO-d6) δ: 8.71-8.68 (2H, m), 7.95 (1H, d, J = 7.8 Hz), 7.56-7.47 (3H, m), 6.86 (2H, d, J = 8.2 Hz), 5.58 (2H, s), 2.50 (3H, s). |
| 71 | A57 | B | 6.50 | 308.1386 | 308.1394 | $C_{18}H_{17}N_3O_2$ | (CD3OD-d4) δ: 8.72-8.67 (2H, m), 7.96 (1H, d, J = 8.0 Hz), 7.58-7.54 (1H, m), 7.19-7.12 (3H, m), 6.55 (1H, d, J = 7.4 Hz), 5.65 (2H, s), 2.66 (3H, s), 2.22 (3H, s). |
| 72 | A58 | B | 6.65 | 308.1383 | 308.1394 | $C_{18}H_{17}N_3O_2$ | (CD3OD-d4) δ: 8.71-8.65 (2H, m), 7.96 (1H, d, J = 7.9 Hz), 7.58-7.54 (1H, m), 7.16 (1H, t, J = 7.6 Hz), 7.06 (1H, d, J = 7.4 Hz), 6.75 (1H, s), 6.69 (1H, d, J = 7.4 Hz), 5.67 (2H, s), 2.61 (3H, s), 2.25 (3H, s). |
| 73 | A59 | B | 7.13 | 322.1552 | 322.1550 | $C_{19}H_{19}N_3O_2$ | (CD3OD-d4) δ: 8.72-8.65 (2H, m), 7.94 (1H, d, J = 8.0 Hz), 7.57-7.54 (1H, m), 7.23-7.12 (3H, m), 6.54 (1H, d, J = 7.8 Hz), 5.72 (2H, s), 2.66 (3H, s), 2.56 (2H, q, J = 7.6 Hz), 1.14 (3H, t, J = 7.5 Hz). |
| 74 | A60 | B | 7.31 | 362.1114 | 362.1111 | $C_{18}H_{14}F_3N_3O_2$ | (CD3OD-d4) δ: 8.57-8.49 (2H, m), 7.81 (1H, d, J = 8.0 Hz), 7.66 (1H, d, J = 7.7 Hz), 7.53 (1H, t, J = 7.2 Hz), 7.46-7.38 (2H, m), 6.73 (1H, d, J = 7.9 Hz), 5.92 (2H, s), 2.59 (3H, s). |
| 75 | A61 | B | 7.42 | 362.1106 | 362.1111 | $C_{18}H_{14}F_3N_3O_2$ | (DMSO-d6) δ: 8.72-8.68 (2H, m), 7.97 (1H, d, J = 7.8 Hz), 7.63-7.50 (3H, m), 7.32 (1H, s), 7.13 (1H, d, J = 7.7 Hz), 5.71 (2H, s), 2.50 (3H, s). |

TABLE 21

| Example | Compound No. | Scheme | HPLC Retention time | Obs. Mass (M⁺ + H) | Pred. Mass (M⁺ + H) | Formula(M) | ¹H-NMR |
|---|---|---|---|---|---|---|---|
| 76 | A62 | B | 7.47 | 378.1070 | 378.1060 | $C_{18}H_{14}F_3N_3O_3$ | (CD3OD-d4) δ: 8.72-8.64 (2H, m), 7.95 (1H, d, J = 7.4 Hz), 7.60-7.54 (1H, m), 7.41-7.36 (1H, m), 7.33-7.27 (2H, m), 6.83 (1H, d, J = 6.8 Hz), 5.76 (2H, s), 2.64 (3H, s). |
| 77 | A63 | B | 7.71 | 378.1061 | 378.1060 | $C_{18}H_{14}F_3N_3O_3$ | (DMSO-d6) δ: 8.72-8.68 (2H, m), 7.96 (1H, d, J = 7.8 Hz), 7.56-7.50 (1H, m), 7.43 (1H, t, J = 8.0 Hz), 7.23 (1H, d, J = 8.4 Hz), 6.93-6.87 (2H, m), 5.67 (2H, s), 2.50 (3H, s). |
| 78 | A64 | B | 5.73 | 319.1198 | 319.1190 | $C_{18}H_{14}N_4O_2$ | (DMSO-d6) δ: 8.76-8.67 (2H, m), 8.00 (1H, d, J = 7.9 Hz), 7.83 (1H, d, J = 7.6 Hz), 7.62 (1H, t, J = 7.7 Hz), 7.56-7.52 (1H, m), 7.44 (1H, t, J = 7.7 Hz), 6.76 (1H, d, J = 8.0 Hz), 5.75 (2H, s), 2.50 (3H, s). |
| 79 | A65 | B | 5.71 | 319.1191 | 319.1190 | $C_{18}H_{14}N_4O_2$ | (DMSO-d6) δ: 8.61-8.56 (2H, m), 7,82 (1H, d, J = 8.0 Hz), 7.66 (1H, d, J = 7.7 Hz), 7.49-7.40 (2H, m), 7.31 (1H, s), 7.15 (1H, d, J = 8.2 Hz), 5.84 (2H, s), 2.44 (3H, s). |
| 80 | A66 | A | 8.78 | 394.1543 | 394.1550 | $C_{25}H_{19}N_3O_2$ | |
| 81 | A67 | A | 8.96 | 412.0598 | 412.0614 | $C_{21}H_{15}Cl_2N_3O_2$ | |
| 82 | A68 | B | 7.64 | 362.0456 | 362.0458 | $C_{17}H_{13}Cl_2N_3O_2$ | (CD3OD-d4) δ: 8.73-8.69 (2H, m), 7.99 (1H, d, J = 8.0 Hz), 7.62-7.58 (1H, m), 7.45 (1H, d, J = 8.3 Hz), 7.16 (1H, s), 6.86 (1H, d, J = 8.3 Hz), 5.66 (2H, s), 2.61 (3H, s). |
| 83 | A69 | B | 6.88 | 362.0468 | 362.0458 | $C_{17}H_{13}Cl_2N_3O_2$ | (DMSO-d6) δ: 8.68 (1H, s), 8.61 (1H, s), 7.94 (1H, d, J = 8.0 Hz), 7.46-7.26 (4H, m), 5.57 (2H, s), 2.38 (3H, s). |
| 84 | A70 | B | 7.52 | 362.0452 | 362.0458 | $C_{17}H_{13}Cl_2N_3O_2$ | (CD3OD-d4) δ: 8.76-8.70 (2H, m), 8.00 (1H, d, J = 8.0 Hz), 7.64-7.60 (1H, m), 7.50 (1H, d, J = 8.0 Hz), 7.27 (1H, t, J = |

TABLE 21-continued

| Example | Compound No. | Scheme | HPLC Retention time | Obs. Mass (M⁺ + H) | Pred. Mass (M⁺ + H) | Formula(M) | $^1$H-NMR |
|---|---|---|---|---|---|---|---|
| | | | | | | | 7.9 Hz), 6.74 (1H, d, J = 7.8 Hz), 5.74 (2H, s), 2.66 (3H, s). |

TABLE 22

| Example | Compound No. | Scheme | HPLC Retention time | Obs. Mass (M⁺ + H) | Pred. Mass (M⁺ + H) | Formula(M) | $^1$H-NMR |
|---|---|---|---|---|---|---|---|
| 85 | A71 | B | 7.72 | 362.0459 | 362.0458 | $C_{17}H_{13}Cl_2N_3O_2$ | (DMSO-d6) δ: 8.70-8.69 (2H, m), 7.93 (1H, d, J = 7.9 Hz), 7.56-7.50 (2H, m), 6.94 (2H, s), 5.59 (2H, s), 2.50 (3H, s). |
| 86 | A72 | B | 6.16 | 346.0756 | 346.0753 | $C_{17}H_{13}ClFN_3O_2$ | (CD3OD-d4) δ: 8.71-8.69 (2H, m), 8.00 (1H, d, J = 7.9 Hz), 7.58-7.54 (1H, m), 7.27-7.20 (1H, m), 7.12 (1H, d, J = 8.0 Hz), 6.92 (1H, t, J = 9.0 Hz), 5.98 (2H, s), 2.59 (3H, s). |
| 87 | A73 | B | 6.93 | 346.0753 | 346.0753 | $C_{17}H_{13}ClFN_3O_2$ | (CD3OD-d4) δ: 8.85-8.66 (2H, m), 8.02 (1H, d, J = 7.9 Hz), 7.68-7.63 (1H, m), 7.27 (1H, dd, J = 8.5 Hz, 2.5 Hz), 7.06 (1H, td, J = 8.4 Hz, 2.4 Hz), 6.90-6.85 (1H, m), 5.72 (2H, s), 2.67 (3H, s). |
| 88 | A74 | B | 7.00 | 346.0754 | 346.0753 | $C_{17}H_{13}ClFN_3O_2$ | (DMSO-d6) δ: 8.77-8.69 (2H, m), 8.01 (1H, d, J = 8.0 Hz), 7.58-7.54 (1H, m), 7.48 (1H, t, J = 7.4 Hz), 7.13 (1H, t, J = 7.9 Hz), 6.67 (1H, t, J = 7.1 Hz), 5.65 (2H, s), 2.50 (3H, s). |
| 89 | A75 | B | 7.11 | 346.0749 | 346.0753 | $C_{17}H_{13}ClFN_3O_2$ | (DMSO-d6) δ: 8.74-8.69 (2H, m), 7.97 (1H, d, J = 8.0 Hz), 7.59-7.54 (1H, m), 7.34 (1H, t, J = 8.9 Hz), 7.20-7.17 (1H, m), 6.88-6.84 (1H, m), 5.59 (2H, s), 2.50 (3H, s). |
| 90 | A76 | B | 7.15 | 346.0751 | 346.0753 | $C_{17}H_{13}ClFN_3O_2$ | (DMSO-d6) δ: 8.74-8.70 (2H, m), 7.98 (1H, d, J = 8.0 Hz), 7.60-7.55 (1H, m), 7.33 (1H, d, J = 8.7 Hz), 6.87 (1H, s), 6.76 (1H, d, J = 9.3 Hz), 5.61 (2H, s), 2.50 (3H, s). |
| 91 | A77 | B | 7.63 | 362.0452 | 362.0458 | $C_{17}H_{13}Cl_2N_3O_2$ | (DMSO-d6) δ: 8.67-8.63 (2H, m), 7.87 (1H, d, J = 7.8 Hz), 7.65 (1H, s), 7.53-7.48 (1H, m), 7.37 (1H, d, J = 8.3 Hz), 6.60 (1H, d, J = 8.4 Hz), 5.55 (2H, s), 2.54 (3H, s). |

TABLE 23

| Example | Compound No. | Scheme | HPLC Retention time | Obs. Mass (M⁺ + H) | Pred. Mass (M⁺ + H) | Formula(M) | $^1$H-NMR |
|---|---|---|---|---|---|---|---|
| 92 | A78 | A | 7.53 | 342.1006 | 342.1004 | $C_{18}H_{16}ClN_3O_2$ | (DMSO-d6) δ: 8.67 (2H, s), 7.92 (1H, d, J = 7.8 Hz), 7.54-7.51 (1H, m), 7.35-7.31 (1H, m), 7.10 (1H, d, J = 7.8 Hz), 6.42 (1H, s), 5.58 (2H, s), 2.51 (3H, s), 2.17 (3H, s). |
| 93 | A79 | A | 7.42 | 368.0017 | 368.0022 | $C_{15}H_{11}Cl_2N_3O_2S$ | |
| 94 | A80 | A | 7.40 | 368.0006 | 368.0022 | $C_{15}H_{11}Cl_2N_3O_2S$ | (DMSO-d6) δ: 8.80 (1H, s), 8.74 (1H, d, J = 3.9 Hz), 8.08-8.04 (1H, m), 7.60 (1H, dd, J = 8.3, 4.9 Hz), 7.11 (1H, s), 5.67 (2H, s), 2.45 (3H, s). |
| 95 | A81 | A | 7.50 | 350.0952 | 350.0958 | $C_{19}H_{15}N_3O_2S$ | (DMSO-d6) δ: 8.70 (1H, d, J = 2.0 Hz), 8.61 (1H, dd, J = 4.9, 1.5 Hz), 7.95 (1H, dt, J = 7.8, 2.0 Hz), 7.81-7.75 (2H, m), 7.51-7.43 (2H, m), 7.31 (1H, t, J = 7.8 Hz), 6.65 (1H, d, J = 7.3 Hz), 5.82 (2H, s), 2.52 (3H, s). |
| 96 | A82 | B | 8.51 | 376.1116 | 376.1114 | $C_{21}H_{17}N_3O_2S$ | (DMSO-d6) δ: 8.64-8.62 (1H, m), 8.57 (1H, dd, J = 4.9, 1.5 Hz), 7.87 (1H, d, J = 7.6 Hz), 7.80-7.75 (2H, m), 7.50 (1H, d, J = 5.4 Hz), 7.44-7.38 (1H, m), 7.32 (1H, t, J = 7.8 Hz), 6.61 (1H, d, J = 7.3 Hz), 5.77 |

TABLE 23-continued

| Example | Compound No. | Scheme | HPLC Retention time | Obs. Mass (M⁺ + H) | Pred. Mass (M⁺ + H) | Formula(M) | ¹H-NMR |
|---|---|---|---|---|---|---|---|
| | | | | | | | (2H, s), 2.74-2.67 (1H, m), 1.01-0.93 (4H, m). |
| 97 | A83 | B | 8.24 | 378.1271 | 378.1271 | $C_{21}H_{19}N_3O_2S$ | |
| 98 | A84 | A | 9.31 | 404.0664 | 404.0675 | $C_{19}H_{12}F_3N_3O_2S$ | |
| 99 | A85 | A | 7.73 | 368.0886 | 368.0864 | $C_{19}H_{14}FN_3O_2$ | (DMSO-d6) δ: 8.73 (1H, d, J = 2.0 Hz), 8.64 (1H, dd, J = 4.9, 1.5 Hz), 7.98 (1H, dt, J = 7.8, 2.0 Hz), 7.87 (1H, d, J = 5.4 Hz), 7.63 (1H, dd, J = 9.3, 2.4 Hz), 7.52-7.45 (2H, m), 6.61 (1H, dd, J = 9.8, 2.0 Hz), 5.81 (2H, s), 2.52 (3H, s). |

TABLE 24

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 100 | A86 | B | 8.81 | 394.1018 | 394.1020 | $C_{21}H_{16}FN_3O_2S$ | (DMSO-d6) δ: 12.96 (1H, s), 8.63 (1H, d, J = 2.4 Hz), 8.58 (1H, dd, J = 4.9, 1.5 Hz), 7.88-7.84 (2H, m), 7.62 (1H, dd, J = 9.3, 2.4 Hz), 7.47 (1H, d, J = 5.4 Hz), 7.43-7.38 (1H, m), 6.53 (1H, dd, J = 9.3, 2.4 Hz), 5.77 (2H, s), 2.73-2.67 (1H, m), 1.01-0.92 (4H, m). |
| 101 | A87 | A | 6.90 | 376.0613 | 376.0614 | $C_{18}H_{15}Cl_2N_3O_2$ | (DMSO-d6) δ: 8.61 (1H, d, J = 4.9 Hz), 8.35 (1H, s), 7.65 (1H, d, J = 8.3 Hz), 7.40-7.32 (2H, m), 7.25 (1H, d, J = 8.3 Hz), 7.01 (1H, s), 6.34 (1H, q, J = 6.8 Hz), 2.43 (3H, s), 1.95 (3H, d, J = 6.8 Hz). |
| 102 | A89 | D | 8.75 | 425.9395 | 425.9406 | $C_{16}H_{10}BrCl_2N_3O_2$ | (DMSO-d6) δ: 13.58 (1H, s), 8.70-8.64 (2H, m), 7.89 (1H, d, J = 8.0 Hz), 7.53-7.48 (2H, m), 7.39 (1H, dd, J = 8.8, 2.4 Hz), 6.76 (1H, d, J = 2.4 Hz), 5.57 (2H, s). |
| 103 | A92 | F | 9.66 | 442.0528 | 442.0520 | $C_{22}H_{14}Cl_2FN_3O_2$ | (DMSO-d6) δ: 8.74 (1H, d, J = 2.0 Hz), 8.69 (1H, d, J = 4.9 Hz), 7.97 (1H, d, J = 7.8 Hz), 7.66-7.38 (6H, m), 7.22 (1H, td, J = 8.5, 2.3 Hz), 6.77 (1H, d, J = 2.4 Hz), 5.61 (2H, s). |
| 104 | A93 | F | 9.51 | 442.0517 | 442.0520 | $C_{22}H_{14}Cl_2FN_3O_2$ | (DMSO-d6) δ: 8.73 (1H, d, J = 2.0 Hz), 8.68 (1H, d, J = 5.0 Hz), 7.96 (1H, d, J = 8.0 Hz), 7.85-7.79 (2H, m), 7.56-7.50 (2H, m), 7.40 (1H, dd, J = 8.8, 2.4 Hz), 7.25 (2H, t, J = 8.8 Hz), 6.75 (1H, d, J = 2.4 Hz), 5.61 (2H, s) |
| 105 | A94 | F | 6.72 | 425.0559 | 425.0567 | $C_{21}H_{14}Cl_2N_4O_2$ | (DMSO-d6) δ: 9.24 (1H, s), 8.83-8.68 (4H, m), 8.00-7.88 (2H, m), 7.59-7.51 (2H, m), 7.41 (1H, dd, J = 8.8, 2.4 Hz), 6.85 (1H, d, J = 2.4 Hz), 5.66 (2H, s). |

TABLE 25

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 106 | A95 | F | 6.50 | 425.0553 | 425.0567 | $C_{21}H_{14}Cl_2N_4O_2$ | (DMSO-d6) δ: 8.87 (2H, d, J = 6.3 Hz), 8.75 (1H, d, J = 2.0 Hz), 8.71 (1H, dd, J = 4.9, 1.5 Hz), 8.33 (2H, d, J = 6.3 Hz), 7.99-7.95 (1H, m), 7.58-7.50 (2H, m), 7.41 (1H, dd, J = 8.3, 2.4 Hz), 6.88 (1H, d, J = 2.4 Hz), 5.64 (2H, s). |
| 107 | A96 | F | 8.07 | 378.0410 | 378.0407 | $C_{17}H_{13}Cl_2N_3O_2$ | (DMSO-d6) δ: 8.66 (2H, s), 7.88 (1H, d, J = 8.0 Hz), 7.53-7.48 (2H, m), 7.39 (1H, dd, J = 8.5, 2.2 Hz), 6.66 (1H, d, J = 2.4 Hz), 5.55 (2H, s), 3.99 (3H, s). |
| 108 | A97 | F | 7.25 | 408.0500 | 408.0512 | $C_{18}H_{15}Cl_2N_3O_4$ | |
| 109 | A98 | F | 10.06 | 446.0271 | 446.0281 | $C_{18}H_{12}Cl_2F_3N_3O_3$ | |

TABLE 25-continued

| Example | Compound No. | Scheme | HPLC Retention time | Obs. Mass ($M^+ + H$) | Pred. Mass ($M^+ + H$) | Formula (M) | $^1$H-NMR |
|---|---|---|---|---|---|---|---|
| 110 | A99 | F | 10.48 | 454.0722 | 454.0720 | $C_{23}H_{17}Cl_2N_3O_3$ | |
| 111 | A100 | F | 10.12 | 458.0473 | 458.0469 | $C_{22}H_{14}Cl_2FN_3O_3$ | |
| 112 | A101 | I | 8.65 | 373.0243 | 373.0254 | $C_{17}H_{10}Cl_2N_4O_2$ | (DMSO-d6) δ: 8.71 (1H, d, J = 4.9 Hz), 8.67 (1H, s), 7.91 (1H, dd, J = 7.8, 1.5 Hz), 7.56-7.47 (2H, m), 7.39 (1H, d, J = 8.8 Hz), 6.93 (1H, s), 5.62 (2H, s). |
| 113 | A102 | F | 8.46 | 374.0443 | 374.0458 | $C_{18}H_{13}Cl_2N_3O_2$ | |
| 114 | A103 | F | 8.85 | 414.0765 | 414.0771 | $C_{21}H_{17}Cl_2N_3O_2$ | |
| 115 | A104 | F | 8.97 | 394.0164 | 394.0178 | $C_{17}H_{13}Cl_2N_3O_2S$ | (DMSO-d6) δ: 13.16 (1H, s), 8.67 (2H, s), 7.89 (1H, d, J = 7.8 Hz), 7.54-7.48 (2H, m), 7.39 (1H, dd, J = 8.5, 2.2 Hz), 6.64 (1H, s), 5.55 (2H, s), 2.54 (3H, s). |

TABLE 26

| Example | Compound No. | Scheme | HPLC Retention time | Obs. Mass ($M^+ + H$) | Pred. Mass ($M^+ + H$) | Formula (M) | $^1$H-NMR |
|---|---|---|---|---|---|---|---|
| 116 | A105 | F | 9.68 | 408.0340 | 408.0335 | $C_{18}H_{15}Cl_2N_3O_2S$ | (DMSO-d6) δ: 13.15 (1H, s), 8.67 (2H, s), 7.88 (1H, d, J = 7.8 Hz), 7.53-7.48 (2H, m), 7.39 (1H, dd, J = 8.8, 2.4 Hz), 6.62 (1H, s), 5.55 (2H, s), 3.15 (2H, q, J = 7.3 Hz), 1.34 (3H, t, J = 7.3 Hz). |
| 117 | A106 | F | 6.84 | 410.0131 | 410.0127 | $C_{17}H_{13}Cl_2N_3O_3S$ | |
| 118 | A107 | F | 7.29 | 424.0292 | 424.0284 | $C_{18}H_{15}Cl_2N_3O_3S$ | |
| 119 | A109 | A | 9.54 | 434.1025 | 434.1033 | $C_{21}H_{21}Cl_2N_3O_3$ | (DMSO-d6) δ: 8.68 (2H, s), 7.94 (1H, dt, J = 8.0, 1.8 Hz), 7.57-7.47 (2H, m), 7.37 (1H, dd, J = 8.8, 2.4 Hz), 6.35 (1H, d, J = 2.0 Hz), 5.63 (2H, s), 2.13-2.02 (2H, m), 1.87-1.75 (2H, m), 0.82 (6H, t, J = 7.3 Hz). |
| 120 | A112 | A | 8.62 | 465.0559 | 465.0549 | $C_{20}H_{18}Cl_2N_4O_3S$ | (DMSO-d6) δ: 8.71-8.66 (2H, m), 7.94 (1H, dt, J = 8.0, 1.8 Hz), 7.54-7.45 (2H, m), 7.39 (1H, dd, J = 8.8, 2.4 Hz), 6.73 (1H, d, J = 2.0 Hz), 5.49 (2H, s), 2.90-2.83 (1H, m), 2.44 (3H, s), 1.06-0.89 (4H, m). |
| 121 | A113 | A | 7.62 | 399.1484 | 399.1485 | $C_{20}H_{22}N_4O_3S$ | (DMSO-d6) δ: 8.77 (1H, d, J = 2.4 Hz), 8.70 (1H, dd, J = 4.9, 2.0 Hz), 8.02 (1H, dt, J = 8.0, 2.0 Hz), 7.58-7.54 (1H, m), 7.01 (1H, d, J = 7.8 Hz), 6.94 (1H, d, J = 7.8 Hz), 6.37 (1H, s), 5.41 (2H, s), 2.97 (3H, s), 2.44 (3H, s), 2.15 (3H, s), 2.04 (3H, s). |
| 122 | A114 | A | 8.44 | 425.1634 | 425.1642 | $C_{22}H_{24}N_4O_3S$ | |

TABLE 27

| Example | Compound No. | Scheme | HPLC Retention time | Obs. Mass ($M^+ + H$) | Pred. Mass ($M^+ + H$) | Formula (M) | $^1$H-NMR |
|---|---|---|---|---|---|---|---|
| 123 | A115 | A | 7.42 | 427.0881 | 427.0893 | $C_{20}H_{18}N_4O_3S_2$ | (DMSO-d6) δ: 8.83 (1H, d, J = 2.0 Hz), 8.67 (1H, dd, J = 4.9, 1.5 Hz), 8.09 (1H, dt, J = 7.8, 2.0 Hz), 7.80 (1H, d, J = 7.8 Hz), 7.73 (1H, d, J = 5.4 Hz), 7.56-7.51 (1H, m), 7.47 (1H, d, J = 5.4 Hz), 7.31 (1H, t, J = 7.6 Hz), 6.82 (1H, d, J = 7.3 Hz), 5.71 (2H, s), 2.95 (3H, s), 2.42 (3H, s). |
| 124 | A116 | A | 8.21 | 453.1048 | 453.1050 | $C_{22}H_{20}N_4O_3S_2$ | (DMSO-d6) δ: 8.80 (1H, d, J = 2.0 Hz), 8.65 (1H, dd, J = 4.9, 2.0 Hz), 8.05 (1H, dt, J = 8.0, 1.8 Hz), 7.80 (1H, d, J = 7.8 Hz), 7.73 (1H, d, J = 5.4 Hz), 7.54-7.45 (2H, m), 7.31 (1H, t, J = 7.8 Hz), 6.81 (1H, d, J = 7.3 Hz), 5.71 (2H, s), 2.78-2.70 (1H, m), 2.42 (3H, s), 0.97-0.77 (4H, m). |
| 125 | A117 | B | 8.38 | 453.1050 | 453.1050 | $C_{22}H_{20}N_4O_3S_2$ | (DMSO-d6) δ: 8.74 (1H, d, J = 1.5 Hz), 8.62 (1H, dd, J = 4.9, 1.5 Hz), 7.98 (1H, dt, J = 8.0, 2.0 Hz), 7.81-7.70 (2H, m), |

TABLE 27-continued

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| | | | | | | | 7.49-7.43 (2H, m), 7.31 (1H, t, J = 7.8 Hz), 6.80 (1H, d, J = 7.3 Hz), 5.65 (2H, s), 2.96 (3H, s), 2.25-2.15 (1H, m), 0.99-0.90 (4H, m). |
| 126 | A118 | B | 9.15 | 479.1203 | 479.1206 | $C_{24}H_{22}N_4O_3S_2$ | |
| 127 | A120 | A | 8.01 | 374.1497 | 374.1499 | $C_{22}H_{19}N_3O_3$ | |
| 128 | A121 | A | 9.09 | 378.1002 | 378.1004 | $C_{21}H_{16}ClN_3O_2$ | (DMSO-d6) δ: 12.94 (1H, s), 8.60 (1H, d, J = 2.4 Hz), 8.55 (1H, d, J = 2.0 Hz), 8.05-7.95 (3H, m), 7.83 (1H, d, J = 8.3 Hz), 7.62-7.56 (2H, m), 7.40 (1H, t, J = 7.8 Hz), 6.54 (1H, d, J = 6.8 Hz), 6.12 (2H, s), 2.53 (3H, s). |
| 129 | A122 | A | 7.48 | 358.1550 | 358.1550 | $C_{22}H_{19}N_3O_2$ | |

TABLE 28

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 130 | A123 | A | 8.34 | 362.1308 | 362.1299 | $C_{21}H_{16}FN_3O_2$ | |
| 131 | A124 | A | 7.69 | 358.1552 | 358.1550 | $C_{22}H_{19}N_3O_2$ | |
| 132 | A125 | A | 8.30 | 374.1501 | 374.1499 | $C_{22}H_{19}N_3O_3$ | |
| 133 | A126 | A | 9.81 | 360.1343 | 360.1343 | $C_{21}H_{17}N_3O_3$ | |
| 134 | A127 | A | 6.36 | 359.1497 | 359.1503 | $C_{21}H_{18}N_4O_2$ | |
| 135 | A128 | A | 7.78 | 372.1342 | 372.1343 | $C_{22}H_{17}N_3O_3$ | |
| 136 | A129 | A | 7.58 | 387.1813 | 387.1816 | $C_{23}H_{22}N_4O_2$ | |
| 137 | A130 | A | 9.81 | 436.1667 | 436.1656 | $C_{27}H_{21}N_3O_3$ | (DMSO-d6) δ: 8.45-8.41 (2H, m), 8.01-7.97 (2H, m), 7.80 (1H, d, J = 8.3 Hz), 7.62-7.58 (2H, m), 7.35-7.30 (2H, m), 7.13 (2H, t, J = 7.8 Hz), 7.02 (1H, t, J = 7.1 Hz), 6.83 (2H, d, J = 8.3 Hz), 6.54 (1H, d, J = 6.8 Hz), 6.06 (2H, s), 2.53 (3H, s). |
| 138 | A131 | A | 9.59 | 466.1769 | 466.1761 | $C_{28}H_{23}N_3O_4$ | (DMSO-d6) δ: 8.40 (1H, d, J = 2.0 Hz), 8.36 (1H, d, J = 2.4 Hz), 8.02-7.95 (2H, m), 7.81 (1H, d, J = 8.3 Hz), 7.63-7.58 (2H, m), 7.30 (1H, t, J = 7.6 Hz), 7.07-6.97 (2H, m), 6.87 (1H, dd, J = 7.8, 1.5 Hz), 6.78 (1H, d, J = 8.3 Hz), 6.71-6.65 (1H, m), 6.48 (1H, d, J = 7.3 Hz), 5.99 (2H, s), 3.49 (3H, s), 2.52 (3H, s). |
| 139 | A132 | A | 8.93 | 384.0581 | 384.0568 | $C_{19}H_{14}ClN_3O_2S$ | (DMSO-d6) δ: 8.68 (1H, d, J = 2.0 Hz), 8.65 (1H, d, J = 1.5 Hz), 8.06 (1H, t, J = 2.0 Hz), 7.99-7.95 (1H, m), 7.73-7.68 (1H, m), 7.42-7.37 (2H, m), 7.02 (1H, s), 5.85 (2H, s), 2.51 (3H, s). |

TABLE 29

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 140 | A133 | A | 8.37 | 368.0856 | 368.0864 | $C_{19}H_{14}FN_3O_2S$ | (DMSO-d6) δ: 8.63 (1H, d, J = 3.5 Hz), 8.57 (1H, t, J = 1.5 Hz), 7.99-7.95 (1H, m), 7.92-7.86 (1H, m), 7.72-7.67 (1H, m), 7.42-7.37 (2H, m), 6.98 (1H, s), 5.85 (2H, s), 2.50 (3.0H, s). |
| 141 | A134 | A | 8.75 | 380.0369 | 380.0363 | $C_{17}H_{12}Cl_2FN_3O_2$ | (DMSO-d6) δ: 13.11 (1H, s), 8.67 (1H, d, J = 2.4 Hz), 8.48 (1H, s), 7.89-7.84 (1H, m), 7.50 (1H, d, J = 7.8 Hz), 7.39-7.35 (1H, m), 6.57 (1H, s), 5.61 (2H, s), 2.49 (3H, s). |
| 142 | A135 | A | 9.44 | 396.0076 | 396.0068 | $C_{17}H_{12}Cl_3N_3O_2$ | (DMSO-d6) δ: 8.71 (1H, d, J = 2.4 Hz), 8.56 (1H, d, J = 2.0 Hz), 8.02 (1H, t, J = 2.0 Hz), 7.50 (1H, d, J = 8.3 Hz), 7.38 (1H, dd, J = 8.8, 2.4 Hz), 6.62 (1H, d, J = 2.4 Hz), 5.61 (2H, s), 2.50 (3H, s). |

TABLE 29-continued

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 143 | A136 | A | 11.07 | 434.0085 | 434.0081 | $C_{17}H_9Cl_2F_4N_3O_2$ | (DMSO-d6) δ: 14.22 (1H, s), 8.73 (1H, d, J = 2.4 Hz), 8.54 (1H, t, J = 1.5 Hz), 7.98-7.93 (1H, m), 7.47 (1H, d, J = 8.8 Hz), 7.38 (1H, dd, J = 8.8, 2.4 Hz), 6.85 (1H, d, J = 2.4 Hz), 5.65 (2H, s). |
| 144 | A137 | A | 11.75 | 449.9786 | 449.9785 | $C_{17}H_9Cl_3F_3N_3O_2$ | (DMSO-d6) δ: 8.76 (1H, d, J = 2.0 Hz), 8.61 (1H, d, J = 2.0 Hz), 8.10 (1H, 1, J = 2.2 Hz), 7.47 (1H, d, J = 8.3 Hz), 7.38 (1H, dd, J = 8.8, 2.4 Hz), 6.87 (1H, d, J = 2.4 Hz), 5.65 (2H, s). |
| 145 | A138 | A | 9.85 | 412.1271 | 412.1267 | $C_{22}H_{16}F_3N_3O_2$ | (DMSO-d6) δ: 8.94 (1H, s), 8.89 (1H, s), 8.15 (1H, s), 8.03-7.95 (2H, m), 7.84 (1H, d, J = 8.3 Hz), 7.61-7.56 (2H, m), 7.43-7.38 (1H, m), 6.62 (1H, d, J = 7.3 Hz), 6.14 (2H, s), 2.56 (3H, s). |
| 146 | A139 | A | 10.23 | 430.0328 | 430.0331 | $C_{18}H_{12}Cl_2F_3N_3O_2$ | (DMSO-D6) δ: 13.18 (1H, s), 9.05 (1H, s), 8.91 (1H, d, J = 1.5 Hz), 8.18 (1H, s), 7.50 (1H, d, J = 8.8 Hz), 7.38 (1H, dd, J = 8.8, 2.4 Hz), 6.66 (1H, d, J = 2.4 Hz), 5.63 (2H, s), 2.51 (3H, s). |

TABLE 30

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 147 | A140 | A | 12.09 | 484.0049 | 484.0049 | $C_{18}H_9Cl_2F_6N_3O_2$ | (DMSO-D6) δ: 9.11 (1H, s), 8.97 (1H, d, J = 2.0 Hz), 8.29 (1H, s), 7.46 (1H, d, J = 8.3 Hz), 7.37 (1H, dd, J = 8.8, 2.4 Hz), 6.92 (1H, d, J = 2.4 Hz), 5.66 (2H, s). |
| 148 | A141 | A | 9.01 | 402.0460 | 402.0474 | $C_{19}H_{13}ClFN_3O_2S$ | (DMSO-d6) δ: 8.66 (1H, d, J = 2.4 Hz), 8.59 (1H, t, J = 1.7 Hz), 7.98 (1H, dd, J = 7.8, 1.0 Hz), 7.95-7.91 (1H, m), 7.47 (1H, dd, J = 7.8, 1.0 Hz), 7.37 (1H, t, J = 7.8 Hz), 6.91 (1H, s), 6.10 (2H, s), 2.52 (3H, s). |
| 149 | A142 | A | 9.60 | 418.0180 | 418.0178 | $C_{19}H_{13}Cl_2N_3O_2S$ | (DMSO-D6) δ: 8.67 (2H, dd, J = 12.9, 2.2 Hz), 8.10 (1H, t, J = 2.2 Hz), 7.98 (1H, d, J = 7.8 Hz), 7.47 (1H, d, J = 7.8 Hz), 7.37 (1H, t, J = 8.0 Hz), 6.93 (1H, s), 6.10 (2H, s), 2.52 (3H, s). |
| 150 | A143 | A | 10.31 | 452.0446 | 452.0442 | $C_{20}H_{13}ClF_3N_3O_2S$ | (DMSO-D6) δ: 13.05 (1H, s), 9.00 (2H, s), 8.27 (1H, s), 7.98 (1H, d, J = 7.8 Hz), 7.47 (1H, d, J = 7.8 Hz), 7.37 (1H, t, J = 7.8 Hz), 6.96 (1H, s), 6.11 (2H, s), 2.53 (3H, s). |
| 151 | A144 | B | 10.20 | 406.1318 | 406.1317 | $C_{23}H_{20}ClN_3O_2$ | (DMSO-D6) δ: 8.61 (1H, d, J = 2.4 Hz), 8.54 (1H, d, J = 2.0 Hz), 8.04-7.96 (3H, m), 7.83 (1H, d, J = 8.3 Hz), 7.62-7.56 (2H, m), 7.42 (1H, t, J = 7.6 Hz), 6.53 (1H, d, J = 7.3 Hz), 6.10 (2H, s), 3.76-3.67 (1H, m), 1.30 (6H, d, J = 7 Hz). |
| 152 | A145 | B | 10.97 | 404.1157 | 404.1160 | $C_{23}H_{18}ClN_3O_2$ | (DMSO-D6) δ: 12.96 (1H, s), 8.60 (1H, d, J = 2.4 Hz), 8.50 (1H, d, J = 2.0 Hz), 8.04-7.95 (3H, m), 7.83 (1H, d, J = 8.3 Hz), 7.61-7.56 (2H, m), 7.42 (1H, t, J = 7.8 Hz), 6.55 (1H, d, J = 7.3 Hz), 6.09 (2H, s), 2.77-2.71 (1H, m), 1.04-0.96 (4H, m). |

TABLE 31

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 153 | A146 | B | 10.76 | 424.1367 | 424.0381 | $C_{19}H_{16}Cl_3N_3O_2$ | (DMSO-D6) δ: 8.72 (1H, t, J = 2.0 Hz), 8.56 (1H, t, J = 1.7 Hz), 8.04-8.01 (1H, m), 7.50 (1H, dd, J = 8.5, 1.7 Hz), 7.38 (1H, dt, |

TABLE 31-continued

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 154 | A147 | B | 11.47 | 422.0221 | 422.0224 | C$_{19}$H$_{14}$Cl$_3$N$_3$O$_2$ | J = 8.3, 1.7 Hz), 6.55 (1H, s), 5.61 (2H, s), 3.71-3.64 (1H, m), 1.26 (6H, d, J = 6.8 Hz). (DMSO-d6) δ: 13.14 (1H, s), 8.70 (1H, d, J = 2.4 Hz), 8.51 (1H, d, J = 2.0 Hz), 7.97 (1H, t, J = 2.0 Hz), 7.50 (1H, d, J = 8.8 Hz), 7.38 (1H, dd, J = 8.3, 2.4 Hz), 6.61 (1H, d, J = 2.4 Hz), 5.57 (2H, s), 2.73-2.66 (1H, m), 0.99-0.93 (4H, m). |
| 155 | A148 | B | 9.01 | 376.1453 | 376.1456 | C$_{22}$H$_{18}$FN$_3$O$_2$ | (DMSO-D6) δ: 8.60 (1H, d, J = 2.9 Hz), 8.50 (1H, s), 8.05-7.82 (4H, m), 7.62-7.55 (2H, m), 7.41 (1H, t, J = 7.8 Hz), 6.53 (1H, d, J = 6.8 Hz), 6.12 (2H, s), 2.97 (2H, q, J = 7.5 Hz), 1.27 (3H, t, J = 7.6 Hz). |
| 156 | A149 | B | 9.61 | 392.1156 | 392.1160 | C$_{22}$H$_{18}$ClN$_3$O$_2$ | (DMSO-D6) δ: 8.62 (1H, d, J = 1.5 Hz), 8.56 (1H, s), 8.05-7.95 (3H, m), 7.83 (1H, d, J = 8.3 Hz), 7.62-7.56 (2H, m), 7.41 (1H, t, J = 7.8 Hz), 6.55 (1H, d, J = 7.3 Hz), 6.12 (2H, s), 2.97 (2H, q, J = 7.5 Hz), 1.27 (3H, t, J = 7.3 Hz). |
| 157 | A150 | B | 9.34 | 394.0528 | 394.0520 | C$_{18}$H$_{14}$Cl$_2$FN$_3$O$_2$ | (DMSO-D6) δ: 8.69 (1H, d, J = 2.7 Hz), 8.50 (1H, t, J = 1.8 Hz), 7.89 (1H, dt, J = 9.4, 1.8 Hz), 7.50 (1H, d, J = 8.3 Hz), 7.37 (1H, dd, J = 8.8, 2.7 Hz), 6.56 (1H, d, J = 2.7 Hz), 5.62 (2H, s), 2.92 (2H, q, J = 7.5 Hz), 1.23 (3H, t, J = 7.6 Hz). |
| 158 | A151 | B | 10.04 | 410.0229 | 410.0224 | C$_{18}$H$_{14}$Cl$_3$N$_3$O$_2$ | (DMSO-d6) δ: 8.73 (1H, d, J = 2.4 Hz), 8.57 (1H, d, J = 2.0 Hz), 8.05 (1H, t, J = 2.2 Hz), 7.50 (1H, d, J = 8.8 Hz), 7.38 (1H, dd, J = 8.8, 2.4 Hz), 6.61 (1H, d, J = 2.4 Hz), 5.62 (2H, s), 2.93 (2H, q, J = 7.5 Hz), 1.23 (3H, t, J = 7.3 Hz). |

TABLE 32

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 159 | A152 | B | 9.57 | 390.1601 | 390.1612 | C$_{23}$H$_{20}$FN$_3$O$_2$ | (DMSO-d6) δ: 8.59 (1H, d, J = 2.4 Hz), 8.49 (1H, t, J = 1.7 Hz), 8.05-7.95 (2H, m), 7.86-7.80 (2H, m), 7.63-7.56 (2H, m), 7.41 (1H, t, J = 7.6 Hz), 6.52 (1H, d, J = 7.3 Hz), 6.11 (2H, s), 3.76-3.69 (1H, m), 1.30 (6H, d, J = 6.8 Hz). |
| 160 | A153 | B | 10.23 | 388.1446 | 388.1456 | C$_{23}$H$_{18}$FN$_3$O$_2$ | (DMSO-d6) δ: 12.97 (1H, s), 8.57 (1H, d, J = 2.9 Hz), 8.44 (1H, t, J = 1.7 Hz), 8.06-7.94 (2H, m), 7.85-7.76 (2H, m), 7.62-7.56 (2H, m), 7.42 (1H, t, J = 7.8 Hz), 6.53 (1H, d, J = 6.8 Hz), 6.09 (2H, s), 2.77-2.71 (1H, m), 1.05-0.95 (4H, m). |
| 161 | A154 | B | 10.01 | 408.0675 | 408.0676 | C$_{19}$H$_{16}$Cl$_2$FN$_3$O$_2$ | (DMSO-d6) δ: 13.18 (1H, s), 8.68 (1H, d, J = 2.4 Hz), 8.48 (1H, s), 7.86 (1H, dt, J = 9.6, 2.1 Hz), 7.50 (1H, d, J = 8.8 Hz), 7.37 (1H, dd, J = 8.8, 2.4 Hz), 6.49 (1H, d, J = 2.4 Hz), 5.60 (2H, s), 3.72-3.63 (1H, m), J = 1.26 (6H, d, J = 6.8 Hz). |
| 162 | A155 | B | 10.65 | 406.0509 | 406.0520 | C$_{19}$H$_{14}$Cl$_2$FN$_3$O$_2$ | (DMSO-d6) δ: 8.67 (1H, d, J = 2.9 Hz), J = 8.44 (1H, t, J = 2.1 Hz), 7.82 (1H, dt, J = 9.4, 2.1 Hz), 7.50 (1H, d, J = 8.8 Hz), 7.38 (1H, dd, J = 8.8, 2.4 Hz), 6.58 (1H, d, J = 2.4 Hz), 5.58 (2H, s), 2.73-2.66 (1H, m), 0.99-0.94 (4H, m). |
| 163 | A156 | A | 7.67 | 376.0598 | 376.0614 | C$_{18}$H$_{15}$Cl$_2$N$_3$O$_2$ | (DMSO-d6) δ: 8.48 (1H, d, J = 2.4 Hz), 8.37 (1H, d, J = 2.4 Hz), 7.70 (1H, t, J = 2.4 Hz), 7.51 (1H, d, J = 8.3 Hz), 7.39 (1H, dd, J = 8.3, 2.4 Hz), 6.55 (1H, d, J = 2.4 Hz), 5.57 (2H, s), 2.49 (3H, s), 2.28 (3H, s) |
| 164 | A157 | A | 8.03 | 392.0556 | 392.0563 | C$_{18}$H$_{15}$Cl$_2$N$_3$O$_3$ | (DMSO-d6) δ: 8.35 (1H, d, J = 2.9 Hz), 8.17 (1H, d, J = 1.5 Hz), 7.51 (1H, d, J = 8.8 Hz), 7.39-7.37 (2H, m), 6.55 (1H, d, J = 2.4 Hz), 5.57 (2H, s), 3.75 (3H, s), 2.49 (3H, s). |

TABLE 33

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 165 | A158 | A | 8.95 | 387.0414 | 387.0410 | $C_{18}H_{12}Cl_2N_4O_2$ | (DMSO-d6) δ: 8.37 (1H, d, J = 4.9 Hz), 8.08 (1H, t, J = 8.5 Hz), 7.47 (1H, t, J = 6.1 Hz), 7.43 (1H, d, J = 8.8 Hz), 7.34 (1H, dd, J = 8.3, 2.4 Hz), 6.54 (1H, d, J = 2.4 Hz), 5.48 (2H, s), 2.49 (3H, s). |
| 166 | A159 | A | 7.40 | 376.0605 | 376.0614 | $C_{18}H_{15}Cl_2N_3O_2$ | (DMSO-d6) δ: 8.39 (1H, d, J = 2.0 Hz), 7.65 (1H, dd, J = 8.0, 2.2 Hz), 7.47 (1H, d, J = 8.8 Hz), 7.34 (1H, dd, J = 8.3, 2.4 Hz), 7.27 (1H, d, J = 8.3 Hz), 6.42 (1H, d, J = 2.4 Hz), 5.74 (2H, s), 2.48 (3H, s), 2.45 (3H, s). |
| 167 | A160 | A | 10.21 | 380.0368 | 380.0363 | $C_{17}H_{12}Cl_2FN_3O_2$ | (DMSO-d6) δ: 9.09 (1H, d, J = 2.0 Hz), 8.89 (1H, d, J = 2.0 Hz), 8.44 (1H, t, J = 2.0 Hz), 7.48 (1H, d, J = 8.3 Hz), 7.36 (1H, dd, J = 8.8, 2.4 Hz), 6.61 (1H, d, J = 2.4 Hz), 5.62 (2H, s), 2.49 (3H, s). |
| 168 | A161 | A | 8.60 | 392.0558 | 392.0563 | $C_{18}H_{15}Cl_2N_3O_3$ | (DMSO-d6) δ: 8.16 (1H, d, J = 2.0 Hz), 7.74 (1H, dd, J = 8.3, 2.4 Hz), 7.50 (1H, d, J = 8.3 Hz), 7.36 (1H, dd, J = 8.8, 2.4 Hz), 6.87 (1H, d, J = 8.8 Hz), 6.47 (1H, d, J = 2.4 Hz), 5.62 (2H, s), 3.85 (3H, s), 2.47 (3H, s). |
| 169 | A162 | A | 8.32 | 392.0558 | 392.0563 | $C_{18}H_{15}Cl_2N_3O_3$ | (DMSO-d6) δ: 8.27 (1H, dd, J = 4.9, 2.0 Hz), 7.74 (1H, dd, J = 7.3, 2.0 Hz), 7.41 (1H, d, J = 8.3 Hz), 7.32 (1H, dd, J = 8.5, 2.7 Hz), 7.07 (1H, dd, J = 7.3, 4.9 Hz), 6.54 (1H, d, J = 2.4 Hz), 5.35 (2H, s), 3.63 (3H, s), 2.46 (3H, s). |
| 170 | A163 | A | 7.50 | 405.0881 | 405.0880 | $C_{19}H_{18}Cl_2N_4O_2$ | |
| 171 | A164 | A | 9.34 | 396.0061 | 396.0068 | $C_{17}H_{12}Cl_3N_3O_2$ | |
| 172 | A165 | A | 8.19 | 440.0247 | 440.0233 | $C_{18}H_{15}Cl_2N_3O_4S$ | |

TABLE 34

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 173 | A166 | A | 8.04 | 431.1020 | 431.1036 | $C_{21}H_{20}Cl_2N_4O_2$ | (DMSO-d6) δ: 7.96 (1H, d, J = 2.4 Hz), 7.82 (1H, d, J = 2.0 Hz), 7.53 (1H, d, J = 8.3 Hz), 7.40 (1H, dd, J = 8.8, 2.4 Hz), 6.74 (1H, t, J = 2.2 Hz), 6.53 (1H, d, J = 2.0 Hz), 5.57 (2H, s), 3.16-3.09 (4H, m), 2.49 (3H, s), 1.91-1.89 (4H, m). |
| 174 | A167 | A | 9.62 | 407.0306 | 407.0308 | $C_{17}H_{12}Cl_2N_4O_4$ | (DMSO-d6) δ: 13.17 (1H, s), 9.41 (1H, d, J = 2.4 Hz), 9.04 (1H, d, J = 2.0 Hz), 8.54 (1H, t, J = 2.2 Hz), 7.53 (1H, d, J = 8.8 Hz), 7.40 (1H, dd, J = 8.8, 2.4 Hz), 6.66 (1H, d, J = 2.4 Hz), 5.63 (2H, s), 2.52 (3H, s). |
| 175 | A168 | A | 8.44 | 402.0777 | 402.0771 | $C_{20}H_{17}Cl_2N_3O_2$ | (DMSO-d6) δ: 13.05 (1H, s), 8.49 (1H, s), 8.39 (1H, s), 7.53 (1H, d, J = 8.3 Hz), 7.40 (1H, dd, J = 8.3, 2.4 Hz), 7.30 (1H, s), 6.57 (1H, d, J = 2.0 Hz), 5.51 (2H, s), 2.49 (3H, s), 1.98-1.91 (1H, m), 0.99-0.93 (2H, m), 0.57-0.52 (2H, m). |
| 176 | A169 | C | 9.75 | 381.9908 | 381.9911 | $C_{16}H_{10}Cl_3N_3O_2$ | (DMSO-d6) δ: 13.20 (1H, brs), 8.71 (1H, d, J = 2.4 Hz), 8.58 (1H, d, J = 2.0 Hz), 8.04 (1H, t, J = 2.2 Hz), 7.92 (1H, s), 7.50 (1H, d, J = 8.3 Hz), 7.37 (1H, dd, J = 8.3, 2.4 Hz), 6.55 (1H, d, J = 2.4 Hz), 5.70 (2H, s). |
| 177 | A170 | A | 9.92 | 448.0892 | 448.0891 | $C_{19}H_{12}F_7N_3O_2$ | (DMSO-d6) δ: 8.65 (1H, d, J = 2.4 Hz), 8.42 (1H, s), 8.00 (1H, d, J = 8.3 Hz), 7.91-7.84 (2H, m), 6.83 (1H, s), 5.83 (2H, s), 2.52 (3H, s). |
| 178 | A171 | C | 9.03 | 366.0205 | 366.0207 | $C_{16}H_{10}Cl_2FN_3O_2$ | (DMSO-d6) δ: 8.68 (1H, d, J = 2.9 Hz), 8.51 (1H, d, J = 2.5 Hz), 7.92-7.88 (2H, m), 7.50 (1H, d, J = 8.3 Hz), 7.37 (1H, dd, J = 8.8, 2.4 Hz), 6.52 (1H, s), 5.71 (2H, s). |

TABLE 35

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 179 | A172 | A | 6.93 | 378.0404 | 378.0407 | $C_{17}H_{13}Cl_2N_3O_3$ | (DMSO-d6) δ: 10.51 (1H, s), 8.24 (1H, d, J = 2.4 Hz), 8.12 (1H, d, J = 1.5 Hz), 7.53 (1H, d, J = 8.8 Hz), 7.40 (1H, dd, J = 8.5, 2.2 Hz), 7.27 (1H, t, J = 2.0 Hz), 6.63 (1H, d, J = 2.0 Hz), 5.54 (2H, s), 2.51 (3H, s). |
| 180 | A173 | A | 10.55 | 464.0596 | 464.0595 | $C_{19}H_{12}ClF_6N_3O_2$ | (DMSO-d6) δ: 8.69 (1H, d, J = 2.4 Hz), 8.49 (1H, d, J = 1.5 Hz), 8.03-7.99 (2H, m), 7.89 (1H, d, J = 8.3 Hz), 6.84 (1H, s), 5.83 (2H, s), 2.52 (3H, s). |
| 181 | A174 | A | 8.63 | 406.0728 | 406.0720 | $C_{19}H_{17}Cl_2N_3O_3$ | (DMSO-d6) δ: 8.36 (1H, d, J = 2.4 Hz), 8.20 (1H, s), 7.51 (1H, d, J = 8.8 Hz), 7.43-7.37 (2H, m), 6.62 (1H, d, J = 2.0 Hz), 5.58 (2H, s), 4.02 (2H, q, J = 7.0 Hz), 2.51 (3H, s), 1.28 (3H, t, J = 6.8 Hz). |
| 182 | A175 | A | 9.09 | 420.0891 | 420.0876 | $C_{20}H_{19}Cl_2N_3O_3$ | (DMSO-d6) δ: 8.34 (1H, d, J = 2.4 Hz), 8.22 (1H, d, J = 1.5 Hz), 7.51 (1H, d, J = 8.8 Hz), 7.41-7.38 (2H, m), 6.67 (1H, d, J = 2.0 Hz), 5.58 (2H, s), 4.55-4.49 (1H, m), 2.52 (3H, s), 1.20 (6H, d, J = 6.3 Hz). |
| 183 | A176 | A | 9.67 | 438.0773 | 438.0771 | $C_{23}H_{17}Cl_2N_3O_2$ | (DMSO-d6) δ: 9.00 (1H, d, J = 2.4 Hz), 8.65 (1H, d, J = 1.5 Hz), 8.07 (1H, t, J = 2.2 Hz), 7.62 (2H, d, J = 7.3 Hz), 7.53-7.38 (5H, m), 6.72 (1H, d, J = 2.4 Hz), 5.64 (2H, s), 2.54 (3H, s). |
| 184 | A177 | A | 9.61 | 439.9573 | 439.9563 | $C_{17}H_{12}BrCl_2N_3O_2$ | (DMSO-d6) δ: 8.78 (1H, d, J = 2.4 Hz), 8.58 (1H, d, J = 2.0 Hz), 8.13-8.10 (1H, m), 7.50 (1H, d, J = 8.3 Hz), 7.38 (1H, dd, J = 8.8, 2.4 Hz), 6.61 (1H, d, J = 2.0 Hz), 5.60 (2H, s), 2.49 (3H, s). |
| 185 | A178 | A | 8.26 | 340.1457 | 340.1456 | $C_{19}H_{18}FN_3O_2$ | (DMSO-d6) δ: 8.66 (1H, d, J = 2.4 Hz), 8.52 (1H, s), 7.82 (1H, d, J = 9.8 Hz), 7.05 (1H, d, J = 7.3 Hz), 6.93 (1H, d, J = 7.3 Hz), 6.18 (1H, s), 5.55 (2H, s), 2.50 (3H, s), 2.14 (3H, s), 2.12 (3H, s). |

TABLE 36

| Example | Compound No. | Scheme | HPLC Retention time | Obs. Mass (M⁺ + H) | Pred. Mass (M⁺ + H) | Formula(M) | ¹H-NMR |
|---|---|---|---|---|---|---|---|
| 186 | A179 | A | 8.86 | 356.1165 | 356.1160 | $C_{19}H_{18}ClN_3O_2$ | (DMSO-d6) δ: 8.68 (1H, d, J = 2.4 Hz), 8.57 (1H, d, J = 1.5 Hz), 7.97 (1H, t, J = 2.2 Hz), 7.05 (1H, d, J = 7.8 Hz), 6.93 (1H, d, J = 7.8 Hz), 6.19 (1H, s), 5.55 (2H, s), 2.50 (3H, s), 2.13 (3H, s), 2.12 (3H, s). |
| 187 | A180 | A | 7.48 | 336.1699 | 336.1707 | $C_{20}H_{21}N_3O_2$ | (DMSO-d6) δ: 8.54 (1H, s), 8.48 (1H, s), 7.82 (1H, s), 7.05 (1H, d, J = 7.3 Hz), 6.94 (1H, d, J = 7.3 Hz), 6.23 (1H, s), 5.53 (2H, s), 2.52 (3H, s), 2.29 (3H, s), 2.13 (6H, s). |
| 188 | A181 | A | 8.22 | 390.0770 | 390.0771 | $C_{19}H_{17}Cl_2N_3O_2$ | (DMSO-d6) δ: 8.58 (1H, d, J = 2.0 Hz), 8.51 (1H, d, J = 2.0 Hz), 7.76 (1H, t, J = 2.0 Hz), 7.52 (1H, d, J = 8.3 Hz), 7.40 (1H dd, J = 8.8, 2.4 Hz), 6.67 (1H, d, J = 2.4 Hz), 5.58 (2H, s), 2.63 (2H, q, J = 7.5 Hz), 2.52 (3H, s), 1.10 (3H, t, J = 7.6 Hz). |
| 189 | A182 | A | 8.75 | 408.0345 | 408.0335 | $C_{18}H_{15}Cl_2N_3O_2S$ | (DMSO-d6) δ: 8.54 (1H, d, J = 2.4 Hz), 8.37 (1H, d, J = 2.0 Hz), 7.64 (1H, t, J = 2.0 Hz), 7.52 (1H, d, J = 8.8 Hz), 7.40 (1H, dd, J = 8.8, 2.4 Hz), 6.64 (1H, d, J = 2.4 Hz), 5.56 (2H, s), 2.51 (3H, s), 2.39 (3H, s). |
| 190 | A183 | A | 8.16 | 404.0567 | 404.0563 | $C_{19}H_{15}Cl_2N_3O_3$ | (DMSO-d6) δ: 13.11 (1H, s), 9.15 (1H, d, J = 2.0 Hz), 8.86 (1H, d, J = 2.0 Hz), 8.22 (1H, t, J = 2.0 Hz), 7.52 (1H, d, J = 8.3 Hz), 7.40 (1H, dd, J = 8.3, 2.4 Hz), 6.63 (1H, d, J = 2.4 Hz), 5.59 (2H, s), 2.56 (3H, s), 2.51 (3H, s). |
| 191 | A184 | A | 9.92 | 502.0747 | 502.0731 | $C_{24}H_{18}Cl_2FN_3O_4$ | (DMSO-d6) δ: 13.08 (1H, s), 8.54 (1H, d, J = 2.4 Hz), 8.45 (1H, d, J = 1.5 Hz), 7.48 (1H, d, J = 8.8 Hz), 7.36 (1H, dd, J = 8.3, 2.4 Hz), 7.26-7.19 (1H, m), 6.92-6.83 (3H, |

TABLE 36-continued

| Example | Compound No. | Scheme | HPLC Retention time | Obs. Mass (M$^+$ + H) | Pred. Mass (M$^+$ + H) | Formula(M) | $^1$H-NMR |
|---|---|---|---|---|---|---|---|
| | | | | | | | m), 6.45 (1H, d, J = 2.4 Hz), 5.40 (2H, s), 3.69 (3H, s), 2.47 (3H, s). |

TABLE 37

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 192 | A185 | A | 9.33 | 420.0890 | 420.0876 | $C_{20}H_{19}Cl_2N_3O_3$ | (DMSO-d6) δ: 13.20 (1H, s), 8.37 (1H, d, J = 2.9 Hz), 8.21 (1H, s), 7.52 (1H, d, J = 8.3 Hz), 7.42-7.37 (2H, m), 6.63 (1H, d, J = 2.4 Hz), 5.58 (2H, s), 3.89 (2H, t, J = 6.6 Hz), 2.51 (3H, s), 1.72-1.62 (2H, m), 0.92 (3H, t, J = 7.3 Hz). |
| 193 | A186 | A | 6.77 | 422.0655 | 422.0669 | $C_{19}H_{17}Cl_2N_3O_4$ | (DMSO-d6) δ: 8.41 (1H, d, J = 2.4 Hz), 8.22 (1H, s), 7.54-7.48 (2H, m), 7.39 (1H, dd, J = 8.3, 2.0 Hz), 6.66 (1H, s), 5.59 (2H, s), 4.00 (2H, t, J = 4.6 Hz), 3.68 (2H, t, J = 4.6 Hz), 2.52 (3H, s). |
| 194 | A187 | A | 7.15 | 436.0820 | 436.0825 | $C_{20}H_{19}Cl_2N_3O_4$ | (DMSO-d6) δ: 8.40 (1H, s), 8.22 (1H, d, J = 1.5 Hz), 7.53-7.47 (2H, m), 7.42-7.36 (1H, m), 6.69 (1H, d, J = 2.4 Hz), 5.59 (2H, s), 4.03 (2H, t, J = 6.3 Hz), 3.51 (2H, t, J = 6.3 Hz), 2.52 (3H, s), 1.86-1.78 (2H, m). |
| 195 | A188 | A | 9.97 | 434.1023 | 434.1033 | $C_{21}H_{21}Cl_2N_3O_3$ | (DMSO-d6) δ: 13.06 (1H, s), 8.34 (1H, s), 8.19 (1H, s), 7.52 (1H, d, J = 8.3 Hz), 7.40 (1H, d, J = 8.3 Hz), 7.31 (1H, s), 6.59 (1H, s), 5.56 (2H, s), 3.66 (2H, d, J = 6.3 Hz), 2.49 (3H, s), 1.99-1.90 (1H, m), 0.91 (6H, d, J = 6.3 Hz). |
| 196 | A189 | A | 11.35 | 474.1351 | 474.1346 | $C_{24}H_{25}Cl_2N_3O_3$ | (DMSO-d6) δ: 8.35 (1H, s), 8.21 (1H, s), 7.52 (1H, d, J = 8.3 Hz), 7.40 (1H, dd, J = 8.8, 2.4 Hz), 7.33 (1H, s), 6.64 (1H, d, J = 2.0 Hz), 5.56 (2H, s), 3.69 (2H, d, J = 6.3 Hz), 2.51 (3H, s), 1.75-1.60 (6H, m), 1.26-1.11 (3H, m), 1.02-0.90 (2H, m). |
| 197 | A190 | A | 9.98 | 468.0860 | 468.0876 | $C_{24}H_{19}Cl_2N_3O_3$ | (DMSO-d6) δ: 13.12 (1H, s), 8.50 (1H, s), 8.30 (1H, s), 7.50 (2H, d, J = 8.8 Hz), 7.40-7.31 (6H, m), 6.57 (1H, d, J = 2.4 Hz), 5.55 (2H, s), 5.11 (2H, s), 2.49 (3H, s). |

TABLE 38

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 198 | A192 | E | 8.01 | 439.0492 | 439.0490 | $C_{19}H_{17}Cl_3N_4O_2$ | |
| 199 | A194 | E | 8.38 | 465.0640 | 465.0646 | $C_{21}H_{19}Cl_3N_4O_2$ | (DMSO-d6) δ: 10.13 (1H, s), 8.76 (1H, d, J = 2.4 Hz), 8.62 (1H, d, J = 1.5 Hz), 8.10 (1H, t, J = 2.2 Hz), 7.51 (1H, d, J = 8.3 Hz), 7.40 (1H, dd, J = 8.8, 2.4 Hz), 6.70 (1H, d, J = 2.4 Hz), 5.70 (2H, s), 4.69 (2H, d, J = 5.4 Hz), 3.62 (2H, s), 3.23 (2H, s), 2.10-1.85 (4H, m). |
| 200 | A195 | E | 8.60 | 479.0782 | 479.0803 | $C_{22}H_{21}Cl_3N_4O_2$ | (DMSO-d6) δ: 9.81 (1H, s), 8.77 (1H, d, J = 2.4 Hz), 8.62 (1H, d, J = 1.5 Hz), 8.10 (1H, t, J = 2.2 Hz), 7.51 (1H, d, J = 8.8 Hz), 7.39 (1H, dd, J = 8.3, 2.4 Hz), 6.72 (1H, d, J = 2.4 Hz), 5.69 (2H, s), 4.58 (2H, d, J = 3.9 Hz), 3.52 (2H, d, J = 11.7 Hz), 3.12-3.00 (2H, m), 1.89-1.64 (5H, m), 1.47-1.35 (1H, m). |
| 201 | A196 | E | 8.16 | 481.0583 | 481.0596 | $C_{21}H_{19}Cl_3N_4O_3$ | (DMSO-d6) δ: 8.76 (1H, d, J = 2.0 Hz), 8.61 (1H, d, J = 2.0 Hz), 8.08 (1H, t, J = 2.0 Hz), 7.51 (1H, d, J = 8.3 Hz), 7.39 (1H, dd, J = 8.8, 2.4 Hz), 6.73 (1H, d, J = 2.4 |

TABLE 38-continued

| Example | Compound No. | Scheme | HPLC Retention time | Obs. Mass (M+ + H) | Pred. Mass (M+ + H) | Formula (M) | $^1$H-NMR |
|---|---|---|---|---|---|---|---|
| | | | | | | | Hz), 5.70 (2H, s), 4.62 (2H, s), 3.85 (4H, s), 3.35 (4H, s). |
| 202 | A197 | E | 7.52 | 494.0897 | 494.0912 | $C_{22}H_{22}Cl_3N_5O_2$ | (DMSO-d6) δ: 8.75 (1H, d, J = 2.4 Hz), 8.60 (1H, d, J = 1.5 Hz), 8.05 (1H, s), 7.50 (1H, d, J = 8.3 Hz), 7.39 (1H, dd, J = 8.8, 2.4 Hz), 6.64 (1H, d, J = 2.0 Hz), 5.67 (2H, s), 4.20 (2H, s), 3.60-2.85 (8H, m), 2.79 (3H, s). |
| 203 | A198 | E | 7.90 | 495.0749 | 495.0752 | $C_{22}H_{21}Cl_3N_4O_3$ | (DMSO-d6) δ: 8.76 (1H, d, J = 2.4 Hz), 8.61 (1H, d, J = 1.5 Hz), 8.08 (1H, s), 7.51 (1H, d, J = 8.3 Hz), 7.39 (1H, dd, J = 8.8, 2.4 Hz), 6.70 (1H, d, J = 2.4 Hz), 5.70 (2H, s), 4.60-4.52 (2H, m), 3.96-3.91 (1H, m), 3.70-3.62 (1H, m), 3.55-3.25 (3H, m), 3.16-3.05 (1H, m), 2.00-1.50 (3H, m). |

TABLE 39

| Example | Compound No. | Scheme | HPLC Retention time | Obs. Mass (M+ + H) | Pred. Mass (M+ + H) | Formula (M) | $^1$H-NMR |
|---|---|---|---|---|---|---|---|
| 204 | A199 | E | 8.14 | 462.0289 | 462.0286 | $C_{20}H_{14}Cl_3N_5O_2$ | (DMSO-d6) δ: 9.20 (1H, s), 8.73 (1H, d, J = 2.4 Hz), 8.53 (1H, d, J = 2.0 Hz), 7.99 (1H, t, J = 2.2 Hz), 7.78 (1H, t, J = 1.7 Hz), 7.68 (1H, t, J = 1.7 Hz), 7.51 (1H, d, J = 8.3 Hz), 7.39 (1H, dd, J = 8.5, 2.7 Hz), 6.73 (1H, d, J = 2.4 Hz), 5.73 (2H, s), 5.67 (2H, s). |
| 205 | A200 | E | 10.37 | 462.0289 | 462.0286 | $C_{20}H_{14}Cl_3N_5O_2$ | (DMSO-d6) δ: 13.67 (1H, s), 8.71 (1H, d, J = 2.4 Hz), 8.54 (1H, d, J = 2.0 Hz), 8.01 (1H, t, J = 2.0 Hz), 7.74 (1H, d, J = 2.0 Hz), 7.50 (1H, d, J = 8.8 Hz), 7.42-7.36 (2H, m), 6.63 (1H, d, J = 2.0 Hz), 6.23 (1H t, J = 2.0 Hz), 5.65 (2H, s), 5.61 (2H, s). |
| 206 | A201 | E | 7.75 | 411.0171 | 411.0177 | $C_{17}H_{13}Cl_3N_4O_2$ | (DMSO-d6) δ: 8.76 (1H, d, J = 2.4 Hz), 8.56 (1H, d, J = 1.5 Hz), 8.32 (3H, s), 8.03 (1H, t, J = 2.2 Hz), 7.53 (1H, d, J = 8.8 Hz), 7.40 (1H, dd, J = 8.3, 2.4 Hz), 6.64 (1H, d, J = 2.4 Hz), 5.73 (2H, s), 4.33 (2H, s). |
| 207 | A202 | E | 7.83 | 522.1228 | 522.1225 | $C_{24}H_{26}Cl_3N_5O_2$ | (DMSO-d6) δ: 8.74 (1H, d, J = 2.0 Hz), 8.60 (1H, d, J = 1.5 Hz), 8.05 (1H, s), 7.51 (1H, d, J = 8.3 Hz), 7.39 (1H, dd, J = 8.5, 2.2 Hz), 6.64 (1H, d, J = 2.0 Hz), 5.67 (2H, s), 4.19 (2H, s), 3.56-2.75 (10H, m), 1.67-1.56 (2H, m), 0.92-0.86 (3H, m). |
| 208 | A203 | E | 8.48 | 558.0535 | 558.0531 | $C_{22}H_{22}Cl_3N_5O_4S$ | (DMSO-d6) δ: 8.75 (1H, d, J = 2.0 Hz), 8.60 (1H, d, J = 1.5 Hz), 8.06 (1H, t, J = 1.7 Hz), 7.50 (1H, d, J = 8.8 Hz), 7.39 (1H, dd, J = 8.8, 2.4 Hz), 6.70 (1H, d, J = 2.0 Hz), 5.71 (2H, s), 4.54 (2H, s), 3.45-3.30 (8H, m), 3.00 (3H, s). |

TABLE 40

| Example | Compound No. | Scheme | HPLC Retention time | Obs. Mass (M+ + H) | Pred. Mass (M+ + H) | Formula (M) | $^1$H-NMR |
|---|---|---|---|---|---|---|---|
| 209 | A204 | E | 8.72 | 572.0678 | 572.0687 | $C_{23}H_{24}Cl_3N_5O_4S$ | (DMSO-d6) δ: 8.75 (1H, d, J = 2.4 Hz), 8.60 (1H, d, J = 2.0 Hz), 8.07 (1H, t, J = 2.0 Hz), 7.51 (1H, d, J = 8.8 Hz), 7.39 (1H, dd, J = 8.5, 2.7 Hz), 6.71 (1H, d, J = 2.4 Hz), 5.71 (2H, s), 4.59 (2H, s), 3.55-3.30 (8H, m), 3.18 (2H, q, J = 7.3 Hz), 1.22 (3H, t, J = 7.3 Hz). |

TABLE 40-continued

| Example | Compound No. | Scheme | HPLC Retention time | Obs. Mass (M+ + H) | Pred. Mass (M+ + H) | Formula (M) | $^1$H-NMR |
|---|---|---|---|---|---|---|---|
| 210 | A206 | C | 7.49 | 362.0458 | 362.0458 | $C_{17}H_{13}Cl_2N_3O_2$ | (DMSO-d6) δ: 8.56 (1H, s), 8.49 (1H, s), 7.97 (1H, s), 7.84 (1H, s), 7.51 (1H, d, J = 8.3 Hz), 7.39 (1H, d, J = 8.3 Hz), 6.55 (1H, s), 5.66 (2H, s), 2.32 (3H, s). |
| 211 | A208 | A | 8.96 | 412.0430 | 412.0426 | $C_{18}H_{13}Cl_2F_3N_3O_2$ | (DMSO-d6) δ: 13.13 (1H, s), 8.84 (1H, d, J = 1.0 Hz), 8.77 (1H, d, J = 1.0 Hz), 8.04 (1H, s), 7.51 (1H, d, J = 8.8 Hz), 7.39 (1H, dd, J = 8.5, 2.7 Hz), 7.15 (1H, t, J = 55.1 Hz), 6.62 (1H, d, J = 2.4 Hz), 5.60 (2H, s), 2.50 (3H, s). |
| 212 | A210 | A | 8.43 | 425.9818 | 425.9810 | $C_{17}H_{10}Cl_3N_3O_4$ | (DMSO-d6) δ: 8.78 (1H, d, J = 2.4 Hz), 8.58 (1H, d, J = 1.5 Hz), 8.09 (1H, t, J = 2.2 Hz), 7.47 (1H, d, J = 8.8 Hz), 7.37 (1H, dd, J = 8.8, 2.4 Hz), 6.86 (1H, d, J = 2.4 Hz), 5.74 (2H, s). |
| 213 | A211 | E | 9.37 | 426.0167 | 426.0174 | $C_{18}H_{14}Cl_3N_3O_3$ | (DMSO-d6) δ: 8.73 (1H, d, J = 2.4 Hz), 8.56 (1H, d, J = 2.0 Hz), 8.03 (1H, t, J = 2.0 Hz), 7.51 (1H, d, J = 8.3 Hz), 7.39 (1H, dd, J = 8.3, 2.4 Hz), 6.61 (1H, d, J = 2.4 Hz), 5.62 (2H, dd, J = 25.9, 17.6 Hz), 5.33 (1H, q, J = 6.5 Hz), 1.43 (3H, d, J = 6.8 Hz). |
| 214 | A212 | A | 10.27 | 424.0621 | 424.0626 | $C_{19}H_{16}Cl_2FN_3O_3$ | (DMSO-d6) δ: 8.70 (1H, d, J = 2.4 Hz), 8.49 (1H, s), 7.91-7.86 (1H, m), 7.50 (1H, d, J = 8.8 Hz), 7.38 (1H, dd, J = 8.8, 2.4 Hz), 6.58 (1H, d, J = 2.4 Hz), 5.63 (2H, s), 1.62 (6H, s). |

TABLE 41

| Example | Compound No. | Scheme | HPLC Retention time | Obs. Mass (M+ + H) | Pred. Mass (M+ + H) | Formula (M) | $^1$H-NMR |
|---|---|---|---|---|---|---|---|
| 215 | A213 | A | 11.11 | 440.0325 | 440.0330 | $C_{19}H_{16}Cl_3N_3O_3$ | (DMSO-d6) δ: 8.74 (1H, s), 8.56 (1H, s), 8.04 (1H, s), 7.50 (1H, d, J = 8.8 Hz), 7.38 (1H, dd, J = 8.5, 2.2 Hz), 6.60 (1H, s), 5.63 (2H, s), 1.62 (6H, s). |
| 216 | A214 | A | 8.32 | 420.0872 | 420.0876 | $C_{20}H_{19}Cl_2N_3O_3$ | (DMSO-d6) δ: 8.56 (1H, s), 8.45 (1H, s), 7.81 (1H, s), 7.51 (1H, d, J = 8.8 Hz), 7.39 (1H, dd, J = 8.5, 2.7 Hz), 6.57 (1H, d, J = 2.4 Hz), 5.60 (2H, s), 2.32 (3H, s), 1.62 (6H, s) |
| 217 | A215 | A | 11.73 | 452.0927 | 452.0939 | $C_{21}H_{20}Cl_2FN_3O_3$ | |
| 218 | A216 | A | 12.59 | 468.0641 | 468.0643 | $C_{21}H_{20}Cl_3N_3O_3$ | (DMSO-d6) δ: 8.74 (1H, d, J = 2.4 Hz), 8.58 (1H, d, J = 2.0 Hz), 8.07 (1H, t, J = 2.0 Hz), 7.49 (1H, d, J = 8.8 Hz), 7.36 (1H, dd, J = 8.3, 2.4 Hz), 6.38 (1H, d, J = 2.0 Hz), 5.67 (2H, s), 2.11-2.01 (2H, m), 1.86-1.76 (2H, m), 0.81 (6H, t, J = 7.3 Hz). |
| 219 | A217 | A | 9.60 | 448.1202 | 448.1189 | $C_{22}H_{23}Cl_2N_3O_3$ | (DMSO-d6) δ: 8.57 (1H, s), 8.50 (1H, s), 7.85 (1H, s), 7.49 (1H, d, J = 8.8 Hz), 7.37 (1H, dd, J = 8.3, 2.4 Hz), 6.37 (1H, d, J = 2.0 Hz), 5.64 (2H, s) 2.33 (3H, s), 2.12-2.01 (2H, m), 1.86-1.75 (2H, m), 0.81 (6H, t, J = 7.1 Hz). |
| 220 | A218 | E | 14.74 | 424.0015 | 424.0017 | $C_{18}H_{12}Cl_3N_3O_3$ | (DMSO-d6) δ: 14.34 (1H, s), 8.76 (1H, d, J = 2.4 Hz), 8.60 (1H, s), 8.10 (1H, s), 7.47 (1H, d, J = 8.3 Hz), 7.39 (1H, dd, J = 8.8, 2.4 Hz), 6.87 (1H, d, J = 2.0 Hz), 5.60 (2H, s), 2.64 (3H, s). |
| 221 | A219 | D | 8.82 | 396.0059 | 396.0068 | $C_{17}H_{12}Cl_3N_3O_2$ | (DMSO-d6) δ: 13.61 (1H, s), 8.53 (1H, d, J = 1.5 Hz), 8.42 (1H, d, J = 2.0 Hz), 7.77 (1H, s), 7.51 (1H, d, J = 8.8 Hz), 7.39 (1H, dd, J = 8.8, 2.4 Hz), 6.78 (1H, d, J = 2.4 Hz), 5.58 (2H, s), 2.30 (3H, s). |

TABLE 42

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 222 | A220 | D | 11.28 | 415.9532 | 415.9522 | $C_{16}H_9Cl_4N_3O_2$ | (DMSO-d6) δ: 13.67 (1H, s), 8.75 (1H, d, J = 2.4 Hz), 8.59 (1H, d, J = 1.5 Hz), 8.07 (1H, t, J = 2.2 Hz), 7.49 (1H, d, J = 8.3 Hz), 7.39 (1H, dd, J = 8.8, 2.4 Hz), 6.85 (1H, d, J = 2.4 Hz), 5.62 (2H, s). |
| 223 | A222 | A | 8.02 | 394.0528 | 394.0520 | $C_{18}H_{14}Cl_2FN_3O_2$ | (DMSO-d6) δ: 8.61 (1H, d, J = 2.9 Hz), 8.21 (1H, s), 7.47 (1H, dt, J = 8.9, 2.2 Hz), 7.36 (1H, d, J = 8.8 Hz), 7.27 (1H, dd, J = 8.3, 2.4 Hz), 7.02 (1H, d, J = 2.4 Hz), 6.36 (1H, q, J = 6.8 Hz), 2.40 (3H, s), 1.93 (3H, d, J = 6.8 Hz). |
| 224 | A223 | A | 8.60 | 410.0216 | 410.0224 | $C_{18}H_{14}Cl_3N_3O_2$ | (DMSO-d6) δ: 8.63 (1H, d, J = 2.0 Hz), 8.32 (1H, s), 7.50 (1H, s), 7.37 (1H, d, J = 8.3 Hz), 7.28 (1H, dd, J = 8.5, 2.2 Hz), 6.96 (1H, d, J = 2.4 Hz), 6.39 (1H, q, J = 6.8 Hz), 2.40 (3H, s), 1.90 (3H, d, J = 6.8 Hz). |
| 225 | A224 | A | 7.25 | 390.0774 | 390.0771 | $C_{19}H_{17}Cl_2N_3O_2$ | (DMSO-d6) δ: 8.44 (1H, s), 8.22 (1H, s), 7.35 (1H, d, J = 8.3 Hz), 7.29-7.22 (2H, m), 6.94 (1H, s), 6.39 (1H, q, J = 6.8 Hz), 2.41 (3H, s), 2.22 (3H, s), 1.92 (3H, d, J = 6.8 Hz). |
| 226 | A225 | A | 8.91 | 385.9922 | 385.9928 | $C_{15}H_{10}Cl_2FN_3O_2S$ | |
| 227 | A226 | A | 9.66 | 401.9637 | 401.9632 | $C_{15}H_{10}Cl_3N_3O_2S$ | |
| 228 | A227 | A | 7.75 | 382.0170 | 382.0178 | $C_{16}H_{13}Cl_2N_3O_2S$ | |
| 229 | A228 | A | 8.99 | 385.9929 | 385.9928 | $C_{15}H_{10}Cl_2FN_3O_2S$ | (DMSO-d6) δ: 8.74 (1H, d, J = 2.4 Hz), 8.63 (1H, s), 8.05-8.00 (1H, m), 7.10 (1H, s), 5.69 (2H, s), 2.43 (3H, s). |
| 230 | A229 | A | 9.74 | 401.9641 | 401.9632 | $C_{15}H_{10}Cl_3N_3O_2S$ | (DMSO-d6) δ: 8.78 (1H, d, J = 2.4 Hz), 8.70 (1H, d, J = 1.5 Hz), 8.18 (1H, t, J = 2.2 Hz), 7.11 (1H, s), 5.68 (2H, s), 2.43 (3H, s). |
| 231 | A230 | A | 7.69 | 382.0169 | 382.0178 | $C_{16}H_{13}Cl_2N_3O_2S$ | (DMSO-d6) δ: 8.62 (1H, s), 8.61 (1H, s), 7.91 (1H, s), 7.12 (1H, s), 5.67 (2H, s), 2.44 (3H, s), 2.37 (3H, s). |

TABLE 43

| Example | Compound No. | Scheme | HPLC Retention time | Obs. Mass (M$^+$ + H) | Pred. Mass (M$^+$ + H) | Formula (M) | $^1$H-NMR |
|---|---|---|---|---|---|---|---|
| 232 | A231 | A | 7.84 | 356.1152 | 356.1160 | $C_{19}H_{18}ClN_3O_2$ | (DMSO-d6) δ: 8.54 (1H, s), 8.46 (1h, d, J = 2.0 Hz), 7.82 (1H, s), 7.33 (1H, d, J = 8.3 Hz), 7.10 (1H, d, J = 8.3 Hz), 6.44 (1H, s), 5.58 (2H, s), 2.52 (3H, s), 2.30 (3H, s), 2.18 (3H, s). |
| 233 | A232 | A | 9.50 | 376.0619 | 376.0614 | $C_{18}H_{15}Cl_2N_3O_2$ | (DMSO-d6) δ: 8.68 (1H, d, J = 2.0 Hz), 8.54 (1H, d, J = 2.0 Hz), 7.99 (1H, t, J = 2.0 Hz), 7.31 (1H, d, J = 8.3 Hz), 7.08 (1H, d, J = 8.3 Hz), 6.39 (1H, s), 5.60 (2H, s), 2.49 (3H, s), 2.16 (3H, s). |
| 234 | A233 | A | 9.34 | 384.0579 | 384.0568 | $C_{19}H_{14}ClN_3O_2S$ | (DMSO-d6) δ: 13.02 (1H, s), 8.62 (1H, d, J = 2.4 Hz), 8.57 (1H, d, J = 1.5 Hz), 8.00 (1H, t, J = 2.2 Hz), 7.80-7.74 (2H, m), 7.49 (1H, d, J = 5.4 Hz), 7.30 (1H, t, J = 7.6 Hz), 6.65 (1H, d, J = 7.3 Hz), 5.85 (2H, s), 2.50 (3H, s). |
| 235 | A234 | A | 8.73 | 368.0855 | 368.0864 | $C_{19}H_{14}FN_3O_2S$ | (DMSO-d6) δ: 8.60 (1H, d, J = 2.4 Hz), 8.52 (1H, s), 7.87 (1H, dt, J = 9.8, 2.2 Hz), 7.80-7.74 (2H, m), 7.49 (1H, d, J = 5.4 Hz), 7.30 (1H, t, J = 7.6 Hz), 6.65 (1H, d, J = 7.3 Hz), 5.86 (2H, s), 2.51 (3H, s). |
| 236 | A235 | B | 10.50 | 412.0871 | 412.0881 | $C_{21}H_{18}ClN_3O_2S$ | |
| 237 | A236 | B | 11.18 | 410.0717 | 410.0725 | $C_{21}H_{16}ClN_3O_2S$ | |
| 238 | A237 | G | 10.16 | 406.0147 | 406.0136 | $C_{16}H_{10}Cl_3N_7$ | (DMSO-d6) δ: 8.72 (1H, d, J = 2.4 Hz), 8.64 (1H, d, J = 2.0 Hz), 8.11 (1H, t, J = 2.2 Hz), 7.97 (1H, s), 7.49 (1H, d, J = 8.8 Hz), 7.34 (1H, dd, J = 8.3, 2.4 Hz), 6.57 (1H, d, J = 2.4 Hz), 5.88 (2H, s). |

TABLE 43-continued

| Example | Compound No. | Scheme | HPLC Retention time | Obs. Mass (M+ + H) | Pred. Mass (M+ + H) | Formula (M) | 1H-NMR |
|---|---|---|---|---|---|---|---|
| 239 | A238 | A | 6.96 | 322.1555 | 322.1550 | $C_{19}H_{19}N_3O_2$ | |
| 240 | A239 | A | 7.18 | 344.1396 | 344.1394 | $C_{21}H_{17}N_3O_2$ | |
| 241 | A240 | A | 9.39 | 374.1500 | 374.1499 | $C_{22}H_{19}N_3O_3$ | |

TABLE 44

| Example | Compound No. | Scheme | HPLC Retention time | Obs. Mass (M+ + H) | Pred. Mass (M+ + H) | Formula (M) | 1H-NMR |
|---|---|---|---|---|---|---|---|
| 242 | A241 | A | 8.03 | 358.1556 | 358.1550 | $C_{22}H_{19}N_3O_2$ | |
| 243 | A242 | A | 9.59 | 378.1014 | 378.1004 | $C_{21}H_{16}ClN_3O_2$ | |
| 244 | A243 | A | 8.71 | 344.1384 | 344.1394 | $C_{21}H_{17}N_3O_2$ | |
| 245 | A244 | A | 7.14 | 362.0457 | 362.0458 | $C_{17}H_{13}Cl_2N_3O_2$ | (DMSO-d6) δ: 8.68 (2H, d, J = 5.9 Hz), 7.55-7.49 (3H, m), 7.40 (1H, dd, J = 8.5, 2.7 Hz), 6.55 (1H, d, J = 2.4 Hz), 5.61 (2H, s), 2.50 (3H, s). |
| 246 | A245 | A | 9.11 | 362.0454 | 362.0458 | $C_{17}H_{13}Cl_2N_3O_2$ | (DMSO-d6) δ: 13.03 (1H, s), 8.46 (1H, d, J = 5.0 Hz), 8.16 (1H, d, J = 7.8 Hz), 7.91 (1H, td, J = 7.8, 2.0 Hz), 7.51 (1H, d, J = 8.3 Hz), 7.40-7.36 (1H, m), 7.31 (1H, dd, J = 8.8, 2.4 Hz), 6.35 (1H, d, J = 2.4 Hz), 6.24 (2H, s), 2.50 (3H, s). |
| 247 | A246 | A | 9.77 | 392.0563 | 392.0563 | $C_{18}H_{15}Cl_2N_3O_3$ | |
| 248 | A247 | H | 10.27 | 378.0407 | 378.0407 | $C_{17}H_{13}Cl_2N_3O_3$ | |
| 249 | A248 | H | 9.01 | 378.0401 | 378.0407 | $C_{17}H_{13}Cl_2N_3O_3$ | |
| 250 | A249 | H | 7.27 | 378.0403 | 378.04.7 | $C_{17}H_{13}Cl_2N_3O_3$ | |
| 251 | A250 | H | 11.96 | 412.0024 | 412.0017 | $C_{17}H_{12}Cl_3N_3O_3$ | |
| 252 | A251 | H | 12.17 | 455.9492 | 455.9512 | $C_{17}H_{12}BrCl_2N_3O_3$ | |

TABLE 45

| Example | Compound No. | Scheme | HPLC Retention time | Obs. Mass (M+ + H) | Pred. Mass (M+ + H) | Formula (M) | 1H-NMR |
|---|---|---|---|---|---|---|---|
| 253 | A253 | H | 11.33 | 412.0021 | 412.0017 | $C_{17}H_{12}Cl_3N_3O_3$ | (DMSO-d6) δ: 12.93 (1H, s), 8.34 (1H, dd, J = 4.6, 1.7 Hz), 8.04 (1H, dd, J = 8.0, 1.7 Hz), 7.57-7.53 (2H, m), 7.41 (1H, dd, J = 8.5, 2.7 Hz), 6.78 (1H, d, J = 2.4 Hz), 5.54 (2H, s), 2.32 (3H, s). |
| 254 | A254 | H | 11.49 | 455.9496 | 455.9512 | $C_{17}H_{12}BrCl_2N_3O_3$ | (DMSO-d6) δ: 12.93 (1H, s), 8.32 (1H, dd, J = 4.6, 1.7 Hz), 8.01 (1H, dd, J = 8.0, 1.7 Hz), 7.58-7.53 (2H, m), 7.41 (1H, dd, J = 8.8, 2.4 Hz), 6.80 (1H, d, J = 2.4 Hz), 5.55 (2H, s), 2.32 (3H, s). |
| 255 | A255 | H | 8.98 | 392.0564 | 392.0563 | $C_{18}H_{15}Cl_2N_3O_3$ | (DMSO-d6) δ: 12.86 (1H, s), 8.32 (1H, d, J = 2.4 Hz), 8.29 (1H, s), 7.58-7.52 (2H, m), 7.40 (1H, dd, J = 8.5, 2.7 Hz), 6.75 (1H, d, J = 2.4 Hz), 5.50 (2H, s), 2.34 (3H, s), 2.30 (3H, s). |
| 256 | A256 | H | 8.35 | 392.0560 | 392.0563 | $C_{18}H_{15}Cl_2N_3O_3$ | (DMSO-d6) δ: 8.53 (1H, s), 8.38 (1H, d, J = 4.9 Hz), 7.56 (1H, d, J = 8.3 Hz), 7.46-7.40 (2H, m), 6.76 (1H, d, J = 2.4 Hz), 5.56 (2H, s), 2.31 (3H, s), 2.09 (3H, s). |
| 257 | A257 | H | 10.95 | 412.0022 | 412.0017 | $C_{17}H_{12}Cl_3N_3O_3$ | (DMSO-d6) δ: 12.88 (1H, s), 8.73 (1H, s), 8.47 (1H, d, J = 4.9 Hz), 7.72 (1H, d, J = 5.4 Hz), 7.55 (1H, d, J = 8.8 Hz), 7.42 (1H, dd, J = 8.3, 2.4 Hz), 6.78 (1H, d, J = 2.4 Hz), 5.55 (2H, s), 2.31 (3H, s). |
| 258 | A258 | H | 110.10 | 455.9502 | 455.9512 | $C_{17}H_{12}BrCl_2N_3O_3$ | DMSO-d6) δ: 12.90 (1H, s), 8.69 (1H, s), 8.36 (1H, d, J = 5.4 Hz), 7.85 (1H, d, J = 5.4 Hz), 7.55 (1H, d, J = 8.8 Hz), 7.42 (1H, dd, J = 8.3, 2.0 Hz), 6.81 (1H, d, J = 2.0 Hz), 5.55 (2H, s), 2.31 (3H, s). |

TABLE 46

| Example | Compound No. | Scheme | HPLC Retention time | Obs. Mass (M+ + H) | Pred. Mass (M+ + H) | Formula (M) | $^1$H-NMR |
|---|---|---|---|---|---|---|---|
| 259 | A259 | G | 7.28 | 356.1388 | 356.1394 | $C_{22}H_{17}N_3O_2$ | (DMSO-d6) δ: 8.68 (1H, d, J = 2.4 Hz), 8.61 (1H, dd, J = 4.9, 1.5 Hz), 8.19 (1H, s), 8.12-8.08 (1H, m), 8.04-8.00 (1H, m), 7.94-7.89 (2H, m), 7.66-7.62 (2H, m), 7.50-7.42 (2H, m), 7.26 (1H, d, J = 16.1 Hz), 6.68 (1H, d, J = 7.3 Hz), 6.47 (1H, d, J = 16.1 Hz), 6.00 (2H, s). |
| 260 | A260 | G | 7.15 | 374.0454 | 374.0458 | $C_{18}H_{13}Cl_2N_3O_2$ | (DMSO-d6) δ: 8.72-8.67 (2H, m), 8.08 (1H, s), 7.94 (1H, dt, J = 8.0, 2.0 Hz), 7.58-7.54 (2H, m), 7.44 (1H, dd, J = 8.3, 2.4 Hz), 7.34 (1H, d, J = 15.6 Hz), 6.72 (1H, d, J = 2.4 Hz), 6.46 (1H, d, J = 16.1 Hz), 5.53 (2H, s). |
| 261 | A261 | G | 8.90 | 422.0491 | 422.0491 | $C_{19}H_{17}Cl_2N_3O_2S$ | |
| 262 | A262 | G | 10.90 | 456.0097 | 456.0102 | $C_{19}H_{16}Cl_3N_3O_2S$ | |
| 263 | A263 | G | 11.08 | 468.0098 | 468.0102 | $C_{20}H_{16}Cl_3N_3O_2S$ | |
| 264 | A264 | A | 8.34 | 422.0484 | 422.0491 | $C_{19}H_{17}Cl_2N_3O_2S$ | (DMSO-d6) δ: 8.61-8.56 (2H, m), 7.84 (1H, dt, J = 8.0, 2.0 Hz), 7.59 (1H, s), 7.54-7.49 (1H, m), 7.44 (1H, d, J = 8.3 Hz), 7.34 (1H, dd, J = 8.8, 2.4 Hz), 6.43 (1H, d, J = 2.4 Hz), 5.47 (2H, s), 1.52 (6H, s). |
| 265 | A265 | A | 9.87 | 440.0397 | 440.0397 | $C_{19}H_{16}Cl_2FN_3O_2S$ | (DMSO-d6) δ: 8.54 (1H, d, J = 2.9 Hz), 8.36-8.34 (1H, m), 7.79-7.75 (1H, m), 7.53 (1H, s), 7.44 (1H, d, J = 8.8 Hz), 7.33 (1H, dd, J = 8.3, 2.4 Hz), 6.41 (1H, d, J = 2.9 Hz), 5.50 (2H, s), 1.51 (6H, s). |
| 266 | A266 | A | 10.41 | 456.0103 | 456.0102 | $C_{19}H_{16}Cl_3N_3O_2S$ | |

Example 267

Production of 1-(naphthalen-1-ylmethyl)-2-(pyridin-3-yl)-1H-pyrrole-5-carboxylic acid (Compound B1) (Scheme I)

[Chemical Formula 70]

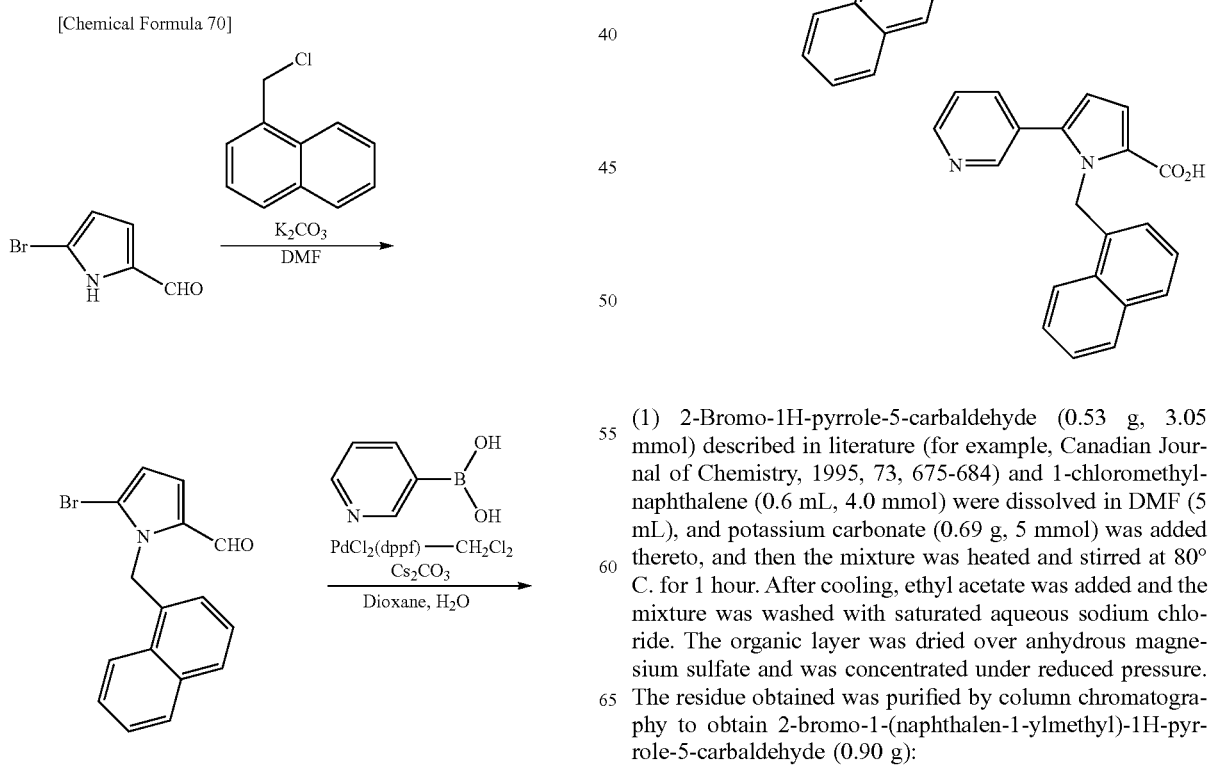

(1) 2-Bromo-1H-pyrrole-5-carbaldehyde (0.53 g, 3.05 mmol) described in literature (for example, Canadian Journal of Chemistry, 1995, 73, 675-684) and 1-chloromethyl-naphthalene (0.6 mL, 4.0 mmol) were dissolved in DMF (5 mL), and potassium carbonate (0.69 g, 5 mmol) was added thereto, and then the mixture was heated and stirred at 80° C. for 1 hour. After cooling, ethyl acetate was added and the mixture was washed with saturated aqueous sodium chloride. The organic layer was dried over anhydrous magnesium sulfate and was concentrated under reduced pressure. The residue obtained was purified by column chromatography to obtain 2-bromo-1-(naphthalen-1-ylmethyl)-1H-pyrrole-5-carbaldehyde (0.90 g):

¹H-NMR (CDCl₃) δ: 9.41 (1H, s), 8.04 (1H, d, J=8.3 Hz), 7.89 (1H, d, J=7.8 Hz), 7.74 (1H, d, J=8.3 Hz), 7.63-7.59 (1H, m), 7.57-7.52 (1H, m), 7.29 (1H, t, J=7.8 Hz), 7.08 (1H, d, J=4.4 Hz), 6.50 (1H, d, J=3.9 Hz), 6.29 (1H, d, J=7.3 Hz), 6.20 (2H, s);

ESI-MS m/z=314 (M⁺+H).

(2) To 2-bromo-1-(naphthalen-1-ylmethyl)-1H-pyrrole-5-carbaldehyde (0.98 g, 3.12 mmol), pyridin-3-ylboronic acid (0.77 g, 6.24 mmol), cesium carbonate (3.05 g, 9.36 mmol), and PdCl₂(dppf) (346 mg, 0.47 mmol) were added dioxane (24 mL) and water (2 mL), and the mixture was heated and stirred at 95° C. for 12 hours under a nitrogen atmosphere. After cooling, the reaction mixture was concentrated under reduced pressure. To the residue was added ethyl acetate and the organic layer was washed with saturated aqueous sodium chloride. After being dried over anhydrous magnesium sulfate, the organic layer was concentrated under reduced pressure. The residue obtained was purified by column chromatography to obtain 1-(naphthalen-1-ylmethyl)-2-(pyridin-3-yl)-1H-pyrrole-5-carbaldehyde (0.89 g):

ESI-MS m/z=313 (M⁺+H).

(3) 1-(Naphthalen-1-ylmethyl)-2-(pyridin-3-yl)-1H-pyrrole-5-carbaldehyde (0.6 g, 1.92 mmol) and 2-methyl-2-butene (2 mL, 6 mmol) were dissolved in a mixed solvent of THF (12 mL) and 1-propanol (24 mL), and the solution was cooled to 0° C. An aqueous solution (12 mL) of a mixture of sodium chlorite (0.9 g, 10 mmol) and sodium dihydrogen phosphate dihydrate (1.56 g, 10 mmol) was added dropwise thereto, and the mixture was stirred at room temperature for 17 hours. Additionally, sodium chlorite (0.18 g, 2 mmol), sodium dihydrogen phosphate dihydrate (0.36 g, 2.3 mmol), 2-methyl-2-butene (5 mL, 15 mmol), and 1-propanol (12 mL) were added and the mixture was heated and stirred at 40° C. for 29 hours. After cooling, the mixture was extracted with ethyl acetate and the organic layer was washed with saturated aqueous sodium chloride. After being dried over anhydrous magnesium sulfate, the organic layer was concentrated under reduced pressure. The residue obtained was purified by a conventional method to obtain 1-(naphthalen-1-ylmethyl)-2-(pyridin-3-yl)-1H-pyrrole-5-carboxylic acid (0.27 g):

¹H-NMR (DMSO-d₆) δ: 12.30 (1H, s), 8.52 (1H, d, J=2.4 Hz), 8.44 (1H, dd, J=4.9, 1.5 Hz), 8.05-7.92 (2H, m), 7.78 (1H, d, J=8.3 Hz), 7.71 (1H, dt, J=7.8, 2.0 Hz), 7.58-7.53 (2H, m), 7.37 (1H, t, J=7.6 Hz), 7.31 (1H, dd, J=8.3, 4.9 Hz), 7.15 (1H, d, J=3.9 Hz), 6.54 (1H, d, J=3.9 Hz), 6.31 (1H, d, J=7.3 Hz), 6.10 (2H, s);

HPLC retention time=8.04 min;
Pred. Mass=329.1285 (M⁺+H, C₂₁H₁₆N₂O₂);
Obs. Mass=329.1288 (M⁺+H).

Compounds from Compound B2 to Compound B35 were synthesized in a manner similar to Example 267.

TABLE 47

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 268 | B2 | I | 8.58 | 343.1446 | 343.1441 | C₂₂H₁₈N₂O₂ | |
| 269 | B3 | I | 8.61 | 412.9968 | 412.9954 | C₁₉H₁₃BrN₂O₂S | (DMSO-D6) δ: 8.60 (1H, d, J = 1.8 Hz), 8.53 (1H, dd, J = 4.9, 1.5 Hz), 8.02-7.99 (1H, m), 7.83 (1H, dt, J = 8.0, 1.8 Hz), 7.62 (1H, dd, J = 7.8, 1.0 Hz), 7.43 (1H, dd, J = 8.3, 4.9 Hz), 7.26 (1H, t, J = 7.8 Hz), 7.13 (1H, d, J = 3.9 Hz), 6.53 (2H, d, J = 4.4 Hz), 6.14 (2H, s). |
| 270 | B4 | I | 7.62 | 343.1434 | 343.1441 | C₂₂H₁₈N₂O₂ | (DMSO-D6) δ: 8.24 (1H, d, J = 2.0 Hz), 8.19 (1H, dd, J = 4.9, 1.5 Hz), 7.70-7.65 (2H, m), 7.52 (1H, d, J = 8.3 Hz), 7.48 (1H, dt, J = 7.6, 1.5 Hz), 7.36-7.32 (2H, m), 7.07-7.01 (3H, m), 6.30 (2H, s), 6.19 (1H, d, J = 4.4 Hz), 2.02 (3H, s). |
| 271 | B5 | I | 8.21 | 343.1428 | 343.1441 | C₂₂H₁₈N₂O₂ | |
| 272 | B6 | I | 8.67 | 407.0378 | 407.0390 | C₂₁H₁₅BrN₂O₂ | |
| 273 | B7 | I | 8.41 | 349.1001 | 349.1005 | C₂₀H₁₆N₂O₂S | |
| 274 | B8 | I | 7.90 | 335.0848 | 335.0849 | C₁₉H₁₄N₂O₂S | (DMSO-d6) δ: 8.65 (1H, d, J = 2.0 Hz), 8.57 (1H, dd, J = 4.9, 1.5 Hz), 7.96-7.92 (2H, m), 7.67-7.62 (1H, m), 7.51 (1H, dd, J = 8.0, 5.1 Hz), 7.39-7.33 (2H, m), 7.11 (1H, d, J = 3.9 Hz), 6.68 (1H, s), 6.51 (1H, d, J = 3.9 Hz), 5.86 (2H, s). |

TABLE 48

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 275 | B9 | I | 8.90 | 403.0725 | 403.0723 | C₂₀H₁₃F₃N₂O₂S | (DMSO-d6) δ: 12.33 (1H, s), 8.58-8.55 (1H, m), 8.50 (1H, d, J = 3.4 Hz), 8.35 (1H, d, J = 7.8 Hz), 7.86-7.78 (2H, m), 7.54 (1H, t, J = 7.8 Hz), 7.38 (1H, dd, J = 7.8, 4.9 Hz), 7.14 (1H, d, J = 4.4 Hz), 6.67 (1H, s), 6.53 (1H, d, J = 3.9 Hz), 5.81 (2H, s). |
| 276 | B10 | I | 8.47 | 369.0451 | 369.0459 | C₁₉H₁₃ClN₂O₂S | (DMSO-d6) δ: 8.61 (1H, d, J = 2.4 Hz), 8.53 (1H, dd, J = 4.9, 1.5 Hz), 7.95 (1H, d, |

TABLE 48-continued

| Example | Compound No. | Scheme | HPLC Retention time | Obs. Mass (M+ + H) | Pred. Mass (M+ + H) | Formula (M) | 1H-NMR |
|---|---|---|---|---|---|---|---|
| | | | | | | | J = 8.0 Hz), 7.84 (1H, dt, J = 7.8, 2.0 Hz), 7.45-7.40 (2H, m), 7.34 (1H, t, J = 7.8 Hz), 7.13 (1H, d, J = 3.9 Hz), 6.54-6.49 (2H, m), 6.09 (2H, s). |
| 277 | B11 | I | 8.25 | 347.0346 | 347.0349 | $C_{17}H_{12}Cl_2N_2O_2$ | (DMSO-d6) δ: 8.61-8.56 (2H, m), 7.82 (1H, d, J = 7.8 Hz), 7.53-7.44 (2H, m), 7.33 (1H, dd, J = 8.5, 2.2 Hz), 7.14 (1H, d, J = 3.9 Hz), 6.54 (1H, d, J = 3.9 Hz), 6.18 (1H, d, J = 1.5 Hz), 5.63 (2H, s). |
| 278 | B12 | I | 7.85 | 307.1437 | 307.1441 | $C_{19}H_{18}N_2O_2$ | (DMSO-d6) δ: 8.58-8.54 (2H, m), 7.82-7.77 (1H, m), 7.49-7.45 (1H, m), 7.09 (1H, dd, J = 3.9, 1.0 Hz), 6.99 (1H, d, J = 7.3 Hz), 6.88 (1H, d, J = 7.8 Hz), 6.49 (1H, d, J = 3.9 Hz), 5.96 (1H, s), 5.54 (2H, s), 2.09 (6H, s). |
| 279 | B13 | I | 8.33 | 361.0520 | 361.0505 | $C_{18}H_{14}Cl_2N_2O_2$ | (DMSO-d6) δ: 8.47 (1H, d, J = 1.5 Hz), 8.38 (1H, d, J = 1.5 Hz), 7.73 (1H, s), 7.46 (1H, d, J = 8.8 Hz), 7.33 (1H, dd, J = 8.8, 2.4 Hz), 7.13 (1H, d, J = 4.0 Hz), 6.53 (1H, d, J = 4.0 Hz), 6.20 (1H, d, J = 2.4 Hz), 5.64 (2H, s), 2.30 (3H, s). |
| 280 | B14 | I | 11.45 | 365.0254 | 365.0254 | $C_{17}H_{11}Cl_2FN_2O_2$ | (DMSO-d6) δ: 8.57 (1H, d, J = 2.4 Hz), 8.36 (1H, s), 7.78 (1H, dt, J = 9.8, 2.2 Hz), 7.45 (1H, d, J = 8.8 Hz), 7.33 (1H, dd, J = 8.8, 2.4 Hz), 7.13 (1H, d, J= 3.9 Hz), 6.58 (1H, d, J = 3.9 Hz), 6.19 (1H, d, J = 2.4 Hz), 5.68 (2H, s). |

TABLE 49

| Example | Compound No. | Scheme | HPLC Retention time | Obs. Mass (M+ + H) | Pred. Mass (M+ + H) | Formula (M) | 1H-NMR |
|---|---|---|---|---|---|---|---|
| 281 | B15 | I | 8.53 | 383.0614 | 383.0616 | $C_{20}H_{15}ClN_2O_2S$ | (DMSO-d6) δ: 8.45 (1H, d, J = 1.5 Hz), 8.43 (1H, s), 7.95 (1H, d, J = 7.8 Hz), 7.80 (1H, s), 7.44 (1H, d, J = 7.8 Hz), 7.35 (1H, dd, J = 8.0, 4.0 Hz), 7.13 (1H, d, J = 4.4 Hz), 6.52-6.51 (2H, m), 6.11 (2H, s), 2.24 (3H, s). |
| 282 | B16 | I | 11.79 | 387.0364 | 387.0365 | $C_{19}H_{12}ClFN_2O_2S$ | (DMSO-d6) δ: 12.45 (1H, s), 8.53 (1H, d, J = 2.4 Hz), 8.47 (1H, s), 7.95 (1H, d, J = 7.8 Hz), 7.83 (1H, dt, J = 9.1, 2.4 Hz), 7.44 (1H, d, J = 7.1 Hz), 7.35 (1H, t, J = 8.0 Hz), 7.12 (1H, d, J = 7.1 Hz), 6.59 (1H, d, J = 4.0 Hz), 6.51 (1H, s), 6.14 (2H, s). |
| 283 | B17 | I | 12.28 | 380.9955 | 380.9959 | $C_{17}H_{11}Cl_3N_2O_2$ | (DMSO-d6) δ: 8.60 (1H, d, J = 2.4 Hz), 8.44 (1H, d, J = 2.0 Hz), 7.91 (1H, t, J = 2.2 Hz), 7.46 (1H, d, J = 8.8 Hz), 7.33 (1H, dd, J = 8.8, 2.7 Hz), 7.13 (1H, d, J = 3.9 Hz), 6.58 (1H, d, J = 3.9 Hz), 6.22 (1H, d, J = 2.4 Hz), 5.67 (2H, s). |
| 284 | B18 | I | 12.61 | 403.0069 | 403.0069 | $C_{19}H_{12}Cl_2N_2O_2S$ | (DMSO-d6) δ: 12.44 (1H, s), 8.56 (1H, d, J = 2.4 Hz), 8.55 (1H, d, J = 2.4 Hz), 7.98-7.95 (2H, m), 7.44 (1H, dd, J = 4.0, 2.2 Hz), 7.35 (1H, t, J = 8.0 Hz), 7.12 (1H, d, J = 4.0 Hz), 6.59 (1H, d, J = 4.0 Hz), 6.53 (1H, s), 6.13 (2H, s). |
| 285 | B19 | I | 6.84 | 330.1236 | 330.1237 | $C_{20}H_{15}N_3O_2$ | (DMSO-d6) δ: 8.88 (1H, dd, J = 4.1, 1.7 Hz), 8.60 (1H, d, J = 1.5 Hz), 8.50 (1H, dd, J = 4.9, 1.5 Hz), 8.39-8.35 (1H, m), 7.92-7.82 (2H, m), 7.60-7.55 (1H, m). 7.51-7.41 (2H, m), 7.15 (1H, d, J = 4.0 Hz), 6.62-6.54 (2H, m), 6.24 (2H, s). |

TABLE 50

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 286 | B20 | I | 8.25 | 335.0839 | 335.0849 | $C_{19}H_{14}N_2O_2S$ | (DMSO-d6) δ: 8.57 (1H, d, J = 2.0 Hz), 8.52 (1H, dd, J = 5.1, 1.2 Hz), 7.84 (1H, d, J = 7.8 Hz), 7.76-7.72 (2H, m), 7.48-7.41 (2H, m), 7.26 (1H, t, J = 7.8 Hz), 7.12 (1H, d, J = 3.9 Hz), 6.52 (1H, d, J = 3.9 Hz), 6.40 (1H, d, J = 7.3 Hz), 5.85 (2H, s). |
| 287 | B21 | I | 8.29 | 349.0990 | 349.1005 | $C_{20}H_{16}N_2O_2S$ | (DMSO-d6) δ: 8.39 (2H, s), 7.75 (2H, d, J = 5.9 Hz), 7.70 (1H, s), 7.47 (1H, d, J = 5.4 Hz), 7.26 (1H, t, J = 7.6 Hz), 7.11 (1H, d, J = 3.9 Hz), 6.51 (1H, d, J = 3.9 Hz), 6.42 (1H, d, J = 6.8 Hz), 5.86 (2H, s), 2.18 (3H, s.) |
| 288 | B22 | I | 11.21 | 353.0761 | 353.0755 | $C_{19}H_{13}FN_2O_2S$ | (DMSO-d6) δ: 12.47 (1H, s), 8.47 (1H, d, J = 2.9 Hz), 8.35 (1H, s), 7.76-7.68 (3H, m), 7.47 (1H, d, J = 5.4 Hz), 7.25 (1H, t, J = 7.6 Hz), 7.12 (1H, d, J = 3.9 Hz), 6.55 (1H, d, J = 3.9 Hz), 6.41 (1H, d, J = 7.3 Hz), 5.90 (2H, s). |
| 289 | B23 | I | 11.96 | 369.0464 | 369.0459 | $C_{19}H_{13}ClN_2O_2S$ | (DMSO-d6) δ: 8.50 (1H, d, J = 2.0 Hz), 8.42 (1H, s), 7.83 (1H, d, J = 1.5 Hz), 7.76-7.72 (2H, m), 7.47 (1H, d, J = 5.4 Hz), 7.26 (1H, t, J = 7.6 Hz), 7.11 (1H, d, J = 4.4 Hz), 6.55 (1H, d, J = 4.4 Hz), 6.43 (1H, d, J = 7.3 Hz), 5.89 (2H, s). |
| 290 | B24 | I | 8.99 | 406.1228 | 406.1220 | $C_{22}H_{19}N_3O_3S$ | |
| 291 | B25 | I | 9.39 | 432.1387 | 432.1376 | $C_{24}H_{21}N_3O_3S$ | |
| 292 | B26 | I | 11.42 | 442.0193 | 442.0190 | $C_{18}H_{14}Cl_2FN_3O_3S$ | |
| 293 | B27 | I | 12.02 | 468.0346 | 468.0346 | $C_{20}H_{16}Cl_2FN_3O_3S$ | |

TABLE 51

| Example | Compound No. | Scheme | HPLC Retention time | Obs. Mass (M⁺ + H) | Pred. Mass (M⁺ + H) | Formula (M) | ¹H-NMR |
|---|---|---|---|---|---|---|---|
| 294 | B28 | I | 8.88 | 424.0303 | 424.0284 | $C_{18}H_{15}Cl_2N_3O_3S$ | |
| 295 | B29 | I | 12.10 | 457.9887 | 457.9894 | $C_{18}H_{14}Cl_3N_3O_3S$ | |
| 296 | B30 | I | 12.68 | 484.0060 | 484.0051 | $C_{20}H_{16}Cl_3N_3O_3S$ | |
| 297 | B31 | I | 9.52 | 450.0450 | 450.0440 | $C_{20}H_{17}Cl_2N_3O_3S$ | |
| 298 | B32 | I | 9.50 | 464.0601 | 464.0597 | $C_{21}H_{19}Cl_2N_3O_3S$ | |
| 299 | B33 | I | 8.14 | 355.1439 | 355.1441 | $C_{23}H_{18}N_2O_2$ | (DMSO-d6) δ: 8.53 (1H, d, J = 2.0 Hz), 8.49 (1H, dd, J = 4.9, 1.5 Hz), 8.14-8.09 (1H, m), 8.02-7.98 (1H, m), 7.87 (1H, d, J = 8.3 Hz), 7.78 (1H, d, J = 7.8 Hz), 7.64-7.59 (2H, m), 7.45-7.41 (2H, m), 7.28 (1H, d, J = 15.6 Hz), 7.15 (1H, d, J = 3.9 Hz), 6.68 (1H, d, J = 3.9 Hz), 6.51 (1H, d, J = 6.8 Hz), 6.27 (1H, d, J = 15.6 Hz), 5.84 (2H, s). |
| 300 | B34 | I | 8.32 | 387.0658 | 387.0662 | $C_{20}H_{16}Cl_2N_2O_2$ | (DMSO-d6) δ: 8.36 (1H, s), 8.25 (1H, s), 7.54-7.50 (2H, m), 7.40-7.34 (2H, m), 7.09 (1H, d, J = 3.9 Hz), 6.55 (1H, d, J = 4.4 Hz), 6.31-6.26 (2H, m), 5.38 (2H, s), 2.26 (3H, s). |
| 301 | B35 | I | 11.39 | 391.0407 | 391.0411 | $C_{19}H_{13}Cl_2FN_2O_2$ | (DMSO-d6) δ: 8.53 (1H, d, J = 2.9 Hz), 8.35 (1H, d, J = 1.5 Hz), 7.71 (1H, dt, J = 9.9, 2.2 Hz), 7.52 (1H, d, J = 8.3 Hz), 7.39-7.35 (2H, m), 7.11 (1H, d, J = 3.9 Hz), 6.65 (1H, d, J = 3.9 Hz), 6.34-6.27 (2H, m), 5.44 (2H, s). |

Example 302

Test for Inhibition of Uric Acid Transport Using Human URAT1-Expressing Cells (1) Preparation of the Test Compound The test compound was dissolved in DMSO (produced by Sigma) to a concentration of 20 mM and was subsequently used by diluting to desired concentrations.

(2) Test for Inhibition of Uric Acid Transport Using Human URAT1-Expressing Cells Full-length cDNA of human URAT1 (hURAT1) (produced by OriGene Technologies, Inc., NCBI Reference Sequence: NM 144585) was subcloned into an expression vector, pCMV6-Kan/Neo (produced by OriGene Technologies, Inc.), and hURAT1 gene was transfected into human embryonic kidney-derived cells (HEK 293 cells) by liposome method using Lipofectamine 2000 (produced by Invitrogen Corporation), whereupon HEK 293 cells expressing human URAT1 gene were screened by its Geneticin resistance. By a method similar to the following method, functional expression of human URAT1 gene was confirmed by using transport of $^{14}$C-labeled uric acid into the cells as an index.

The HEK 293 cells expressing human URAT1 were seeded in a 24-well cell culture dish to a density of $3\times10^5$ cells/mL/well and were cultured in Dulbecco's modified Eagle's medium (D-MEM medium) containing 10% fetal bovine serum at 37° C. for 2 days. Thereafter, the following test for inhibition of uric acid transport was performed.

After the medium was removed by aspiration from each well, the medium was replaced with a solution obtained by substituting NaCl in Hank's Balanced Salt Solution (HBSS) with Na gluconate (hereinafter, HBSS/Na-gluconate) and the cells were preincubated at 37° C. for about 10 minutes. HBSS/Na-gluconate was removed by aspiration and a $^{14}$C-uric acid solution that was warmed at 37° C. in advance containing various concentrations of the Example compound described in (1) and a radioactive ligand ($^{14}$C-labeled uric acid; final concentration 25 μM) was added and an uptake reaction was carried out by incubating at 37° C. for 5 min. After the incubation, $^{14}$C-labeled uric acid solution was removed by aspiration and the cells were washed three times with ice-cold HBSS. The HEK 293 cells expressing human URAT1 were lysed in 0.2 mol/L aqueous NaOH (hereafter, the cell sample) and the cell samples were collected. The cell sample and a liquid scintillation liquid, ULTIMA GOLD (produced by PerkinElmer, Inc.) were mixed and the radioactivity was measured by a liquid scintillation counter (Beckman Coulter, Inc.).

The uric acid transport rate of the Example compound at each concentration (% of control uptake) was calculated relative to the radioactivity (radioactivity in human URAT1 expressing HEK 293 cells without addition of the Example compound (DMSO addition)) showing URAT1-specific uric acid transport as 100%, and the concentration ($IC_{50}$) of the Example compound at which the uric acid transport rate is inhibited by 50% was determined. The results are shown in the following table. In addition, the symbols (*, , and *) in the table represent the following inhibitory activity values:

$IC_{50} \leq 0.2$ μM: ***
$0.2$ μM $< IC_{50} \leq 2$ μM: **
$2$ μM $< IC_{50} \leq 20$ μM: *

TABLE 52

| Compound No. | Inhibitory Activity |
|---|---|
| A1 | ** |
| A2 | ** |
| A3 | ** |
| A4 | * |
| A5 | * |
| A6 | ** |
| A7 | ** |
| A8 | ** |
| A9 | ** |
| A10 | ** |
| A11 | ** |
| A12 | * |
| A13 | *** |
| A14 | *** |
| A15 | *** |
| A16 | * |
| A17 | ** |
| A18 | *** |
| A19 | *** |
| A22 | ** |
| A23 | ** |
| A24 | ** |
| A25 | *** |
| A26 | *** |
| A27 | ** |
| A28 | * |
| A30 | * |
| A31 | ** |
| A32 | * |
| A33 | ** |
| A34 | ** |
| A35 | ** |
| A36 | ** |
| A37 | *** |
| A38 | *** |
| A39 | *** |
| A40 | ** |
| A41 | ** |
| A42 | ** |
| A43 | *** |
| A44 | ** |
| A45 | *** |
| A46 | ** |
| A47 | * |
| A48 | * |
| A49 | * |
| A50 | * |
| A51 | * |
| A52 | * |
| A53 | * |
| A54 | ** |
| A55 | ** |
| A56 | * |
| A57 | * |
| A58 | * |
| A59 | * |
| A60 | * |
| A61 | * |
| A62 | * |
| A63 | * |
| A64 | * |
| A65 | * |
| A66 | * |
| A67 | ** |
| A68 | ** |
| A70 | ** |
| A71 | *** |
| A72 | * |
| A73 | * |
| A74 | * |
| A75 | * |
| A76 | ** |
| A77 | ** |
| A78 | *** |
| A79 | ** |
| A80 | ** |
| A81 | ** |
| A82 | ** |
| A83 | ** |
| A84 | ** |

TABLE 53

| Compound No. | Inhibitory Activity |
|---|---|
| A85 | *** |
| A86 | *** |
| A87 | * |
| A88 | *** |
| A89 | *** |
| A90 | *** |
| A91 | *** |

TABLE 53-continued

| Compound No. | Inhibitory Activity |
|---|---|
| A92 | * * * |
| A93 | * * * |
| A94 | * * |
| A95 | * |
| A96 | * * * |
| A97 | * |
| A98 | * * * |
| A99 | * * * |
| A100 | * * * |
| A101 | * * * |
| A102 | * * |
| A103 | * * |
| A104 | * * * |
| A105 | * * * |
| A106 | * |
| A107 | * |
| A108 | * * * |
| A109 | * * |
| A110 | * * |
| A111 | * |
| A112 | * |
| A115 | * |
| A116 | * |
| A117 | * * |
| A118 | * * |
| A119 | * * |
| A120 | * |
| A121 | * * |
| A124 | * |
| A125 | * |
| A130 | * * |
| A131 | * |
| A132 | * * |
| A133 | * * |
| A134 | * * * |
| A135 | * * * |
| A136 | * * * |
| A137 | * * * |
| A138 | * * |
| A139 | * * * |
| A140 | * * * |
| A141 | * * |
| A142 | * * * |
| A143 | * * * |
| A144 | * * * |
| A145 | * * * |
| A146 | * * * |
| A147 | * * * |
| A148 | * * |
| A149 | * * * |
| A150 | * * * |
| A151 | * * * |
| A152 | * * |
| A153 | * * |
| A154 | * * * |
| A155 | * * * |
| A156 | * * * |
| A157 | * * * |
| A158 | * * |
| A159 | * * |
| A160 | * * |
| A161 | * * |
| A162 | * * |
| A163 | * |
| A164 | * * |
| A165 | * |
| A166 | * * * |
| A167 | * * * |
| A168 | * * * |
| A169 | * * * |
| A170 | * * |
| A171 | * * * |
| A172 | * * |

TABLE 54

| Compound No. | Inhibitory Activity |
|---|---|
| A173 | * * * |
| A174 | * * * |
| A175 | * * |
| A176 | * * * |
| A177 | * * * |
| A178 | * * |
| A179 | * * * |
| A180 | * * * |
| A181 | * * * |
| A182 | * * * |
| A183 | * * * |
| A184 | * |
| A185 | * * * |
| A186 | * |
| A187 | * |
| A188 | * * * |
| A189 | * * |
| A190 | * * |
| A191 | * * * |
| A192 | * * |
| A193 | * * * |
| A194 | * * * |
| A195 | * * * |
| A196 | * * * |
| A197 | * * * |
| A198 | * |
| A199 | * * |
| A200 | * * * |
| A201 | * |
| A202 | * * * |
| A203 | * * |
| A204 | * * * |
| A205 | * * * |
| A206 | * * * |
| A207 | * * * |
| A208 | * * * |
| A209 | * * * |
| A210 | * * * |
| A211 | * * * |
| A212 | * * * |
| A213 | * * * |
| A214 | * * * |
| A215 | * * * |
| A216 | * * * |
| A217 | * * * |
| A218 | * * * |
| A219 | * * * |
| A220 | * * * |
| A221 | * * * |
| A222 | * |
| A223 | * * |
| A224 | * |
| A225 | * * * |
| A226 | * * * |
| A227 | * * * |
| A228 | * * |
| A229 | * * |
| A230 | * * |
| A231 | * * * |
| A232 | * * * |
| A233 | * * * |
| A234 | * * |
| A235 | * * * |
| A236 | * * * |
| A237 | * * * |
| A238 | * * |
| A239 | * |
| A240 | * * |
| A241 | * |
| A242 | * |
| A243 | * |
| A244 | * * |
| A245 | * * * |
| A246 | * * |
| A247 | * * |
| A248 | * * * |
| A250 | * * * |

TABLE 54-continued

| Compound No. | Inhibitory Activity |
|---|---|
| A251 | * * * |
| A252 | * * * |
| A253 | * * * |

TABLE 55

| Compound No. | Inhibitory Activity |
|---|---|
| A254 | * * * |
| A255 | * * * |
| A256 | * * * |
| A257 | * * * |
| A258 | * * * |
| A259 | * |
| A260 | * |
| A261 | * |
| A262 | * * |
| A263 | * * |
| A264 | * |
| A265 | * |
| A266 | * * |
| B1 | * * * |
| B2 | * * * |
| B3 | * * * |
| B4 | * * |
| B6 | * * * |
| B7 | * * * |
| B8 | * * * |
| B9 | * * * |
| B10 | * * * |
| B11 | * * * |
| B12 | * * * |
| B13 | * * * |
| B14 | * * * |
| B15 | * * * |
| B16 | * * * |
| B17 | * * * |
| B18 | * * * |
| B19 | * * |
| B20 | * * * |
| B21 | * * * |
| B22 | * * * |
| B23 | * * * |
| B24 | * * * |
| B25 | * * * |
| B26 | * * * |
| B27 | * * * |
| B28 | * * * |
| B29 | * * * |
| B30 | * * * |
| B31 | * * * |
| B32 | * * * |
| B33 | * * * |
| B34 | * * * |
| B35 | * * * |

Test for Drug Efficacy in Cebus Apella

Example 303

A test compound (3 mg/kg to 30 mg/kg) prepared by suspending in a 0.5% methylcellulose solution was administered to Cebus apella into stomach via the nasal cavity using a disposable catheter and a syringe barrel. Blood samples were taken before administration and 30 minutes, 1 hour, 2 hours, 4 hours, 8 hours, 12 hours, and 24 hours after administration; and urine samples were collected for the time intervals of immediately to 4 hours after administration, from 4 hours to 8 hours after administration, from 8 hours to 16 hours after administration, and from 16 hours to 24 hours after administration. Concentrations of uric acid and creatinine in the blood and urine samples collected were measured by an automatic analyzer (JEOL Ltd.). Uric acid and creatine were measured using L-type Wako UA.F (Wako Pure Chemicals Industries, Ltd.) and L-type Creatine F (Wako Pure Chemicals Industries, Ltd.) respectively. Uric acid clearance was calculated from the uric acid concentrations in blood and urine and, similarly, creatinine clearance was calculated from the creatinine concentrations. From these values, the uric acid excretion rate was determined according to the following equation:

Uric acid excretion rate (%)=(uric acid clearance/creatinine clearance)×100

In the present test, the excellent uricosuric effect was confirmed for compounds A1, A2, A7, A13, A14, A15, A19, A26, A81, A119, A121, A134, A135, A137, A139, A147, A156, A169, A233, B1, and B11.

From the above-mentioned results, it is shown that the pyridine derivative of the present invention possesses a superior uricosuric effect.

INDUSTRIAL APPLICABILITY

The pyridine derivative of the present invention or the prodrug thereof, or the pharmaceutically acceptable salt thereof, or the solvate thereof is used as a pharmaceutical.

The invention claimed is:
1. A pyridine derivative represented by the following formula (I) or a pharmaceutically acceptable salt thereof,

[Chemical Formula 1]

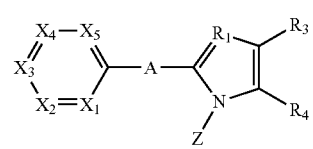

(I)

wherein:
A represents a single bond;
$R_1$ represents a nitrogen atom, $X_2$ is N; $X_1$, $X_3$, $X_4$ and $X_5$ are $CR_2$;
$R_2$ each independently represent a hydrogen atom, an alkyl group having 1 to 6 carbon atoms, an alkenyl group having 2 to 6 carbon atoms, an alkynyl group having 2 to 6 carbon atoms, a halogen atom, a trifluoromethyl group, a difluoromethyl group, a cyano group, an alkylcarbonyl group having 2 to 7 carbon atoms, an alkylsulfonyl group having 1 to 6 carbon atoms, a nitro group, an amino group, a dialkylamino group having 1 to 6 carbon atoms, a formyl group, a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom);
$R_3$ represents a hydrogen atom, an alkyl group having 1 to 6 carbon atoms (which may optionally be substituted with one or more of a hydroxyl group, an amino group, a dialkylamino group having 1 to 6 carbon atoms, an alkenyl group having 2 to 6 carbon atoms, an alkynyl group having 2 to 6 carbon atoms, an alkoxy group having 1 to 6 carbon atoms (which may optionally be substituted with one or more of a hydroxyl group and a halogen atom), an alkylcarbonyl group having 2 to 7 carbon atoms, an alkylthio group having 1 to 6 carbon atoms, an alkylsulfinyl group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a phenoxy group (which may optionally be substituted with one or more of an alkyl group having 1 to 6 carbon atoms, an alkoxy group having 1 to 6 carbon atoms, and a halogen atom), a carboxyl group, or —$CO_2R_5$;

$R_4$ represents a carboxyl group, —$CONHSO_2R_5$, —$CO_2R_5$, or any of the following substituents:

[Chemical Formula 2]

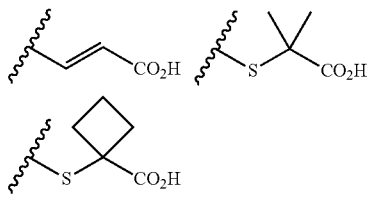

$R_5$ in $R_3$ and $R_4$ each independently represents an alkyl group having 1 to 6 carbon atoms;

Z represents any of the following substituents designated Z1 to Z2:

[Chemical Formula 3]

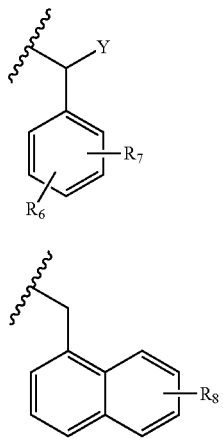

wherein:

$R_6$ and $R_7$ each independently represent a hydrogen atom, a halogen atom, an alkyl group having 1 to 6 carbon atoms, a trifluoromethyl group, a trifluoromethoxy group, or a cyano group, with the proviso that the case where $R_6$ and $R_7$ are simultaneously hydrogen atoms is excluded;

$R_8$ represents a hydrogen atom, a halogen atom, an alkyl group having 1 to 6 carbon atoms, or a trifluoromethyl group; and Y represents a hydrogen atom or an alkyl group having 1 to 6 carbon atoms.

2. The pyridine derivative or the pharmaceutically acceptable salt thereof, according to claim 1, wherein, among four $CR_2$'s, three are CH's and $R_2$ of the remaining one $CR_2$ is a hydrogen atom, an alkyl group having 1 to 6 carbon atoms, a halogen atom, a trifluoromethyl group, a difluoromethyl group, a cyano group, a nitro group, a dialkylamino group having 1 to 6 carbon atoms a hydroxyl group, an alkoxy group having 1 to 6 carbon atoms (which may optionally be substituted with one or more of a hydroxyl group, a phenyl group, a cyclohexyl group, and a halogen atom), an alkylthio group having 1 to 6 carbon atoms, a phenyl group (which may optionally be substituted with one or more of an alkyl group having 1 to 6 carbon atoms, an alkoxy group having 1 to 6 carbon atoms, and a halogen atom), or a phenoxy group (which may optionally be substituted with one or more of an alkyl group having 1 to 6 carbon atoms, an alkoxy group having 1 to 6 carbon atoms, and a halogen atom).

3. The pyridine derivative or the pharmaceutically acceptable salt thereof, according to claim 2, wherein $R_2$ is a hydrogen atom, a methyl group, an ethyl group, a cyclopropyl group, a methoxy group, an ethoxy group, a propoxy group, an isopropoxy group, an isobutyloxy group, a benzyloxy group, a methylthio group, a fluorine atom, a chlorine atom, a bromine atom, a cyano group, a hydroxyl group, a trifluoromethyl group, a difluoromethyl group, a nitro group, a phenyl group, or a phenoxy group.

4. The pyridine derivative or the pharmaceutically acceptable salt thereof according to claim 1, wherein, among four $CR_2$'s, three are CH's and the remaining $CR_2$ is located at $X_4$.

5. The pyridine derivative or the pharmaceutically acceptable salt thereof, according to claim 1, wherein $R_3$ is a hydrogen atom, an alkyl group having 1 to 6 carbon atoms (which may optionally be substituted with one or more of a hydroxyl group, an amino group, a dialkylamino group having 1 to 6 carbon atoms, an alkoxy group having 1 to 6 carbon atoms, an alkylthio group having 1 to 6 carbon atoms, a halogen atom, a trifluoromethyl group, a difluoromethyl group, a cyano group, a phenyl group (which may optionally be substituted with one or more of an alkyl group having 1 to 6 carbon atoms, an alkoxy group having 1 to 6 carbon atoms, and a halogen atom), a carboxyl group, or —$CO_2R_5$.

6. The pyridine derivative or the pharmaceutically acceptable salt thereof, according to claim 5, wherein $R_3$ is a hydrogen atom, a methyl group, an ethyl group, an isopropyl group, a cyclopropyl group, a chlorine atom, a bromine atom, an iodine atom, a trifluoromethyl group, a difluoromethyl group, a methoxy group, a phenyl group, a cyano group, a carboxyl group, —$CO_2R_5$, a hydroxymethyl group, a 1-hydroxyethyl group, a 2-hydroxypropan-2-yl group, a 3-hydroxypentan-3-yl group, a dimethylaminomethyl group, or a diethylaminomethyl group.

7. The pyridine derivative or the pharmaceutically acceptable salt thereof, according to claim 1, wherein $R_4$ is a carboxyl group —$CONHSO_2CH_3$, —$CONHSO_2$-cyclopropyl, or —$CO_2R_5$.

8. The pyridine derivative or the pharmaceutically acceptable salt thereof, according to claim 1, wherein Z is Z1, and $R_6$ and $R_7$ are, on a phenyl ring, chlorine substituents at 2- and 5-positions, chlorine substituents at 3- and 5-positions, methyl substituents at 2- and 5-positions, trifluoromethyl substituents at 2- and 5-positions, or chlorine and methyl substituents at 2- and 5-positions, respectively; or Z is Z2, and $R_8$ is, on a naphthalene ring, a hydrogen atom, a 2-methyl group, a 4-methyl group, an 8-methyl group, or an 8-bromo group.

9. A pyridine derivative selected from the following compounds (1) to (193) or a pharmaceutically acceptable salt thereof:

(1) 1-(2,5-dimethylbenzyl)-4-methyl-2-(pyridin-3-yl)-1H-imidazole-5-carboxylic acid;

(2) 4-methyl-1-(naphthalen-1-ylmethyl)-2-(pyridin-3-yl)-1H-imidazole-5-carboxylic acid;

(3) ethyl 4-methyl-1-(naphthalen-1-ylmethyl)-2-(pyridin-3-yl)-1H-imidazole-5-carboxylate;

(7) 4-chloro-1-(naphthalen-1-ylmethyl)-2-(pyridin-3-yl)-1H-imidazole-5-carboxylic acid;

(8) 4-ethyl-1-(naphthalen-1-ylmethyl)-2-(pyridin-3-yl)-1H-imidazole-5-carboxylic acid;

(9) 4-cyclopropyl-1-(naphthalen-1-ylmethyl)-2-(pyridin-3-yl)-1H-imidazole-5-carboxylic acid;

(10) 1-(2,5-dichlorobenzyl)-4-methyl-2-(pyridin-3-yl)-1H-imidazole-5-carboxylic acid;

(11) 1-(2,5-dichlorobenzyl)-4-ethyl-2-(pyridin-3-yl)-1H-imidazole-5-carboxylic acid;

(12) 4-cyclopropyl-1-(2,5-dichlorobenzyl)-2-(pyridin-3-yl)-1H-imidazole-5-carboxylic acid;

(13) 4-methyl-1-((4-methylnaphthalen-1-yl) methyl)-2-(pyridin-3-yl)-1H-imidazole-5-carboxylic acid;

(14) 4-cyclopropyl-1-((4-methylnaphthalen-1-yl)methyl)-2-(pyridin-3-yl)-1H-imidazole-5-carboxylic acid;

(15) 1-(2,5-dichlorobenzyl)-2-(pyridin-3-yl)-4-(trifluoromethyl)-1H-imidazole-5-carboxylic acid;

(17) 4-chloro-1-((4-methylnaphthalen-1-yl)methyl)-2-(pyridin-3-yl)-1H-imidazole-5-carboxylic acid;

(18) 4-isopropyl-1-(naphthalen-1-ylmethyl)-2-(pyridin-3-yl)-1H-imidazole-5-carboxylic acid;

(19) 4-isopropyl-1-((4-methylnaphthalen-1-yl)methyl)-2-(pyridin-3-yl)-1H-imidazole-5-carboxylic acid;

(20) 1-(2,5-dichlorobenzyl)-4-isopropyl-2-(pyridin-3-yl)-1H-imidazole-5-carboxylic acid;

(31) 1-(2-chloro-5-fluorobenzyl)-4-methyl-2-(pyridin-3-yl)-1H-imidazole-5-carboxylic acid;

(32) 1-(5-chloro-2-fluorobenzyl)-4-methyl-2-(pyridin-3-yl)-1H-imidazole-5-carboxylic acid;

(33) 1-(2-chloro-5-(trifluoromethyl)benzyl)-4 methyl-2-(pyridin-3-yl)-1H-imidazole-5-carboxylic acid;

(34) 1-(5-chloro-2-(trifluoromethyl)benzyl)-4-methyl-2-(pyridin-3-yl)-1H-imidazole-5-carboxylic acid;

(35) 1-(2,5-dichlorobenzyl)-2-(pyridin-3-yl)-1H-imidazole-5-carboxylic acid;

(36) 1-(2,5-bis(trifluoromethyl)benzyl)-4-methyl-2-(pyridin-3-yl)-1H-imidazole-5-carboxylic acid;

(37) 1-(2-bromobenzyl)-4-methyl-2-(pyridin-3-yl)-1H-imidazole-5-carboxylic acid;

(38) 1-(3-bromobenzyl)-4-methyl-2-(pyridin-3-yl)-1H-imidazole-5-carboxylic acid;

(40) 1-(3,4-dichlorobenzyl)-4-methyl-2-(pyridin-3-yl)-1H-imidazole-5-carboxylic acid;

(41) 1-(2,3-dichlorobenzyl)-4-methyl-2-(pyridin-3-yl)-1H-imidazole-5-carboxylic acid;

(42) 1-(3,5-dichlorobenzyl)-4-methyl-2-(pyridin-3-yl)-1H-imidazole-5-carboxylic acid;

(43) 1-(3-chloro-5-fluorobenzyl)-4-methyl-2-(pyridin-3-yl)-1H-imidazole-5-carboxylic acid;

(44) 1-(2,4-dichlorobenzyl)-4-methyl-2-(pyridin-3-yl)-1H-imidazole-5-carboxylic acid;

(45) 1-(2-chloro-5-methylbenzyl)-4-methyl-2-(pyridin-3-yl)-1H-imidazole-5-carboxylic acid;

(54) 4-chloro-1-(2,5-dichlorobenzyl)-2-(pyridin-3-yl)-1H-imidazole-5-carboxylic acid;

(55) 4-bromo-1-(2,5-dichlorobenzyl)-2-(pyridin-3-yl)-1H-imidazole-5-carboxylic acid;

(56) 1-(2,5-dichlorobenzyl)-4-iodo-2-(pyridin-3-yl)-1H-imidazole-5-carboxylic acid;

(57) 1-(2,5-dichlorobenzyl)-4-phenyl-2-(pyridin-3-yl)-1H-imidazole-5-carboxylic acid;

(58) 1-(2,5-dichlorobenzyl)-4-(3-fluorophenyl)-2-(pyridin-3-yl)-1H-imidazole-5-carboxylic acid;

(59) 1-(2,5-dichlorobenzyl)-4-(4-fluorophenyl)-2-(pyridin-3-yl)-1H-imidazole-5-carboxylic acid;

(61) 1-(2,5-dichlorobenzyl)-4-methoxy-2-(pyridin-3-yl)-1H-imidazole-5-carboxylic acid;

(62) 1-(2,5-dichlorobenzyl)-2-(pyridin-3-yl)-4-(2,2,2-trifluoroethoxy)-1H-imidazole-5-carboxylic acid;

(63) 1-(2,5-dichlorobenzyl)-2-(pyridin-3-yl)-4-(p-tolyloxy)-1H-imidazole-5-carboxylic acid;

(64) 1-(2,5-dichlorobenzyl)-4-(4-fluorophenoxy)-2-(pyridin-3-yl)-1H-imidazole-5-carboxylic acid;

(65) 4-cyano-1-(2,5-dichlorobenzyl)-2-(pyridin-3-yl)-1H-imidazole-5-carboxylic acid;

(66) 1-(2,5-dichlorobenzyl)-2-(pyridin-3-yl)-4-vinyl-1H-imidazole-5-carboxylic acid;

(67) 4-(1-cyclopenten-1-yl)-1-(2,5-dichlorobenzyl)-2-(pyridin-3-yl)-1H-imidazole-5-carboxylic acid;

(68) 1-(2,5-dichlorobenzyl)-4-(methylthio)-2-(pyridin-3-yl)-1H-imidazole-5-carboxylic acid;

(69) 1-(2,5-dichlorobenzyl)-4-(ethylthio)-2-(pyridin-3-yl)-1H-imidazole-5-carboxylic acid;

(70) 1-(2,5-dichlorobenzyl)-4-(2-hydroxypropan-2-yl)-2-(pyridin-3-yl)-1H-imidazole-5-carboxylic acid;

(71) 1-(2,5-dichlorobenzyl)-4-(3-hydroxypentan-3-yl)-2-(pyridin-3-yl)-1H-imidazole-5-carboxylic acid;

(75) 2-(5-fluoropyridin-3-yl)-4-methyl-1-(naphthalen-1-ylmethyl)-1H-imidazole-5-carboxylic acid;

(76) 2-(5-chloropyridin-3-yl)-4-methyl-1-(naphthalen-1-ylmethyl)-1H-imidazole-5-carboxylic acid;

(77) 4-methyl-1-(naphthalen-1-ylmethyl)-2-(5-phenoxypyridin-3-yl)-1H-imidazole-5-carboxylic acid;

(80) 1-(2,5-dichlorobenzyl)-2-(5-fluoropyridin-3-yl)-4-methyl-1H-imidazole-5-carboxylic acid;

(81) 2-(5-chloropyridin-3-yl)-1-(2,5-dichlorobenzyl)-4-methyl-1H-imidazole-5-carboxylic acid;

(82) 1-(2,5-dichlorobenzyl)-2-(5-fluoropyridin-3-yl)-4-(trifluoromethyl)-1H-imidazole-5-carboxylic acid;

(83) 2-(5-chloropyridin-3-yl)-1-(2,5-dichlorobenzyl)-4-(trifluoromethyl)-1H-imidazole-5-carboxylic acid;

(84) 4-methyl-1-(naphthalen-1-ylmethyl)-2-(5-(trifluoromethyl)pyridin-3-yl)-1H-imidazole-5-carboxylic acid;

(85) 1-(2,5-dichlorobenzyl)-4-methyl-2-(5-(trifluoromethyl)pyridin-3-yl)-1H-imidazole-5-carboxylic acid;

(86) 1-(2,5-dichlorobenzyl)-4-(trifluoromethyl)-2-(5-(trifluoromethyl)pyridin-3-yl)-1H-imidazole-5-carboxylic acid;

(90) 2-(5-chloropyridin-3-yl)-4-isopropyl-1-(naphthalen-1-ylmethyl)-1H-imidazole-5-carboxylic acid;

(91) 2-(5-chloropyridin-3-yl)-4-cyclopropyl-1-(naphthalen-1-ylmethyl)-1H-imidazole-5-carboxylic acid;

(92) 2-(5-chloropyridin-3-yl)-1-(2,5-dichlorobenzyl)-4-isopropyl-1H-imidazole-5-carboxylic acid;

(93) 2-(5-chloropyridin-3-yl)-4-cyclopropyl-1-(2,5-dichlorobenzyl)-1H-imidazole-5-carboxylic acid;

(94) 4-ethyl-2-(5-fluoropyridin-3-yl)-1-(naphthalen-1-ylmethyl)-1H-imidazole-5-carboxylic acid;

(95) 2-(5-chloropyridin-3-yl)-4-ethyl-1-(naphthalen-1-ylmethyl)-1H-imidazole-5-carboxylic acid;
(96) 1-(2,5-dichlorobenzyl)-4-ethyl-2-(5-fluoropyridin-3-yl)-1H-imidazole-5-carboxylic acid;
(97) 2-(5-chloropyridin-3-yl)-1-(2,5-dichlorobenzyl)-4-ethyl-1H-imidazole-5-carboxylic acid;
(98) 2-(5-fluoropyridin-3-yl)-4-isopropyl-1-(naphthalen-1-ylmethyl)-1H-imidazole-5-carboxylic acid;
(99) 4-cyclopropyl-2-(5-fluoropyridin-3-yl)-1-(naphthalen-1-ylmethyl)-1H-imidazole-5-carboxylic acid;
(100) 1-(2,5-dichlorobenzyl)-2-(5-fluoropyridin-3-yl)-4-isopropyl-1H-imidazole-5-carboxylic acid;
(101) 4-cyclopropyl-1-(2,5-dichlorobenzyl)-2-(5-fluoropyridin-3-yl)-H-imidazole-5-carboxylic acid;
(102) 1-(2,5-dichlorobenzyl)-4-methyl-2-(5-methylpyridin-3-yl)-1H-imidazole-5-carboxylic acid;
(103) 1-(2,5-dichlorobenzyl)-2-(5-methoxypyridin-3-yl)-4-methyl-1H-imidazole-5-carboxylic acid;
(104) 2-(5-cyanopyridin-3-yl)-1-(2,5-dichlorobenzyl)-4-methyl-1H-imidazole-5-carboxylic acid;
(105) 1-(2,5-dichlorobenzyl)-4-methyl-2-(6-methylpyridin-3-yl)-1H-imidazole-5-carboxylic acid;
(106) 1-(2,5-dichlorobenzyl)-2-(2-fluoropyridin-3-yl)-4-methyl-1H-imidazole-5-carboxylic acid;
(107) 1-(2,5-dichlorobenzyl)-2-(6-methoxypyridin-3-yl)-4-methyl-1H-imidazole-5-carboxylic acid;
(108) 1-(2,5-dichlorobenzyl)-2-(2-methoxypyridin-3-yl)-4-methyl-1H-imidazole-5-carboxylic acid;
(109) 2-(6-chloropyridin-3-yl)-1-(2,5-dichlorobenzyl)-4-methyl-1H-imidazole-5-carboxylic acid;
(111) 1-(2,5-dichlorobenzyl)-4-methyl-2-(5-nitropyridin-3-yl)-1H-imidazole-5-carboxylic acid;
(112) 2-(5-cyclopropylpyridin-3-yl)-1-(2,5-dichlorobenzyl)-4-methyl-1H-imidazole-5-carboxylic acid;
(113) 2-(5-chloropyridin-3-yl)-1-(2,5-dichlorobenzyl)-1H-imidazole-5-carboxylic acid;
(114) 1-(2,5-bis(trifluoromethyl)benzyl)-2-(5-fluoropyridin-3-yl)-4-methyl-1H-imidazole-5-carboxylic acid;
(115) 1-(2,5-dichlorobenzyl)-2-(5-fluoropyridin-3-yl)-1H-imidazole-5-carboxylic acid;
(116) 1-(2,5-dichlorobenzyl)-2-(5-hydroxypyridin-3-yl)-4-methyl-1H-imidazole-5-carboxylic acid;
(117) 1-(2,5-bis(trifluoromethyl)benzyl)-2-(5-chloropyridin-3-yl)-4-methyl-1H-imidazole-5-carboxylic acid;
(118) 1-(2,5-dichlorobenzyl)-2-(5-ethoxypyridin-3-yl)-4-methyl-1H-imidazole-5-carboxylic acid;
(119) 1-(2,5-dichlorobenzyl)-2-(5-isopropoxypyridin-3-yl)-4-methyl-1H-imidazole-5-carboxylic acid;
(120) 1-(2,5-dichlorobenzyl)-4-methyl-2-(5-phenylpyridin-3-yl)-1H-imidazole-5-carboxylic acid;
(121) 2-(5-bromopyridin-3-yl)-1-(2,5-dichlorobenzyl)-4-methyl-1H-imidazole-5-carboxylic acid;
(122) 1-(2,5-dimethylbenzyl)-2-(5-fluoropyridin-3-yl)-4-methyl-1H-imidazole-5-carboxylic acid;
(123) 2-(5-chloropyridin-3-yl)-1-(2,5-dimethylbenzyl)-4-methyl-1H-imidazole-5-carboxylic acid;
(124) 1-(2,5-dimethylbenzyl)-4-methyl-2-(5-methylpyridin-3-yl)-1H-imidazole-5-carboxylic acid;
(125) 1-(2,5-dichlorobenzyl)-2-(5-ethylpyridin-3-yl)-4-methyl-1H-imidazole-5-carboxylic acid;
(126) 1-(2,5-dichlorobenzyl)-4-methyl-2-(5-(methylthio)pyridin-3-yl)-1H-imidazole-5-carboxylic acid;
(127) 2-(5-acetylpyridin-3-yl)-1-(2,5-dichlorobenzyl)-4-methyl-1H-imidazole-5-carboxylic acid;
(128) 1-(2,5-dichlorobenzyl)-4-methyl-2-(5-propoxypyridin-3-yl)-1H-imidazole-5-carboxylic acid;
(129) 1-(2,5-dichlorobenzyl)-2-(5-isobutoxypyridin-3-yl)-4-methyl-1H-imidazole-5-carboxylic acid;
(130) 2-(5-(cyclohexylmethoxy)pyridin-3-yl)-1-(2,5-dichlorobenzyl)-4-methyl-1H-imidazole-5-carboxylic acid;
(131) 2-(5-(benzyloxy)pyridin-3-yl)-1-(2,5-dichlorobenzyl)-4-methyl-1H-imidazole-5-carboxylic acid;
(132) 2-(5-chloropyridin-3-yl)-1-(2,5-dichlorobenzyl)-4-(hydroxymethyl)-1H-imidazole-5-carboxylic acid;
(133) 2-(5-chloropyridin-3-yl)-1-(2,5-dichlorobenzyl)-4-((dimethylamino)methyl)-1H-imidazole-5-carboxylic acid;
(134) 2-(5-chloropyridin-3-yl)-1-(2,5-dichlorobenzyl)-4-((diethylamino)methyl)-1H-imidazole-5-carboxylic acid;
(144) 2-(5-bromopyridin-3-yl)-1-(2,5-dichlorobenzyl)-1H-imidazole-5-carboxylic acid;
(145) 1-(2,5-dichlorobenzyl)-2-(5-methylpyridin-3-yl)-1H-imidazole-5-carboxylic acid;
(146) 2-(5-chloropyridin-3-yl)-1-(2,5-dichlorobenzyl)-4-(difluoromethyl)-1H-imidazole-5-carboxylic acid;
(147) 1-(2,5-dichlorobenzyl)-2-(5-(difluoromethyl) pyridin-3-yl)-4-methyl-1H-imidazole-5-carboxylic acid;
(148) 2-(5-chloropyridin-3-yl)-1-(2,5-dichlorobenzyl)-4-ethynyl-1H-imidazole-5-carboxylic acid;
(149) 2-(5-chloropyridin-3-yl)-1-(2,5-dichlorobenzyl)-1H-imidazole-4,5-dicarboxylic acid;
(150) 2-(5-chloropyridin-3-yl)-1-(2,5-dichlorobenzyl)-4-(1-hydroxyethyl)-1H-imidazole-5-carboxylic acid;
(151) 1-(2,5-dichlorobenzyl)-2-(5-fluoropyridin-3-yl)-4-(2-hydroxypropan-2-yl)-1H-imidazole-5-carboxylic acid;
(152) 2-(5-chloropyridin-3-yl)-1-(2,5-dichlorobenzyl)-4-(2-hydroxypropan-2-yl)-1H-imidazole-5-carboxylic acid;
(153) 1-(2,5-dichlorobenzyl)-4-(2-hydroxypropan-2-yl)-2-(5-methylpyridin-3-yl)-1H-imidazole-5-carboxylic acid;
(154) 1-(2,5-dichlorobenzyl)-2-(5-fluoropyridin-3-yl)-4-(3-hydroxypentan-3-yl)-1H-imidazole-5-carboxylic acid;
(155) 2-(5-chloropyridin-3-yl)-1-(2,5-dichlorobenzyl)-4-(3-hydroxypentan-3-yl)-1H-imidazole-5-carboxylic acid;
(156) 1-(2,5-dichlorobenzyl)-4-(3-hydroxypentan-3-yl)-2-(5-methylpyridin-3-yl)-1H-imidazole-5-carboxylic acid;
(157) 4-acetyl-2-(5-chloropyridin-3-yl)-1-(2,5-dichlorobenzyl)-1H-imidazole-5-carboxylic acid;
(158) 4-chloro-1-(2,5-dichlorobenzyl)-2-(5-methylpyridin-3-yl)-1H-imidazole-5-carboxylic acid;
(159) 4-chloro-2-(5-chloropyridin-3-yl)-1-(2,5-dichlorobenzyl)-1H-imidazole-5-carboxylic acid;
(161) 2-(5-chloropyridin-3-yl)-1-(1-(2,5-dichlorophenyl)ethyl)-4-methyl-1H-imidazole-5-carboxylic acid;
(168) 1-(2-chloro-5-methylbenzyl)-4-methyl-2-(5-methylpyridin-3-yl)-1H-imidazole-5-carboxylic acid;
(169) 1-(2-chloro-5-methylbenzyl)-2-(5-chloropyridin-3-yl)-4-methyl-1H-imidazole-5-carboxylic acid;
(191) 2-((2-(5-chloropyridin-3-yl)-1-(2,5-dichlorobenzyl)-1H-imidazole-5-yl)thio)-2-methylpropanoic acid;
(192) 1-((2-(5-chloropyridin-3-yl)-1-(2,5-dichlorobenzyl)-1H-imidazol-5-yl)thio)cyclobutanecarboxylic acid; and
(193) 2-((5-(5-chloropyridin-3-yl)-1-(2,5-dichlorobenzyl)-1H-imidazol-2-yl)thio)-2-methylpropanoic acid.

10. A pharmaceutical composition comprising the pyridine derivative, or the pharmaceutically acceptable salt thereof, according to claim 1.

* * * * *